United States Patent
Tiwari et al.

(10) Patent No.: US 12,241,070 B2
(45) Date of Patent: Mar. 4, 2025

(54) SERINE RECOMBINASES MEDIATING STABLE INTEGRATION INTO PLANT GENOMES

(71) Applicant: GREENVENUS, LLC, Davis, CA (US)

(72) Inventors: Shiv B. Tiwari, Blacksburg, VA (US); Arianne Tremblay, Blacksburg, VA (US); Jonathan Carson, Blacksburg, VA (US); Sekhar Boddupalli, Blacksburg, VA (US); Rio Stamler, Blacksburg, VA (US); Amanda Edwards, Blacksburg, VA (US); Kornelie Frech, Blacksburg, VA (US)

(73) Assignee: GREENVENUS, LLC, Davis, CA (US)

( * ) Notice: Subject to any disclaimer, the term of this patent is extended or adjusted under 35 U.S.C. 154(b) by 496 days.

(21) Appl. No.: 17/290,114

(22) PCT Filed: Oct. 31, 2019

(86) PCT No.: PCT/US2019/059107
§ 371 (c)(1),
(2) Date: Apr. 29, 2021

(87) PCT Pub. No.: WO2020/092733
PCT Pub. Date: May 7, 2020

(65) Prior Publication Data
US 2021/0395761 A1      Dec. 23, 2021

Related U.S. Application Data

(60) Provisional application No. 62/914,633, filed on Oct. 14, 2019, provisional application No. 62/913,318, filed on Oct. 10, 2019, provisional application No. 62/849,368, filed on May 17, 2019, provisional application No. 62/754,745, filed on Nov. 2, 2018.

(51) Int. Cl.
*C12N 15/82* (2006.01)
*C12N 9/22* (2006.01)

(52) U.S. Cl.
CPC .......... *C12N 15/8213* (2013.01); *C12N 9/22* (2013.01); *C12N 15/8241* (2013.01)

(58) Field of Classification Search
None
See application file for complete search history.

(56) References Cited

U.S. PATENT DOCUMENTS

| 10,081,817 | B2 * | 9/2018 | Padidam | .............. | C12N 15/907 |
| 2006/0172377 | A1 | 8/2006 | Padidam | | |
| 2009/0133158 | A1 | 5/2009 | Lahaye et al. | | |
| 2013/0067618 | A1 | 3/2013 | Ader et al. | | |
| 2014/0237681 | A1 | 8/2014 | Gordon-Kamm et al. | | |
| 2017/0114370 | A1 * | 4/2017 | Padidam | .............. | A61P 31/18 |
| 2017/0183654 | A1 | 6/2017 | Wong et al. | | |
| 2018/0163195 | A1 | 6/2018 | Wong et al. | | |
| 2018/0171346 | A1 | 6/2018 | Gordon-Kamm et al. | | |

OTHER PUBLICATIONS

Ow, 2002, Plant Molecular Biology, 48:183-2002.*
Olorunniji et al, 2017, Nucleic Acids Research, 45:8635-8645.*
Thomson et al, 2010, BMC Biotechnology, 10:1-12.*
International Preliminary Report on Patentability and Written Opinion for Application No. PCT/US2019/059107 (issued Apr. 27, 2021).
Abe et al., "Developmentally-Regulated Excision of the SPβ Prophage Reconstitutes a Gene Required for Spore Envelope Mutation in Bacillus subtilis," PLoS Genetics 10(10): e1004636 (2014).
Armas et al., "A rapid and efficient in vitro regeneration system for lettuce (*Lactuca sativa* L.)," Plant Methods 13:58 (2017).
Collier et al., "A versatile and robust Agrobacterium-based gene stacking system generates high-quality transgenic *Arabidopsis* plants," The Plant Journal 95(4): 573-583 (2018).
Groth et al., "A phage integrase directs efficient site-specific integration in human cells," Proc Natl Acad Sci USA 97(11): 5995-6000 (2000).
Jie et al., " Myo-inositol increases the plating efficiency of protoplast derived from cotyledon of cabbage (*Brassica oleracea* var. capitata)," J Plant Biotechnol 38: 69-76 (2011).
Kapusi et al., "phiC31 Integrase-Mediated Site-Specific Recombination in Barley," PLoS One 7(9): e45353 (2012).
Lai et al., "Genomics of Compositae weeds: EST libraries, microarrays, and evidence of introgression," American Journal of Botany 99(2): 209-218 (2011).
Lazarevic et al., "Nucleotide sequence of the Bacillus subtilis temperate bacteriophage SPbeta2c," Microbiology 145(5): 1055-1067 (1999).
Mandali et al., "The site-specific integration reaction of Listeria phage A118 integrase, a serine recombinase," Mobile DNA 4: 2 (2013).
Olorunniji et al., "Control of serine integrase recombination directionality by fusion with the directionality factor," Nucleic Acids Research 45(14): 8635-8645 (2017).
Smith et al., "Diversity in the serine recombinases," Molecular Microbiology 44(2): 299-307 (2002).

(Continued)

*Primary Examiner* — Jason Deveau Rosen
(74) *Attorney, Agent, or Firm* — Troutman Pepper Locke LLP (Rochester)

(57) ABSTRACT

Described is a serine recombinase that integrates large sections of foreign DNA into plant chromosomes through non-homologous recombination through attP or attB sites on the foreign DNA but without the engineering of corresponding attB or attP site on the plant chromosome. The serine recombinase-based method has several advantages over other systems, such as *Agrobacterium*. Also described are related methods, composition, and plants containing exogenous DNA.

21 Claims, 48 Drawing Sheets
Specification includes a Sequence Listing.

(56) References Cited

OTHER PUBLICATIONS

Thomson et al., "The Bxbl recombination system demonstrates heritable transmission of site-specific excision in *Arabidopsis*," BMC Biotechnol 12:9 (2012).
Tiwari et al., "Transfection assays with protoplasts containing integrated reporter genes," Methods Mol Biol 323: 237-44 (2006).
Woo et al., "DNA-free genome editing in plants with preassembled CRISPR-Cas9 ribonucleoproteins," Nature Biotechnol 32: 1162-1164 (2015).
Zhang et al., "Control of Directionality in *Streptomyces* Phage QBT1 Integrase-Mediated Site-Specific Recombination," PLoS One 8(11): e80434 (2013).
International Search Report issued in PCT/US2019/059107, dated Feb. 14, 2020.
First Office Action from Chinese Application No. 201980087590.7 and translation dated Dec. 7, 2023.
Second Office Action from Chinese Application No. 201980087590.7 and translation dated Jul. 9, 2024.

* cited by examiner

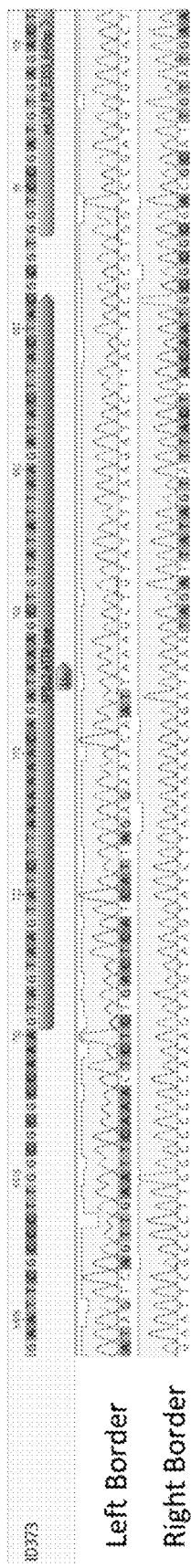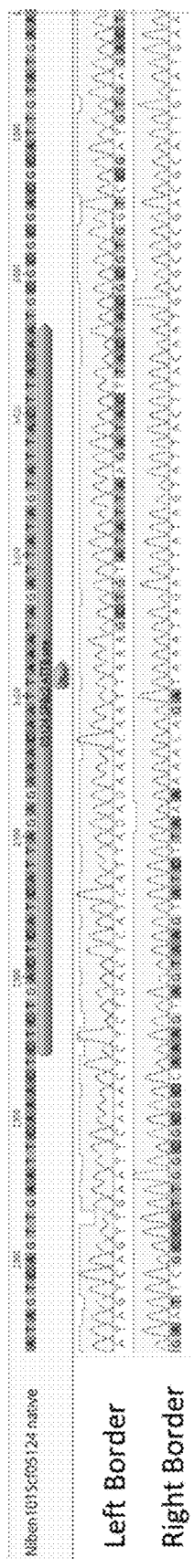
FIG. 14

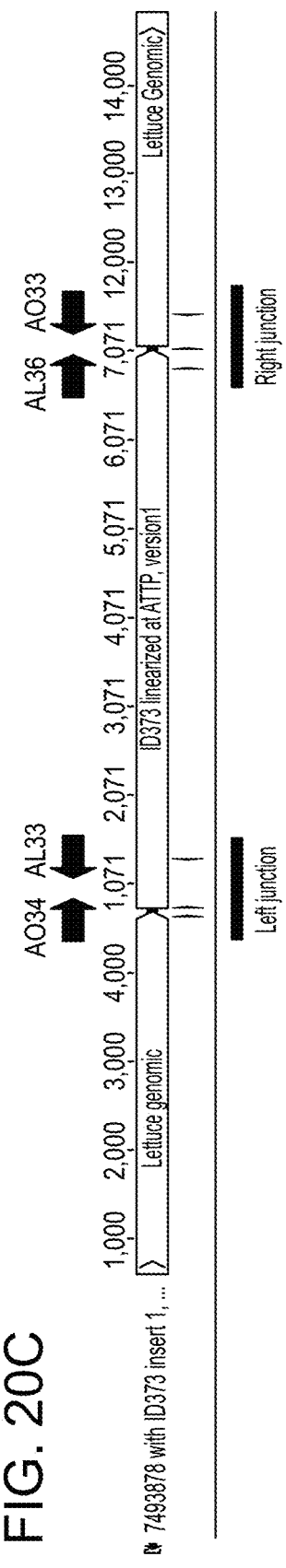
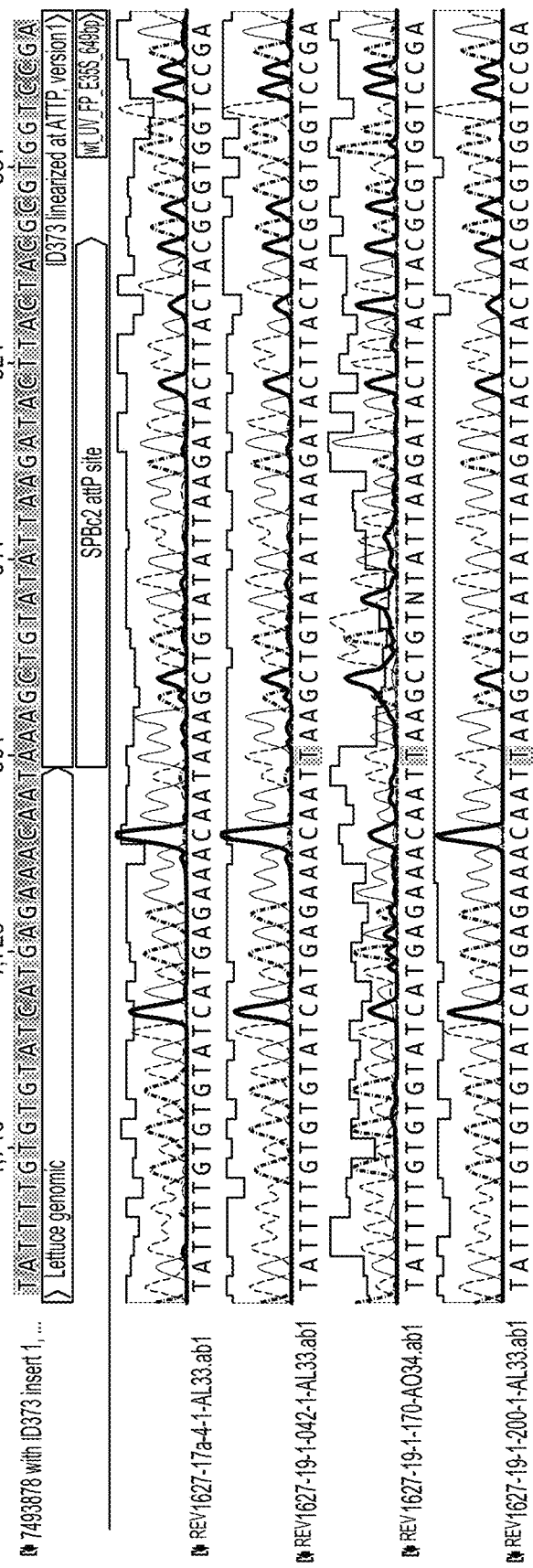
FIG. 20C
FIG. 20D

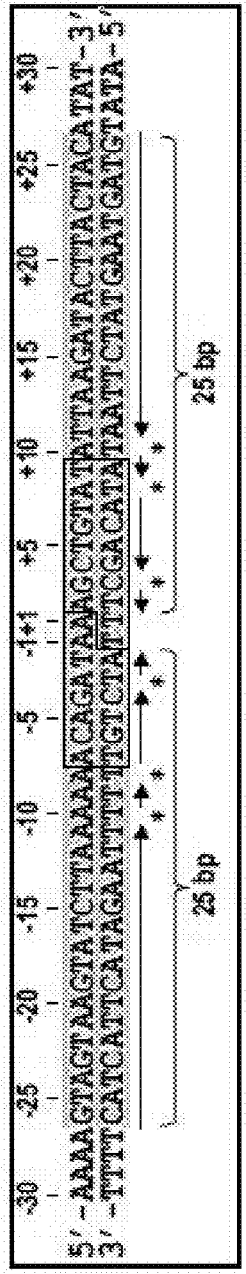
FIG. 25C  attP (SPβ)
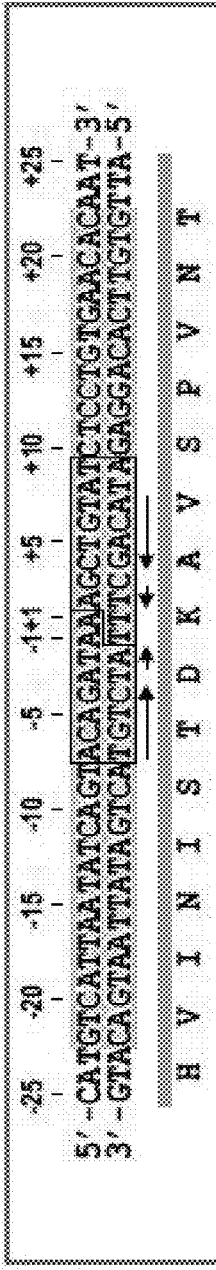
FIG. 25D  attB (spsM)
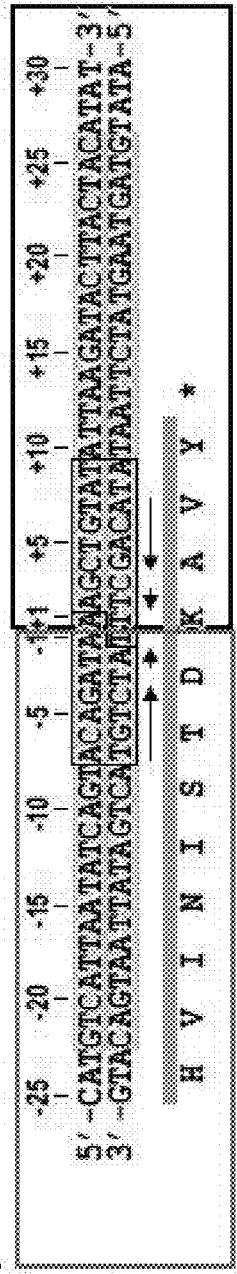
FIG. 25E  attL (5'-spsM)
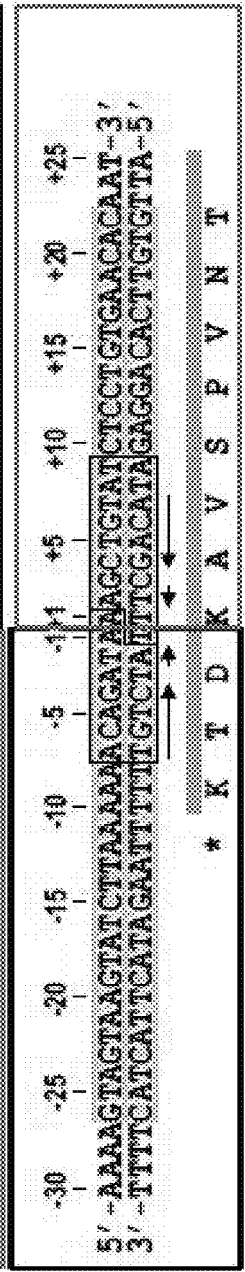
FIG. 25F  attR (spsM-3')

ATAACGAAAGATTTGGCCATGACTGCAGCATTGCCACCATACGAAGATACTGTTGCTTCGTAGCTCATCA
AAAACTGCTTCGGGTCTGAGTGGCCATCA (SEQ ID NO:56)

1. AC229795 - Rice Genome Hit
   ATGTGTTGAATTCACACAGTGG-TTGCTACTTGGTGCTAATTGCTACCAGTTGCTTAGCTAGTAGTGTTATTACAGGATTGGTGATCTACTCGGGTTGTCAGGATTGCTTGG
   K source Oryza minuta 2. PacBio Read from Protoplast pools ATGTGTTGAATTCACACAGTGGTTGCTACTTGGTGCTAATTGCTACCAGTTGCT-AGCTAGTAGTGTTATTACAGGATTGGTGAGCTACTCGGCTGTGTATATTAAGATACTTACTACGCGT
3. SPBc2 attP integration vector                          ATGTGTTGAATTCACACAGTGGTTGCTACTTGGTGCTAATTGCTACCAGTTGCTTTGCTACTTGGTGCTACTTGGTGCTAATTGCTACCAGTTGCTTGG GATGTATGGTAAGTATATTAAGATACTTACTACGCGT
                                                                                                                            SPBc2 attP

FIG. 32C

| Reference Genome | Genomic Location | Sequence |
|---|---|---|
| Nipponbare | Chr. 6: 25696769 | TCCGATTGAAGTTTAGTAGGAGTATAGTGTAGTGTTAGTGTACACTGTCTTTA AGATCACATTAAGAACTAATAGACCCTGTAAACCCTTTCATCTAGCAG |
| Nipponbare | Chr. 9: 21180289 | GGTAAAGGCGATGATGTGTACTCTCTTGGGTTGCCTATTGGGTGCATATCCTTG GCAGGGCTCATGTTGTTCAGTTAATAAAGATATTAAGTAGCTACCTA |
| Nipponbare | Chr. 8: 28050778 | TACCTTTAATTTAGTAGTACATGACATTGTGAACATCAGCATAAGTATCGTCTTATT GAGATACATATTTTATCTCACGTTAGCACGTTTTTTTAAGTACTA |
| Nipponbare | Chr. 12: 27510360 | ACCGAATGCTGCGTGGGAGTACATTGTTCAGATCGTAGGTGGCGCTGTCTTGT CTGCCCGCCCATTTAACTTCCTTCCGCCATCACGAACCTGATCAACG |

| Alignment position | 1.......... | 11......... | 21......... | 31...... |
|---|---|---|---|---|
| NC_024459_1 | aa-TTACATG | AGAAACAATT | AAGAAGAGTT | TAGAAAAGAA |
| NC_024461_1 | at-TATTTTT | AGAAACAATA | AATGGGTTTT | TAAAATAGCA |
| NC_024462_1 | -TGTATCTAG | TGAAACTATA | AATTGGTAAT | TCTAAGTAAC |
| NC_024462_2 | -TGTTGCGTG | AGAAACAATT | AAATAGATCC | AACAATACAA |
| NC_024462_3 | -TGAAATTTT | AGAAACCATT | AAAATGTATT | TAGAAGCTTC |
| NC_024463_1 | -TGTCATGAA | AGCAACAATA | AAATTGATTT | TCTAATTAAt |
| NC_024465_1 | -TGGCATATG | AGAAACAATA | AAAGCGATCA | TATCATATTA |
| NC_024465_2 | -TGTTGTGTG | AGAAACAATT | AAACAGATCC | AACAATACAA |
| NC_024465_3 | -TGTTGTGTG | AGAAACAATT | AAACAGATCC | AACAATACAA |
| NC_024466_1 | -TGTTGCATG | AGAAACAATT | AAACAGAAAC | TATGATTGTA |
| NC_024467_1 | aTAAAAA-AC | AGAAACTATT | AAACAGAAAC | TATGATTGTA |
| NC_024467_2 | ACAAAAA-AC | AGAAACTATT | AAACAGAAAC | TATAAGTCCA |
| NC_024467_3 | C-ATAGGATA | AAAAACAATA | AAGGAGTTAT | TTTGATTATg |
| NC_024468_1 | a-GTCATTTG | AGAAACAATA | AAACAGAAAC | TATGATTGTA |
| NC_024468_2 | ACAAAAA-AC | AGAAACTATT | AAAAGGCTCT | TAGCAGTCAC |
| NC_024468_3 | -TATACTTAA | AAAAACAATT | ********** | ********** |

FIG. 36

```
Alignment position       1.........11.........21.........31.......

NC_016088_1         1    aGGAATATAA GAAACAATAA AAATGACACT AATATGAAG
NC_016089_1         1    ACTAAAAAGA TAAACAATTA AATAGTTTAT ATAAGAATA
NC_016089_2         1    AACTATAGGA GAAACAATTA AGAAGAATCT ACAATTTGT
NC_016089_3         1    TTTAATATAA AAAACAATAA AGAGGAAAAT CATATTGAA
NC_016090_1         1    TATAACAAGT AAAACAATAA AAAGGAAAAT AATAATGAT
NC_016090_2         1    TAAAATAAAA GAAACAATAA AAGCGTTTTT TTTATTAAA
NC_016091_1         1    GATAGGGAAA AAAACTATAA AAAGGATTTT TTAATTATA
NC_016091_2         1    CATATTATTA AAAACTATTA ATCGTTTTT ATAATTATT
NC_038241_1         1    ATTAATACGA GAAACAATTA AAAAAATCTT ATAAAAAAG
NC_038241_2         1    AAGATAATAA GAAACAATTA AAAAGTTTAT AATATGAAT
NC_038241_3         1    TGGATTAAAA TAAACAATTA AAAGGATCAT TAAAGTCAG
NC_038242_1         1    TTTATTATTA GAAACTATAA ATAGGGTTTT CTAATTTTT
NC_038242_2         1    GAGCATAAAA GAAACAATTA AAAGGGGATT GGAATAAAA
NC_038243_1         1    TTTTATAAAA AAAACAATTA AAAGGGTCAT AATAGTGCT
NC_038243_2         1    TTAAATATTA GAAACTATTA AAAAGTTATT AAAAAATTT
NC_038243_3         1    TTTATAAAGA AAAACAATAA AAGGGAGTAT ATTATAATG
NC_038244_1         1    TGTAAATAAA GTAACAATTA AAACGATCTT GTCATTACT
NC_038244_2         1    TGTACATTTT TAAACAATTA AAAGGTTAGT ATAAGAATA
NC_038244_3         1    TGTAATAAAA AAAACAATAA TAAAGAAGTT ATAATTCTC
NC_038245_1         1    CATCAAATGA AAAACAATTA AAAGGTCTTA AAAATACAC
NC_038245_2         1    TTTAAATGCA GAAACTATAA CAAAGTTCTT ATAATTAAA
NC_038245_3         1    TTGTTTGTTA AAAACAATTA AAAGGTCATT AAAATTAGT
NC_038246_1         1    ACTTACATAA GAAACAATTA AGTTGTTGCT CAAATTATA
NC_038247_1         1    TTTTTTATCA GCAACTATTA AAATGATAGT AAAAATTAA
NC_038247_2         1    TTTCTTAATA CAAACAATTA AAAGGTTAAC AAAAATATA
NC_038248_1         1    CATTGATTAA GAAACTATAA AAAAGTATTT ATTATGAAA
NC_038248_2         1    TTTCTGCATA AAAACAATAA AAAGGAAAGT ATTAGTAAG
NC_038248_3         1    TTTAAGTGAA GAAACAATTA AAGAGAGGGT AGAAGAACA
NC_038248_4         1    GACTCGAAGT GAAACAATTA AAAAGTATCT AGGATTAAA
NC_038249_1         1    GATATTGATA AAAACAATTA AAAGGAGATT ATCATTTGT
NC_038249_2         1    GACTCGAAGT GAAACAATTA AAAAGTATCT AAGATTAAA
NC_038250_1         1    TGTAGTATTT GAAACCATTA CAATGAAATT ATGATTCAG
NC_038250_2         1    AATTGTCAGA GAAACAATTA AATGGAATTG TATATTGTC
NC_038250_3         1    GACTTGAAGT GAAACAATTA AAAAGTATCT AGGATTAAA
NC_038251_1         1    AATTGTCAGA GAAACAATTA AATGGAATTG CACATTGCC
NC_038251_2         1    TCTTTACTGA GAAACAATTA AATGGAAAGA AAAATAAGA
NC_038252_1         1    GTTATCATTT GAAACAATTA TAATGCACTT ATTATAAAC
NC_038253_1         1    cTCTTCAATA GAAACCATTA AAAAGGATCT AGAATTAAA
NC_038253_2         1    TTTATAAAAA AAAACTATTA AAATGTATTG ATTATTTCT
NC_038253_3         1    TCTGAATGCA GAAACCATAA AATAGAATAT AGAATTGAG
NC_038253_4         1    AAAAATATTA GAAACTATTA AAAAGTTACT AAAAAAAAC
NC_038253_5         1    ACTACCTAAA GCAACAATAA AAAGGGAAAT ATCATTCTA
NC_038255_1         1    TCTAAACTGA TAAACAATTA AACGGTGTTT ATATTTATA
                         ********** ********** ********** *********
                         ********** ********** ********** *********
                         ********** ********** ********** *********
                         *  ****  * ********** ********** *********
                         *  **  *  * ********** *** *     * * *****
                              *   *  ********** *** *     * *  ****
                                    *  ****** * ***  *     * *   **
                                     *  ****  ** *  *      *      *
                                        **** **  *   *            *
                                           *** ** *
```

FIG. 37

SERINE RECOMBINASES MEDIATING STABLE INTEGRATION INTO PLANT GENOMES

This application is a national stage application under 35 U.S.C. § 371 of International Patent Application No. PCT/2019/059107, filed Oct. 31, 2019, which claims the priority benefit of U.S. Provisional Patent Application Ser. No. 62/914,633, filed Oct. 14, 2019, U.S. Provisional Patent Application Ser. No. 62/913,318, filed Oct. 10, 2019, U.S. Provisional Patent Application Ser. No. 62/849,368, filed May 17, 2019, and U.S. Provisional Patent Application Ser. No. 62/754,745, filed Nov. 2, 2018, which are hereby incorporated by reference in their entirety.

REFERENCE TO SEQUENCE LISTING

This application incorporates by reference a "Sequence Listing" (identified below) which is submitted concurrently herewith in text file format via the U.S. Patent Office's Electronic Filing System (EFS). The text file copy of the replacement Sequence Listing submitted herewith is labeled "257432.001100_ST25.txt", is a file of 114,689 bytes in size, and was created on Apr. 15, 2024. This Sequence Listing is incorporated by reference in its entirety herein.

BACKGROUND OF THE INVENTION

Site specific recombinases are common among prokaryotes and lower eukaryotes, but are not found in higher, multicellular eukaryotes such as plants. Site-specific recombinases catalyze recombination reactions between two DNA fragments containing short specific sequences. This process differs from the homology-dependent recombinases which catalyze recombination between two larger homologous sequences.

The site-specific recombinases broadly fall into two major categories: tyrosine recombinases (also called as λ integrase system) and serine recombinases (also called resolvase or integrase family). These two recombinase families operate on different recombination mechanisms and have no sequence or structural similarity. Each family appears to have evolved separately.

Tyrosine recombinases are widely present in most prokaryotes, fungi and ciliates. Over 1000 members are known, and include Cre-lox system from bacteriophage P1 and Flp-FRT system from yeast. Cre-lox and Flp-FRT are widely used in site-specific integration of foreign genes as well as excision of unwanted gene cassette flanked by recombinase sites. Tyrosine recombinases have a reversible recombination reaction, and therefore can be used for both integration and excision. Tyrosine recombination requires artificially engineering recombinase sites into plant chromosomes for integrating a desired gene cassette. The lox site comprises an 8 bp spacer between two 13 bp inverted repeats, while FRT comprises an 8 bp spacer between two 13 bp repeats. Frt and lox sites share no sequence similarity with each other's. The presence of such recombination sites in engineered plants and animals is an additional step in genetic engineering.

The serine-recombinases are encoded by bacteriophages and evolved to integrate the phage genome into the bacterial chromosome using a phage specific attP (phage) site (reviewed Smith & Thorpe, *Molecular Microbiology* (2002), 44, 299-307). Successful integration requires the presence of a second site, attB (bacterial), in bacterial host chromosome. Recombination between attP and attB modifies the sites and results in attL (left) and attR (right) (as shown in FIG. 1), which cannot be cleaved by serine recombinases alone, requiring an additional Recombination Directionality Factor (RDF). Thus, serine recombination is irreversible and unidirectional in the absence of a cognate RDF. Both attB and attP sites are required for integration and the specific att-PlattB pairs are, in general, specific to the particular recombinase or work only with close family members. There are over 72 different serine recombinases, which cluster into three main families along phylogenic lines, referred to as (a) large serine recombinases (b) resolvase/invertases and (c) IS607-like (Smith & Thorpe, id.)

Directional and irreversible recombination by serine recombinases makes them an attractive tool for gene integration in eukaryotic chromosomes, synthetic biology application such as directional gene stacking, and excision of unwanted genes from an integrated gene cassette in chromosomes. The att sites are often small (<50bps) and can be introduced at desired location in the genome or in the cloning cassettes. Provided that both attB and attP sites are present, which usually requires artificially engineering an att site into the target species, serine recombinases are able to function in yeast, plants and animal (Groth et. al., 2000; Kapusi et. al., 2012; Thomson et. al., 2012; Mandali et. al., 2013; Collier et. al., 2018).

Intrexon has characterized six different serine recombinases (ΦRv1, ΦC31, Bxb1, SF370.1, A118, and SPβc2) belonging to broader class of large serine-recombinases. Several members are shown to integrate large pieces of DNA (up to 300Kb) into mammalian chromosomes, which make them an attractive tool for engineering entire metabolic pathways in desired organisms. Intrexon also identified several prokaryotic att site-like sequences present in mammalian chromosomes. To distinguish mammalian att site-like sequences from prokaryotic att sites, these mammalian att sites were called pseudosites. By using both SPβc2 and SF370.1, it was demonstrated that putative att site-like sequences are active and can be used to integrate the gene directly into mammalian chromosomes (US20,060, 172377A1).

In plants; successful recombination has been demonstrated by different classes of serine recombinases on artificially engineered prokaryotic att Sites in plant genomes (Thomson et. al., 2012; Kapusi et. al., 2012; Collier et. al., 2018). There is no demonstration that a serine recombinase can integrate foreign DNA into plant genomes without artificially engineering a prokaryotic att site in the genome.

BRIEF SUMMARY OF THE INVENTION

Described are compositions and methods for the genetic manipulation of plants. A serine recombinase that integrates large sections of foreign DNA into specific loci on plant chromosomes through non-homologous recombination through attP or attB sites on the foreign DNA, without the prior engineering of corresponding attB or attP site on the plant chromosome, has numerous advantages.

Described is a method for incorporating an exogenous DNA into a plant, comprising co-delivering of an exogenous DNA comprising an attP or attB site and a polynucleotide encoding a serine recombinase operably linked to a promoter that is active in the plant into a plant cell. The method may further comprise selecting for the integration of the exogenous DNA into one or more att sites on the plant chromosome, particularly a pseudo attB or pseudo attP site.

In a related method, described is a method for obtaining site-specific insertion of exogenous DNA into a plant cell genome, the method comprising contacting a first attachment site on the exogenous DNA with a second attachment site on the plant cell genome in the presence of a prokaryotic serine recombinase polypeptide resulting in recombination between the genomic and exogenous attachment sites, wherein the plant attachment site is a pseudo att site, and the exogenous recombination site is attP or attB.

The exogenous DNA may be up to 25 kb, up to 50 kb, up to 75 kb, up to 100 kb, up to 150 kb, up to 200 kb, up to 250 kb, or up to 300 kb. The exogenous DNA preferably comprises an attP site, preferably having the sequence of SEQ ID NO:7.

In the methods and compositions herein, the serine recombinase has an amino acid sequence at least 65%, 70%, 75%, 80%, 85%, 90%, 95%, 98%, or 99% identical to SEQ ID NO: 1; and may also have an amino acid sequence at least 75%, 80%, 85%, 90%, 95%, 98%, 99% similar to SEQ ID NO: 1. The serine recombinase may be SPβc2. The serine recombinase may be provided directly to the cell, or may be encoded on a nucleic acid (e.g. a plasmid) co-transfected into the cell with the exogenous DNA.

The methods herein may be practiced on any plant cell. Preferably, the cell is a protoplast. The invention covers a transgenic protoplast made according to the methods herein. A transgenic protoplast or other plant cell may be cultured to obtain a transgenic plant. Accordingly, the invention includes a transgenic plant obtained according to any of the methods herein.

In related methods, a serine recombinase may be used to insert a polynucleotide construct an attP or attB site such that the integrated nucleotide contains attL and attR sites. This method comprises introducing into the plant cell a polynucleotide which contains a gene of interest or cassette of interest and also encoding a second serine recombinase and a cognate Recombinase Directionality Factor (RDF) wherein the second serine recombinase and RDF are under the control of an inducible promoter or gene switch. When activated, the promoter drives expression of the second serine recombinase and the RDF to excise the exogenous DNA from the plant genome.

In some embodiments, the serine recombinase and cognate RDF are co-transfected along with the gene of interest or cassette of interest. In other embodiments, the serine recombinase and RDF are introduced by sexual crossing with a plant that constitutively expresses the serine recombinase and RDF or wherein the serine recombinase and RDF are under the control of an inducible promoter or gene switch. In other embodiments, the serine recombinase and RDF are introduced by sequential transfection of the plant cells. In these embodiments, the serine recombinase and RDF may be constitutively expressed or may be under the control of an inducible promoter or gene switch.

In some embodiments, the second serine recombinase is SPβc2. In some embodiments, the inducible promoter is activated by temperature, drought, copper, a developmental process, or a chemical ligand. In some embodiments, the RDF comprises the amino acid sequence of SEQ ID NO: 31.

In another related method, a serine recombinase is used to insert a polynucleotide construct an attP or attB site such that the integrated nucleotide contains att and attR sites. This method comprises co-delivering the polynucleotide which contains a gene of interest or cassette of interest and also encoding the cognate Recombinase Directionality Factor (RDF) for the serine recombinase wherein the RDF and the cognate serine recombinase are under the control of an inducible promoter or gene switch. When activated, the promoter drives expression of the serine recombinase and RDF to excise the exogenous DNA from the plant genome in a scarless excision.

In some embodiments, the serine recombinase is SPβc2. In some embodiments, the serine recombinase and its cognate RDF are expressed as a fusion protein. In some embodiments, the inducible promoter is activated by temperature, drought, copper, a developmental process, or a chemical ligand. In some embodiments, the RDF comprises the amino acid sequence of SEQ ID NO: 31.

In a related method, provided herein is a method for obtaining site-specific recombination in a plant cell, the method comprising:
  a. providing a plant cell that comprises a first attachment site and a second attachment site;
  b. contacting the first and second recombination sites with a prokaryotic serine recombinase polypeptide, resulting in recombination between the recombination sites,
wherein the serine recombinase polypeptide mediates recombination between the first and second attachment sites, the first recombination site is attP or attB, the second recombination site is a pseudo attachment site, and the serine recombinase is SPβc2 serine recombinase.

A further related method herein provides for obtaining site-specific recombination in a plant cell comprising contacting a plant cell with:
  a. an exogenous DNA comprising an attP or attB site and
  b. a serine recombinase polypeptide that is active in the plant.

Also provided herein is a gene expression system comprising a polynucleotide encoding a gene of interest operably linked to a promoter that is operable in a plant cell and an att site for integrating the gene expression system into a plant cell. The att site may be, for example, an attP or attB that is cognate with SPβc2 serine recombinase. The promoter may be, for example, a 35S promoter, a ubiquitin promoter, a 19S promoter, a NOS promoter, an Adh promoter, a sucrose synthase promoter, an R complex promoter or a chlorophyll a/b binding protein promoter. The gene expression system may further comprise inducible promoters including but not limited to those activated by stress, and chemical ligands.

The gene expression system may further comprise a selectable marker gene operably linked to a second promoter, and the second promoter may be the same or different promoter than the promoter operably linked to the gene of interest.

The gene expression system may further comprise an enhancer. The enhancer may be, for example, a *Zea mays* Hetpta repeat of the booster1 gene, an *Arabidopsis thaliana* Block C from the Flowering Locus (FT), an *Arabidopsis thaliana* Region C of Lateral Suppressor (LAS), a *Pisum sativum* P268 PetE, a *Zea mays* PI-rr distal enhancer, a *Zea mays* Vegetative to generative1, a *Pisum sativum* AB80 enhancer, a *Pisum sativum* Enhancer-like element or a plant virus enhancer element. Enhancer elements can also be derived from plant viral promoters such as the 35S enhancer element.

Also provided herein is a plant engineering system comprising a polynucleotide containing at least one SPβc2 att site for integrating into a plant cell, and at least one target site for further insertion of exogenous DNA. The site for further insertion of exogenous DNA may be, for example, tyrosine site-specific recombinase attachment site (e.g. loxP, FRT), or a second serine site-specific recombinase att site that is non cognate with the SPβc2 att site. The plant engineering system may also encode a selectable marker gene.

Upon insertion into the chromosome via the SPβc2 att site, at least one target site for further insertion of exogenous DNA may be used to insert gene expression systems comprising genes that regulate metabolic pathways or components thereof to improve nutritional, flavor, shelf-life, and yield of food, feed, and forage crops.

In a related method, the plant engineering system is co-transfected into a plant cell with SPβc2 serine recombinase that mediates an interaction between the SPβc2 att site on the engineering system and an att site on the plant chromosome, leading to the insertion of the engineering system into the plant chromosome. The resultant transgenic plant cell may be further manipulated to insert further genes via the target site for further genetic manipulation.

In another related method, the invention provides a method of reversibly introducing exogenous DNA into a plant cell genome comprising: (a) introducing into the cell an exogenous DNA that comprises a polynucleotide sequence of interest and an attP and/or attB site; (b) a polynucleotide encoding a serine recombinase operably linked to a promoter that is active in the plant; and (c) a polynucleotide encoding a Recombinase Directionality Factor (RDF) operably linked to an inducible promoter or a gene switch that is active in the plant. In this method, the serine recombinase directs introduction of the exogenous DNA into the plant cell genome and when expression of the RDF is induced, or the switch is turned "on," the combination of the serine recombinase and RDF excises the exogenous DNA from the plant cell. In some embodiments, (a), (b) and (c) are in one polynucleotide construct. In some embodiments, (a), (b) and (c) are on two or more polynucleotide constructs.

In some embodiments, the polynucleotide sequence of interest comprises at least one of a coding sequence for a selectable marker, a dsRNA, antisense RNA, artificial miRNA, one or more gRNA sequences, a gene editing nuclease, a coding sequence for a protein to be expressed in the plant. In some embodiments, the serine recombinase is SPβc2. In some embodiments when the serine recombinase is SPβc2, the RDF may have an amino acid sequence comprising SEQ ID NO: 31.

In some embodiments of the method, (a), (b) and (c) are introduced by an *Agrobacterium* method, a serine recombinase method, by electroporation, by a ribonucleotide protein (RNP) method or by a biolistic method. In some embodiments, the inducible promoter is activated by temperature, drought, copper, a developmental process, or a chemical ligand.

The invention also provides a method of integrating DNA into a plant att pseudosite comprising:
(a) introducing into a plant cell an exogenous DNA comprising:
  i. a polynucleotide sequence of interest; and
  ii. an attP or attB site;
(b) a polynucleotide encoding a serine recombinase operably linked to a promoter that is active in the plant; and
wherein the serine recombinase directs introduction of the exogenous DNA into the plant cell genome at a plant att pseudosite.

In some embodiments, the plant att pseudosite comprises a [core] sequence of SEQ ID NO: 99 or SEQ ID NO:101. In some embodiments, the plant att pseudosite comprises a [consensus] sequence of SEQ ID NO:97, SEQ ID NO:98 or SEQ ID NO:100. In other embodiments, the plant att pseudosite comprises a sequence of any one of SEQ ID NOS: 66-96.

In some embodiments, the serine recombinase is an SPβc2 serine recombinase and the plant is of the genus *Oryza*. In certain embodiments, the att pseudosite comprises a nucleic acid sequence of SEQ ID NO:107, SEQ ID NO: 108, SEQ ID NO: 109, or SEQ ID NO: 110. In some embodiments, the plant is *Oryza sativa*.

In other embodiments, the serine recombinase is an SPβc2 serine recombinase and the plant is of the genus *Lactuca*. In some embodiments, the att pseudosite comprises a nucleic acid sequence of SEQ ID NO:111, SEQ ID NO:112, SEQ ID NO:113, SEQ ID NO:114, SEQ ID NO: 115 or SEQ ID NO:116. In certain embodiments, the plant is *Lactuca sativa*.

In still other embodiments, the serine recombinase is an SPβc2 serine recombinase and the plant is of the genus *Nicotiana*. In some embodiments, the att pseudosite comprises a nucleic acid sequence of SEQ ID NO: 132, SEQ ID NO: 133, SEQ ID NO: 134, SEQ ID NO: 135, SEQ ID NO: 136, SEQ ID NO: 137, SEQ ID NO: 138 or SEQ ID NO: 139. In some embodiments, the plant is *Nicotiana benthamiana*.

In still other embodiments, the serine recombinase is an SF370 serine recombinase. In certain embodiments, the att pseudosite comprises the nucleic acid sequence of SEQ ID NO:124. In other embodiments, the att pseudosite comprises the nucleic acid sequence of SEQ ID NO: 123.

The invention also provides a polynucleotide encoding a fusion protein comprising a first nucleic sequence encoding a large serine recombinase operably linked to a second nucleic acid sequence encoding a cognate recombinase directionality factor (RDF) of said large serine recombinase. In some embodiments, the first nucleic acid and said second nucleic acid are joined by a polynucleotide liner sequence. In certain embodiments, the first nucleic acid encodes an amino acid sequence of SEQ ID NO:41. In some embodiments, the first nucleic acid sequence comprises the nucleic acid sequence of SEQ ID NO:36. In certain embodiments, the second nucleic acid encodes an amino acid sequence of SEQ ID NO:31. In some embodiments, the second nucleic acid sequence comprises the nucleic acid sequence of SEQ ID NO:29. IN some embodiments, the polynucleotide further comprises a third nucleic acid encoding HA and NLS tags. In some embodiments, the polynucleotide encodes an amino acid sequence of SEQ ID NO: 40. In some embodiments, the polynucleotide comprises the nucleic acid sequence of SEQ ID NO: 35.

BRIEF DESCRIPTION OF THE DRAWINGS

FIG. 2A is a schematic drawing of effector constructs expressing recombinase fusion proteins. Each recombinase was modified with a C-terminal HA (influenza hemagglutinin) peptide and SV40 nuclear localization signal (NLS). Expression was under the control of Cauliflower mosaic virus (CaMV) 35S promoter and nopaline synthase (NOS) terminator. Expected sizes of each of the five recombinase fusion proteins is shown in Table 2. As a control, the recombinase was replaced with the chloramphenicol acetyl transferase (CAT) gene. FIG. 2B is a complete map of the SPβc2 effector plasmid, including the vector backbone (SEQ ID NO: 5).

FIG. 4A is a schematic diagram of the reporter plasmids to test the ability of recombinase to act on specific attB or attP sites. Each reporter plasmid contained a Green Fluorescent Protein (GFP) reporter under the control of the Cauliflower mosaic virus (CaMV) 35S promoter and nopaline synthase (NOS) terminator. Each plasmid also contained a neomycin phosphotransferase II (NPTII) gene, which confers resistance to neomycin and kanamycin, under the control of a Cassava Vein Mosaic Virus (CsVMV) promoter and F3R (the 3'UTR of Ubi3 gene from potato). The common design was modified to add attP (1) or attB (2) site 5' to the GFP reporter gene, while a control plasmid (3) lacked any att site. Because each serine recombinase recognizes a specific cognate attP/attB, the attP or attB for each reporter plasmid was adapted to the cognate serine recombinase. FIG. 4B is a complete map of the reporter plasmid, containing the attP site for SPβc2 recombinase, and including the vector backbone (SEQ ID NO: 4).

FIG. 5A: The number of colonies was measured 5 weeks after transfection demonstrating that transfection had a negative impact on viability compared with no DNA, but that the different plasmids did not have a significant difference in viability between each other. FIG. 5B: After 5 weeks of culturing, GFP expression was measured. Protoplasts co-transfected with attP+SPβc2 recombinase had at least 20-fold more GFP colonies than controls.

FIG. 6A: GFP-positive beads obtained for each plasmid set during 22 day sub-culturing shows that attP+SPβc2 retains GFP expression over protoplasts transfected with other DNA. FIG. 6B: A small number of GFP-expressing microcolonies were observed after transfection with attP+CAT, but none of these were resistant to kanamycin. Compared with attP+CAT, transfection with attP+SPβc2 gave 42×more GFP-expressing colonies after growth without kanamycin selection. GFP-expressing microcolonies are resistant to kanamycin, as shown by growth in kanamycin (35 or 50 µg/ml) applied at 8 to 15 days (post-transfection). The GFP and kanamycin positive colonies were counted after 5 weeks.

FIG. 8A: With the attP reporter plasmid, SPβc2 but not CAT produced kanamycin resistant, GFP positive colonies. FIG. 8B A single Kanamycin resistant GFP-positive callus was obtained from the attB reporter plasmid in the presence of SPβc2. FIG. 8C shows the number of calli after transfection grown on non-selective media. FIG. 8D shows that transgenic calli were positive for both kanamycin resistance and GFP expression.

FIG. 9A: PCR on genomic DNA demonstrates the presence of both NPTII and GFP regions. FIG. 9B: Fluorescence shows expression of GFP in transgenic lettuce, but not wild type lettuce.

FIG. 10A shows the position of primers on the map of the attP reporter plasmid. FIG. 10B shows a table of expected amplicons and FIG. 10C shows a gel with the result of PCR amplification on transgenic lettuce plant (TG), wild type (WT) lettuce and plasmid control.

FIG. 14A shows a schematic drawing of the inserted transgene containing a 35S promoter, (35S pro); green fluorescent protein (GFP) coding sequence; a nopaline synthase termination sequence (No. . . . S); a cassava vein mosaic virus promoter (CaVSV Pro); a pUC origin of replication (pUC origin); and a coding sequence for Spectinomycin resistance (Spectinomycin resistan . . . ). The *Nicotiana benthamiana* genomic DNA (gDNA) flanking the insert is shown as "Benthi gDNA. " FIG. 14B shows sequence chromatograms obtained from the left (SEQ ID NO: 174) and right (SEQ ID NO: 175) borders of the transgene integration site aligned to the circular attP vector. ID373 corresponds to nucleotides 5578-5672 of SEQ ID NO: 4. FIG. 14C shows the same sequence chromatograms aligned to the WT *N. benthamiana* reference genome ("Niben101Scf05124 native" corresponds to nucleotides 4-98 of SEQ ID NO: 132). Sequence for Left Border corresponds to SEQ ID NO: 174 and sequence for Right Border corresponds to SEQ ID NO: 175. FIGS. 14D and E shows identical linearization of the attP vector from 6 independent transgenic events. For FIG. 14D, lines 1 to 6 correspond in order to SEQ ID NOs: 176-181. For FIG. 14E, lines 1 to 6 correspond in order to SEQ ID NOs: 182-187.

FIG. 32: Identification of ATTR junctions from PacBio amplicon reads. Panel A shows PacBio CCS sequence reads reference assembled to the complete SPβc2 attP site (nucleotides 5593-5655 of SEQ ID NO:4). Boxed reads indicate putative gDNA junctions within the attP site. For the sequences shown below SPβc2 attP: lines 1-5, 7-10, 12, 14, 16, 18, 22, 24, 25, 28, 29, 31-35, 38-41, 43-45, 48, and 49 correspond to nucleotides 5574-5672 of SEQ ID NO:4; Line 6 corresponds to SEQ ID NO:213; Line 11 corresponds to SEQ ID NO:214; Line 13 corresponds to SEQ ID NO:215; Line 15 corresponds to SEQ ID NO:216; Line 17 corresponds to SEQ ID NO:217; Line 19 corresponds to SEQ ID NO:218; Line 20 corresponds to SEQ ID NO: 219; Line 21 corresponds to SEQ ID NO:220; Line 23 corresponds to SEQ ID NO:221; Line 26 corresponds to SEQ ID NO:222; Line 27 corresponds to SEQ ID NO:223; Lines 30 and 37 correspond to SEQ ID NO:224; Line 36 corresponds to SEQ ID NO:225; Line 42 corresponds to SEQ ID NO:226; Line 46 corresponds to SEQ ID NO:227; Line 47 corresponds to SEQ ID NO: 228; and Line 50 corresponds to SEQ ID NO:229. Panel B shows selected amplicon reads that were BLAST searched against the Rice Genome and aligned with genomic sequence (top) and the SPβc2 attP integration vector (bottom). For the sequences shown in Panel B: "1. AC229795-Rice Genome Hit" corresponds to SEQ ID NO:230, "2. PacBio Read from Protoplast Pools" corresponds to SEQ ID NO:231, and "3. SPβc2 attP integration vector" corresponds to nucleotides 5592-5656 of SEQ ID NO:4. Panel C shows rice SPβc2 pseudo-sites (junction locations are marked by boldface and underlining). For the sequences shown in Panel C: the sequences in order from top to bottom correspond to SEQ ID NOs: 102-105.

FIG. 36: An alignment of the 16 *Zea mays* matches is shown. The '*' signs below the alignment show the nucleotide similarity at each position of the alignment. If all nucleotides are identical, 10 '*' signs are displayed. For nine positions within the alignment, all nucleotides are identical. All other positions of the alignment have a lower nucleotide similarity. For the sequences shown: "NC_024459_1" corresponds to SEQ ID NO: 235; "NC_024461_1" corresponds to SEQ ID NO: 236; "NC_024462_1" corresponds to SEQ ID NO: 237; "NC_024462_2" corresponds to SEQ ID NO: 238; "NC_024462_3" corresponds to SEQ ID NO: 239; "NC_024463_1" corresponds to SEQ ID NO: 240; "NC_024465_1" corresponds to SEQ ID NO: 241; "NC 024465_2" and "NC_024465_3" correspond to SEQ ID NO: 242; "NC_024466_1" corresponds to SEQ ID NO: 243; "NC_024467_1" corresponds to SEQ ID NO: 244; "NC 024467_2" and "NC_024468_2" correspond to SEQ ID NO: 245; "NC 024467_3" corresponds to SEQ ID NO: 246; "NC_024468_1" corresponds to SEQ ID NO: 247; and "NC_024468_3" corresponds to SEQ ID NO: 248.

FIG. 37: An alignment of the 43 *Glycine max* matches is shown. The '*' signs below the alignment show the nucleotide similarity at each position of the alignment. If all nucleotides are identical, 10 '*' signs are displayed. For nine positions within the alignment, all nucleotides are identical. All other positions of the alignment have a lower nucleotide similarity. The sequences in order from top to bottom correspond with SEQ ID NOs: 249-291.

DETAILED DESCRIPTION OF THE INVENTION

Definitions

Figure 1:
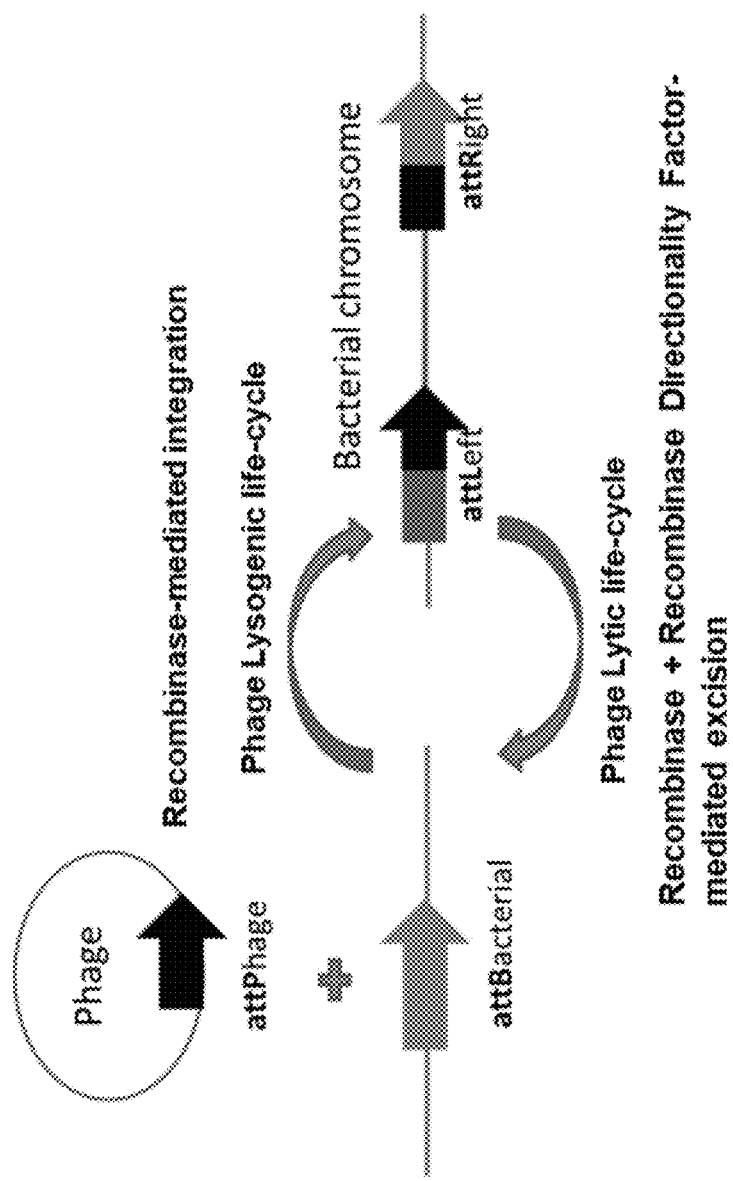
FIG. 1 is a schematic representation of serine recombinase-mediated integration between specific attP and attB sites that inserts the bacteriophage genome into bacterial chromosome initiating the lysogenic phase of growth, and creates the attL and attR sites. attL and attR are not acted on by serine recombinase alone. During the lytic cycle of phage growth, integration is reversed by co-expression of the serine recombinase and recombination directionality factor (RDF).

In this disclosure, a number of terms and abbreviations are used. The following definitions are provided and should be helpful in understanding the scope and practice of the present invention.

The term "about" typically encompasses a range up to 10% of a stated value.

Unless otherwise specified, "recombinase" as used herein refers to a group of enzymes that can facilitate site-specific recombination between defined sites, where the sites are physically separated on a single DNA molecule or where the sites reside on separate DNA molecules.

Of particular interest herein is the "serine recombinase" family which has a specific type of recombination sites and a specific mechanism of action. Numerous serine recombinases are known, and they cluster into three main families along phylogenic lines, referred to as (a) large serine recombinases (b) resolvase/invertases and (c) IS607-like (Smith & Thorpe, id.). Representative serine recombinases include BXB1, SF370.1, SPβc2, A188, φC31, TP901-1, Tn3, gamma delta. A "serine recombinase" encompasses fusion proteins that contain the recombinase and other elements, including a nuclear localization signal (NLS), tags to identify the protein or aid in purification such as influenza virus hemagglutinin (HA).

Of particular interest are fusions of the recombinase with an NLS, because the NLS "tags" a protein for import into the nucleus by nuclear transport. The NLS typically consists of one or more short sequences of positively charged lysines or arginines. A consensus sequence for one family of NLS is K-K/R—X-K/R. Examples of NLS include SV40 Large T-Antigen, nucleoplasmin (AVKRPAATKK-AGQAKKKKLD (SEQ ID NO:16)), EGL-13 (MSRRR-KANPTKLSENAKKLAKEVEN (SEQ ID NO:17)), c-Myc (PAAKRVKLD (SEQ ID NO: 18)) and TUS-protein (KLKIKRPVK (SEQ ID NO:19)).

As shown below, the "SPβc2 recombinase" has been found to have a surprising ability to facilitate site specific recombination of an attP bearing DNA into plant genomes without the addition of a canonical attB site. "SPβc2 recombinase" may also be known as YokA, and may be exemplified by the protein having the amino acid sequence of SEQ ID NO: 1. "SPβc2 recombinase" also encompasses fusion proteins containing SEQ ID NO: 1, and proteins with an amino acid at least 95% identical to SEQ ID NO: 1.

As used herein, "SPβc2 family recombinase" includes those recombinases that are at least 60, 65, 70, 75, 80, 85, 90, or 95% identical in amino acid sequence to SEQ ID NO:1. It may also include that are at least 75, 80, 85, 90, or 95% similar to SEQ ID NO:1. Listed in Table 1 are recombinases having high sequence identity and/or similarity. Most sequence variation is observed in the C-terminal portion.

TABLE 1

Select proteins with sequence identity and similarity to SPβc2

| Protein | Identity | similarity |
| --- | --- | --- |
| resolvase [*Bacillus subtilis*] Sequence ID: WP_041053131.1 | 541/545(99%) | 544/545(99%) |
| recombinase family protein [*Bacillus subtilis*] Sequence ID: WP_101502393.1 | 533/545(98%) | 540/545(99%) |

TABLE 1-continued

Select proteins with sequence identity and similarity to SPβc2

| Protein | Identity | similarity |
|---|---|---|
| recombinase family protein [Bacillus sp. LYLB4] | 489/541(90%) | 517/541(95%) |
| resolvase [Bacillus velezensis] Sequence ID: WP_063636678.1 | 489/539(91%) | 514/539(95%) |
| MULTISPECIES: DNA recombinase [Bacillus amyloliquefaciens group] Sequence ID: WP_015417670.1 | 488/541(90%) | 516/541(95%) |
| resolvase [Bacillus sp. LK7] Sequence ID: WP_048367425.1 | 488/539(91%) | 514/539(95%) |
| recombinase family protein [Bacillus velezensis] Sequence ID: WP_105937602.1 | 485/541(90%) | 515/541(95%) |
| Site-specific recombinase [Streptococcus pneumoniae] Sequence ID: COD03578.1 | 427/481(89%) | 455/481(94% |
| recombinase family protein [Bacillus halotolerans] Sequence ID: WP_099043174.1 | 419/542(77%) | 482/542(88%) |
| MULTISPECIES: recombinase family protein [Bacillus] Sequence ID: WP_109962774.1 | 420/542(77%) | 481/542(88%) |
| recombinase family protein [Bacillus subtilis] Sequence ID: WP_086352797.1 | 420/542(77%) | 481/542(88%) |
| resolvase [Bacillus subtilis] Sequence ID: WP_041336396.1 | 18/542(77%) | 479/542(88%) |
| MULTISPECIES: resolvase [Bacillus subtilis group] Sequence ID: WP_013352589.1 | 373/535(70%) | 444/535(82%) |
| Resolvase like protein YokA [Bacillus amyloliquefaciens] Sequence ID: OBR26774.1 | 372/535(70%) | 444/535(82%) |
| resolvase [Bacillus sp. Leaf49] Sequence ID: WP_056704633.1 | 341/531(64%) | 416/531(78%) |
| resolvase [Bacillus amyloliquefaciens] Sequence ID: WP_061573896.1 | 287/540(53%) | 397/540(73%) |
| MULTISPECIES: recombinase family protein [Bacillus] Sequence ID: WP_046132721.1 | 279/533(52%) | 394/533(73%) |
| MULTISPECIES: recombinase family protein [Moorella] Sequence ID: WP_054936363.1 | 240/522(46%) | 343/522(65%) |

Serine recombinases require a pair of "recombination attachment sites," which are specific polynucleotide sequences that are recognized by and acted upon by the recombinase enzyme. These may be named generically as an "att site" or "att." The serine-recombinases are originally encoded by bacteriophages and evolved to integrate the phage genome into the bacterial chromosome and require an "attP" site (originally from phage) and a second "attB" site (from the bacterial host chromosome). The attP and attB sites are not homologous. Recombination between attP and attB modifies the sites and results in attL (left) and attR (right), which cannot be cleaved by serine recombinases alone, requiring an additional Recombination Directionality Factor (RDF) (reviewed Smith & Thorpe, *Molecular Microbiology* (2002), 44, 299-307).

Not only are attB and attP sites different, but attP and attB sites are relatively specific for each serine recombinase, being substrates for one serine recombinase or closely related serine recombinases. Thus an att site may also be denoted by the serine recombinase that acts upon it. For example, SPβc2 recognizes and recombines "SPβc2 attP" and "SPβc2 attB".

Structurally, recombination sites typically include left and right arms separated by a core or spacer region. Thus, an attB recombination site consists of BOB', where B and B' are the left and right arms, respectively, and O is the core region. Similarly, attP is POP', where P and P' are the arms and O is again the core region. Upon recombination between the attB and attP sites, and concomitant integration of a nucleic acid at the target, the recombination sites that flank the integrated DNA are referred to as "attL" and "attR." The attL and attR sites, using the terminology above, thus consist of BOP' and POB', respectively. In some representations herein, the "O" is omitted and attB and attP, for example, are designated as BB' and PP', respectively.

A "pseudo attachment site" is a site that does not conform to the canonical attachment site sequence but may serve as a site for recombination, often at lower frequency or under specific situation. For example, a "pseudo attB" may recombine with an attP; and pseudo attP may recombine with an attB; but at lower frequencies than attPlattB recombination.

A "target att site" is a site that will recombine with a cognate att site. For example, attB is the target for attP, and attP is the target for attB.

As used herein, "cognate" relates to the ability of a serine recombinase to recognize a specific attP site and attB site and mediate recombination. There are thousands of possible attP and attB sites (and pseudo sites) but, for any given attP site, and for a given serine recombinase, a very limited number of attB sites will recombine. Such attB sites are "cognate" with the attP site if they recombine. Likewise, the serine recombinase is cognate with the attP and attB pair. The use of cognate and non-cognate att sites provides a basis for controlling recombination.

When a first DNA containing an att site is able to recognize and recombine with a second DNA containing a cognate att site, the first DNA may be considered the "targeting DNA" and the second DNA the "target DNA." Typically, the targeting DNA is foreign, exogenous DNA and is frequently in the form of a plasmid (i.e. "targeting plasmid"). The att site on the targeting DNA may also be referred to as the "targeting att" or "targeting att site." The target DNA is typically a plant genome, particularly a plant chromosome that bears an att site that is cognate with the att site on the targeting plasmid. The cognate att site on the chromosome is a "target att site" or, simply, a "target site."

The targeting DNA or targeting plasmid is typically a construct containing a targeting att site and DNA of interest for targeting into the chromosome. The targeting DNA may contain additional nucleic acid fragments such as control sequences, marker sequences, selection sequences and the like as discussed below. When the targeting plasmid contains a reporter or selection sequence, the targeting plasmid may be referred to as a "reporter plasmid" or "reporter DNA."

Serine recombinase is required to mediate recombination between att sites (e.g. on the targeting plasmid and the chromosomal target). The serine recombinase may be provided as a protein or, more typically, on a nucleic acid encoding the recombinase. A nucleic acid encoding the recombinase, and suitable promoters, regulators and the like is referred to herein as an "effector." Because the effector is a recombinase, it may also be called a "recombinase plasmid."

The term "substantially free" means that a composition comprising "A" (where "A" is a single protein, DNA molecule, vector, recombinant host cell, etc.) is substantially free of one or more contaminating proteins, DNA molecules, vectors, etc., such that is comprises when at least about 75%, preferably 90%, 95%, 99% of A by weight. The term "purified" does not require the material to be present in a form exhibiting absolute purity, exclusive of the presence of other compounds. Rather, it is a relative definition.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated".

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

The term "fragment" will be understood to mean a nucleotide sequence of reduced length relative to the reference nucleic acid and comprising, over the common portion, a nucleotide sequence identical to the reference nucleic acid. Such a nucleic acid fragment may be, where appropriate, included in a larger polynucleotide of which it is a constituent.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook (cf. "Molecular Cloning: A Laboratory Manual," second edition, edited by Sambrook, Fritsch, & Maniatis, Cold Spring Harbor Laboratory, (1989)). Hybridization and washing conditions are well known and exemplified in Sambrook et al., 1989), particularly Chapter 11 and Table 11.1 therein (entirely incorporated herein by reference). The conditions of temperature and ionic strength determine the "stringency" of the hybridization.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences, and involves repetitive cycles denaturation, annealing and extension.

A DNA "coding sequence" is a double-stranded DNA sequence that is transcribed and translated into a polypeptide when placed under the control of suitable regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription. The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule with which it shares significant stretches of sequence homology. This process is mediated by e.g. RecA in bacteria, and RAD51 in eukaryotes. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

The term "plasmid" refers to an extra chromosomal element often carrying a gene that is not part of the central metabolism of the cell, and usually in the form of circular double-stranded DNA molecules.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

DNA may be introduced into the desired cells by methods known in the art. For example *Agrobacterium* mediated Ti transfer; polyethylene glycol mediated transfection; electroporation; and gene guns.

The term "transfection" means the uptake of exogenous or heterologous RNA or DNA by a cell. A cell has been "transfected" by exogenous or heterologous RNA or DNA when such RNA or DNA has been introduced inside the cell.

The term "co-transfection" means that the cell is transfected with more than one heterologous RNA or DNA.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), red fluorescent protein (RFP), chloramphenicol acetyltransferase ((AT), β-galactosidase (LacZ), β-glucuronidase ((us), and the like. One category of reporter gene is a selectable marker.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

Another type of selectable marker is an auxotrophic marker that allows cells to synthesize an essential component (such an amino acid) while grown in media that lacks that essential component.

"Promoter" refers to a DNA sequence capable of controlling the expression of a coding sequence or functional RNA. In general, a promoter sequence is 5' to a coding sequence. A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

Promoters may be derived in their entirety from a native gene, or be composed of different elements derived from different promoters found in nature, or even comprise synthetic DNA segments. Different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters"

or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention. Cauliflower mosaic virus (CaMV) 35S and opine promoters (including nopaline synthase (nos), octopine synthase (oct) and mannopine synthase (mas)) are derived from plant pathogens and may be used in multiple species. In monocots plant ubiquitin (Ubi), rice actin 1 (Act-1) and maize alcohol dehydrogenase 1 (Adh-1) are commonly used.

In addition, these expression sequences may be modified by addition of enhancer or regulatory sequences and the like.

Enhancers that may be used in embodiments of the invention include a *Zea mays* Hetpta repeat of the booster1 gene, an *Arabidopsis thaliana* Block C from the Flowering Locus (FT), an *Arabidopsis thaliana* Region C of Lateral Suppressor (LAS), a *Pisum sativum* P268 PetE, a *Zea mays* PI-rr distal enhancer, a *Zea mays* Vegetative to generative1, a *Pisum sativum* AB80 enhancer, or a *Pisum sativum* Enhancer-like element.

Termination control regions, i.e., terminator or polyadenylation sequences, may also be derived from various genes native to the preferred hosts. In a preferred embodiment of the invention, the termination control region may be derived from NOS, AF3R, 35S, and ubiquitin genes.

The terms "3' non-coding sequences" or "3' untranslated region (UTR)" refer to DNA sequences located downstream (3') of a coding sequence and may comprise polyadenylation [poly (A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but are designed by one having ordinary skill in the art.

"RNA transcript" refers to the product resulting from RNA polymerase-catalyzed transcription of a DNA sequence. When the RNA transcript is a perfect complimentary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. A "protein" is a polypeptide that performs a structural or functional role in a living cell. An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The concepts of percent identity and percent similarity of two polypeptide sequences is well understood in the art. For example, two polypeptides 10 amino acids in length which differ at three amino acid positions (e.g., at positions 1, 3 and 5) are said to have a percent identity of 70%. However, the same two polypeptides would be deemed to have a percent similarity of 80% if, for example at position 5, the amino acids moieties, although not identical, were "similar" (i.e., conserved amino acid substitutes possessing similar biochemical characteristics). Many programs for analysis of nucleotide or amino acid sequence similarity, such as fast and BLAST specifically list percent identity of a matching region as an output parameter.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482-489, 1981) to find the best segment of similarity between two sequences.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667.). Homologous proteins typically have high sequence identity and similarity. Homologous DNA sequences typically have high identity, with variation most often found in redundant codons.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) J. Mol. Biol. 215:403-410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences may be performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method may be selected: KTUPLE 1, GAP PENALTY-3, WINDOW-5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., J. Mol. Biol. 215:403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters, which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"SF370 Recombinase" refers to the *Streptococcus pyogenes* phage 370.1 large serine recombinase (such as, for example that provided in Accession ID: WP_010922052.1).
Compositions and Methods for Introducing DNA into Plant Genomes A leading method of introducing DNA into the genome of plants is through the use of *Agrobacterium*. There are, however, a number of downsides to the use of the *Agrobacterium* system. First, *Agrobacterium*-mediated gene transfer is accompanied by deletions of the ends of the DNA being transferred, and that the size and chance of deletions increase with the size of the DNA being transferred, with a practical upper limit at around 25 kb. Second, *Agrobacterium* mediated transfer leads to the integration of transgenes randomly at different locations in the genome. As a result, is commonly necessary to screen 100s-1000s of transgenic events to identify those that have inserted the entire section of foreign DNA, and at a suitable site in the genome. This requirement adds to the time and money of constructing a transgenic plant. Finally, the *Agrobacterium* method does not redirect the next transgene to the same locus.

Compared with *Agrobacterium* serine recombinases offer advantages. The ability to integrate large sections of DNA is only limited by the ability to transfer DNA into the cell. Integration is governed by the presence of att site matching, and therefore occurs only at the locations with a pre-existing att site. Finally, if the foreign DNA integrated into the chromosome carries another but different att site, it is possible to add further DNA into the same locus.

To date, serine recombinase-mediated integration into plants was not possible because of the lack of suitable att sites in the plant chromosome. Therefore, before serine recombinase mediated transformation could be performed on a plant, the plant would have to be first engineered to add a suitable att site to the chromosome.

The requirement of this additional step is not only costly and time consuming, but is particularly problematic in screening in diverse backgrounds. For example, the effect of a given transgene in a plant may vary between different cultivars of the same species. It is difficult to screen multiple cultivars if each cultivar must engineered twice: once to add the att site, and again to add the transgene.

The present disclosure provides compositions and methods for incorporating DNA into plants that overcome the problems both of *Agrobacterium* mediated modification, and prior serine recombinase methods. Applicants have found that DNA bearing an att site, especially an SPβc2 attP site, are able to incorporate into plants in the presence of SPβc2 recombinase. The present disclosure also demonstrates that SF370 serine recombinase is able to integrate DNA into plant cells in which the DNA to be incorporated includes an SF370 attP site. The present disclosure facilitates the simple, one step introduction of large sections of exogenous DNA into one or a limited number of sites. Insertions of up to 20 kb, up to 30 kb, up to 40 kb, up to 50 kb, up to 75 kb, up to 100 kb, and up to 150 kb. The simplicity of the method makes it feasible to screen multiple cultivars to identify those with surprising interactions with the exogenous DNA.

Furthermore, the use of serine recombinase (e.g., SPβc2 and SF370) in recombinase-mediated integration is unidirectional, catalyzing recombination between two complementary recombination sites, but cannot catalyze recombination between the hybrid sites that are formed by this recombination. Because the recombinases used in the methods of the invention cannot catalyze the reverse reaction, the integration is stable. Such methods are useful, for example, for obtaining stable integration into the eukaryotic chromosome of a transgene that is present on the plasmid. The unidirectionality of the reaction is a benefit over tyrosine recombinases, such as the Cre lox or FLP-FRT systems.

Further, it is also possible to specifically remove the exogenous DNA by addition of both the recombinase and an equally specific Recombination Directionality Factor (RDF). The expression of the recombinase and the RDF may result in the specific and scarless excision of the entire exogenous DNA or a portion of the exogenous DNA depending on how the attL/attR sites are situated in the exogenous DNA. In one embodiment, one recombinase variant could be used to integrate an attP vector into the plant genome at a pseudo attB site, while a distinct recombinase and its cognate RDF variant could be used to excise a portion of the transgene cassette (such as a selectable marker) through artificial attL and attR sites engineered into the vector flanking the portion to be excised that are recognized by the serine recombinase/cognate RDF pair. For example, a serine recombinase other than SPβc2 could be used to integrate a genetic construct into the genome of a cell. After regeneration of the transgenic event, the selectable marker, for example, could be removed by the co-expression of SPβc2 serine recombinase and its cognate RDF which would act on the attR and attL sites flanking the selectable marker. These strategies would also be compatible with other primary transformation strategies such as *Agrobacterium* transformation or particle bombardment, for example. Removal of the selectable marker would allow the use of the same selectable marker for further manipulation of the cell, whereas without the removal of the selectable marker, a different selectable marker would be needed for further manipulation.

In one embodiment, the invention provides a method of reversibly introducing exogenous DNA into a plant cell genome comprising: (a) introducing into the cell an exogenous DNA that comprises a polynucleotide sequence of interest and an attP and/or an attB site; (b) a polynucleotide encoding a serine recombinase operably linked to a promoter that is active in the plant; and (c) a polynucleotide encoding a cognate Recombinase Directionality Factor (RDF) to the serine recombinase operably linked to an inducible promoter or a gene switch that is active in the plant. The sequences may be present on one polynucleotide construct or on two or more polynucleotide constructs. When expressed, the serine recombinase directs introduction of the exogenous DNA into the plant cell genome. When the RDF is induced (or the switch is turned "on") the combination of the serine recombinase and RDF excises the exogenous DNA from the plant cell.

In some embodiments, a serine recombinase protein may be co-introduced into the cell instead of a polynucleotide encoding the serine recombinase.

The polynucleotides of this method may be introduced by any method known in the art such as, but not limited to the *Agrobacterium* method, a serine recombinase method, by electroporation, by a ribonucleotide protein (RNP) method or by a biolistic method.

In some embodiments, the inducible promoter is activated by temperature, drought, copper, a developmental process, or a chemical ligand.

In some embodiments, the serine recombinase is SPβc2. In some embodiments when the serine recombinase is SPβc2, the RDF may have an amino acid sequence comprising SEQ ID NO: 31.

The polynucleotide sequence of interest may be any sequence of interest such as that encoding a polynucleotide such as a dsRNA, antisense RNA, artificial miRNA, or a guide RNA (gRNA), or a protein-encoding comprises at least one of a coding sequence for a selectable marker, a gene editing nuclease, a coding sequence for a protein to be expressed in the plant. Expression of a gRNA and a gene editing nuclease, for example, may be used to edit the plant's genome. Expression of a protein of interest may impart a phenotypic trait to the plant that it did not have before transformation, for example.

The methods of the present invention involve contacting a pair of recombination attachment sites, attB and attP (or att pseudo sites), that are present in a eukaryotic cell with a corresponding recombinase. The recombinase then mediates recombination between the recombination attachment sites. Depending upon the relative locations of the recombination attachment sites, any one of a number of events can occur as a result of the recombination. For example, if the recombination attachment sites are present on different nucleic acid molecules, the recombination can result in integration of one nucleic acid molecule into a second molecule. Thus, one can obtain integration of a plasmid that contains one recombination site into a eukaryotic cell chromosome that includes the corresponding recombination site. The recombination attachment sites can also be present on the same nucleic acid molecule. In such cases, the resulting product typically depends upon the relative orientation of the attachment sites. For example, recombination between sites that are in the parallel or direct orientation will generally result in excision of any DNA that lies between the recombination attachment sites. In contrast, recombination between attachment sites that are in the reverse orientation can result in inversion of the intervening DNA. Likewise, the resulting rearranged nucleic acid is stable in that the recombination is irreversible in the absence of an additional factor or factors, generally encoded by the particular bacteriophage and/or by the host cell of the bacteriophage from which the recombinase is derived, that is not normally found in eukaryotic cells. One example of an application for which this method is useful involves the placement of a promoter between the recombination attachment sites. If the promoter is initially in the opposite orientation relative to a coding sequence that is to be expressed by the promoter and the recombination sites that flank the promoter are in the inverted orientation, contacting the recombination attachment sites will result in inversion of the promoter, thus placing the promoter in the correct orientation to drive expression of the coding sequence. Similarly, if the promoter is initially in the correct orientation for expression and the recombination attachment sites are in the same orientation, contacting the recombination attachment sites with the recombinase can result in excision of the promoter fragment, thus stopping expression of the coding sequence.

The methods of the invention are also useful for obtaining translocations of chromosomes. For example, in these embodiments, one recombination attachment site is placed on one chromosome and a second recombination attachment site that can serve as a substrate for recombination with the first recombination attachment site is placed on a second chromosome. Upon contacting the recombination attachment sites with a recombinase, recombination occurs that results in swapping of the two chromosome arms. For example, one can construct two strains of an organism, one strain of which includes the first recombination attachment site and the second strain that contains the second recombination attachment site. The two strains are then crossed, to obtain a progeny strain that includes both of the recombination attachment sites. Upon contacting the attachment sites with the recombinase, chromosome arm swapping occurs.

Recombinases

The recombinases used in the practice of the present invention can be introduced into a target cell before, concurrently with, or after the introduction of a targeting vector. The recombinase can be directly introduced into a cell as a protein, for example, using liposomes, coated particles, or microinjection. Alternately, a polynucleotide, either DNA or messenger RNA, encoding the recombinase can be introduced into the cell using a suitable expression vector. The targeting vector components described above are useful in the construction of expression cassettes containing sequences encoding a recombinase of interest. However, expression of the recombinase can be regulated in other ways, for example, by placing the expression of the recombinase under the control of a regulatable promoter (i.e., a promoter whose expression can be selectively induced or repressed), or use of gene switch.

Recombinase polypeptides, and nucleic acids that encode the recombinase polypeptides of the present invention, are described in the Examples, and can be obtained using routine methods known to those of skill in the art.

SPβc2 has an amino acid sequence SEQ ID NO: 1 and may be encoded by a nucleotide having the sequence of nucleotides 15 to 1649 of SEQ ID NO: 3 SPβc2 may also function as a fusion protein, such as fusions with nuclear transfer factor and motifs to facilitate recognition and purification of the protein. A suitable SPβc2 fusion protein may have the amino acid sequence of SEQ ID NO: 2 and be encoded by a nucleotide having the sequence of SEQ ID NO: 3. SEQ ID NO: 3 also contains an SBF1 restriction site (cctgcagg), a Kozak sequence (GCCACC), an HA tag sequence (SEQ ID NO:34), an NLS sequence (SEQ ID NO:33) and a ClaI restriction site (atcgat).

The recombinase may also have an amino acid sequence that is at least 65%, 75%, 80%, 85%, 90% 95%, 98%, or 99% identical to that of SEQ ID NO: 1. The recombinase may also have an amino acid sequence that is at least 75%, 80%, 85%, 90% 95%, 98%, or 99% similar to SEQ ID NO: 1.

The recombination attachment sites comprise an isolated polynucleotide sequence comprising a nucleic acid that is at least 90%, 91%, 92%, 93%, 94%, 95%, 96%, 97%, 98%, 99% or 100% identical to the SEQ ID NO: 6 or SEQ ID NO: 7, preferably SEQ ID NO: 7.

SF370 has an amino acid sequence of SEQ ID NO: 125. This amino acid sequence may be encoded by a nucleic acid sequence such as SEQ ID NO:126.

Vectors/Constructs

The targeting and effector constructs herein may contain additional nucleic acid fragments such as control sequences, marker sequences, selection sequences and the like.

In general, the targeting construct will have one or more of the following features: a promoter, promoter-enhancer sequences, a selection marker sequence, an origin of replication, an inducible element sequence, an epitope—tag sequence, and the like.

Promoter and promoter-enhancer sequences are DNA sequences to which RNA polymerase binds and initiates transcription. The promoter determines the polarity of the transcript by specifying which strand will be transcribed. Bacterial promoters consist of consensus sequences, −35 and −10 nucleotides relative to the transcriptional start, which are bound by a specific sigma factor and RNA polymerase. Eukaryotic promoters are more complex. Most promoters utilized in expression vectors are transcribed by RNA polymerase II. General transcription factors (GTFS) first bind specific sequences near the start and then recruit the binding of RNA polymerase II. In addition to these minimal promoter elements, small sequence elements are recognized specifically by modular DNA-binding/trans-activating proteins (e.g. AP-1, SP-1) that regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV). Viral promoters may be preferred as they are generally particularly strong promoters.

Promoters may be, furthermore, either constitutive or regulatable (i.e., inducible or repressible). Inducible elements are DNA sequence elements which act in conjunction with promoters and bind either repressors (e.g. lacO/LAC Iq repressor system in *E. coli*) or inducers (e.g. gall/GAL4 inducer system in yeast). In either case, transcription is "shut off" until the promoter is repressed or induced, at which point transcription is "turned-on."

Examples of constitutive promoters include 35S CaMV promoter, the cassava vein mosaic virus (DCsVMV) promoter, the figwort mosaic virus (DFMV) promoter, the *mirabilis* mosaic virus (DMMV) promoter the peanut chlorotic streak virus (DPCLSV) promoter U6 promoter, 19S promoter, NOS promoter, an adh promoter, a sucrose synthase promoter, an R complex promoter, chlorophyll a/b binding protein promoter, and the actin promoter. Exemplary promoters for use in the present invention are selected such that they are functional in cell type (and/or animal or plant) into which they are being introduced.

Because the targeting plasmid is non-replicating in plants, the only means for replication of the targeting DNA is to incorporate into the plant genome. A "reporter" is an element that provides a means to identify transfected cells and those in which the targeting plasmid has been inserted. The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. The skilled artisan may choose the reporter gene for its relative merits in the system of interest. For example, fluorescent proteins such as GFP and RFP can be readily detected with fluorescence, but may interfere with normal metabolic functions. β-glucuronidase (Gus) is very sensitive but requires a colorimetric indicator. One category of reporter gene is a selectable marker, such as resistance to antibiotics or herbicide. Other categories of selectable markers include developmental genes such as BBM or WUS and hormone synthesis genes such as IPT.

The constructs contain an origin of replication. Typically, the origin of replication functions in one type of host but does not function in another host. Preferably, the origin of replication will function in an organism used for producing the construct (e.g. bacteria or yeast), but will not grow in organism being subject to genetic manipulation (i.e. plant). These may be said to be "permissive" in bacteria or yeast, and "nonpermissive" in plants. Suitable origins of replication for use in constructs herein include *E. coli* oriC, colE1 plasmid origin, 2u and ARS (both useful in yeast systems).

Epitope tags are short peptide sequences that are recognized by epitope specific antibodies. A fusion protein comprising a recombinant protein and an epitope tag can be simply and easily purified using an antibody bound to a chromatography resin. The presence of the epitope tag furthermore allows the recombinant protein to be detected in subsequent assays, such as Western blots, without having to produce an antibody specific for the recombinant protein itself. Examples of commonly used epitope tags include V5, glutathione-S-transferase (GST), hemagglutinin (HA), the peptide Phe-His-His-Thr-Thr (SEQ ID NO: 20), chitin binding domain, a combination of HA and NLS tags (SEQ ID NO:44) and the like.

Constructs may also contain a multiple cloning site or polylinker for convenient cloning of DNA into the vector at a specific position. Constructs may contain components for genes for crop improvements, protections from pests etc.

The constructs can be constructed utilizing methodologies known in the art of molecular biology (see, for example, Ausubel or Maniatis) in view of the teachings of the specification. As described above, the targeting constructs are assembled by inserting, into a suitable vector backbone, a recombination attachment site, polynucleotides encoding sequences of interest operably linked to a promoter of interest; and, optionally a sequence encoding a positive selection marker. Suitable prokaryotic vectors include plasmids such as those capable of replication in *E. coli* (for example, pBR322, ColE1, pSC101, PACYC 184, itVX, PRSET, pBAD (Invitrogen, Carlsbad, Calif.) and the like). See Sambrook 1989 supra. *Bacillus* plasmids include pC194, pC221, pT127, and the like, and are disclosed by Gryczan (In: The Molecular Biology of the Bacilli, Academic Press, NY (1982), pp. 307-329).

A preferred method of obtaining polynucleotides, including suitable regulatory sequences (e.g., promoters) is PCR. General procedures for PCR are taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. After amplification, the resulting fragments can be detected by agarose gel electrophoresis followed by visualization with ethidium bromide staining and ultraviolet illumination.

Gene Expression Constructs

The ability to readily incorporate an exogenous DNA into a plant chromosome can be used for a plant gene expression system. The gene expression system may comprise a polynucleotide encoding a gene of interest operably linked to a promoter that is operable in a plant cell and an att site for integrating the gene expression system into a plant cell. The att site may be, for example, an attP or attB that is cognate with SPβc2 serine recombinase. In other embodiments, for example, the att site is an attP or attB that is cognate with SF370 recombinase. The promoter may be constitutive, inducible, or regulated by e.g., a gene switch. The gene expression system may further comprise other regulatory elements, such as enhancers. Insertion and tracking of the gene expression system may be facilitated by reporter genes, such as selectable markers. Such reporter genes are operably linked to a second promoter, and the second promoter may be the same or different promoter than the promoter operably linked to the gene of interest.

In some embodiments, the nucleic acid sequence encoding the serine recombinase actually encodes a fusion protein of the serine recombinase with its cognate RDF, optionally joined by a linker sequence. As such the serine recombinase RDF fusion polypeptide may be encoded by a polynucleotide comprising a first nucleic sequence encoding a large serine recombinase operably linked to a second nucleic acid sequence encoding a cognate recombinase directionality factor (RDF) of said large serine recombinase. In some embodiments, the first nucleic acid and said second nucleic acid are joined by a polynucleotide liner sequence. In some embodiments, the first nucleic acid encodes an amino acid sequence of SEQ ID NO:41. The first nucleic acid sequence that can encode the amino acid sequence of SEQ ID NO:41 includes, but is not limited to the nucleic acid sequence of SEQ ID NO:36. In some embodiments, the second nucleic acid encodes an amino acid sequence of SEQ ID NO:31. The polynucleotides that may encode this amino acid sequence includes, but is not limited to the nucleic acid sequence of SEQ ID NO:29.

In some embodiments, the polynucleotide further comprises a third nucleic acid encoding HA and NLS tags, (e.g., HA and NLS tags having the amino acid sequence of SEQ ID NO: 40, which may be encoded by a polynucleotide sequence, for example, of SEQ ID NO:35.

In some embodiments, the serine recombinase-RDF fusion protein is under the control of an inducible promoter or gene switch to regulate excision upon addition of a stimulus, including, but not limited to a chemical ligand. In some embodiments, the serine recombinase-RDF fusion protein is delivered through subsequent transformation (sequential) of the plant cell or through sexual cross with a line that constitutively expresses the serine recombinase-RDF fusion protein.

Plant Engineering System

The ability to readily incorporate an exogenous DNA into a plant chromosome can also be used for facilitating the addition of further exogenous DNA. Established methods of gene exchange require the presence of target site for insertion of new exogenous DNA, such as a tyrosine site specific recombinase attachment site (e.g. loxP, FRT), and serine recombinase attachment sites attB and attP). Plants do not naturally possess such sites. The present methods and constructs provide for a plant engineering system with the ability to readily add such a target site for further manipulation into the chromosome.

In particular, the plant engineering system comprises a polynucleotide containing an SPβc2 att site for incorporation into the plant chromosome, and also comprises at least one target site for further insertion of exogenous DNA. As used herein, "target site for further insertion of exogenous DNA" includes sites for loxP, FRT, attB and attP sites, provided that any attB or attP site differs from and is non-cognate with the SPβc2 att site for incorporation into the plant chromosome.

Thus, a method involves co-transfection of a plant cell with (a) a DNA encoding a serine recombinase and (b) a plant engineering system DNA comprising (i) an SPβc2 att site for incorporation into the plant chromosome, and (ii) a target site for further insertion of exogenous DNA. Following transfection, the plant cell is grown and screened to confirm the presence of the plant engineering system. Transgenic plant cells may be grown to transgenic plant(s), and used for further insertion of exogenous DNA.

In other embodiments, the method involves co-transfection of a plant cell with (a) a DNA encoding a serine recombinase and (b) a plant engineering system DNA comprising (i) an SF370 att site for incorporation into the plant chromosome, and (ii) a target site for further insertion of exogenous DNA. Following transfection, the plant cell is grown and screened to confirm the presence of the plant engineering system. Transgenic plant cells may be grown to transgenic plant(s), and used for further insertion of exogenous DNA.

Methods

Disclosed herein are means for targeted insertion of a polynucleotide (or nucleic acid sequence(s)) of interest into a genome by, for example, (i) providing a recombinase, wherein the recombinase is capable of facilitating recombination between a first recombination site and a second recombination site, (ii) providing a targeting construct having a first recombination sequence and a polynucleotide of interest, (iii) introducing the recombinase and the targeting construct into a cell which contains in its nucleic acid the second recombination site, wherein the introducing is done under conditions that allow the recombinase to facilitate a recombination event between the first and second recombination sites.

Also described is a related method for site-specific recombination comprising: providing a first recombination site and a second recombination site; contacting the first and second recombination sites with a prokaryotic recombinase polypeptide, resulting in recombination between the recombination sites, wherein the recombinase polypeptide can mediate recombination between the first and second recombination sites, the first recombination site is attP or attB, the second recombination site is attB, attP, or a pseudo att site, and the recombinase is SPβc2, and/or at least 65%, 70%, 75%, 80%, 85%, 90%, 95%, 96%, 97%, 98%, or 99% identical to the amino acid sequence of to SEQ ID NO: 1, provided that when the first recombination attachment site is attB, the second recombination attachment site is attP or pseudo attP, and when the first recombination attachment site is attP, the second recombination attachment site is attB or pseudo attB; or when the both sites are pseudo att sites.

The present invention further comprises methods for obtaining a plant cell having a stably integrated polynucleotide sequence, the method comprising: introducing a polynucleotide that comprises a first recombination att site, into a plant cell that comprises a nucleic acid sequence and a second recombination att site, and contacting the first and the second recombination sites with a prokaryotic recombinase polypeptide, wherein the recombinase polypeptide can mediate site-specific recombination between the first and second recombination sites, and the recombinase is SPβc2, and/or at least 65%, 70%, 75%, 80%, 85%, 90%, 95%, 96%, 97%, 98%, or 99% identical, and/or at least 75%, 80%, 85%, 90%, 95%, 96%, 97%, 98%, or 99% similarity to SEQ ID NO: 1, wherein the first att site is attP and the second att site is a cognate pseudo attB. In other embodiments, the recombinase is SF370, and/or at least 65%, 70%, 75%, 80%, 85%, 90%, 95%, 96%, 97%, 98%, or 99% identical, and/or at least 75%, 80%, 85%, 90%, 95%, 96%, 97%, 98%, or 99% similarity to SEQ ID NO: 125, wherein the first att site is attP and the second att site is a cognate pseudo attB.

Uses of Transgenic Cells and Plants

A transgenic plant cell possesses a modified genome, in which the targeting DNA has inserted into a target site on the plant chromosome. Such transgenic cells and plants have multiple uses, including screening, producing metabolites or small molecules, producing novel proteins, improved resistance to disease, improved growth, improved nutritional profiles, and more.

Screening

The transgenic cells and plants are useful as tools to screen for substances capable of modulating the activity of a protein encoded by a nucleic acid fragment of interest. It is generally easier to screen large numbers of transgenic cells. Thus, provided herein are methods of screening comprising contacting genetically engineered cells of the invention with a test substance and monitoring the cells for a change in cell phenotype, cell proliferation, cell differentiation, enzymatic activity of the protein or the interaction between the protein and a natural binding partner of the protein when compared to test cells not contacted with the test substance.

A variety of test substances can be evaluated using the genetically engineered cells of the invention including peptides, proteins, antibodies, low molecular weight organic compounds, natural products derived from, for example, fungal or plant cells, and the like. By "low molecular weight organic compound" it is, meant a chemical species with a molecular weight of generally less than 500-1000. Sources of test substances are well known to those of skill in the art.

Various assay methods employing cells are also well known by those skilled in the art. They include, for example, assays for enzymatic activity (Hirth, et al, U.S. Pat. No. 5,763,198, issued Jun. 9, 1998), assays for binding of a test substance to a protein expressed by the genetically engineered cells, assays for transcriptional activation of a reporter gene, and the like.

Cells modified by the methods of the present invention can be maintained under conditions that, for example, (i) keep them alive but do not promote growth, (ii) promote growth of the cells, and/or (iii) cause the cells to differentiate or dedifferentiate. Cell culture conditions are typically permissive for the action of the recombinase in the cells, although regulation of the activity of the recombinase may also be modulated by culture conditions (e.g., raising or lowering the temperature at which the cells are cultured). For a given cell, cell-type, tissue, or organism, culture conditions are known in the art.

Further Modification

The transgenic cell may be used for further modification. For example, while the exogenous DNA carried a first att site that permitted insertion into the chromosome at the second att site, the exogenous DNA may further carry a third att site that is non-cognate with the first and second att sites. The third att is, typically, also non-cognate with any other att site or pseudo site on the chromosome. The third att site can, therefore, be used as an attachment site for further modification with a different serine recombinase.

Transgenic Plants

In another embodiment, the present invention comprises transgenic plants and method of obtaining such plants. A "transgenic" plant is a genetically engineered plant containing material from at least one unrelated organism. The transgenic plant encompasses all stages of development, including embryonic, seed, mature plants, and offspring of genetically engineered plants. The term "chimeric" plant used to refer to plants in which some but not all cells of the plant possess the heterologous gene. The term transgenic as used herein additionally includes any organism whose genome has been altered by in vitro manipulation to induce a specific gene knockout. The term "gene knockout" as used herein, refers to the targeted disruption of a gene in vivo with loss of function that has been achieved by use of the invention vector.

A transgenic plant may be used for screening interactions with drugs, pathogens or other external factors. A transgenic plant may also be used for the altered properties mediated by the transgene(s).

Suitable plants may include, for example, alfalfa sprouts, apples, apricots, artichokes, Asian pears, asparagus, atemoyas, avocados, bamboo shoots, bananas, beans, bean sprouts, beets, Belgian endive, bitter melons, bell peppers, blackberries, blueberries, bok choy, boniato, boysenberries, broccoflowers, broccoli, broccolini, Brussel sprouts, butter lettuce, cabbage, cantaloupe, carambola, carrots, casaba melons, cauliflower, celery, chayotes, cherimoyas, cherries, coconuts, coffee, collard greens, corn, cranberries, cucumbers, dates, eggplant, endive, escarole, feijoa, fennel, figs, garlic, gooseberries, grapefruit, grapes, green beans, green onions, collard greens, mustard greens, guava, hominy, honeydew melons, horned, melons, iceberg lettuce, Jerusalem artichokes, jicama, kale, kiwifruit, kohlrabi, kumquats, leeks, lemons, lettuce, lima beans, limes, longan, loquats, lychees, mandarins, malangas, marijuana, mandarin oranges, mangos, mulberries, mushrooms, napas, nectarines, okra, onions, oranges, papayas, parsnip, passion fruits, pawpaws, peaches, peanut, pears, sugar snap peas, green peas, peppers, persimmons, pineapples, plantains, plums, pomegranates, potatoes, prickly pears, pummelos, pumpkins, quince, radicchio, radishes, raspberries, red cabbage, rhubarb, romaine lettuce, rutabaga, shallots, snow peas, soybeans, spinach, sprouts, squash, strawberries, string beans, sweet potatoes, tangelo, tangerines, tomatillo, tomatoes, turnip, ugli fruit, watermelons, water chestnuts, watercress, waxed beans, yams, yellow squash, *yucca*/cassava, zucchini squash, African daisy, Agapanthus, *Ageratum houstonianum*, Alchemilla, *Allium, Alyssum, Amaranthus*, Amaryllis, Anemone, Angelonia, Anthurium, *Artemisia*, Asclepias syriaca, Aster, *Astilbe*, Astrantia, Aubreita *deltoidea*, baby's breath, bachelor button, balloon flower, bee balm, *begonia*, bellflower, blanket flower, Bergenia, black-eyed Susan, blanket flower, blazing star, bleeding heart, bluebell, blue-eyed grass, blue star flower, Bouvardia, *Bougainvillea*, broom, Buddleja, bush morning glory, buttercup, butterfly weed, butterfly bush, Calendula, California poppy, calla lily, ('alliandra, *Camellia, Campanula*, candytuft, *canna* lily, cape primrose, cardinal flower, carnation, catmint, *Celosia, Chrysanthemum*, Clarkia, clover, *clematis*, cockscomb, columbine, coneflower, coral bells, Coreopsis, Cosmos, Cotoneaster, *Crocus*, creeping *phlox*, Crocosmia, crown imperial, cuckoo flower, Cyclamen, Dahlia, day lily, Delphinium, Echium, English bluebell, Erigeron, evening primrose, *Euphorbia*, flannel flower, flax flower, floss flower, forget-me-not, Forsythia, foxglove, Frangipani, Freesia, Fuschia, *Gardenia*, Geranium, gas plant, Gaura, gayfeather, *Gerbera, Gladiolus*, globeflower, goldenrod, grape hyacinth, *Gypsophila*, heather, Hebe, Helenium, Heliotrope, Hellebore, hemp, Hibiscus, hollyhock, honeysuckle, Hosta, Hyacinth, *Hydrangea, Hypericum*, hardy Geranium, hybrid tea roses, Iceland poppy, ice plant, *Ilex, Impatiens*, Ipheion *uniflorum*, Iris, Ixia, *Ixora*, Jaborosa, Jacob's ladder, Jamesia americana, jasmine, Jupiter's beard, kaffir lily, *Kalmia*, kangaroo paw, *Kerria*, Knautia *macedonica, Kniphofia, Kolkwitzia*, lady's slipper, *Lamium*, Lantana, larkspur, Lavatera, lavender, Lechenaultia, lilac, lily, lily of the valley, Linaria, Lisianthus, *Lobelia*, loosestrife, Lotus, Lunaria, lupin, *Magnolia*, Maltese cross, Mandevilla, Marguerite daisy, marigold, *Matthiola*, mayflower, Meconopsis, *Mimosa*, Mina lobate, mock orange, monk's hood, moonflower, morning glory, Muscari, *Narcissus, Nasturtiums, Nemesia*, Nemophila, Nerine, New Guinea impatien, *Nicotiana*, Nierembergia, Nigella, Nolana, *Oleander*, orchid, oriental lily, oriental poppy, Osteospermum, oyster plant, ox eye daisy, painted daisy, pansy, passion flower, peace lily, *Pelargonium*, Penstemon, peony, Persian buttercup, Peruvian lily, *petunia*, pincushion flower, pink lady's slipper, Poinsettia, *Polyanthus*, poppy anemone, *Portulaca grandiflora, Primula*, Quaker ladies, Queen Anne's lace, Queen's cup, Queen of the meadow, quince, rain lily, *Ranunculus, Rhododendron*, rock rose, Rondeletia, rose, rose of Sharon, *Salvia splendens, Saponaria, Scabiosa*, Scaevola, scented Geranium, Scilla, Sedum, shasta daisy, shrub roses, Silene, silver lace vine, snapdragon, snowball bush, snowdrop, snowflake, statice, strawflower, sun drop, sunflower, sweet pea, *Syringa*, tea rose, tiger flower, tiger lily, Tithonia, *Trillium*, Triteleia, Tritonia *crocata*, trumpet vine, tuberose, tulip, urn plant, Ursinia, Uva *ursi, Verbena, Veronica, incana, Vinca, Viola* tri-colour, Violet, Virginia creeper, wallflower, wandflower, water lily, *Watsonia*, wax plant, Wedelia, Weigela, wild rose, wild violet, winter aconite, winterberry, winter jasmine, wishbone flower, *wisteria*, wooly violet, Xerophyllum, Xylobium, Xylosma, yarrow, yellow angel, yellow bell, yellow-eyed grass, yellowhorn, *Zenobia, Zinnia*, barley, buckwheat, bulgur wheat, corn, durum wheat, einkorn, emmer, farro, fonio, kamut, millet, oats, rice, rye, semolina wheat, sorghum, spelt, teff, triticale, wheat, bamboo shoots, barley grass, lemongrass, sugarcane, wheatgrass, Amaranth, Coxcomb, pitseed goosefoot, *quinoa*, chia, Acacia seed, wattleseed, Kentucky bluegrass, perennial ryegrass, tall fescue, fine fescue, creeping bent grass, creeping red fescue, hard fescue, chewings fescue, Bermuda grass, buffalo grass, kikuyu grass, St. Augustine, and *Zoysia*. In particular, the gene expression system and method of the invention are useful for introducing quality traits in fruits, such as, but not limited to browning in apple, pears, cherry and avocado; disease resistance traits in fruits, for example, *Erwinia* resistance apples, citrus-greening resistant oranges and other citrus fruits; self-fertilizing traits such as in cherries and plums; and seedless or reduced seed size traits, in such fruits as, for example, mangoes, peaches, and avocados; rapid-growth/early flowering traits (applicable to most fruit trees).

Valuable agricultural plants include rice, wheat, soybeans, tomatoes, sugarcane, maize (corn), potatoes, vegetables, not elsewhere specified, grapes, cotton, apples, bananas, cassava (*yucca*), mangos, mangosteens, guavas, coffee, oil palm, onions, beans, peanuts, olives, rapeseed, chilis and peppers (green and dry), rubber, tea, oranges, cucumbers, yams, peaches, nectarines, lettuce, chicory, cacao (chocolate), sunflower seed, sugar beets, watermelons, asparagus, carrots, turnips, coconuts, tangerines, almonds, lemons, limes, strawberries, walnuts.

Given public concerns about GMO food, there are generally lower barriers for transgenic plants used for industrial produce or not for human food. Such plants include grasses such as bamboo, misacanthus and switch grass, jatropha, hemp, castor bean, and flax.

Transgenic Properties

Transgenic properties include resistance to pests such as but not limited to insects, fungi and bacteria; and pesticides. Transgenic plants may also be made to knock out unwanted genes or to add traits or modify traits related to flowering, drought resistance, herbicide resistance, pest resistance, disease resistance, floral color, intensity of floral color, floral aroma, accumulation of specific nutrients, fruit aroma, taste, nutritional value, or for expression of an exogenous gene.

For example, a plasmid bearing the SPβc2 att site can also be used for altering the expression of genes that improve plant shelf-life, flavor, aroma and appearance of plants. Genes involved in increased shelf life include those reducing ethylene level and/or sensitivity (e.g. 1-Aminocyclopropane-1-carboxylic acid synthase (ACS) gene, ethylene receptors, ethylene oxidation), reducing senescence (e.g., ef-1, DHS), reducing the browning in cut fruits and vegetables (e.g. polyphenol oxidase, PPO or Phenylealanine Ammonia Lyase, PAL gene). Genes involved in flavor and taste include those increasing sugar content (genes for sugar and organic acids biosynthesis and transport) or reducing the bitterness (e.g, genes of Sesquiterpenoid pathways) of plant tissue. Genes involved in aroma and appearance include those responsible for producing aromatic volatiles compounds resulting from amino acid and carotenoid biosynthetic pathways. Genes involved in nutritional value of plants could be those that upregulate production of carotenoids (e.g., PSY) and tocopherols (e.g., homogentisate geranylgeranyltransferase; homogentisate phytyltransferase; and homogentisate solanesyltransferase).

A plasmid bearing the SPβc2 att site can also be used for trait engineering applications in crops, fruits and vegetables. Genes involved in improving agronomic performances such as drought, cold and heat tolerance, increasing yield via improving photosynthetic efficiency or nutrient utilization or genes involved in increasing plant biomass can be engineered and expressed in plants. Such genes can be expressed alone or in combination of multiple genes or traits.

Other agronomic traits include herbicide tolerance and genes involved in crop protections from pests. The herbicide tolerance genes include those that detoxify herbicides (e.g., dicamba mono-oxygenase) or those that increase insensitivity to herbicide action (5-enolpyruvylshikimate 3-phosphate synthase, EPSP). The crop protection genes could be insecticidal proteins (e.g. Cry family toxins such as Bt toxin.) or those protecting from various plant diseases (e.g. defensin family, dsRNA etc).

The ability to incorporate large sections of DNA makes the present invention particularly useful for the transfer of metabolic gene clusters. Metabolic Gene Clusters (MGCs) are genomically co-localized and potentially co-regulated genes of a particular metabolic pathway. Several of these clusters encode molecules involved in defense against pests, herbivores and/or pathogens. For example, the marneral gene cluster (50 kb) and thalianol gene cluster (70 kb) from *Arabidopsis thaliana*; the momilactone (180 kb) and phytocassane (250 kb) gene clusters in rice (*Oryza sativa*); DIMBOA (250 kb) gene cluster from *Zea mays* (corn); terpene gene cluster (100 kb) solanine/tomatine gene clusters (150 and 30 kb) from *Solanum lycopersicum* (tomato); solanine/tomatine gene clusters (250 and 30 kb) from *Solanum tuberosum* (potato).

There are a number of techniques available to clone large gene clusters. The Bacterial Artificial Chromosome (BAC) based on an F plasmid ori may be used for 150-350 kb cloning; the related P1-derived Artificial Chromosome (PAC), based on PI bacteriophage, typically contains 100-300 kb fragments; and Yeast artificial chromosomes (YACs) may range from 100-1000 kb. Thus, for example, the DIMBOA gene cluster from corn can be cloned into e.g. a BAC and used to transfer expression of resistance to pests and pathogens. Alternatively, very large sections of DNA may be reduced by cloning some or all of the relevant genes from the cDNA, thus removing operons. This strategy was used to clone 3 genes from oat (*Avena* sp.) that mediate production of the antifungal compound avenacin. Transferring the avenacin genes to *Avena* longiglumis, which does not produce avenacin, also transferred resistance the fungus G. graminis var. tritici.

One useful example is the production of DIMBOA (2,4-dihydroxy-7-methoxy-1,4-benzoxazin-3-one), which is a naturally occurring compound that is a powerful antibiotic present in maize and related grasses, and provides defense against pests, including fungi and bacteria, and European corn borer larvae. DIMBOA production is typically highest in young seedlings, but decreases at the plant ages. Thus, if DIMBOA related genes are placed under the control of root specific promoters that continue expression into adult life (see dl.sciencesocieties.org/publications/tpg/articles/9/1/plantgenome2015.04.0025 for exemplary root specific genes), and transfected into corn, the resulting plants will express higher levels of DIMBOA in the roots in mature plants and provide a natural defense to corn borers, Another example is the production of $C_4$ rice. Rice naturally uses $C_3$ carbon fixation. $C_4$ fixation is an elaboration of $C_3$, and requires additional genes encoding for both a modified photosynthetic pathway and modification of the leaf architecture to concentrate $CO_2$ at the Rubisco enzyme. Compared to $C_3$, $C_4$ photosynthesis fixes carbon more efficiently, at lower levels of carbon dioxide, and with significantly less water. A $C_4$ plant therefore has increased growth at higher temperatures and is more resistant to drought. Converting rice to $C_4$ would be a significant advance for global food production.

Helpfully, many enzymes and structural features required for $C_4$ photosynthesis are already found in $C_3$ plants, and $C_4$ photosynthesis has evolved independently at least 66 times in at least 18 plant families (Schuler et al. "Engineering $C_4$ photosynthesis into $C_3$ chassis in the synthetic biology age" *The Plant Journal,* 2016; 87, 51-65, at 55). According to Schuler, transcriptomic studies suggest that engineering of $C_4$ will require the removal or suppression of genes that suppress a full $C_4$ cycle. As for new genes, at most 9 genes had been successfully introduced into a plant, whereas the predicted number of transgenes for $C_4$ is expected to be many more. Genome landing pads will be needed to enable the introduction of multigene constructs.

Because the present invention is able to integrate large DNA segments directly into the chromosome of diverse species, it is particularly useful for the $C_4$ rice program. An insert can provide (a) a suite of regulatory RNAs to suppress the expression of genes that interfere with a full $C_4$ cycle (b) transgenes required for $C_4$ and (c) additional "landing sites" to facilitate the insertion of additional genes and regulators. Pseudosites for Serine Recombinase-Mediated Integration Pseudosites that are useful in the integration of nucleic acids into the genome of plants include, but are not limited to the following:

Tobacco

Examples of SPβc2 pseudo attB sites in *Nicotiana* include but are not limited to:

```
                                               (SEQ ID NO: 132)
gttatagtcagttgaattcaaactctctgactcatcattagagaaacaat taaatagattatagtattacttacaatgcgcgcgacgcattgtatgaacc (SEQ ID NO: 133)
ttgctgtcttttcatacttttctaagttgaaagtacttgaaagtacgacc aagaaaatgattatatttgacacagaaaatgcaaggtactttgaatgtga (SEQ ID NO: 134)
ggataagggagggtttagatattttgaaagggttaaggggtaaaatcact aaggggaattaacaatgcacactagggttgccttaaaagtgcctatata (SEQ ID NO: 135)
ctaatatacattgacagtgttaaaaaaaatctattaacgacaatatagag aagagagtacttacatgaatgacgtctactttgactccgtcaattccaac (SEQ ID NO: 136)
taggcttacattcctgatgtactatcccattatgcaataataaagatgca aaataggaaatgtcattgacagctacgagatctatctttattgattcact (SEQ ID NO: 137)
acatggagcaatgatggagaaaaatggtggtcattactactgaagttgtc aaagcaaagctgtcaggtaacatcaaatgatctctaaatcaattagtctt (SEQ ID NO: 138)
gccacaacctaggccaggcaaaggtttcactaatacctgtgatgtttgtc aaaggagtctcctcgactccttcagattctgctctcttggctgtaaggta (SEQ ID NO: 139)
gaagagacgattacatatatgtgtacgcgttggataatcatttgaacctt aaagtctgtctctctcttaacatgtgttcaatagcaatacaaagtgtata
```

In some embodiments, the species of *Nicotiana* is *Nicotiana benthamiana*.

Lettuce

Examples of SPβc2 pseudo attB sites in *Lactuca* include but are not limited to:

```
                                               (SEQ ID NO: 140)
attaaggaggagaatataacatgtattttgtgtgtatcatgagaaacaat tagaaggtacctataattatgaagtcaaagcacaaggatattcttgtaaa (SEQ ID NO: 141)
caatggtgaatatagtccggcgaccaactctgtccactatcagcaacgat aaaaaggtcatgctaagacccacaagcccagtcaccactgctgacataag (SEQ ID NO: 142)
ataagtttagatcttattgaactaggcttgtggtgcttgtttaaggccat aaatcgccttattcaagcgacaaaaatgagacgaataggtggagtcttca (SEQ ID NO: 143)
tccgtcacaaattgcatcactacgactaagatcttcatcaatgattctat taaggagattcttacattgaaggagaagttacataaattctttattattt (SEQ ID NO: 144)
tgaatttcttatgaaggttacaacgcatcgtggattacaagcaattctgt ttagtctgttatgttgttgaatttgaatggatcttgtcctcagttactca (SEQ ID NO: 145)
cacaaaaaattgaccatttctagcaacttcctatgatacgttgatactttt ctaaacattaattacaatgacaaaatgaagtctaccaaatcattcataga (SEQ ID NO: 146)
tatttgtgatgtgacatgacaaataatgatgttacaatattatgtacctc taaatgagatctagcattgaagattgcatgaatattcttgagtgtgttat t
```

In some embodiments, the species of *Lactuca* is *Lactuca sativa*.

Possible Att Sites Identified for Lettuce and Tobacco:

Examples of att sites in lettuce and tobacco include, but are not limited to:

```
                                                (SEQ ID NO: 66)
           GTGCTTGTTTAAGGCCATAAATCGCCTTATTCAAGCGA (SEQ ID NO: 67)
           GTGCTTGTTTAAGGCCATAAATCGCCTTATTCAAGCGA (SEQ ID NO: 68)
           GTTAAGGGGTAAAATCACTAAGGGGGAATTAACAATGC (SEQ ID NO: 69)
           GTTAAGGGGTAAAATCACTAAGGGGGAATTAACAATGC (SEQ ID NO: 70)
           TCCACTATCAGCAACGATAAAAAGGTCATGCTAAGACC (SEQ ID NO: 71)
           TCCACTATCAGCAACGATAAAAAGGTCATGCTAAGACC (SEQ ID NO: 72)
           TCCACTATCAGCAACGATAAAAAGGTCATGCTAAGACC (SEQ ID NO: 73)
           TCCACTATCAGCAACGATAAAAAGGTCATGCTAAGACC (SEQ ID NO: 74)
           TCCACTATCAGCAACGATAAAAAGGTCATGCTAAGACC (SEQ ID NO: 75)
           TCCACTATCAGCAACGATAAAAAGGTCATGCTAAGACC (SEQ ID NO: 76)
           TCCACTATCAGCAACGATAAAAAGGTCATGCTAAGACC (SEQ ID NO: 77)
           TGTATCATGAGAAACAATTAGAAGGTACCTATAATTAT (SEQ ID NO: 78)
           TGTATCATGAGAAACAATTAGAAGGTACCTATAATTAT (SEQ ID NO: 79)
           TGTATCATGAGAAACAATTAGAAGGTACCTATAATTAT (SEQ ID NO: 80)
           TGTATCATGAGAAACAATTAGAAGGTACCTATAATTAT (SEQ ID NO: 81)
           TGTATCATGAGAAACAATTAGAAGGTACCTATAATTAT (SEQ ID NO: 82)
           TGTATCATGAGAAACAATTAGAAGGTACCTATAATTAT (SEQ ID NO: 83)
           TGTATCATGAGAAACAATTAGAAGGTACCTATAATTAT (SEQ ID NO: 84)
           TGTATCATGAGAAACAATTAGAAGGTACCTATAATTAT (SEQ ID NO: 85)
           TGTATCATGAGAAACAATTAGAAGGTACCTATAATTAT
```

-continued

```
                                    (SEQ ID NO: 86)
TGTATCATGAGAAACAATTAGAAGGTACCTATAATTAT (SEQ ID NO: 87)
CATCATTAGAGAAACAATTAAATAGATTATAGTATTAC (SEQ ID NO: 88)
CATCATTAGAGAAACAATTAAATAGATTATAGTATTAC (SEQ ID NO: 89)
CATCATTAGAGAAACAATTAAATAGATTATAGTATTAC (SEQ ID NO: 90)
CATCATTAGAGAAACAATTAAATAGATTATAGTATTAC (SEQ ID NO: 91)
CATCATTAGAGAAACAATTAAATAGATTATAGTATTAC (SEQ ID NO: 92)
CATCATTAGAGAAACAATTAAATAGATTATAGTATTAC (SEQ ID NO: 93)
TTCATCAATGATTCTATTAAGGAGATTCTTACATTGA (SEQ ID NO: 94)
TTCATCAATGATTCTATTAAGGAGATTCTTACATTGA (SEQ ID NO: 95)
ACTTGAAAGTACGACCAAGAAAATGATTATATTTGA (SEQ ID NO: 96)
ACTTGAAAGTACGACCAAGAAAATGATTATATTTGA
```

Consensus sequences for SPβc2 pseudosites are:

ccaaagtagt aagtatctta aaaaacagatwr (SEQ ID NO: 130); and ccaaagtagt aagtatctta aaaaacagataa (SEQ ID NO:131). Thus, a SPβc2 pseudosite in lettuce and tobacco comprises the common element of SEQ ID NO: 130 or SEQ ID NO: 131.

Examples of pseudosites in lettuce for SF370 are:

```
                                            (SEQ ID NO: 64)
    cagcctaacg attattatag attgtgttgg ccgacccttt ttgccagcct tataggtaat aaagttataa gacaatatta caataggtct ttgacatcaa (SEQ ID NO: 65)
    ataaataaat aaaagagggg ttagggcttt gagtcctttt gtcttcgtct gattggagag aaagggaacg aacgaaagca gcaacaattt gtcccatgat
```

Rice

Examples of SPβc2 pseudo attB sites in *Oryza* include but are not limited to:

```
                                            (SEQ ID NO: 107)
tccgattgaagtttagtaggagtatagtgtagtgttagtgtacactgtc tttaagatcacattaagaactaatagacctgtaaacccttttcatctagc ag.

(SEQ ID NO: 108)
ggtaaaggcgatgatgtgtactcttgggttgcctattgggtgcatatcc ttggcagggctcatgttgttcagttaataaagatattaagtagctacct a.
```

```
                                            (SEQ ID NO: 109)
Tacctttaatttagtacatgacattgtgaacatcagcataagtatcgtc ttattgagatacatattttatctcacgttagcacgttttttaagtact a.

(SEQ ID NO: 110)
accgaatgctgcgtggagtacattgttcagatcgtaggtggcgctgtct tgtctgcccgcccatttaacttccttccgccatcacgaacctgatcaac g.
```

In some embodiments, the species of *Oryza* is *Oryza sativa*.

Corn

Examples of SPβc2 pseudo attB sites in *Zea* include but are not limited to:

```
                                            (SEQ ID NO: 56)
    ataacgaaag atttggccat gactgcagca ttgccaccat acgaagatac tgttgcttcg tagctcatca aaaactgctt cgggtctgag tggccatca
```

In some embodiments, the species of *Zea* is *Zea mays*.

In some embodiments, the att site in *Zea* is a sequence that has the consensus sequence of

```
                                            (SEQ ID NO: 98)
    mhrdhnndwn wrmAAChATw AAdnnGhdhh whnvAdhnhn
``` with a core sequence of:

```
                                            (SEQ ID NO: 99)
    mhrdhnndwn wrmAAChATw AAdnnGhdhh w
```

Soybean

Examples of SPβc2 pseudo attB sites in Glycine include but are not limited to:

```
                                            (SEQ ID NO: 100)
    nnnnnnnnnw nhAAChATwA hdnnrnnnnn nnnwddnnn
``` with a core sequence of:

```
                                            (SEQ ID NO: 101)
            wnhAAChATw Ahdnnr.
```

In certain embodiments, the method comprises integrating exogenous DNA into a plant attB pseudosite comprising introducing into a plant cell
  (a) an exogenous DNA comprising:
    (i) a polynucleotide sequence of interest; and
    (ii) an attP site; and
  (b) a polynucleotide encoding a serine recombinase operably linked to a promoter that is active in the plant;
  wherein the serine recombinase directs introduction of the exogenous DNA into the plant cell genome at a plant att pseudosite.

The plant may be a monocot or a dicot. The serine recombinase may be SPβc2 or SF370 serine recombinase. The integration of the exogenous DNA is unidirectional unless one expresses the serine recombinase with its cognate RDF to excise the integrated exogenous DNA from the genome. The serine recombinase and RDF may be expressed separately or as a fusion protein.

The invention may be further understood by reference to the following non-limiting examples.

Examples

Example 1 Plasmid Constructs

1. Recombinase Plasmids

Figure 2:
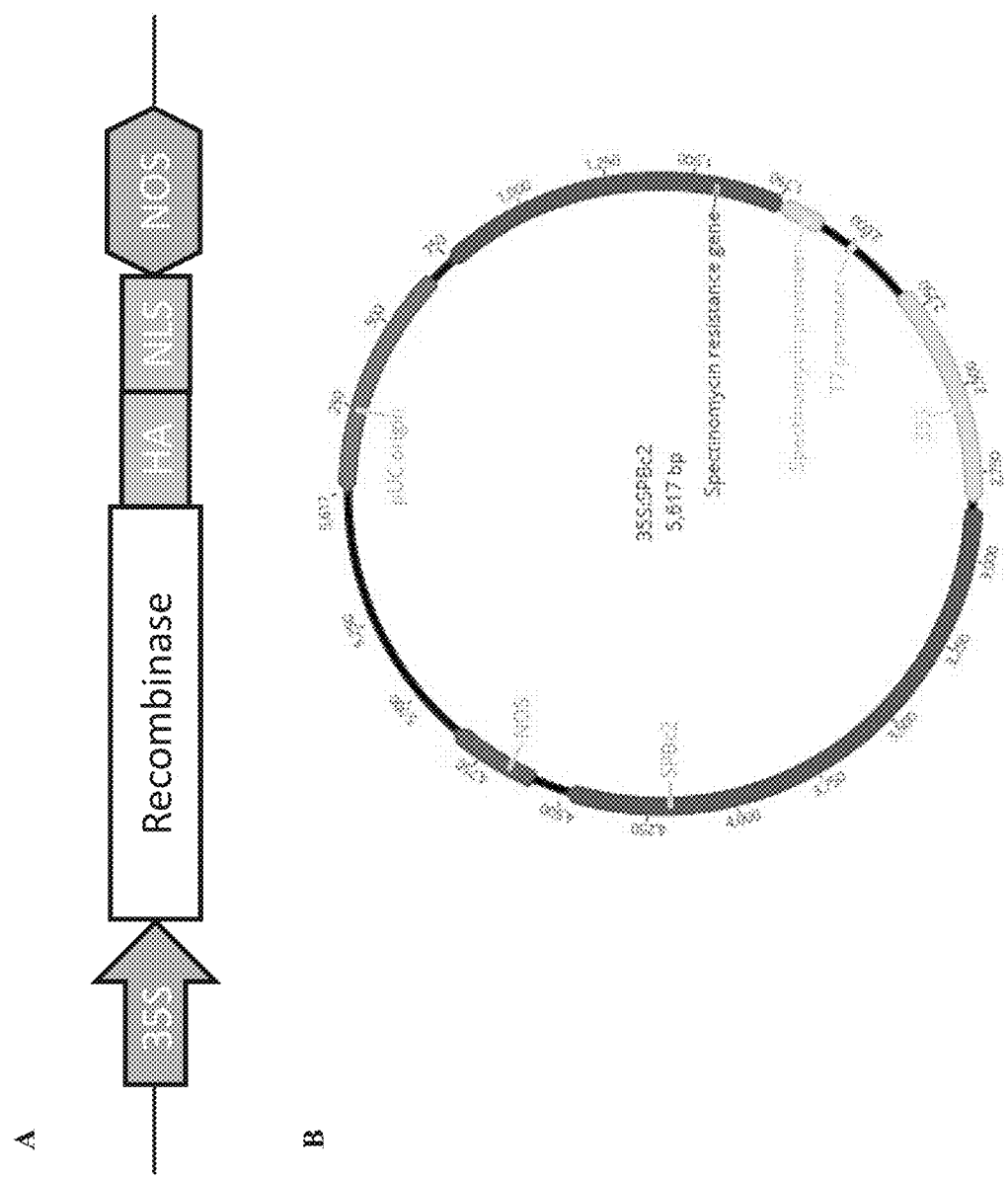
FIG. 2A-B: Effector plasmids expressing recombinase (see Example 1)

Plasmids bearing recombinases were based on a pUC backbone. Each recombinase gene was modified to express a fusion protein with a C-terminal HA (influenza hemagglutinin) peptide and SV40 nuclear localization signal (NLS). Expression was under the control of Cauliflower mosaic virus (CaMV) 35S promoter and nopaline synthase (NOS) terminator. FIG. 2 is a schematic drawing of the recombinase constructs expressing recombinase fusion proteins.

The following Table 2 describes the bacteriophage that was the original source of the recombinase, the structure of the recombinase fusion proteins used in this study, and the amino acid sequence identifiers.

TABLE 2

Sources of recombinases

| Source and Accession ID | Recombinase fusion proteins | Expected size (kDa) |
| --- | --- | --- |
| *Mycobacterium avium* phage Bxb1 Accession ID: NP_075302.1 | BXB1-HA-NLS | 57.8 |
| *Streptococcus pyogenes* phage 370.1 Accession ID: WP_010922052.1 | SF370.1-HA-NLS | 60.7 |
| *Bacillus subtilis* phage SPβc2 Accession ID: WP_004399105.1 | SPβc2- HA-NLS (SEQ ID NO: 2) | 69.4 |
| *Listeria monocytogenes* phage A118 Accession ID: WP_015967157.1 | A188- HA-NLS | 58.9 |
| *Streptomyces* phage ΦC31 Accession ID: WP_107426086.1 | ΦC31-HA-NLS | 73.7 |

To equalize the amount of DNA transfected into cells in experiments where no effector plasmid was used, a plasmid expressing chloramphenicol acetyl transferase (CAT) gene was transfected as a control (Ulmasov et al (1997) "Aux/IAA proteins repress expression of reporter genes containing natural and highly active synthetic auxin response elements" *Plant Cell* 9, 1963-1971). The CAT gene was cloned into the 35S-T7-tobacco mosaic virus (TMV)-3' nopaline synthase vector (i.e., CaMV 35S with a duplicated enhancer 35s promoter combined with the T7 phage promoter followed by the TMV R translational enhancer and the 3' nopaline synthase untranslated region).

2. Serine Recombinases are Expressed in Plant Cells

The effector constructs expressing serine recombinases were grown in *E. coli* and extracted using commercial DNA extraction kit such as Qiagen DNA extraction kit. Plasmids used in transfection were prepared using Qiagen Endo Free Maxi Kit (Catalog no. 12361, Qiagen Inc. CA).

Mesophyll protoplasts were isolated from 3-5 weeks-old aseptically grown lettuce plants as described by Tiwari et al. ("Transfection assays with protoplasts containing integrated reporter genes" *Methods Mol Biol.* 2006; 323:237-44). Purified protoplasts were transfected with the plasmid expressing recombinase using standard polyethylene glycol method as described in Tiwari (id.)

Figure 3:
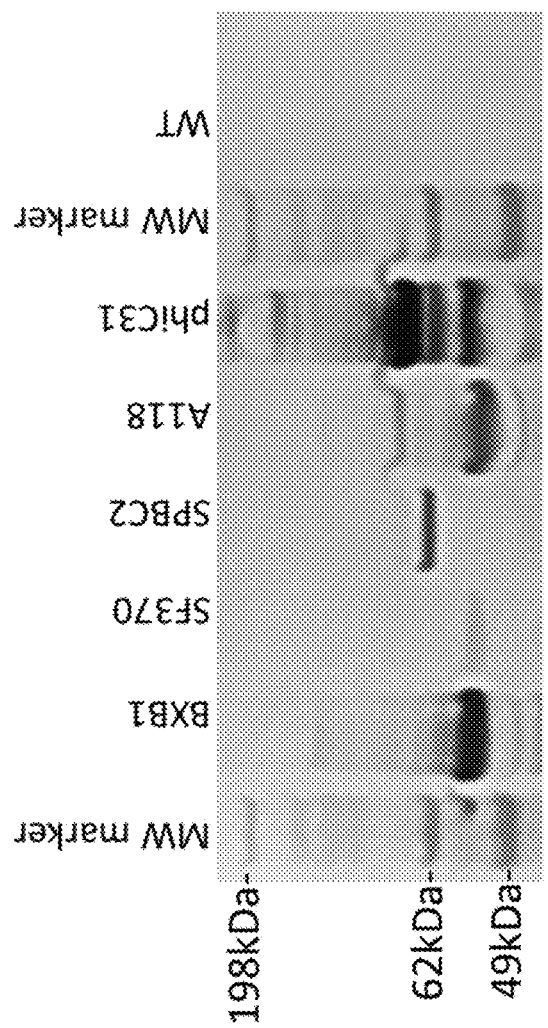
FIG. 3: Western blot showing the expression of different recombinases in lettuce protoplasts, as shown by Western blot against the HA epitope. SF370.1 was expressed at a low level. All other recombinases were expressed at a high level in lettuce protoplasts (see Example 1).

After 18 hours of culturing, protoplasts were harvested, lysed in SDS-buffer and proteins were separated on an SDS-poly acrylamide gel and transferred for Western blot. The presence of recombinases in the gel was detected using HA-epitope antibody (Rat anti-HA clone 3F10 (Sigma #21319000)) FIG. 3 shows the Western blot of recombinase expression, producing proteins at the expected size. SF370.1 was expressed at a low level. All other recombinases were expressed at a high level in lettuce protoplasts.

3. Construction of Reporter Plasmids

Figure 4:
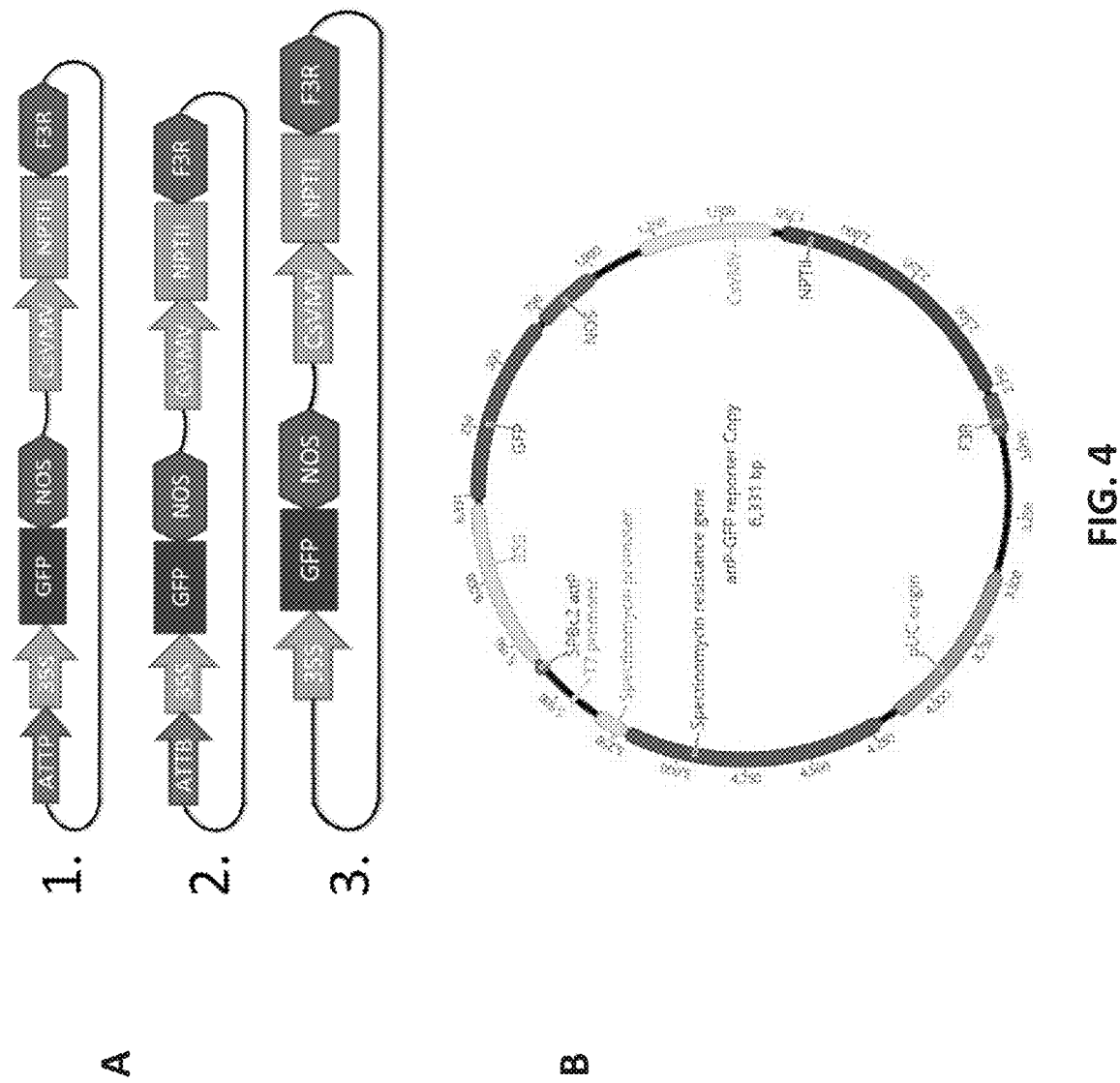
FIG. 4 shows reporter plasmids (see Example 1).

Reporter plasmids were constructed on a pBR322 backbone for replication in bacteria, but are unable to replicate in plants without incorporation into a plant chromosome. To determine if the plasmid has incorporated into the chromosome, the plasmid carried two reporter genes: neomycin phosphotransferase II (NPTII) gene, which confers resistance to neomycin and kanamycin, and Green Fluorescent Protein (GFP). As shown in FIG. 4, each reporter gene was under the control of a promoter and terminator active in plants: Cauliflower mosaic virus (CaMV) 35S promoter and nopaline synthase (NOS) terminator for GFP; Cassava Vein Mosaic Virus (CsVMV) promoter and F3R terminator for NPTII.

FIG. 4 also shows that the reporter plasmids also contained an attP (1), attB (2) or no site (3) 5' to the GFP reporter. SEQ ID NO: 4 shows the reporter plasmid with an SPβc2 attP site at positions 5598-6331. This region is deleted in the plasmid lacking an att site, or substituted with the appropriate attP or attB sequence. Because each serine recombinase recognizes a specific cognate attPlattB, the attP or attB for each reporter plasmid was adapted to the cognate serine recombinase, as shown in the following Table 3.

Because a serine recombinase will only mediate incorporation of the reporter plasmid into the plant chromosome if it recognizes an attPlattB pair, reporter plasmids bearing attP or attB are able to determine the presence of their corresponding attB or attP on the chromosome. The att-free plasmid controls for random integration.

TABLE 3

Serine recombinases and their cognate attB and attP sequences

| Serine recombinase | attB sequence | attP sequence |
| --- | --- | --- |
| BXB1 | TCGGCCGGCTTGTCGACGACGGCGGTCT CCGTCGTCAGGATCATCCGGGC (SEQ ID NO: 12) | GTCGTGGTTTGTCTGGTCAACCACCGCGGTCTC AGTGGTGTACGGTACAAACCCCGAC (SEQ ID NO: 13) |
| SF370.1 | GTTTTCCATTGTTTTTTTGAAGTGTCTG ATGTTCTGTGATATGATAAAAGGGATAA TAACGTTTGTAAAGGAGACTGATAATGG CATGTACAACTATACTCGTCGGTAAAAA | ATTTTTGTATCCAGTTCAATGGATATTTGATAT AATCGTCTTAAAAAGGAGGTCGTGAAATGGATA AAAAAATACAGCGTTTTTCATGTACAACTATAC TAGTTGTAGTGCCTAAATAATGCTTTTAAAACT |

TABLE 3-continued

Serine recombinases and their cognate attB and attP sequences

| Serine recombinase | attB sequence | attP sequence |
|---|---|---|
| | GGCATCTTATGATGGCTCAACCATGGTT GCTCGAACAGAAGATTCTCAAAATGGTG ATTTCACGCCTAAAAAAATGATTGTGGT GAAA (SEQ ID NO: 8) | TAAAAATAATATCGATGTTATCCATAGTAACCT CGACTCTATCTATCAATTGCTTAACTATCCTAG AT (SEQ ID NO: 9) |
| SPβc2 | AGTGCAGCATGTCATTAATATCAGTACA GATAAAGCTGTATCTCCTGTGAACACAA TGGGTG (SEQ ID NO: 6) | AAAGTAGTAAGTATCTTAAAAAACAGATAAAGC TGTATATTAAGATACTTACTAC (SEQ ID NO: 7) |
| A118 | AACTTTTCGGATCAAGCTATGAAGGACG CAAAGAGGGAACTAAACACTT (SEQ ID NO: 10) | TTAGTTCCTCGTTTTCTCTCGTTGGAAGAAGAA GAAACGAGAAACTAAA (SEQ ID NO: 11) |
| ΦC31 | TGCGGGTGCCAGGGCGTGCCCTTGGGCT CCCCGGGCGCGTACTCC (SEQ ID NO: 14) | GTGCCCCAACTGGGGTAACCTTTGAGTTCTCTC AGTTGGGGG (SEQ ID NO: 15) |

Example 2. Genbank Screening of Lettuce and Tobacco Genome Did not Identify attP or attB Sites Public genome databases were screened for the presence of attB, attP and possible pseudo att sites. The Phytozome database (from the U.S. Department of Energy Joint Genome Institute, available at phytozome.jgi.doe.gov/pz/portal.html) was examined for lettuce (*Lactuca sativa*) and tobacco (*Nicotiana benthamiana*) genomes. *Arabidopsis* genomes were searched at *Arabidopsis*.org, the database founded by The *Arabidopsis* Information Resource (TAIR).

These databases were searched for the attB and attP sequences listed in Table 3 with a permitted 2 nucleotide mismatch or spacers to account for possible att "pseudo" sites. The att pseudo sites identified in U.S. Pat. No. 9,034,650 were also screened against the lettuce and tobacco genomes.

No attP or attB sites or canonical pseudosites were identified in *Arabidopsis*, lettuce or tobacco. Accordingly, the serine recombinases should be unable to incorporate the attP or attB bearing reporter plasmids into the chromosome of lettuce or tobacco.

Example 3. SPβc2 Recombinase Integrated a 6.3 Kb Plasmid Containing attP but not attB into Lettuce Genome 1. Methods Cultures of *E. coli*, each containing an effector or reporter plasmid, were grown and the DNA extracted using Qiagen Endo Free Maxi Kit (Catalog no. 12361, Qiagen Inc. CA).

Mesophyll protoplasts were isolated from 3-5 weeks-old aseptically grown lettuce plants as described by Tiwari, 2006 (Tiwari et. al., "Transfection assays with protoplasts containing integrated reporter genes" Methods Mol Biol. 2006; 323:237-44). Purified protoplasts were transfected with the plasmid expressing recombinase using standard polyethylene glycol method as described in Tiwari 2006 (id.).

The protocols for sub-culturing of transfected protoplasts and regeneration were as previously described (Jie et. al., "Myo-inositol increases the plating efficiency of protoplast derived from cotyledon of cabbage (*Brassica oleracea* var. *capitata*)." J Plant Biotechnol (2011) 38:69-76; Armas et al., "A rapid and efficient in vitro regeneration system for lettuce (*Lactuca sativa* L.)." Plant Methods (2017) 13:58). In brief, the transfected protoplasts were cultured in liquid medium for 48-hours in dark. Protoplasts were then encapsulated into gelatin beads and grown under dark for 3 weeks. Cell divisions in the embedded protoplasts were observed after 7 days. Small microcolonies were observed in 3 weeks. After 3 weeks, beads were dissolved and young microcolonies were grown in dark for one week and transferred to light. Microcolonies were regenerated into calli (5-7 weeks) and subsequently into plants. In some experiments, microcolonies (4 weeks old) were grown on kanamycin (25-100 μg/ml) to kill cells that didn't contain a reporter plasmid. GFP fluorescence was monitored at every stage of growth. Calli showing positives for both markers (GFP and kan-resistance) were used for subsequent molecular analysis.

Genomic DNA was isolated from transgenic calli and plants. The presence of integrated plasmid in the lettuce chromosome was determined using PCR primers specific to different regions in the reporter-plasmid. The sequences of PCR primers are listed in Table 4.

TABLE 4

PCR primers against the reporter plasmid

| ID | Name | Sequence |
|---|---|---|
| R3 | P35S_AT_F3608 | CATTTCATTTGGAGAGGACA (SEQ ID NO: 21) |
| AI48 | F3R_AT_R | GAAAACTGATAAGACATTTGC TAAAC (SEQ ID NO: 22) |
| Z93 | Kan_ZL_F_1 | GTACTCTTGCCGACTACAACA TC (SEQ ID NO: 23) |
| AK64 | Rec_Spec_AT_R | GAACCCAGTGGACATAAGC (SEQ ID NO: 24) |
| AK65 | Rec_Spec_AT_F | AGGTTTCATTTAGCGCCTC (SEQ ID NO: 25) |
| R6 | NOSt_AT_R7724 | GATAATCATCGCAAGACCG (SEQ ID NO: 26) |
| AI78 | LsPDS_ATG_AT_F | ATGTCTCTGTTTGGAAATGTT TC (SEQ ID NO: 27) |
| AI80 | LsPDS_1kb_AT_R | CAATGGTGCAGGTAAAACAT (SEQ ID NO: 28) |

2. Screening Identifies the SPβc2 and attP Combination is Active in Lettuce

To determine if a given recombinase can integrate reporter plasmids into the lettuce genome (without artificially engineering an att site), lettuce protoplasts were co-transfected with an effector plasmid expressing a recombinase, and a reporter plasmid bearing an attP, attB or no site. The protoplasts were grown into microcolonies for three weeks and the number of GFP positive colonies counted.

In assessing whether integration has occurred, it should be noted neither kanamycin resistance nor GFP expression alone are definitive proof of integration of the kanamycin and GFP reporter plasmid into the chromosome. Plants can exhibit partial kanamycin resistance, likely due to upregulation of drug efflux pumps. Further, a GFP signal can be detected in transfected protoplasts due to expression of GFP from reporter plasmid that is retained in the cell but has not incorporated into the genome, although such signal will dissipate with cell growth. Therefore, a more reliable indication of stable insertion is the combination of GFP resistance and kanamycin, the level of GFP and/or kanamycin resistance, and confirmation with PCR.

In our initial screening, we did not observe any stable GFP signals over control with protoplasts co-transfected with reporter plasmids and plasmids expressing A118, SF370 and BxB1.

A reporter plasmid containing an attP site and effector plasmid producing SPβc2 recombinase produced 27 colonies, while the SPβc2 effector plasmid with an attB or att-free plasmid produced only one colony each. Thus, the attP with SPβc2 was the only combination producing a significant increase in the number of GFP-positive colonies over control.

Figure 5:
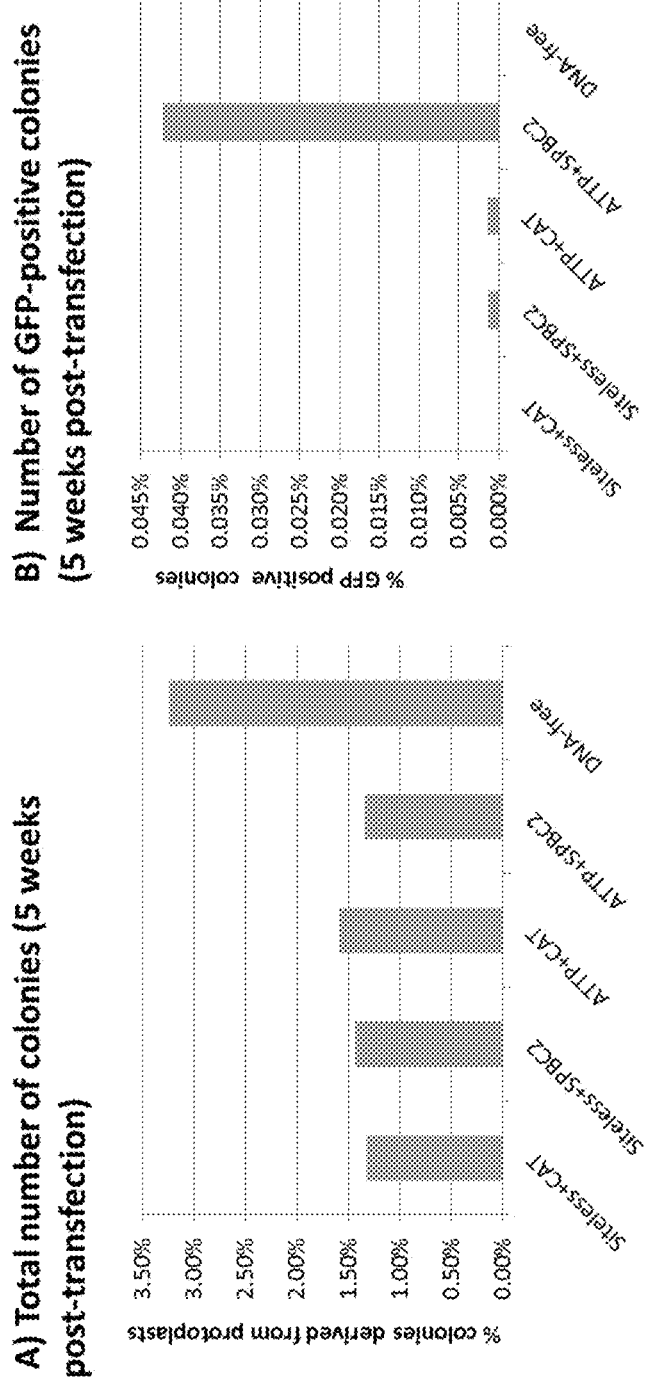
FIG. 5A-5B shows that a reporter plasmid bearing attP is incorporated into the lettuce genome in the presence of SPβc2. Lettuce mesophyll protoplasts were co-transfected with reporter (bearing attP or no att site) and effector plasmids (expressing SPβc2 recombinase or chloramphenicol transferase (CAT) as control) (see Example 3).

To confirm this result, a reporter plasmid containing an attP site or no site (siteless) was co-transfected into lettuce protoplasts along with another effector plasmid expressing SPβc2 recombinase or CAT (control). The protoplasts were grown into microcolonies. The number of colonies was measured at 5 weeks, demonstrating that co-transfection had a negative impact on viability, but that the different plasmids did not have a significant difference in viability between each other (FIG. 5A). Equivalent numbers of microcolonies for each reporter constructs (siteless and attP site) were grown for 5 weeks and the numbers of colonies with GFP florescence were counted.

As shown in FIG. 5B, there is at least a 20-fold enrichment in the number of GFP-positive colonies was seen with reporter plasmid containing an attP site in presence of SPβc2 recombinase. There were only few GFP-positive colonies that appeared with siteless reporter or in absence of SPβc2 recombinase (marked as CAT). These colonies are believed to be due to residual activity of reporter plasmid that has not incorporated into the chromosome.

Figure 6:
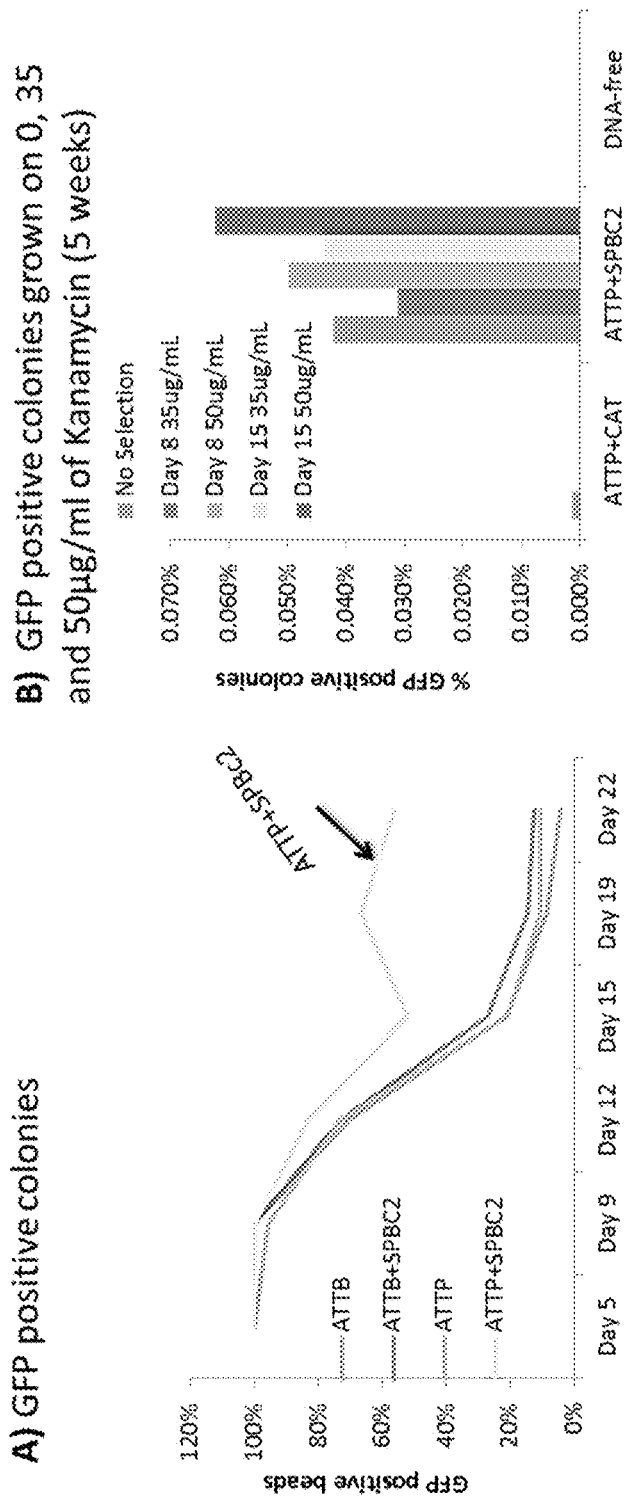
FIG. 6A-6B: SPβc2 mediated integration into lettuce chromosomes acts preferentially on attP. Protoplasts were transfected with reporter plasmids (siteless, attB or attP) along with plasmids expressing SPβc2 or chloramphenicol acetyl transferase (CAT), and cultured as microcolonies (see Example 3).

3. SPβc2 Acts Preferentially on attP Over attB for Incorporating the Reporter Plasmid into the Lettuce Genome We further tested if attB site can also integrate plasmid in lettuce genome. Reporter plasmids with attP and attB sites were co-transfected individually with or without SPβc2 recombinase in lettuce mesophyll protoplasts and encapsulated in gelatin beads. As shown in FIG. 6A, the number of GFP-positive beads declined over 22 days to less than 20%, for protoplasts transfected with the attB-reporter plasmid in presence or absence of SPβc2 recombinase, or the attP reporter without SPβc2. By comparison, the number of beads expressing GFP remained at approximately 60% for protoplasts transfected with SPβc2 and attP plasmids.

At 22 days, GFP-positive beads containing protoplasts co-transfected with SPβc2 and attP were dissolved by suspending in $CaCl_2$) solution to release cell and grown on selection medium containing 35 or 50 μg/ml kanamycin for 8 or 15 days. As a control, beads containing protoplasts transfected with attP+CAT or no DNA were broken open and the cells grown on kanamycin.

The number of GFP positive colonies was counted 5-6 weeks following transfection. As shown in FIG. 6B, attP-reporter plasmid produced 42 fold more GFP-positive colonies in presence of SPβc2-recombinase than without recombinase when grown without kanamycin. When grown in the presence of kanamycin, only protoplasts transfected with attP+SPβc2 gave GFP-positive colonies (FIG. 6B).

This result demonstrates that both kanamycin resistance (NPTII) and GFP marker genes are incorporated into the chromosome, and that kanamycin can be used to enrich the number of transgenic cells.

Figure 7:
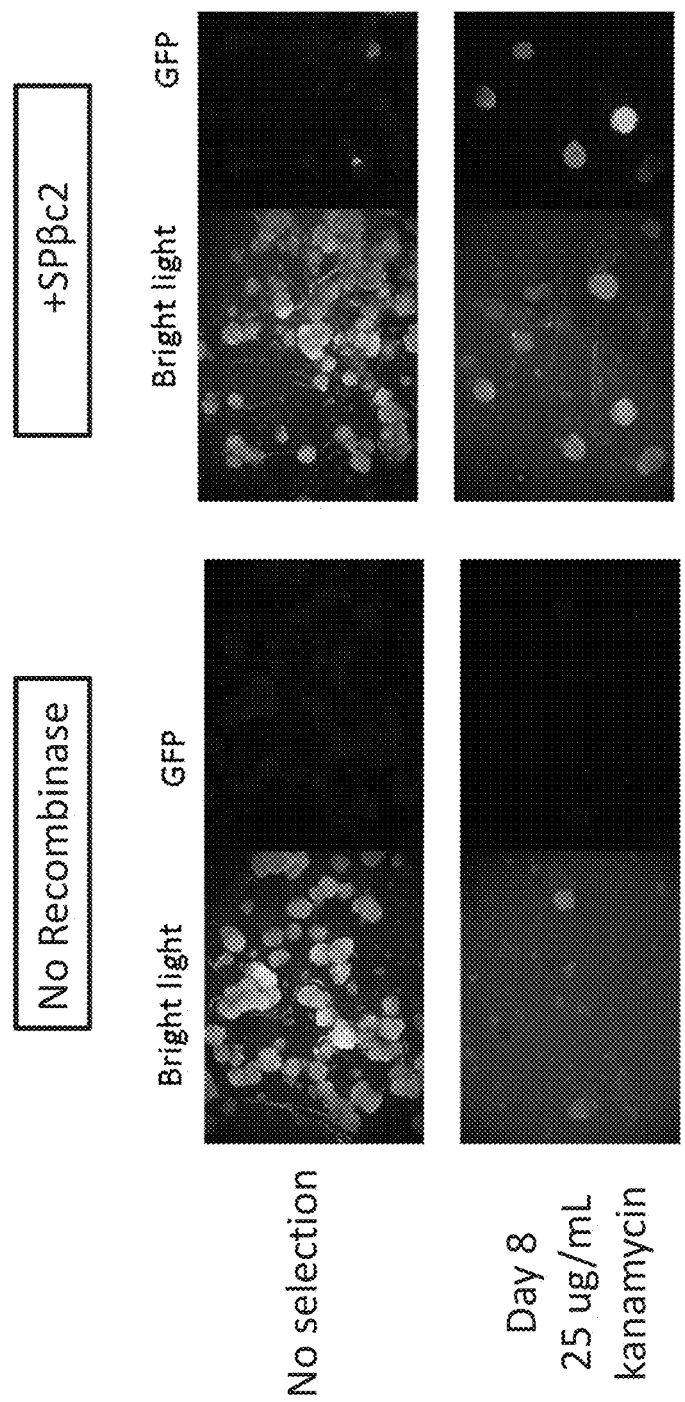
FIG. 7: transgenic lettuce calli generated by attP-reporter plasmid and SPβc2-recombinase were positive for both marker genes (nptII and GFP) present in attP-reporter plasmid. Reporter plasmid with attP was transfected along with plasmids expressing SPβc2 or chloramphenicol acetyl transferase (CAT). Protoplasts were grown into microcolonies with or without kanamycin. Images of calli under bright light or with a GFP filter. No GFP positive colony was obtained with attP-reporter in the absence of SPβc2 (see Example 3).

We further validated the above results by growing colonies in beads at higher concentration of kanamycin (25-50 μg/ml) and for longer periods (>7 weeks) of time. FIG. 7 shows colonies with a weak GFP signal in cells transfected with attP reporter plasmid without SPβc2 recombinase. After kanamycin selection, no GFP positive cells were identified. Cells transfected with attP and SPβc2 plasmids produced many cells with weak GFP signal and a few cells with strong GFP signal. After selection on 25 μg/ml, only the strong GFP-signal cells were observed. Thus, there was a complete integration of attP-reporter plasmid into the lettuce genome, and that kanamycin can be used for enriching integrants.

Table 5 shows the results of counting the number of GFP-positive colonies after growth in 50 μg/ml kanamycin. Compared with the initial number of protoplasts at the time of transfection, approximately 0.06% of protoplasts transfected with attP and SPβc2 plasmids were GFP and Kan positive after 5 weeks. No signal was observed for the attP+CAT and DNA-free controls.

TABLE 5

| Integration frequency (GFP positive cells after 5 weeks/total number of cells used in transfection) | | | |
|---|---|---|---|
| DNA transfected | attP + CAT | attP + SPβc2 | No DNA |
| Integration frequency % | 0 | 0.061 | 0 |

4. Confirmation in Cells from 7 Day Old Seedlings

The seeds of *Lactuca sativa* variant were germinated and protoplasts were prepared from one-week old young seedlings. The isolation of seedling protoplasts, transfection and plant regeneration were carried out according to Woo (2015) *Nature Biotechnology* vol. 33, no. 11).

Figure 8:
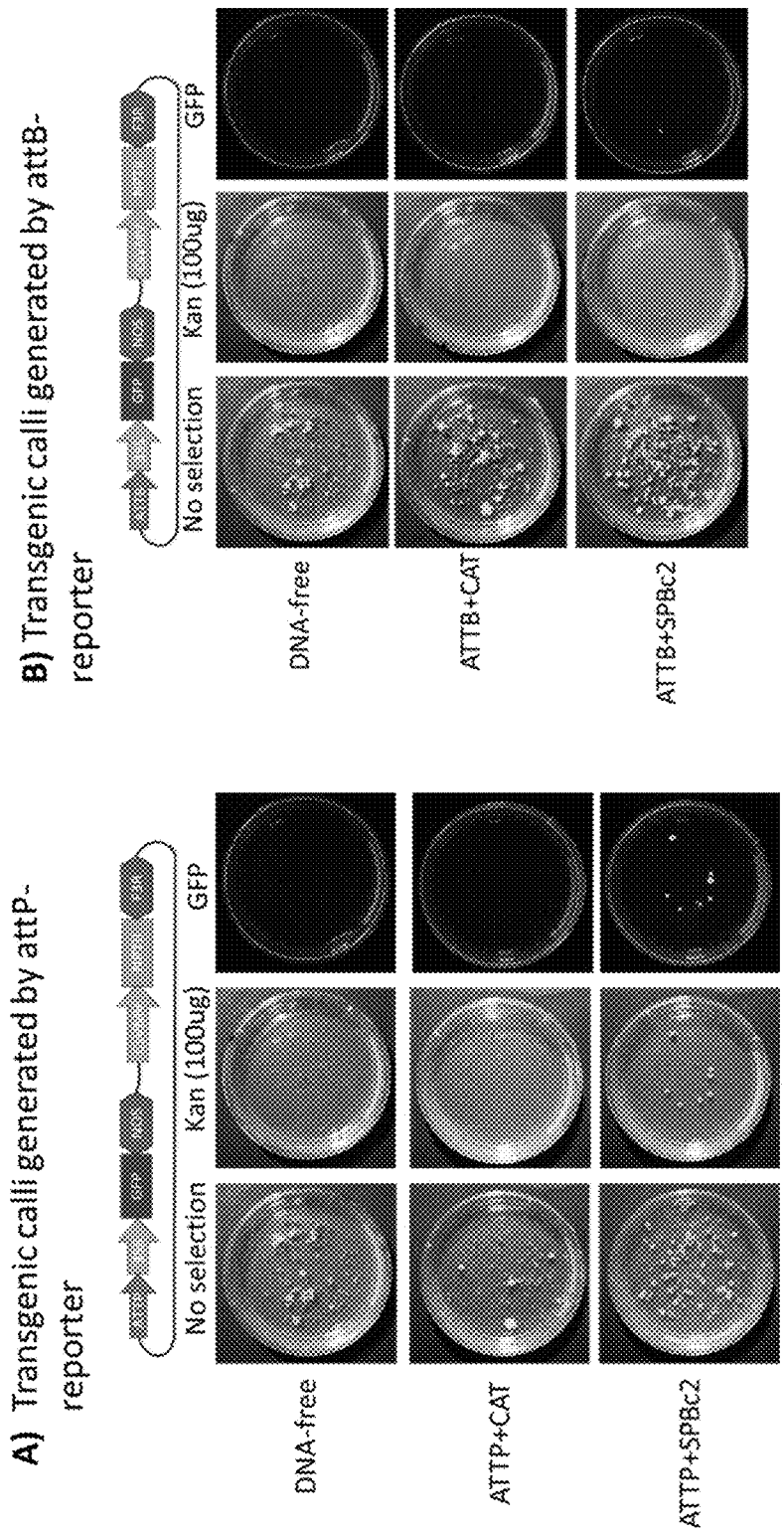
FIG. 8A-D: Transgenic lettuce calli show that SPβc2 mediated integration into lettuce chromosomes acts preferentially on attP. Reporter plasmids (attB or attP) were transfected along with plasmids expressing SPβc2 or chloramphenicol acetyl transferase (CAT) into lettuce protoplast cells derived from 7 day old seedlings (see Example 3).
Figure 8:
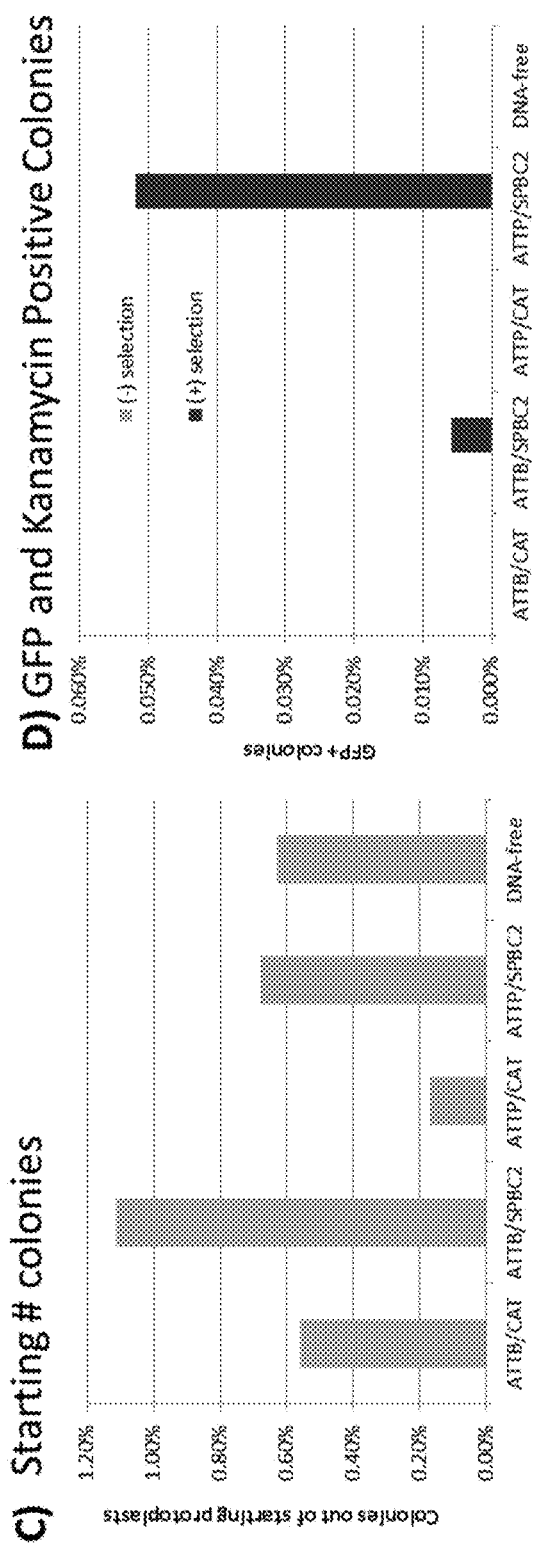

Protoplasts were co-transfected with attP or attB reporter plasmids in the presence of SPβc2 recombinase or CAT. The results with protoplasts from 7 day old seedlings were broadly similar to previous results with protoplasts from leaves. As shown in FIG. 8A, with the attP reporter plasmid, SPβc2 but not CAT produced kanamycin resistant, GFP positive colonies. A single Kanamycin resistant GFP-positive callus was obtained from the attB reporter plasmid in the presence of SPβc2 (FIG. 8B). Counting the number of calli on nonselective media for 5 weeks (FIG. 8C) and after selection with kanamycin (FIG. 8D), shows that transgenic calli were positive for both kanamycin resistance and GFP expression.

The observation of a single positive callus with the attB reporter suggests that an attP-like targeting sequence could be present in plants. The attB-reporter derived callus is being further analyzed to confirm that it contains a reporter plasmid inserted into the chromosome.

5. Transgenic Plant Generated by SPβc2 Recombinase and attP Reporter Plasmid

Figure 9:
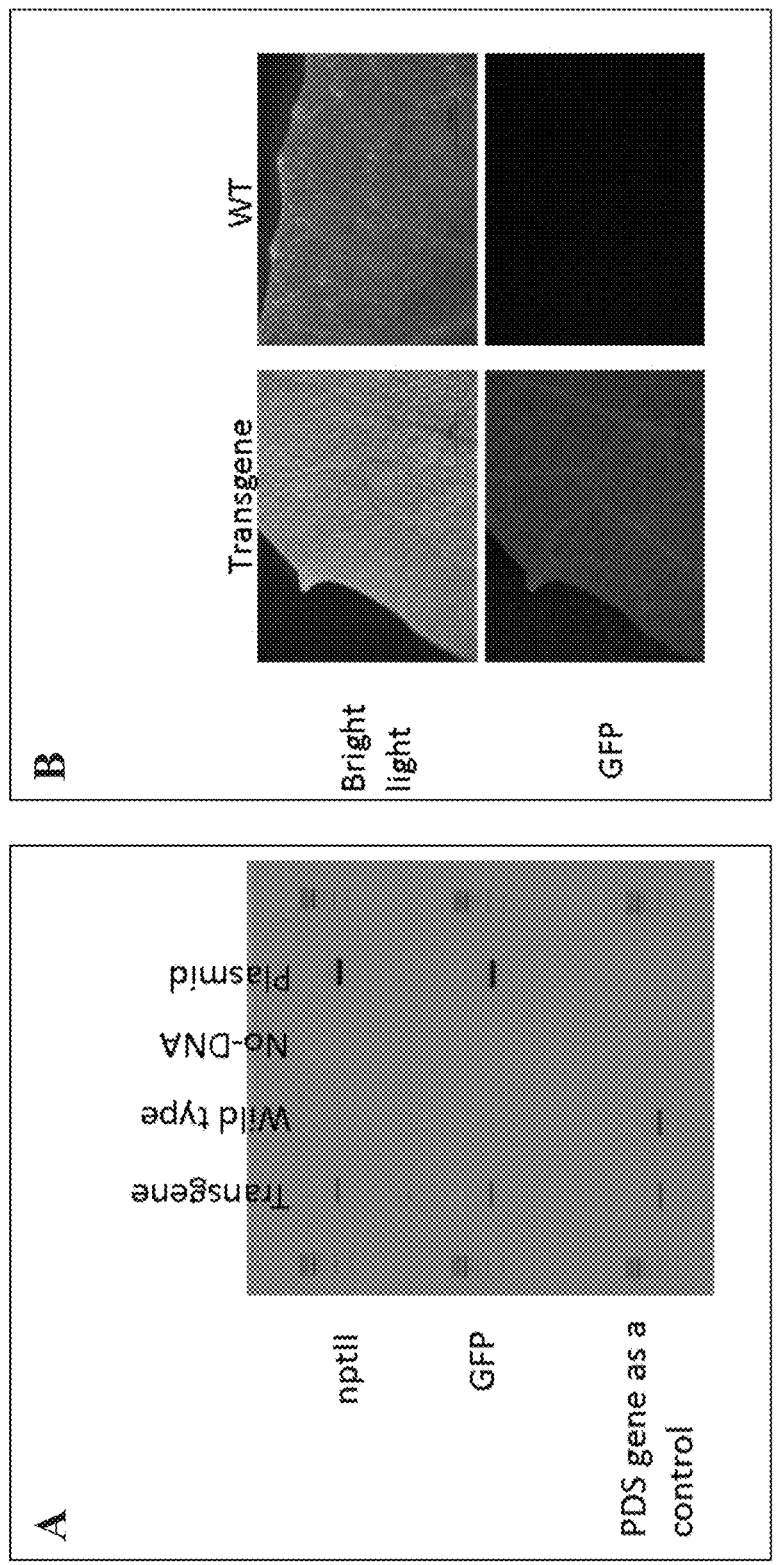
FIG. 9A-B: Transgenic plants generated by attP-reporter plasmid and SPβc2 recombinase contained both kanamycin and GFP marker genes (see Example 3).

A transgenic lettuce plant was regenerated from lettuce mesophyll protoplast cells prepared as described above, and transfected with SPβc2 recombinase and attP-reporter gene. PCR, using the primers described in Table 4 demonstrated the presence of both npIII and gfp signals in genomic DNA from the lettuce leaf, with amplicons the same size as those obtained from the reporter plasmid (FIG. 9A). The phytoene desaturase (PDS) gene was used as a positive control for plant DNA.

The PCR results were further confirmed by the observation of the GFP phenotype in whole leaves. Leaves of the transgenic plant fluoresced under UV light, consistent with GFP production, while wild type lettuce does not (FIG. 9B). Because the reporter plasmid is non replicating, chromosome integration of the reporter plasmid is required for the entire leaf to become GFP-fluorescent.

Figure 10:
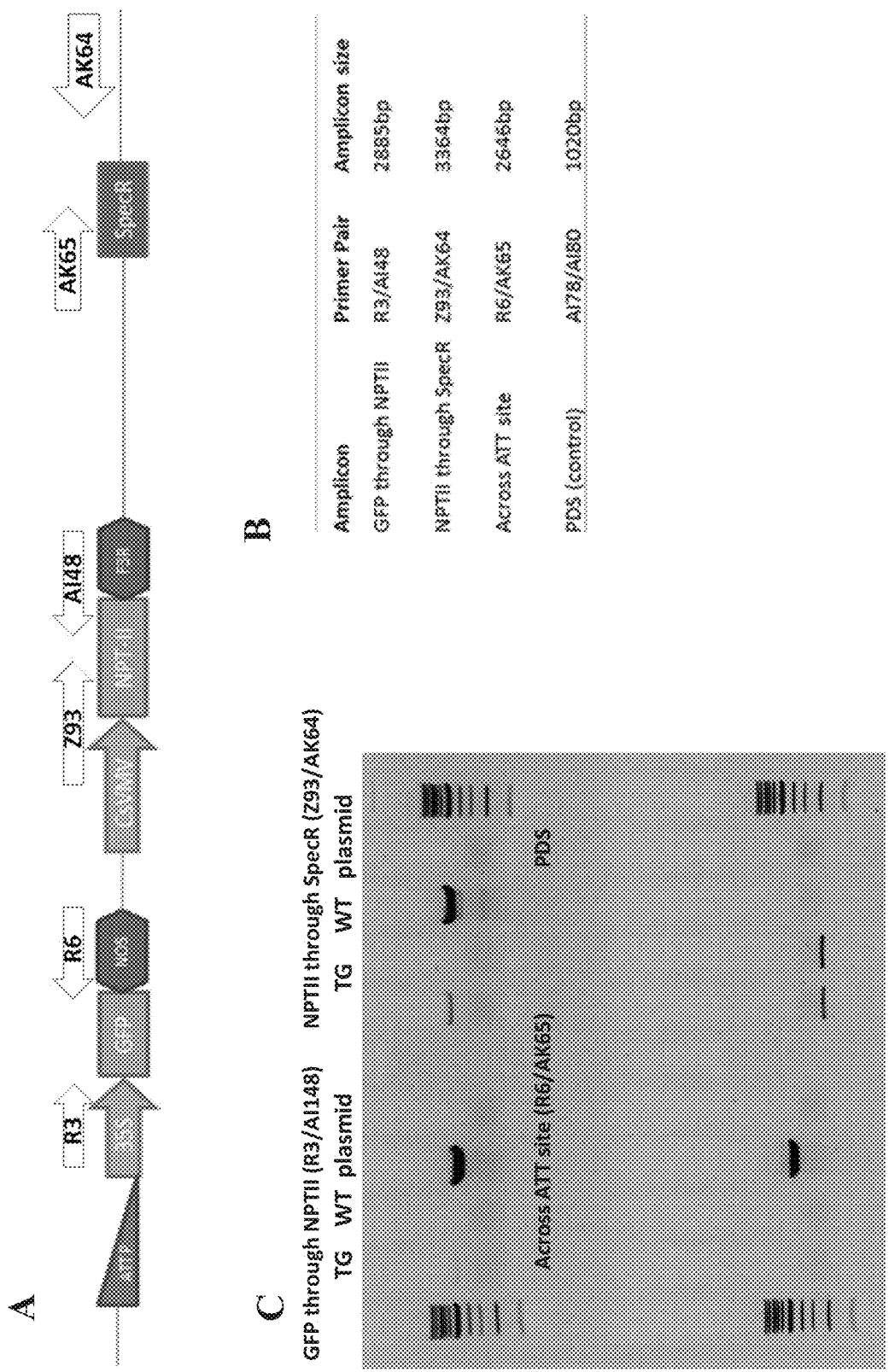
FIG. 10A-C: PCR confirms that transgene has incorporated into the lettuce chromosome (see Example 3).

PCR was further used to confirm that the entire 6.3 kb attP plasmid was integrated into the lettuce genome, and if integration occurred by recombination between the attP region of the plasmid and an attB-like site on the plant chromosome. FIG. 10A is a schematic of the reporter plasmid, showing the relative position genes and of PCR primers used in long transcript PCR amplification. FIG. 10B shows the expected sizes of transcripts and the results of PCR. In the transgenic lettuce plant (TG) and plasmid, amplicons for GFP through NPTII and NPTII to SpecR were identified. Thus, the entire reporter plasmid is present in the transgenic lettuce. Amplification from the SpecR to GFP, passing across attP, generated a transcript from the plasmid but not from the transgenic lettuce (FIG. 10C). This indicates that the reporter plasmid has inserted into the chromosome and linearized at attP. Wild type (WT) lettuce was negative for transgene markers, but both TG and WT lettuce were positive for the PDS control gene.

Figure 11:
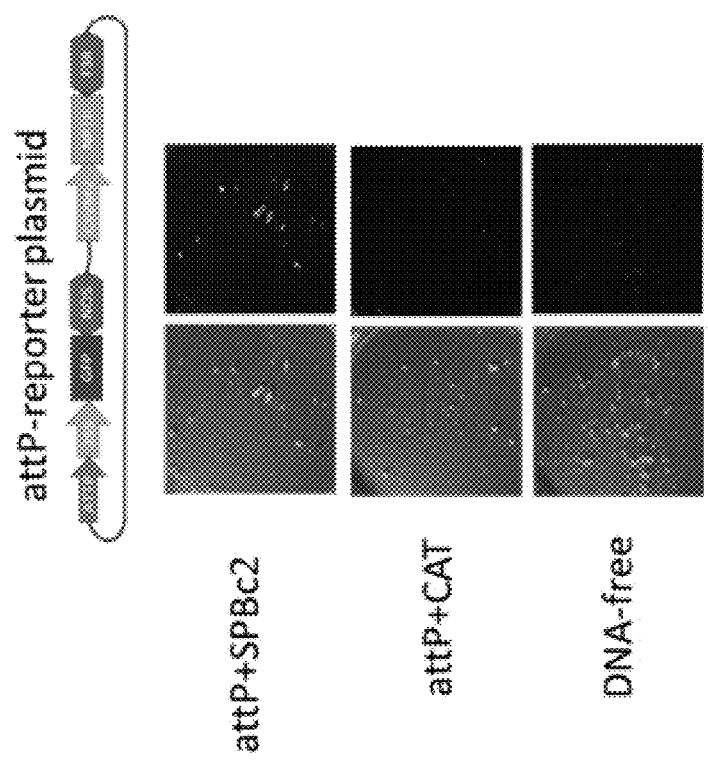
FIG. 11: SPβc2 recombinase and attP-reporter plasmid produce GFP-expressing calli colonies from tobacco relative, *Nicotiana benthamiana*. Co-transfection of tobacco with attP reporter and SPβc2, but not CAT, generated GFP expressing microcalli. Left column shows calli under white light, right column shows GFP fluorescence (see Example 4).

Example 4. SPβc2 Recombinase Integrates attP Bearing Reporter Plasmids into Tobacco Plant Cells To test if SPβc2 recombinase is active in other plant species; we tested recombination in tobacco (*Nicotiana benthamiana*). Following the same protocol used for lettuce, tobacco plant protoplasts were prepared and transfected with attP-bearing reporter plasmid and SPβc2 recombinase effector plasmid, with a control co-transfection with the CAT encoding plasmid. Co-transfection of attP reporter plasmid with SPβc2 generated microcalli expressing GFP. See FIG. 11. No integration was observed with reporter plasmid in absence of SPβc2 recombinase (referred as CAT).

This result was confirmed by the experiment and growing putative transgenic calli on kanamycin at 0, 20, 40, 60, 80 and 100 μg/ml for 7 weeks, while monitoring GFP fluorescence. The results are summarized in Table 6. "Kan" is kanamycin in mg/L, "tot" is total number of microcalli, "GFP" are number of GFP+microcalli

TABLE 6

Number of GFP and Kanamycin positive tobacco microcalli after 7 weeks post transfection.

| Kan (mg/L) | attB/CAT | | attB/SPβc2 | | attP/CAT | | attP/SPβc2 | | No DNA | |
|---|---|---|---|---|---|---|---|---|---|---|
| | Tot | GFP+ | Tot | GFP+ | Tot | GFP+ | Tot | GFP+ | Tot | GFP+ |
| 0 | 18 | 0 | 38 | 1 | 35 | 0 | 44 | 13 | 67 | 0 |
| 20 | 1 | 1 | 4 | 2 | 4 | 1 | 49 | 43 | 0 | 0 |
| 60 | 0 | 0 | 1 | 0 | 0 | 0 | 65 | 60 | 0 | 0 |
| 80 | 0 | 0 | 1 | 0 | 0 | 0 | 15 | 12 | 0 | 0 |
| 100 | 0 | 0 | 0 | 0 | 0 | 0 | 5 | 4 | 0 | 0 |

Figure 12:
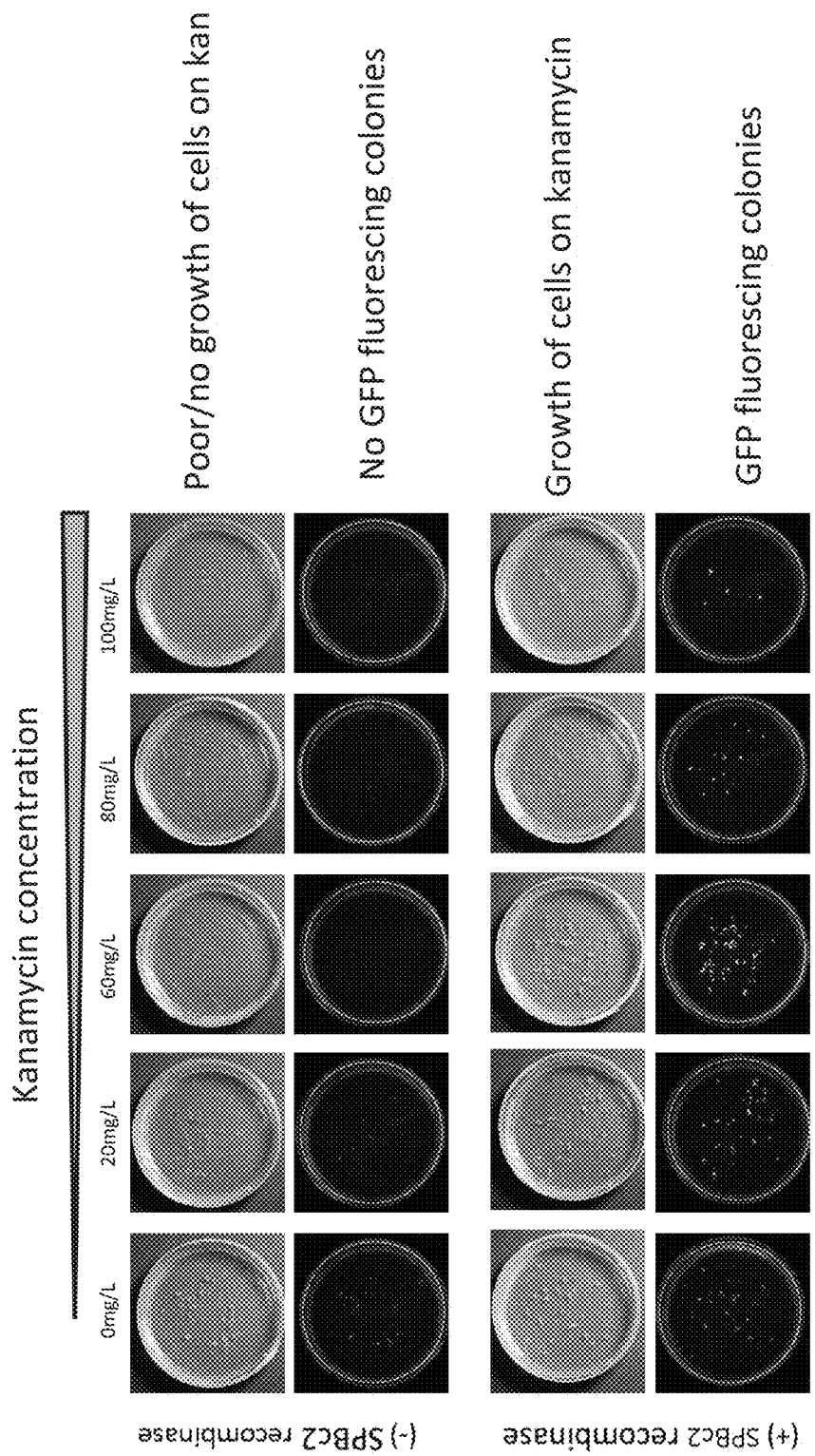
FIG. 12: Transgenic 6 week old *N. benthamiana* calli generated by SPβc2 recombinase and attP-reporter expressed GFP and were able to grow on kanamycin up to at least 100 µg/ml. In the top two rows, calli transfected with attP reporter plasmid and CAT plasmid (i.e. SPβc2 (−)) were cultured on increasing doses of kanamycin. The number of colonies decreased rapidly with increasing kanamycin, as did the number of fluorescent colonies. In the bottom two rows, calli transfected with attP reporter plasmid and SPβc2 plasmid show robust growth and GFP fluorescent, even after growth at 100 µg/ml (see Example 4).
Figure 13:
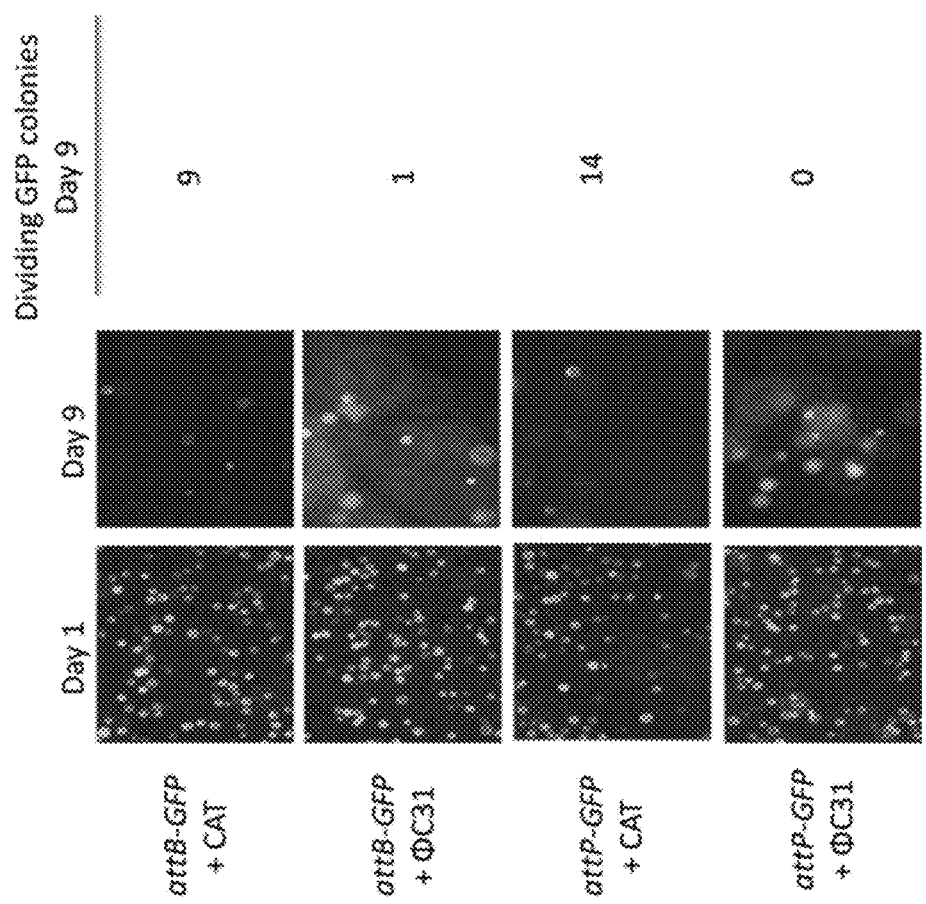
FIG. 13: ¢C31 did not mediate incorporation of reporter plasmid. Reporter and effector constructs (shown at the side of picture) were transfected into lettuce mesophyll protoplasts, and the resulting colonies examined for GFP expression. Limited or no cell division was observed in the protoplast cells expressing ΦC31 protein (see Example 5).

As shown in FIG. 12, no GFP fluorescent microcalli were observed in cells transfected with the attP and CAT plasmids. By contrast, cells transfected with attP and SPβc2 plasmids generate microcalli able to grow on up to 100 μg/ml kanamycin, all of which were produced GFP. The presence of both GFP and NPTII markers together indicates that the entire attP-bearing plasmid has incorporated into the tobacco chromosome. We conclude that SPβc2 is able to integrate attP bearing DNA into the genome of tobacco.

Example 5. Possible Toxic Effects of ΦC31 recombinase

As reported in Example 1, A118, SF370.1, ΦC31 and BxB1 recombinases did not produce stable GFP signals over controls in initial studies. Further analysis suggests that ØC31 may permit integration of reporter plasmids into the lettuce genome, but the resulting protoplast cells did not divide. As shown in FIG. 12, ΦC31 co-transfected with either attP or attB reporter plasmids was associated with a higher number of GFP expressing cells after 9 days, compared to CAT control. However, these cells were unable to further divide.

Expression of ΦC31 recombinase was significantly higher than other recombinases, and may have been able to induce random or semi random integrations of reporter plasmids into the genome, but with further DNA damage. Multiple studies have reported that ΦC31 is able to induce a DNA damage response and chromosomal rearrangements in animal cells. See e.g. Liu J "ΦC3 Iintegrase induces a DNA damage response and chromosomal rearrangements in human adult fibroblasts" BMC Biotechnol. 2009 9:31. If ΦC31 is inducing DNA damage in plants, it may be able to randomly integrate reporter plasmids into the chromosome, but at the risk of serious and uncontrolled mutations.

The experiments are repeated with an effector plasmid expressing ΦC31 recombinase behind a weaker constitutive promoter.

Example 6. Identification of Integration Site and Improved Targeting by Flanking Homology 1. Identification of Pseudo attB Sites Because bio-informatic searches of the lettuce and tobacco genomes did not identify canonical attB sites, we conclude that the reporter plasmid has incorporated into a pseudo attB site. The sequence of the pseudo attB site is identified by genome sequencing. In brief, the genomic DNAs from transgenic calli and plants are prepared, followed by library construction. The enrichment of chromosomal DNAs flanking to the inserted plasmid is done using portion of plasmid sequences as bait. The isolated DNA fragments are sequenced by Illumina HiSeq platform to identify the plant-derived att pseudo sites.

Alternatively, plant cells containing integrated reporter plasmid are cultured and the genomic DNA extracted, and the DNA digested with a restriction enzyme which does not cut in the reporter plasmid. The DNA is then diluted, incubated with DNA ligase to recircularize a plasmid, and transformed into *E. coli*. Spectinomcyin resistant colonies are identified and sequenced from the attP region.

Alternatively, in a method referred to as "Genome Walker Assay," plant cells containing integrated reporter plasmid are cultured, the genomic DNA is extracted, digested with a restriction enzyme, and adaptor sequences are ligated onto the genomic fragments. This library is then queried by PCR using an adaptor specific primer and a primer specific to the inserted DNA sequence. A second "nested" PCR can be performed using internally spaced primers for further amplification of low abundance amplicons. PCR products are then sequenced to identify transgene junctions with the native chromosome sequence.

After identification of the att pseudo site sequence, its location in the lettuce genome is identified from the previously published genomic sequence, and is confirmed by PCR amplification with primers flanking the pseudo attB site and inside the reporter plasmid. The same primer sets are then used on other transgenic lettuce clones to identify whether more than one site serves as pseudo attB sites in the presence of exogenous attP DNA and SPβc2. Additional pseudo attB sites are sequenced and identified as described above.

Having identified more than one pseudo attB site, new attP DNA and SPβc2 transfections are performed and the resulting transgenic colonies screened to determine the relative frequency of insertion into one pseudo attB site over another.

2. Use of Flanking Homology to Select for Target Specific Integration

A given pseudo attB site may be preferred over another site for reasons that include Location within a gene such that insertion of reporter plasmid disrupts normal protein expression;

Chromosomal architecture, such that a transgene is better expressed from one site over another;

Chromosomal location, such that a desirable transgene is co-inherited with other desirable genes.

Example 7. Transfer of β Carotene Genes into Lettuce

Lettuce is an important part of the diet in parts of Asia, accounting for more than half of global consumption. Vitamin A deficiency is also a problem in Asia. Increased β carotene intake can correct for deficiencies in Vitamin A intake. Lettuce is known to produce moderate amounts of β carotene but has not, until now, been proposed as a significant source of β carotene.

The reporter plasmid of FIG. 4 (1), bearing an attP site for SPβc2 recombinase, is modified by the insertion of lox sites (a) between attP and the 35S promoter and (b) 3' of SpecR gene. 3' to the last lox site is added the PSY gene and a 35S promoter. The PSY gene encodes phytoene synthase, and is the rate-limiting enzyme in β carotene synthesis and accumulation in lettuce.

This plasmid is co-transfected into lettuce protoplasts with a plasmid expressing SPβc2 recombinase, and the resulting cells are grown on 25 µg/ml of kanamycin in calli.

After 2 weeks, cells are examined for GFP expression, and positive cells grown for a further 1 week and screened for stable, high level expression of GFP and kanamycin resistance, followed by PCR to confirm the presence of the plasmid insert. Positive calli are grown to mature lettuce plants. The mature plants express GFP, kanamycin resistance, and overexpress PSY.

Protoplasts are prepared from mature lettuce, which is then transfected with a plasmid encoding Cre recombinase, allowing for action on the lox sites in the insert. Protoplasts are then grown without kanamycin selection, and are screened for the loss of GFP expression. Protoplasts are identified with loss of GFP expression and kanamycin sensitivity, and PCR is used to confirm the presence of the transgenic PSY.

The resulting protoplasts are grown into lettuce plants, possessing an intact and functional PSY gene.

This technique can be used for larger gene clusters. *Agrobacterium*-mediated gene transfer often leads to truncated products and requires generation of numerous transgenic events for obtaining a desired intact transgene. Larger plasmids are even harder to transfect by the *Agrobacterium* method, and are typically limited to less than 20 kb. These problems are not present with serine-recombinase mediated integration, and are limited only by the size of DNA that can be reliably transfected into a cell.

Example 8. Use of Serine Recombinases for Genomic Deletion

Having demonstrated that there is at least one SPβc2 recombinase pseudo att site on plant chromosomes, it is possible to use this pseudo site to specifically delete DNA around the pseudo att site.

First, having identified the region of interest for deletion at one site of the pseudo att site, an SPβc2 recombinase attP site is inserted on the other side of the region of interest, in a plant cell. The attP is located in exogenous DNA further containing a reporter gene and optionally containing a third att site that is non-cognate with SPβc2 ("att3"). The exogenous DNA is introduced into the chromosome using homologous site specific recombination, identifying the presence of the insertion by detection of the reporter in transfected plant cells.

Second, a vector expressing SPβc2 recombinase is introduced into the plant cell, such that there is recombination between the pseudo att site on the chromosome and the attP site on the exogenous DNA, leaving a new attR/attL site. Deletion is detected by screening transfectants for loss of the reporter gene located on exogenous DNA. The resulting plant cell is then examined with PCR to confirm that genomic deletion has occurred.

In a further example, the exogenous DNA further possesses an att3 site and is located such recombination between the pseudo att site on the chromosome and the attP site on the exogenous DNA leaves att3 on the chromosome. The att3 site is then available for introduction of new exogenous DNA, such as modified DNA that complements the deleted region.

Example 9. A Plant Engineering System for Further Insertion of Exogenous DNA

A plasmid bearing the SPβc2 attP is further modified to contain the attB site for BXB1, and the resulting plant engineering system is cotransfected into protoplasts with SPβc2. Following the identification of transformed protoplasts containing the plant gene engineering system, the protoplasts are cotransfected with (a) exogenous DNA bearing the BXB1 attP site and (b) exogenous DNA expressing BXB1.

Example 10

1. Generation of *N. benthamiana* Transformants with SPβc2 Recombinase

Wild tobacco relative *Nicotiana benthamiana* (Benthi) events were generated through co-transfection of a SPβc2 expression vector (or control filler vector: CAT) plus a target integration vector containing GFP, NptII, and a SPβc2 attachment site (attP, attB, or site-less control). Colonies were regenerated in the presence of a kanamycin gradient to detect NptII and the presence of GFP was determined through illumination with a blue "biolight" together with an appropriate filter (FIG. 1). Consistent with previous experiments in lettuce the attP/SPβc2 DNA combination resulted in a significantly higher number of kanamycin resistant and GFP positive colonies than any other DNA combination. Enhanced regeneration of transgenic colonies varied between 10 and 65 fold and was dependent on the Kanamycin concentration used for selection. At a Kanamycin concentration of 60 mg/L, the attP/SPβc2 transfection condition resulted in 65 transgenic colonies compared to 0-1 colonies for all other conditions. Of these 65 attP/SPβc2 colonies, 60 were positive for GFP expression while no colonies from any other transfection condition showed GFP expression at 60 mg/L Kanamycin. Notably, 13 out of 44 (~30%) attP/SPβc2 colonies were positive for GFP expression in the absence of any selection. These results highlight the ability of SPβc2 to not only enhance attP transgene integration within plant genomes but to also increase the fidelity of integration, leading to positive expression of multiple transgenes with or without selection. Very few GFP-positive kanamycin-resistant colonies arose from the attB/SPβc2 or Siteless/SPβc2 conditions, indicating a dependence on the attP site for interaction with plant pseudo-attB sites. Likewise, the few positive colonies from the attP/CAT combination compared to the attP/SPβC2 combination demonstrate dependence upon the SPβc2 recombinase for site-specific integration in plant genomes. A total of 126 plants from 91 unique calli events were regenerated, transplanted into soil, and carried forward to seed collection (Table 7).

TABLE 7

Total unique regenerated Benthi events that were carried to seed

| DNA combination transfected | Selection during colony formation | | | |
|---|---|---|---|---|
| | (−) | | (+) | |
| | GFP (−) | GFP (+) | GFP (−) | GFP (+) |
| attB/CAT | 2 | 0 | 0 | 0 |
| attB/SPβC2 | 3 | 0 | 0 | 0 |
| attP/CAT | 5 | 0 | 1 | 0 |
| attP/SPβC2 | 4 | 4 | 22 | 36 |
| Siteless/CAT | 0 | 0 | 1 | 0 |
| Siteless/SPβC2 | 3 | 1 | 0 | 1 |
| DNA-free | 9 | 0 | 0 | 0 |

(+) Selection includes events arising on kanamycin 20-100 mg/L
GFP (−) or GFP (+) were the original scores at the colony stage 1. Identification of Integration Sites Ten regenerated attP/SPβC2 plants were selected for gDNA extraction and TaqMan assay based upon positive GFP signal and/or having originated under kanamycin selection. Five low copy number events with high-quality genomic DNA were advanced to GenomeWalker. In confirmation with TaqMan copy number prediction, 7 unique insertion sites were identified from the 5 events using the GenomeWalker Assay (not shown). An additional integration site, Niben101Scf03735, was identified by performing GenomeWalker on a pool of gDNAs extracted from 64 regenerated att/SPβc2 plants representing 55 unique events. To confirm the GenomeWalker result, primers were designed to the genomic regions upstream and downstream of the insertion sites and used for direct PCR and Sanger sequencing of left (35S side) and right (SpecR side) gDNA: insert junctions (Table 8). The gDNA: insert junctions were confirmed for all but one site identified. Amplification across the native loci showed all insertions to be hemizygous. Direct Sanger sequencing of event specific amplicons confirmed that these are transgene junctions consistent with a Large Serine Recombinase site-specific recombination mechanism whereby all attP vectors were linearized in the middle of the attP site and no loss of vector or host genome sequence was observed following integration (FIGS. 14B-E).

TABLE 8

Diagnostic Primer Sets for Identification of SPβc2 insertion sites in *N. benthamiana*

| 35S border (pair with AL33 or AL34) | | SpecR border (pair with AL35 or AL36) | |
|---|---|---|---|
| Oligo ID | Sequence | Oligo ID | Sequence |
| AL96 | GAAAACTGACCAACCGTATGTTCTCACTAA SEQ ID NO: 159 | Am07 | ATGATAGAATCCGCCTTGTTTATCTAGACG SEQ ID NO: 167 |
| AM05 | GAGATGAGTTTTGCGTACTTCAAGAGGATG SEQ ID NO: 160 | AM11 | AATGCAAATTCACCGTATCAGTAAAGTTCG SEQ ID NO: 168 |
| AM01 | CAAGTTCATTGGATTTTGACTGACTCACCA SEQ ID NO: 161 | AM08 | ACCGTAACGTGATCTTCAAATTAACAATCT SEQ ID NO: 169 |
| AL95 | TCCCAACTTAACAATACGAAAACTAGGGGT SEQ ID NO: 162 | AM06 | GGTGATGATCCATACAGCTTGGTTAAAGAT SEQ ID NO: 170 |
| AM02 | GTAGGCTATCGTCATTTCCTAAGATGTGGA SEQ ID NO: 163 | AM09 | ATCCAAGAATAAGAATCCCACCTCATGTTC SEQ ID NO: 171 |

TABLE 8-continued

Diagnostic Primer Sets for Identification of
SPβc2 insertion sites in N. benthamiana

| 35S border (pair with AL33 or AL34) | | SpecR border (pair with AL35 or AL36) | |
|---|---|---|---|
| Oligo ID | Sequence | Oligo ID | Sequence |
| AM04 | TAGTCAATGCACGCCTTTTCGATCTATATC SEQ ID NO: 164 | AM10 | AATTAACAGACCATGAGCCACAATAACTGA SEQ ID NO: 172 |
| AM03 | CCCCTTACAAGTACCCTCATATTTCTCACA SEQ ID NO: 165 | | No border primer designed due to repetitive sequence |
| AO70 | TTAACGAGGCAACCAATAAGGC SEQ ID NO: 166 | AO69 | AGAGGGAATTAACGCAACTGTG SEQ ID NO: 173 |

To determine whether any of the sites identified by GenomeWalker were preferentially utilized for integration by the SPβc2 recombinase, 64 attP/SPβc2 regenerated events were screened by end-point PCR for amplification of the left (35S side) gDNA: insert border. Of the 8 sites screened, 3 were found to be repeated in multiple unique events (Table 9).

TABLE 9

SPβc2 pseudo-attB sites identified in N. benthamiana

| # of positive events | Scaffold ID | Position Start | Benthi SPβc2 attB recombination site sequence |
|---|---|---|---|
| 6 | Niben101Scf05124 | 125034 | gttatagtcagttgaattcaaactctctgactcatca ttagagaaacaattAAatagattatagtattacttac aatgcgcgcgacgcattgtatgaacc (SEQ ID NO: 132) |
| 2 | Niben101Scf04030 | 73557 | ttgctgtcttttcatactttctaagttgaaagtact tgaaagtacgacCAagaaaatgattatatttgacaca gaaaatgcaaggtactttgaatgtga (SEQ ID NO: 133) |
| 2 | Niben101Scf13522 | 56803 | ggataagggagggtttagatattttgaaagggttaag gggtaaaatcacTAaggggaattaacaatgcacact agggttgccttaaaagtgcctatata (SEQ ID NO: 134) |
| 1 | Niben101Scf11415 | 75574 | ctaatatacattgacagtgttaaaaaaaatctattaa cgacaatataGAagagagtacttacatgaatgacg tctactttgactccgtcaattccaac (SEQ ID NO: 135) |
| 1 | Niben101Scf04574 | 721938 | taggcttacattcctgatgtactatcccattatgcaa taataaagatgCAaaataggaaatgtcattgacagct acgagatctatctttattgattcact (SEQ ID NO: 136) |
| 1 | Niben101Scf00773 | 833045 | acatggagcaatgatggagaaaaatggtggtcattac tactgaagttgtCAaagcaaagctgtcaggtaacatc aaatgatctctaaatcaattagtctt (SEQ ID NO: 137) |
| 1 | Niben101Scf00732 | 841842 | gccacaacctaggccaggcaaaggtttcactaatacc tgtgatgtttgtCAaaggagtctcctcgactccttca gattctgctctcttggctgtaaggta (SEQ ID NO: 138) |
| 1 | Niben101Scf03735 | 798446 | gaagagacgattacatatatgtgtacgcgttggataa tcatttgaacctTAaagtctgtctctctcttaacatg tgttcaatagcaatacaaagtgtata (SEQ ID NO: 139) |

Reference Genome was SolGenomics' v1.0.1 Scaffolds + NrContigs BLAST dataset
Boldface, underlined font in the sequence indicates the insertion site The most often repeated insertion site, Niben101Scf05124, was identified in 5 unique events additional to the original GenomeWalker analyzed event. Left and right gDNA: insert border amplicons from the 5 additional events were sequenced. The insert construct and the pseudosite were consistently linearized in the same location within the att sites as in the original GenomeWalker result. No insertions or deletions in the insert construct or the pseudosite were observed (FIGS. 14D & E).

Events were also queried for presence of the recombinase expression construct (ID363); within the Benthi event population 5 out of 71 recovered events that were originally transfected with ID363 were PCR-positive for ID363 (data not shown).

Example 11. Reversal of Integration with Recombinase Directionality Factor (RDF)

*Nicotiana benthamiana* protoplasts were isolated and an ATTR event was generated by protoplast transfection and SPβc2-mediated introgression of an attP donor vector. Leaf tissue was sliced into thin strips with a razor blade, placed in an enzyme solution (1% Cellulase R10, 0.25% Macerozyme R10, 0.4 M mannitol, 20 mM KCl, 20 mM MES pH 5.7, 10 mM $CaCl_2$), and 0.1% BSA), and vacuum infiltrated for 20 minutes in low-light. After vacuum infiltration, digests were carried out with gentle agitation at room temperature in the dark. Digestion was carried out for 3-4 hours before diluting with equal volume W5 (2 mM MES pH 5.7, 154 mM NaCl, 125 mM $CaCl_2$), 5 mM KCl) and filtering through a 100 uM nylon strainer. Cells were pelleted at 113×g for 2 minutes, washed once with W5, and incubated in the dark on ice in W5. After the 30 minutes on ice, cells were pelleted and resuspended in MMG (0.4 M mannitol, 15 mM $MgCl_2$, and 4 mM MES at pH 5.7) at $3\times10^5$.

PEG-mediated transfections were carried out in 48-well deep dish plates with the number of replicate wells being scaled up or down based upon experimental needs. Per well, 100 uL cells were mixed with 9-18 ug insert DNA and 4.5-9 ug recombinase expression DNA (see Appendix for experiment specifics). 100 uL PEG (40% PEG, 0.4 M mannitol, 0.1 M $Ca(NO_3)_2$ adjusted to pH 10) were added and mixed thoroughly by shaking. After 18 minutes incubation in the dark, 800 uL W5 were added slowly and allowed 8 minutes acclimation before fully mixing. Cells were pelleted at 805×g for 5 minutes, resuspended in 150 uL WI (4 mM MES pH 5.7, 20 mM KCl, and 0.5 M mannitol), and incubated at 25° C. in the dark for up to 3 days.

Figure 14:
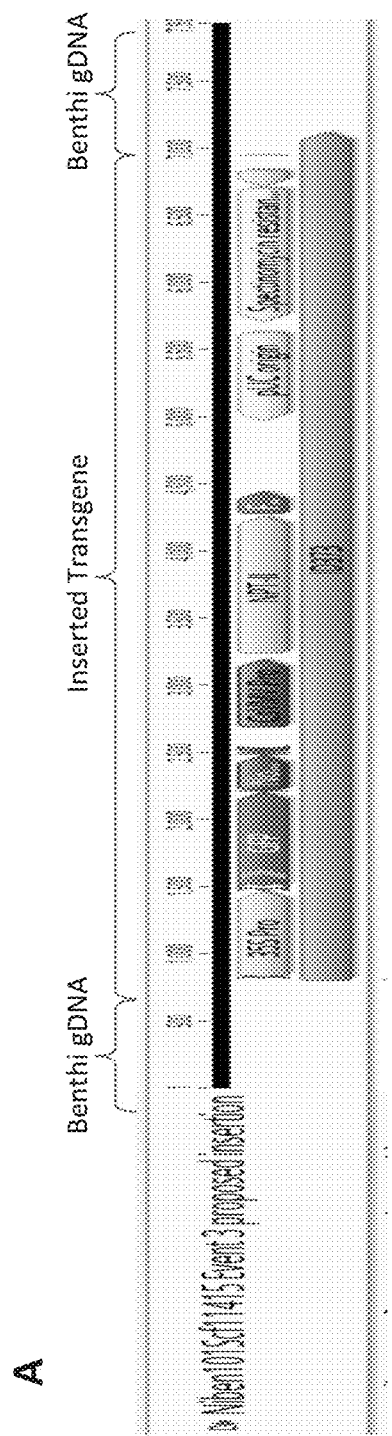
FIG. 14.
Figure 14:
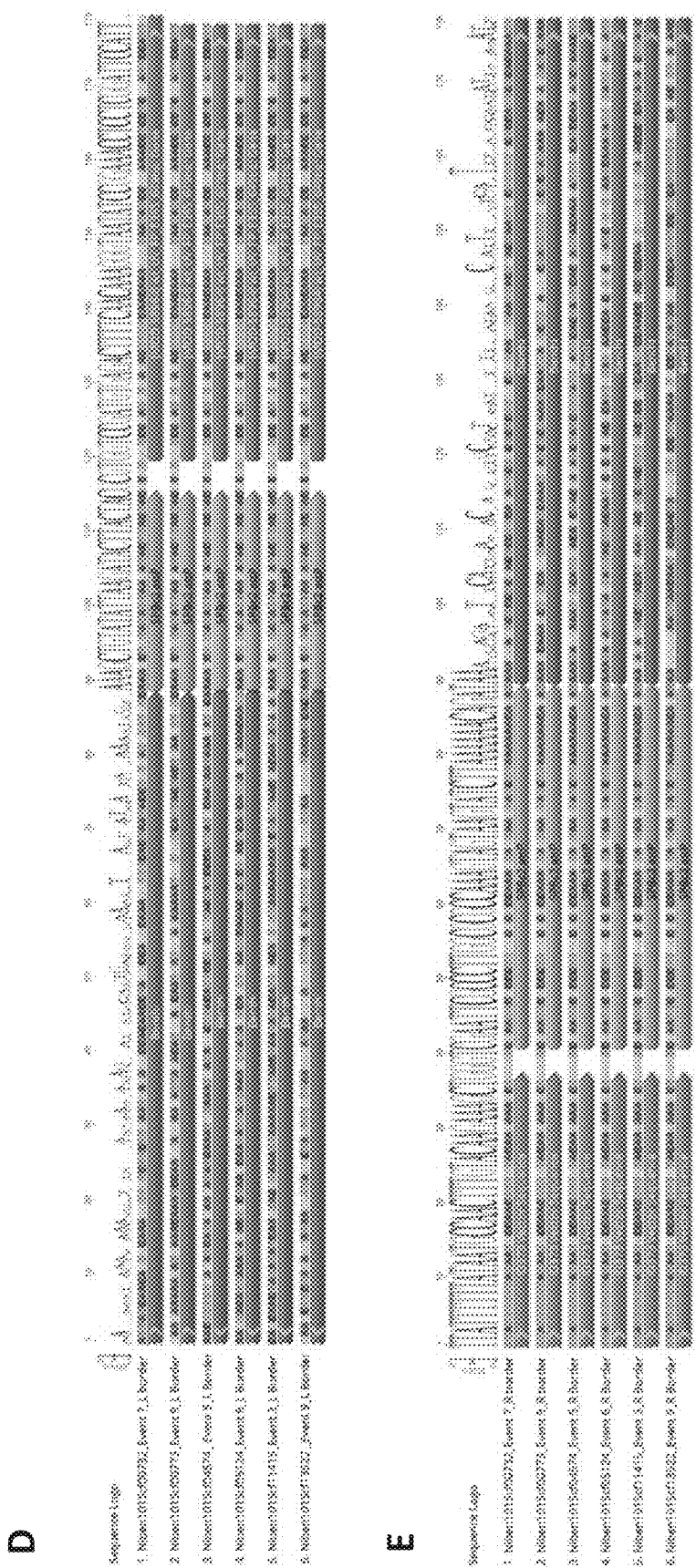
Figure 15:
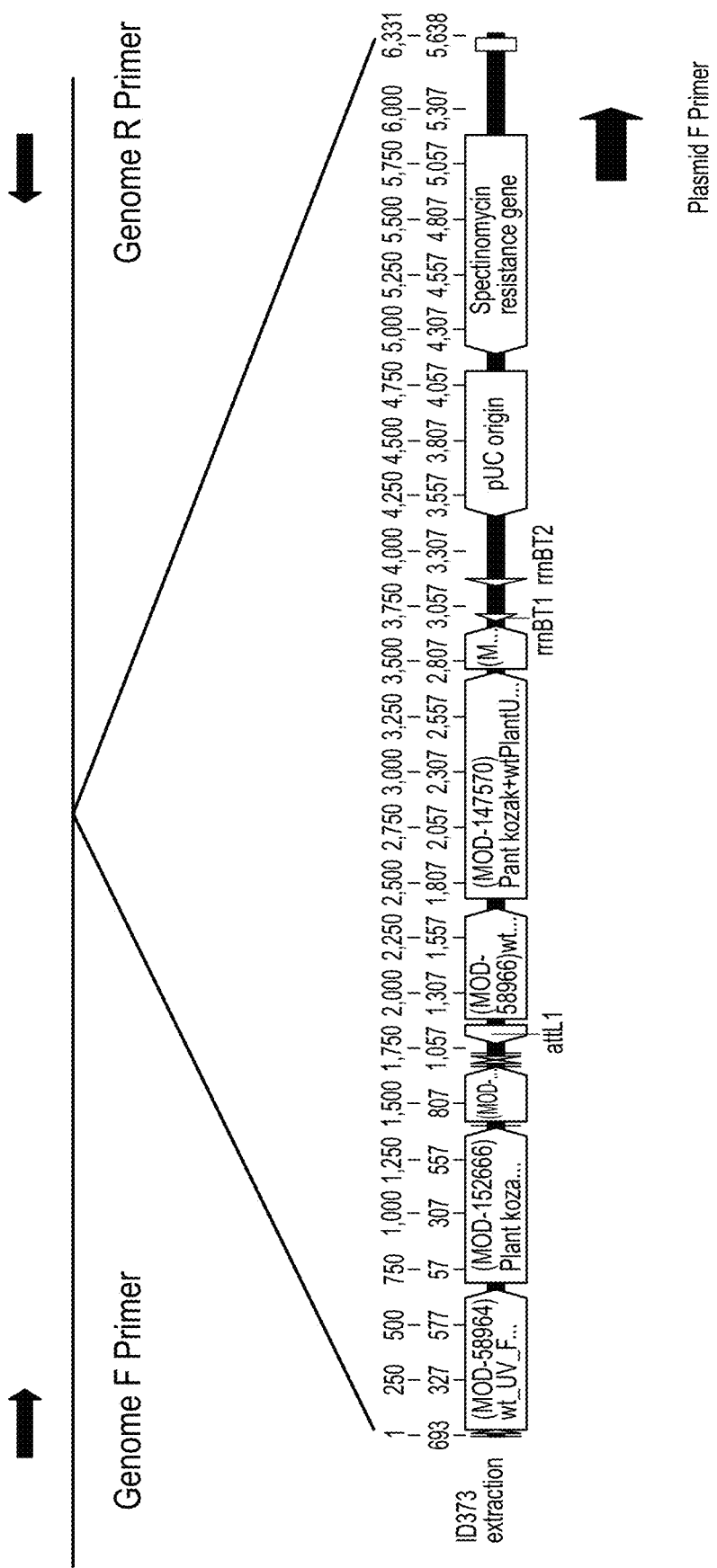
FIG. 15: A schematic drawing of the inserted exogenous vector between the flanking plant genomic DNA and the forward and reverse genome primer positions (Genome F Primer and Genome R Primer, respectively) as well as the Plasmid forward Primer position (Plasmid forward Primer) that were used in a multiplex PCR experiment to determine segregation and inheritance of the transgene across generations (results shown in FIG. 16).
Figure 16:
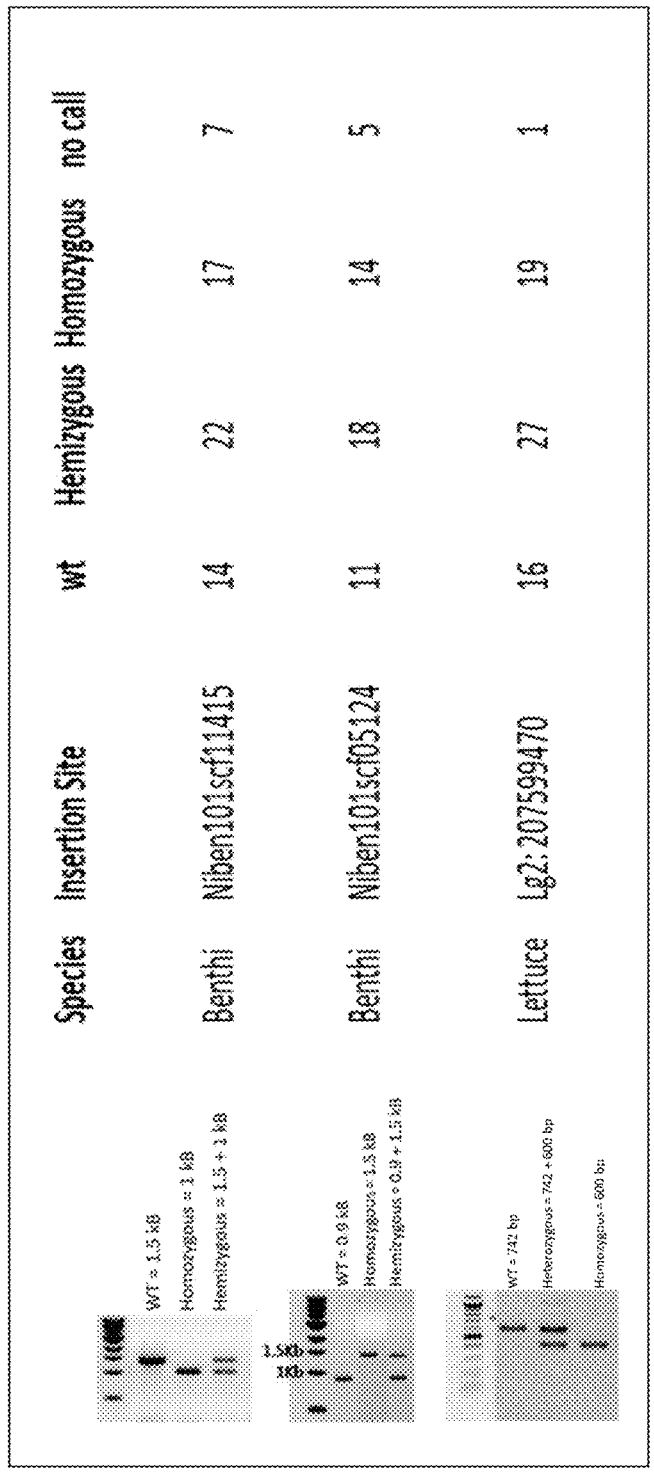
FIG. 16: Representative gels showing results of multiplex PCR using Genome F Primer, Genome R Primer and Plasmid forward Primer (see FIG. 15) to determine wild type (WT), hemizygous or homozygous progeny derived from selfed *N. benthamiana* and Lettuce transgenic $T_0$ plants. For *N. benthamiana* event Niben101scf11415, WT progeny have a single band at approximately 1.5 KB, Homozygous progeny show a single band on the gel of approximately 1 kB, whereas hemizygous progeny show two bands on the PCR gel at 1 kb and 1.5 kb. For *N. benthamiana* event Niben101scf05124, WT progeny have a band at approximately 0.9 kb, Homozygous progeny have a single band at 1.5 kb, and hemizygous progeny have two bands at 0.9 kb and 1.5 kb. For lettuce event LG2: 207599470, WT progeny have a 742 bp band, homozygous progeny have a 600 bp band, and hemizygous progeny have two bands at 742 bp and 600 bp. The table at right shows example results obtained from $T_1$ seedling progeny for each event.

TaqMan confirmed that integration occurred as a single copy, hemizygous event. The inserted construct is shown in FIG. 14, and comprises a GFP sequence under the control of a 35S promoter. A GenomeWalker assay identified a single insertion site with flanking DNA sequence matching the *N. benthamiana* genome. A PCR assay was performed with primers designed to flank the insertion site for wild-type amplification (a 1.5 kb amplicon is expected). PCR was performed using Phusion Green Hot Start II High-Fidelity PCR Mastermix (Thermo #F566) and adhering to the manufacturer's recommendations for reaction set-up and cycling conditions. PCR products of interest were purified with either the Zymo DNA Clean & Concentrator 5 (#D4014) or the Qiagen QIAquick PCR & Gel Cleanup Kit (#28506) and submitted for Sanger sequencing by Genewiz. Sequencing results were analyzed using Geneious. Primers sequences were designed with Primer3. Genomic R primer paired with an insert-specific F primer produces an expected amplicon of 1.0 kb. A multiplex PCR with the three primers shown in FIG. 15 results in the pattern of amplicons shown in the gel in FIG. 16. Sixty T1 seeds of the transformed *N. benthamiana* were germinated, gDNA was isolated and multiplex PCR was performed to determine the segregation of SPβc2 transgene into progeny. The results are shown in Table 10.

TABLE 12

| Totals | | | |
|---|---|---|---|
| WT | Hemizygous | Homozygous | Not determined |
| 14 | 22 | 17 | 7 |

Figure 17:
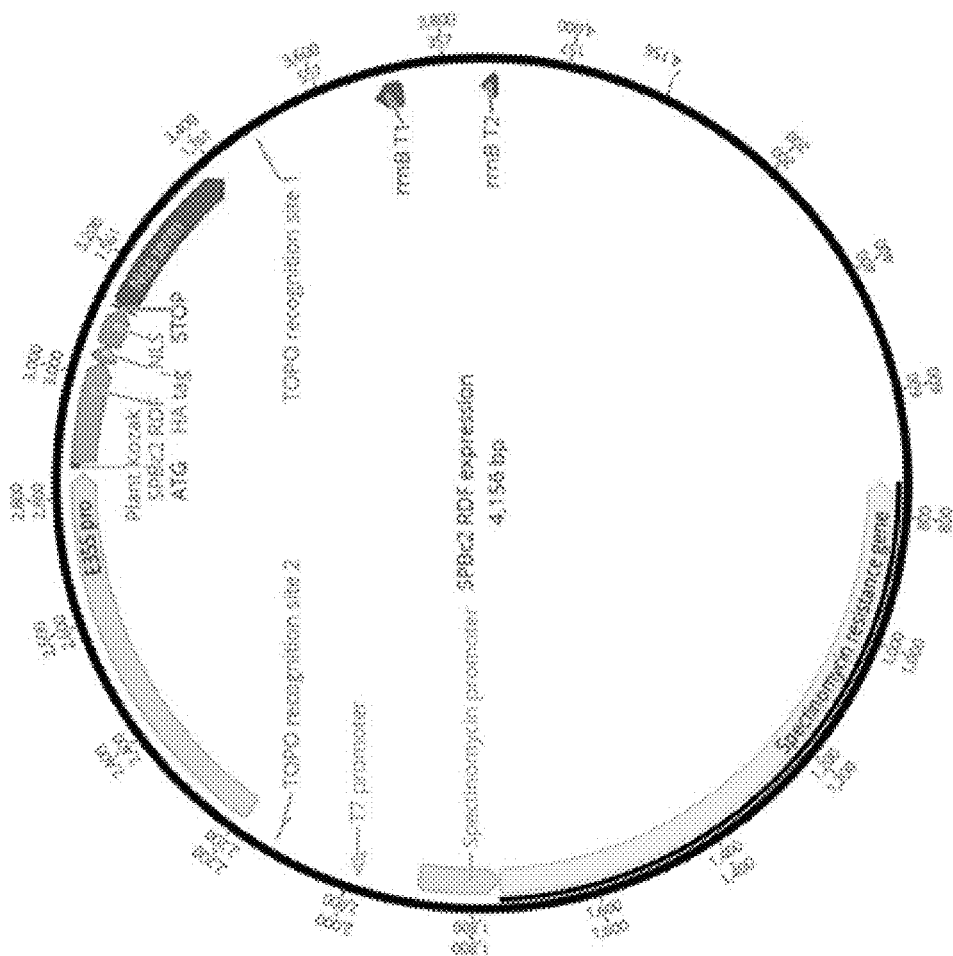
FIG. 17: A schematic of the SPβc2 RDF expression vector of 4, 156 bp DNA.

A plant codon-optimized RDF open reading frame (SEQ ID NO:29) was generated with a 3' HA-tag sequence and nuclear localization signal (NLS) (SEQ ID NO:33). The amino acid sequence of the translated open reading frame and the RDF/HA-tag/NLS sequences are provided as SEQ ID NO:31 and SEQ ID NO:32, respectively. A vector was generated with the RDF construct under the control of a 35S promoter and a nopaline synthase termination sequence (FIG. 17).

Figure 18:
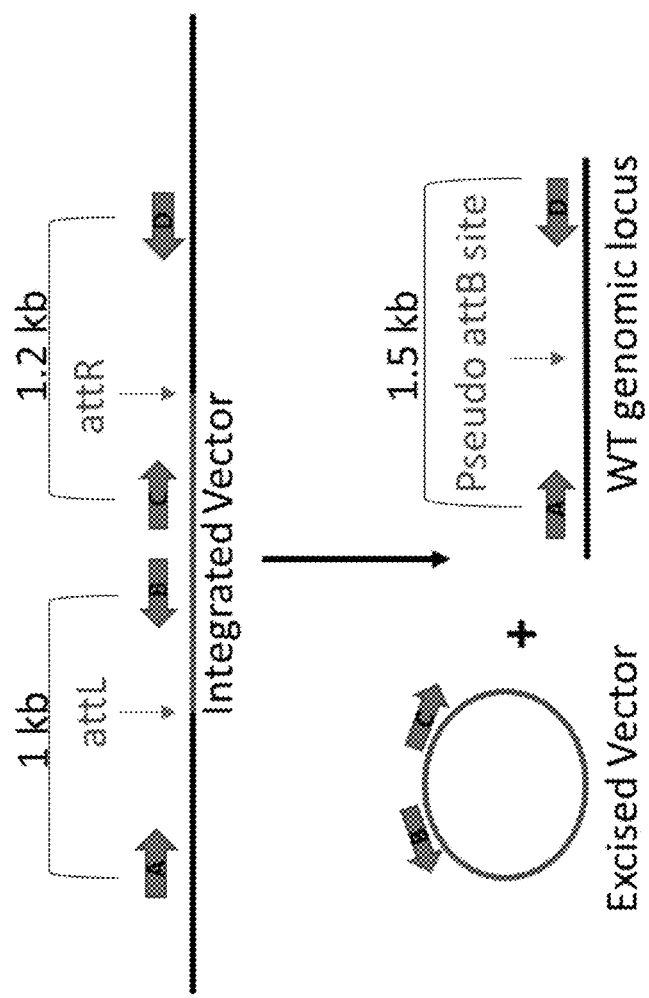
FIG. 18: A schematic of a PCR strategy using primers that span the entire integrated exogenous DNA (primers A and D), primers that span the 5' end of the inserted exogenous DNA and the left flanking *N. benthamiana* genomic DNA (primers A and B) (approximately 1 kb), primers that span the 3' end of the inserted exogenous DNA and the right flanking *N. benthamiana* genomic DNA (primers C and D) (approximately 1.2 kb). The attL and attR sequences at the 5' and 3' end of the exogenous DNA insert are indicated. A WT genomic locus (shown at bottom right) is amplified by primers A and D and gives a band on the gel of approximately 1.5 kb. The excised, circular exogenous DNA (shown at bottom left) may be amplified by primers B and C, but cannot be amplified when integrated into the genomic DNA.

Ten homozygous T1 seedlings of *Nicotiana benthamiana* described above were selected from the segregation analysis. Genotype was confirmed in a multiplex PCR assay a second time to confirm that no WT insertion sites were present. The protoplasts were isolated, pooled and aliquoted equally into 4 portions and each aliquot was transfected with one the following: (1) DNA free control; (b) SPβc2 recombinase; (c) SPβc2 RDF; or (d) SPβc2 recombinase and RDF. Genomic DNA was isolated from the transfected protoplasts and assayed with PCR using primer sets specific to the WT locus (primers A+D), the right border (primers C+D), and the left border (primers A+B) as diagrammed in FIG. 18. PCR amplicons were sequenced to confirm their identity.

Figure 19:
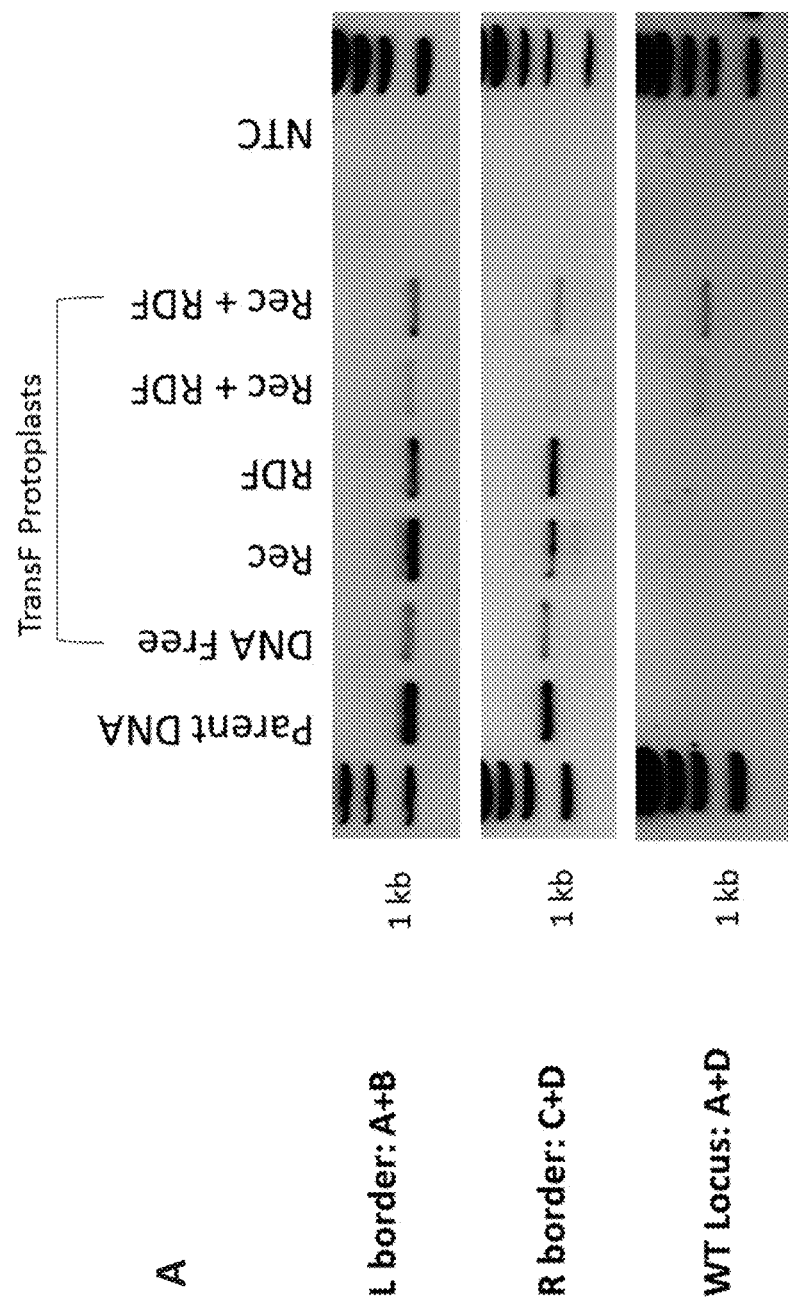
FIGS. 19A-B: Panel A shows a gel separating the reaction products of a PCR using DNA containing the integrated exogenous DNA (Parent DNA) and DNA prepared from cells containing the integrated exogenous DNA treated with no DNA (DNA free), recombinase alone (Rec) or recombinase and RDF (Rec+RDF). The left border was amplified using primers A+B; the right border was amplified using primers C+D; and a WT locus was amplified using primers A+D. WT locus was only observed when the cells were treated with recombinase and RDF. Panel B shows Sanger sequence chromatograms for the WT amplicon, only recovered after Rec+RDF co-transfection, and left border amplicon. Sequences were aligned to the *N. benthamiana* reference genomic sequence and the original attP integration vector to illustrate scarless excision of the integrated DNA. For the sequences shown in FIG. 19B: "1. RDF+Rec TransF protoplasts" corresponds to SEQ ID NO: 188, "2. *N. benthamiana* WT genomic locus" also corresponds to SEQ ID NO: 188, "3. DNA free protoplasts" corresponds to SEQ ID NO: 189 and "4. ID373 attP" corresponds to SEQ ID NO: 190.
Figure 19:
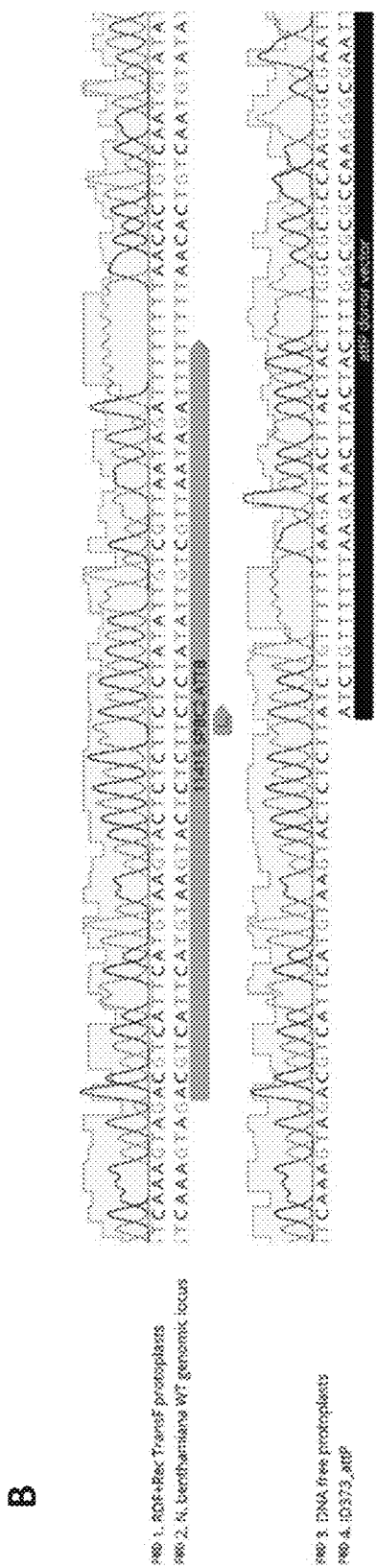

The PCR assay confirmed that co-expression of the recombinase and RDF excised the integrated vector from the genome (FIG. 19A). Sanger sequencing confirmed that the WT locus obtained following co-expression of the recombinase and RDF was identical to the original, non-transformed genomic locus indicating that the excision of the integrated vector was scarless (FIG. 19B).

Example 13

The attP/SPβc2 combination in romaine lettuce was previously demonstrated to significantly increase formation of GFP-positive kanamycin-resistant events over attB, siteless, and minus-recombinase controls. Transfection and culturing of attP/SPβc2 were scaled up to regenerate a population of events for identification of preferred integration sites (Table 11)

TABLE 11

| Lettuce events regenerated for population analysis | | | | |
|---|---|---|---|---|
| DNA Combo | Selection | Original GFP Call | Colonies Transferred | gDNA Extracted from Leaf Tissue |
| attP/SPβc2 | + | + | 170 | 20 |
| | − | − | 20 | 0 |
| | − | + | 2 | 1 |
| | − | − | 84 | 2 |
| DNA-Free | − | − | 119 | 3 |

Figure 20A:
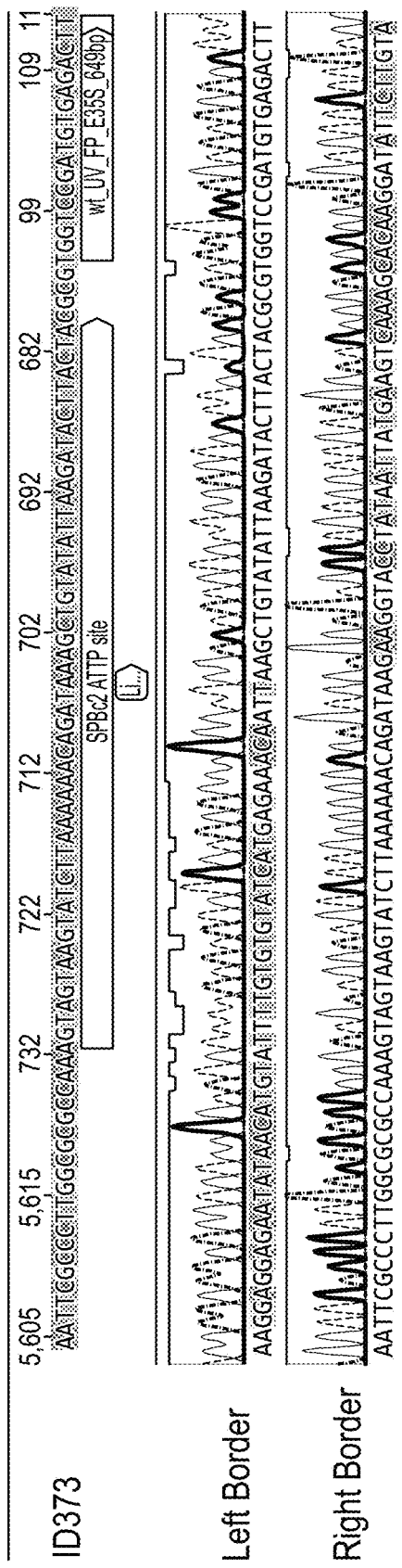
FIG. 20: Example of sequencing data of gDNA: insert junctions. Next-gen sequencing identified an ID373 insertion in Ls7493878 in event 1627-17a-4-1. gDNA: insert junctions were PCR amplified, Sanger sequenced, and mapped to the ID373 circular vector (Panel A) and the native 7493878 (Panel B). Note that the left and right borders of the insertion site form a contiguous alignment with the native site, indicating no loss of genomic sequence during integration. For the sequences shown in Panel A: "ID373" corresponds to nucleotides 5578-5673 of SEQ ID NO:4, "Left Border" corresponds to SEQ ID NO: 191, and "Right Border" corresponds to SEQ ID NO:192. For the sequences shown in Panel B: "7493878 native" corresponds to nucleotides 4-98 of SEQ ID NO: 140, "Left Border" corresponds to SEQ ID NO: 191, and "Right Border" corresponds to SEQ ID NO: 192. Two different possibilities for linearization of att sites in SPβc2-mediated recombination at lettuce site 7493878 were detected in sequencing of left (Panel D) and right (Panel E) gDNA: insert junctions in multiple unique events. Highlighted nucleotides indicate two possible integration positions of the attP site into lettuce pseudo-site 7493878. Panel C shows the gDNA: insert with arrows showing the primers used for sequencing. For the sequences shown in Panel D: "7493878 with ID373 insert" and "1627-17a-4-1-AL33.ab1" correspond to SEQ ID NO: 193, "1627-19-1-042-1-AL33.ab1" and "1627-19-1-200-1-AL33.ab1" correspond to SEQ ID NO: 194, and "1627-19-1-170-AO34.ab1" corresponds to SEQ ID NO: 195. For the sequences shown in Panel E: "7493878 with ID373 insert" and "1627-17a-4-1-A033.ab1" correspond to SEQ ID NO: 196, and "1627-19-1-042-1-AO33.ab1", "1627-19-1-170-AO33.ab1" and "1627-19-1-200-1-AO33.ab1" correspond to SEQ ID NO: 197.
Figure 20B:
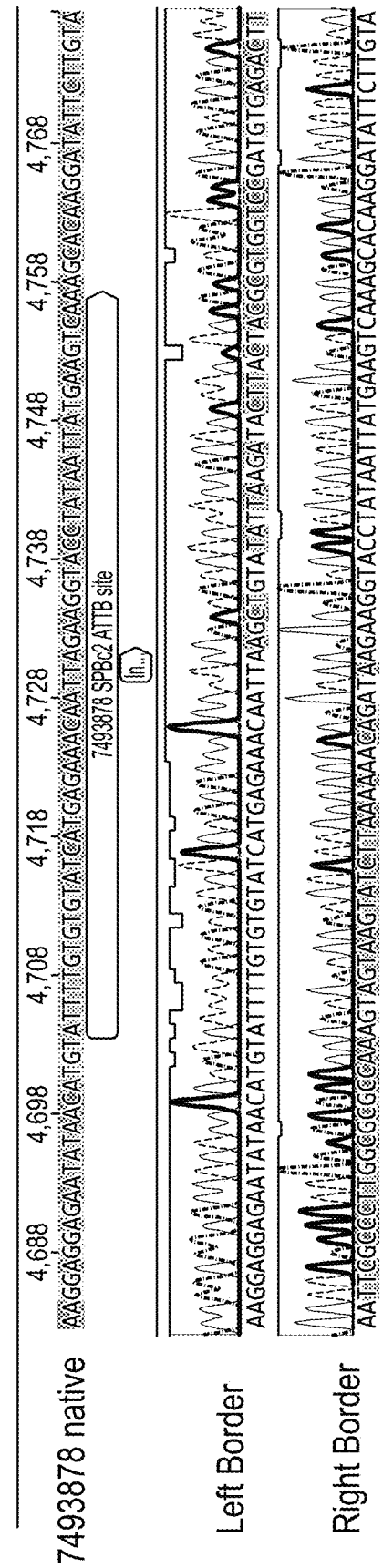

Integration sites in lettuce events were identified by next-gen sequencing for five calli and one regenerated plant. The sites in the regenerated plant were confirmed by GenomeWalker. As for *N. benthamiana* events, primers were designed to the genomic regions upstream and downstream of the insertion sites and used for direct PCR and Sanger sequencing of gDNA: insert junctions (Table 12). Direct PCR followed by Sanger sequencing of amplicons confirmed the gDNA: insert borders for 7 of the 9 integration sites identified by next-gen sequencing (FIG. 20A and FIG. 20B).

In addition to the 20 GFP-positive kanamycin-resistant regenerated events, 35 GFP-positive kanamycin-resistant calli were also sampled for gDNA extraction and insertion analysis. These events were not analyzed by qPCR for NPT-II copy number due to the likelihood of circular non-integrated plasmid being present in the callus tissue. The 55 unique GFP-positive kanamycin-resistant attP/SPβc2 events were screened by end-point PCR for the right gDNA: insert junction (SpecR side) for each of the 7 previously identified

TABLE 12

Diagnostic Primer Sets for Identification of SPβc2 insertion sites in lettuce.

| 35S border (pair with AL33 or AL34) | | SpecR border (pair with AL35 or AL36) | |
| --- | --- | --- | --- |
| Oligo ID | Sequence | Oligo ID | Sequence |
| AO33 | GCGACTTGGGAAGGAGAGTT (SEQ ID NO: 53) | AO34 | GGATGTTAGAGACGGTATTATGTTCAC (SEQ ID NO: 152) |
| AO45 | CCCGGAAACACCTAACAGCT (SEQ ID NO: 147) | AO46 | CACAAACACCGTCATCACCG (SEQ ID NO: 153) |
| AO43 | AGTCCCGTCATCAAACCCAC (SEQ ID NO: 148) | AO44 | ATGCCAAAGTTTGCCAAAGTCT (SEQ ID NO: 154) |
| AL51 | TTTTGCAAACTCCAACGCCA (SEQ ID NO: 149) | AL50 | CTTGTGGGTTGTGGAATTGTCA (SEQ ID NO: 155) |
| AO35 | GAGCCAGAATCCAACTTCCCA (SEQ ID NO: 54) | AO36 | TGCTATTCGTACGGAAGGCG (SEQ ID NO: 156) |
| AO37 | GTGGAGAGGGGAGAGATCGA (SEQ ID NO: 150) | AO38 | TCGAACTCACCAAGCTCCAC (SEQ ID NO: 157) |
| AL60 | CCGCTCTCATCCCTGGTTTT (SEQ ID NO: 151) | AL49 | GCACCTACGTTCAGAGGCTT (SEQ ID NO: 158) |

DNA samples from leaf tissue of the 20 regenerated GFP-positive kanamycin-resistant attP events were analyzed by TaqMan to estimate NptII copy number. Five plasmid-free transfection events and 3 putatively null (GFP-minus and/or non-kanamycin selected) events were included as negative controls.

Figure 20E:
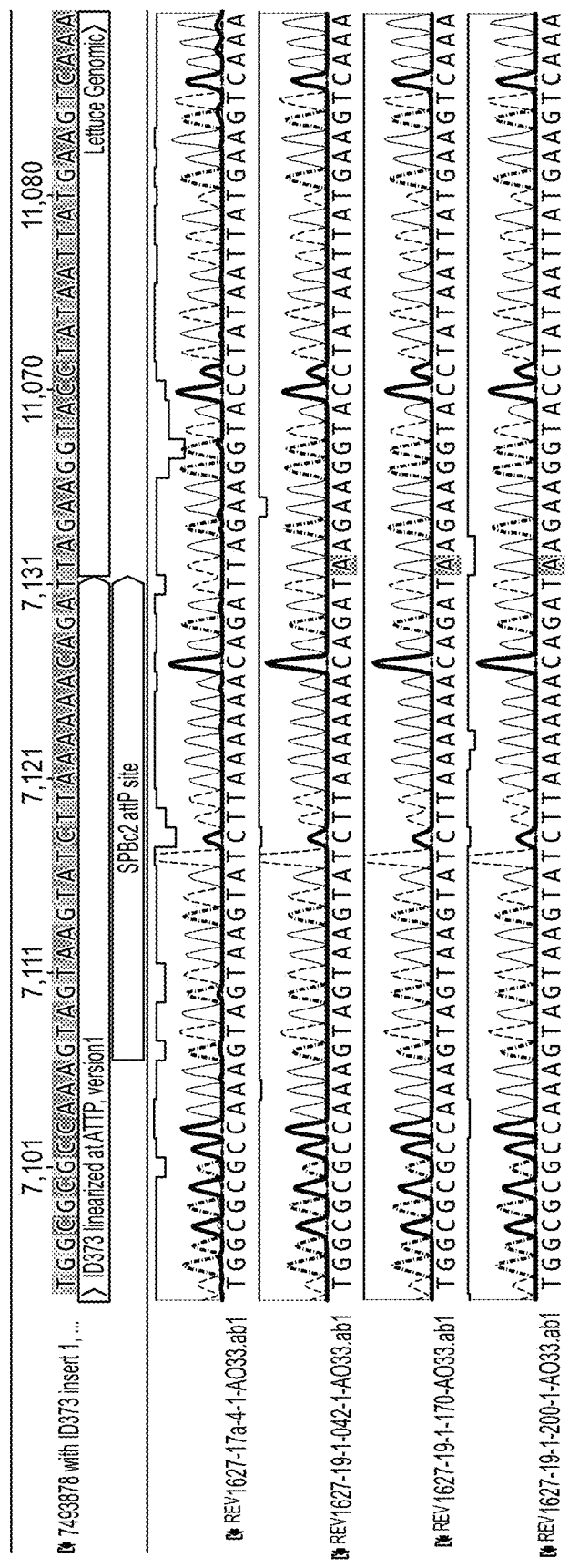

One event was arbitrarily set as the single-copy reference, but regardless of which event was set as the reference, the RQ values fell into 3 groups interpreted as zero copy, low copy, and high copy. The plasmid-free transfection events and putatively null events were all in the zero copy category. Of the GFP-positive kanamycin-resistant events, 4 were high copy, and the remaining 16 were low copy (data not shown).

integration sites. Four of the 7 insertion sites were identified in multiple unique events with one of the integration sites found in 8 events including the 2 events in which it was identified by next-gen sequencing (Table 13). Sanger sequencing of amplicons from both left and right gDNA: insert borders for 3 of the events with integrations in site 7493878 identified a 1 bp difference in the insert: gDNA recombination site compared to the originally identified borders (FIG. 20C-E). As was done in Benthi, the population was also screened for presence of the recombinase expression construct (ID363); it was found in 2 out of the 20 regenerated attP/SPβc2 events (data not shown).

TABLE 13

SPβc2 attB sites identified in lettuce

| # positive events | Chromosome ID | Position Start | Lettuce SPβc2 attB recombination site sequence |
| --- | --- | --- | --- |
| 8 | Dovetail_09Sept_Map_inspected_12-07-2015_1_v8_1g_7 | 7493878 | attaaggaggagaatataacatgtattttgtgt gtatcatgagaaacaaTTagaaggtacctataa ttatgaagtcaaagcacaaggatattcttgtaa a (SEQ ID NO: 140) |
| 7 | Dovetail_09Sept_Map_inspected_12-07-2015_1_v8_1g_2 | 207599470 | caatggtgaatatagtccggcgaccaactctgt ccactatcagcaacgaTAaaaaggtcatgctaa |

TABLE 13-continued

SPβc2 attB sites identified in lettuce

| # positive events | Chromosome ID | Position Start | Lettuce SPβc2 attB recombination site sequence |
|---|---|---|---|
| | | | gacccacaagcccagtcaccactgctgacataa g (SEQ ID NO: 141) |
| 2 | Dovetail_09Sept_Map_inspected_12-07-2015_1_v8_1g_6 | 411877132 | ataagtttagatcttattgaactaggcttgtgg tgcttgtttaaggccaTAaatcgccttattcaa gcgacaaaaatgagacgaataggtggagtcttc a (SEQ ID NO: 142) |
| 2 | Dovetail_09Sept_Map_inspected_12-07-2015_1_v8_1g_4 | 328302882 | tccgtcacaaattgcatcactacgactaagatc ttcatcaatgattctattaAGgagattottaca ttgaaggagaagttacataaattctttattatt t (SEQ ID NO: 143) |
| 1 | Dovetail_09Sept_Map_inspected_12-07-2015_1_v8_1g_9 | 13364626 | tgaatttcttatgaaggttacaacgcatcgtgg attacaagcaattctgtttAGtctgttatgttg ttgaatttgaatggatcttgtcctcagttactc a (SEQ ID NO: 144) |
| 1 | Dovetail_09Sept_Map_inspected_12-07-2015_1_v8_1g_5 | 310607752 | cacaaaaaattgaccatttctagcaacttccta tgatacgttgatactttcTAaacattaattaca atgacaaaatgaagtctaccaaatcattcatag a (SEQ ID NO: 145) |
| 1 | Dovetail_09Sept_Map_inspected_12-07-2015_1_v8_1g_2 | 115327723 | tatttgtgatgtgacatgacaaataatgatgtt acaatattatgtacctctaaATgagatctagca ttgaagattgcatgaatattcttgagtgtgtta tt (SEQ ID NO: 146) |

Reference Genome was Michelmore Lab unmasked vv8 from UC Davis Genome Center.
Boldfaced and underlined font in the sequence indicates the insertion site Example 14

Figure 21:
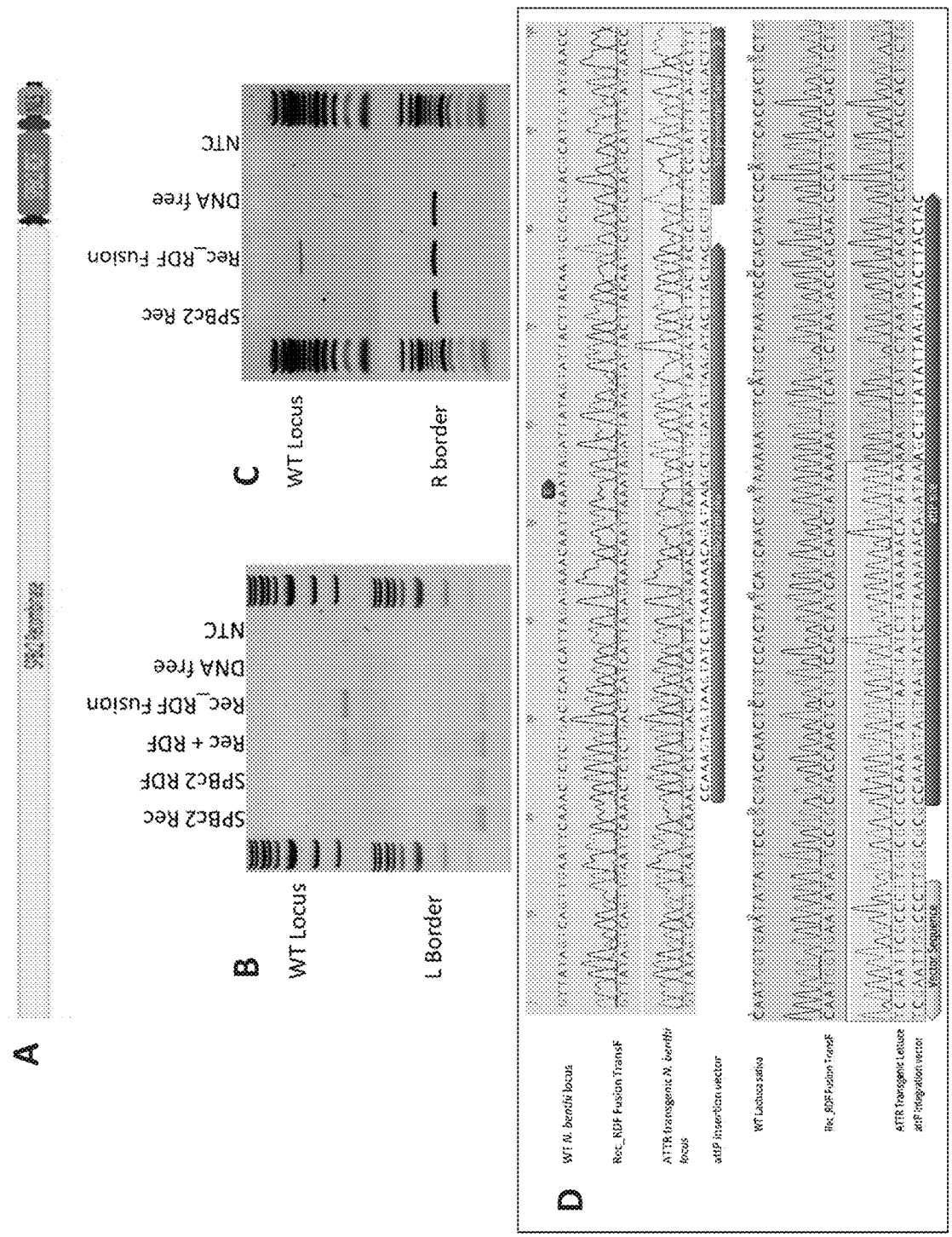
FIG. 21: SPβc2 Rec-RDF fusion protein mediates complete and scarless excision of ATTR transgenes. Panel A shows a schematic of the Rec-RDF fusion protein for unidirectional attL/attR excision comprised of the SPβc2 Recombinase, a 6 amino acid linker sequence, a SPβc2 RDF, an HA epitope tag, and a Nuclear Localization Signal (NLS). Panels B and C show representative PCR results demonstrating restoration of WT locus from homozygous *N. benthamiana* and Lettuce TI seedlings after co-transfection with Rec+RDF or single transfection with the Rec-RDF fusion protein. Panel D shows Sanger sequence confirmation of complete and scarless excision by SPβc2 Rec-RDF in lettuce and *N. benthamiana*. Sequences in darker shading are identical to the original WT genomic loci while boxed sequences are identical to the attP integration vector. For the sequences shown in Panel D: "WT *N. benthi* locus" and "Rec RDF Fusion TransF" correspond to SEQ ID NO: 132, "ATTR transgenic *N. benthi* locus" corresponds to SEQ ID NO:198, "attP insertion vector" corresponds to nucleotides 5596-5674 of SEQ ID NO: 4, "WT *Lactuca sativa*" and the second "Rec_RDF Fusion TransF" (fifth sequence from the top) correspond to nucleotides 1-93 of SEQ ID NO:141, "ATTR Transgenic Lettuce" corresponds to SEQ ID NO: 199, and "attP integration vector" corresponds to SEQ ID NO: 200.

Another construct was made providing a fusion protein of the SPβc2 Serine recombinase fused with a linker to the SPβc2 RDF with HA and NLS tags. The nucleic acid sequence of this construct is provided as SEQ ID NO:35 and the amino acid sequence as SEQ ID NO: 40. The component nucleic acid sequences include the SPβc2 codon-optimized serine recombinase (SEQ ID NO:36), the SPβc2 RDF (SEQ ID NO:38), the linker sequence (SEQ ID NO: 37), and the HA and NLS tags (SEQ ID NO:37). The amino acid sequences corresponding to these are: SPβc2 codon-optimized serine recombinase (SEQ ID N: 41), the SPβc2 RDF (SEQ ID NO: 42), the linker sequence (SEQ ID NO:43), and the HA and NLS tags (SEQ ID NO:44). A diagram of the construct is shown in FIG. 21A. As described above, multiplex PCR was used to identify homozygous progeny from a lettuce event and a benthi event with characterized integration sites. Protoplasts were isolated homozygous individuals, pooled and transfected with SPβc2 Recombinase or Recombinase-RDF fusion construct. Genomic DNA was isolated from the transfected protoplasts and assayed with PCR using primer sets specific to the WT locus (primers A+D), the right border (primers C+D), and the left border (primers A+B) as diagrammed in FIG. 18. PCR amplicons were sequenced to confirm their identity. An example of a PCR conducted as shown above using the fusion construct for *N. benthamiana* (FIG. 21B) and lettuce (FIG. 21C) demonstrates amplification of the native site following transfection with the fusion Recombinase-RDF construct. Sanger sequencing confirmed that the wildtype sequence is perfectly restored upon transfection with the SPβc2 recombinase/RDF fusion construct in *N. benthamiana* and lettuce (FIG. 21D, top and bottom, respectively).

Example 15. Luciferase Assay for RDF-Mediated Excision

Figure 22:
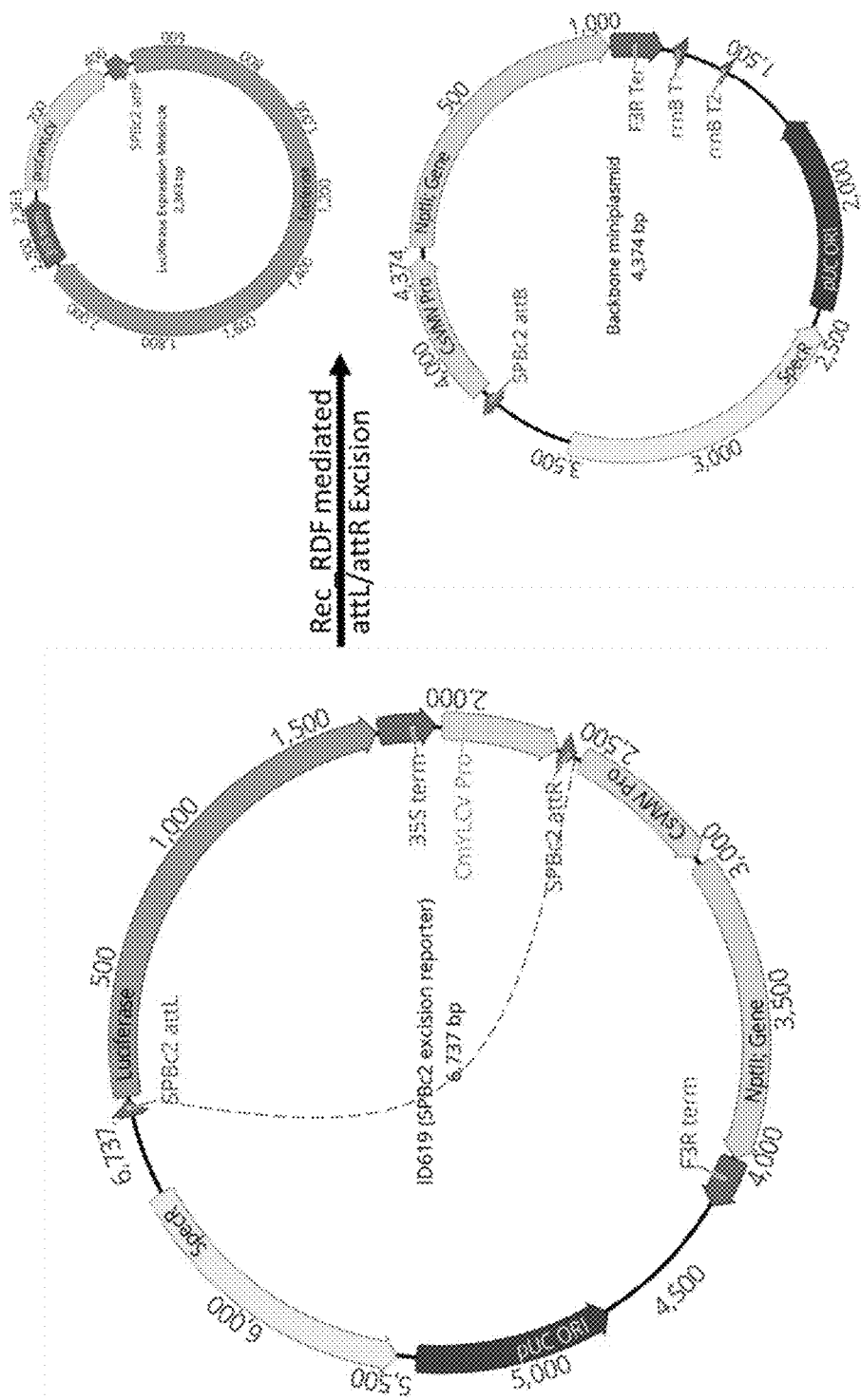
FIG. 22: SPβc2 Rec-RDF Excision Reporter vector map. Left: SPβc2 excision reporter vector map. SPβc2 attL and attR sites are shown as arrowheads with the dotted line connecting the expected recombination sites in the presence of SPβc2 Rec-RDF fusion protein. Right: two distinct circular products are expected following SPβc2 Rec-RDF excision with the top product containing the Luciferase ORF now joined to the CmYLCV promoter and the bottom product containing the Origin of Replication (pUC Ori), Spectinomycin Resistance Gene (SpecR), and Kanamycin Resistance Gene (NptII).

An excision reporter plasmid was created to demonstrate RDF-mediated excision (FIG. 22). FIG. 22 (left) shows the SPβc2 excision reporter vector map in which the SPβc2 attL and attR sites are shown with a dotted blue line connecting the expected recombination sites in the presence of SPβc2 Rec-RDF fusion protein. Two distinct circular products are expected following SPβc2 Rec-RDF excision with the Luciferase Expression minicircle (top) product containing the luciferase ORF which becomes joined to the CmYLCV promoter upon excision, activating reporter gene expression, while the backbone mini-plasmid (bottom, right) product contains the origin of replication (pUC Ori), the spectinomycin resistance gene (SpecR), and the kanamycin resistance gene (NptII).

Figure 23:
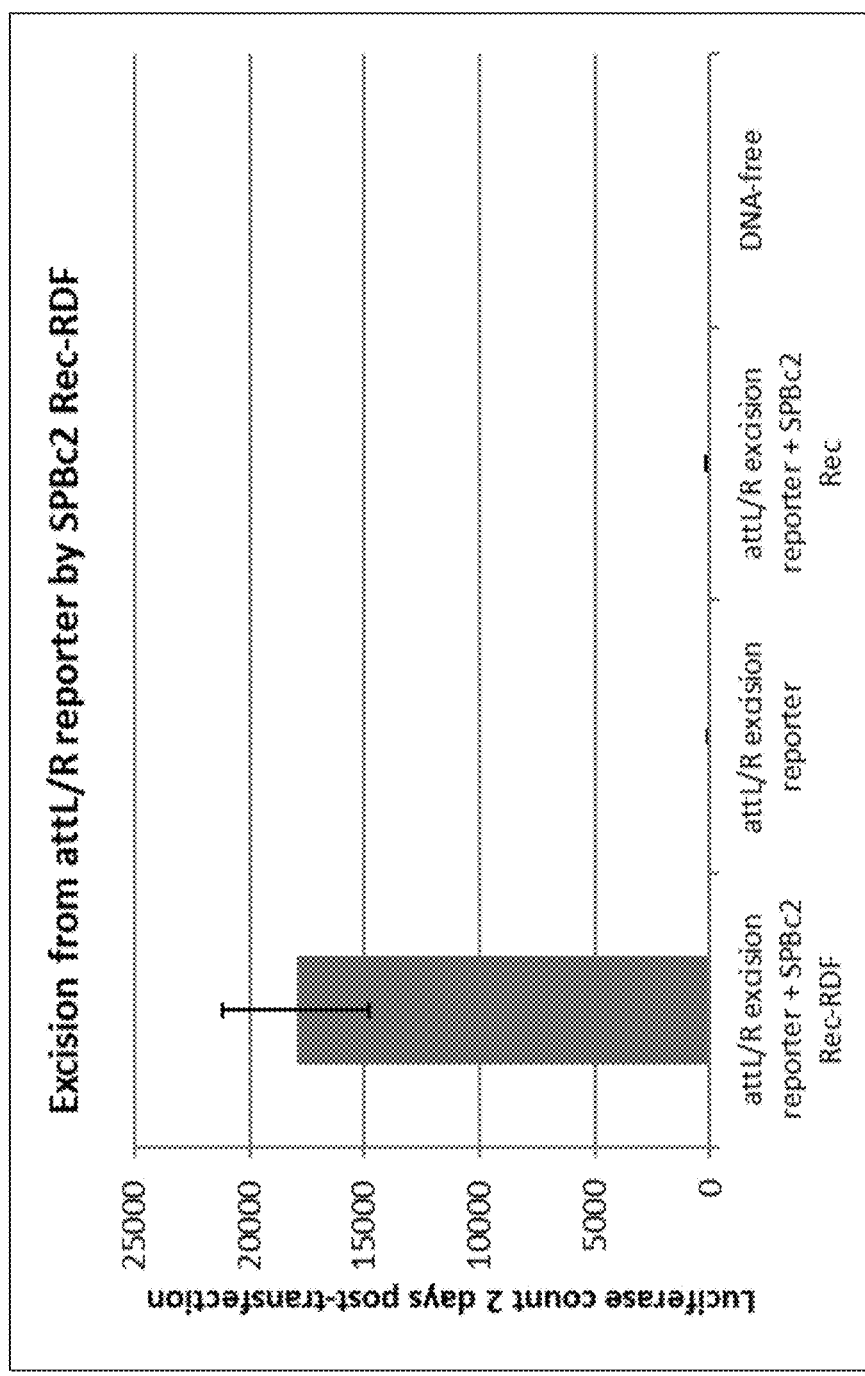
FIG. 23: SPβc2 Rec-RDF fusion protein mediates attL/attR recombination, activating Luciferase expression. Luciferase expression was detected in lettuce mesophyll protoplasts specifically after co-transfection with the Excision Reporter Vector+SPβc2 Rec-RDF fusion protein expression vector.

For the luciferase assay to detect RDF-mediated excision, 50 μL of D-luciferin solution (10 mg/ml in WI buffer) was added to a white 96-well plate along with 50 μL of transfected protoplast solution. Samples were mixed by pipette with wide-bore tips and luminescence was immediately measured using a FIUOstar Omega plate reader. Results are shown in FIG. 23 in which luciferase expression was detected in lettuce mesophyll protoplasts specifically after co-transfection with the Excision Reporter Vector+SPβc2 Rec_RDF fusion protein expression vector, but not when protoplasts contained only the Excision Reporter Vector, or the Excision Reporter Vector+SPβc2 Recombinase, or when the protoplasts were not transfected with any construct. This demonstrated that the RDF-mediated excision was specific and precise.

Figure 24:
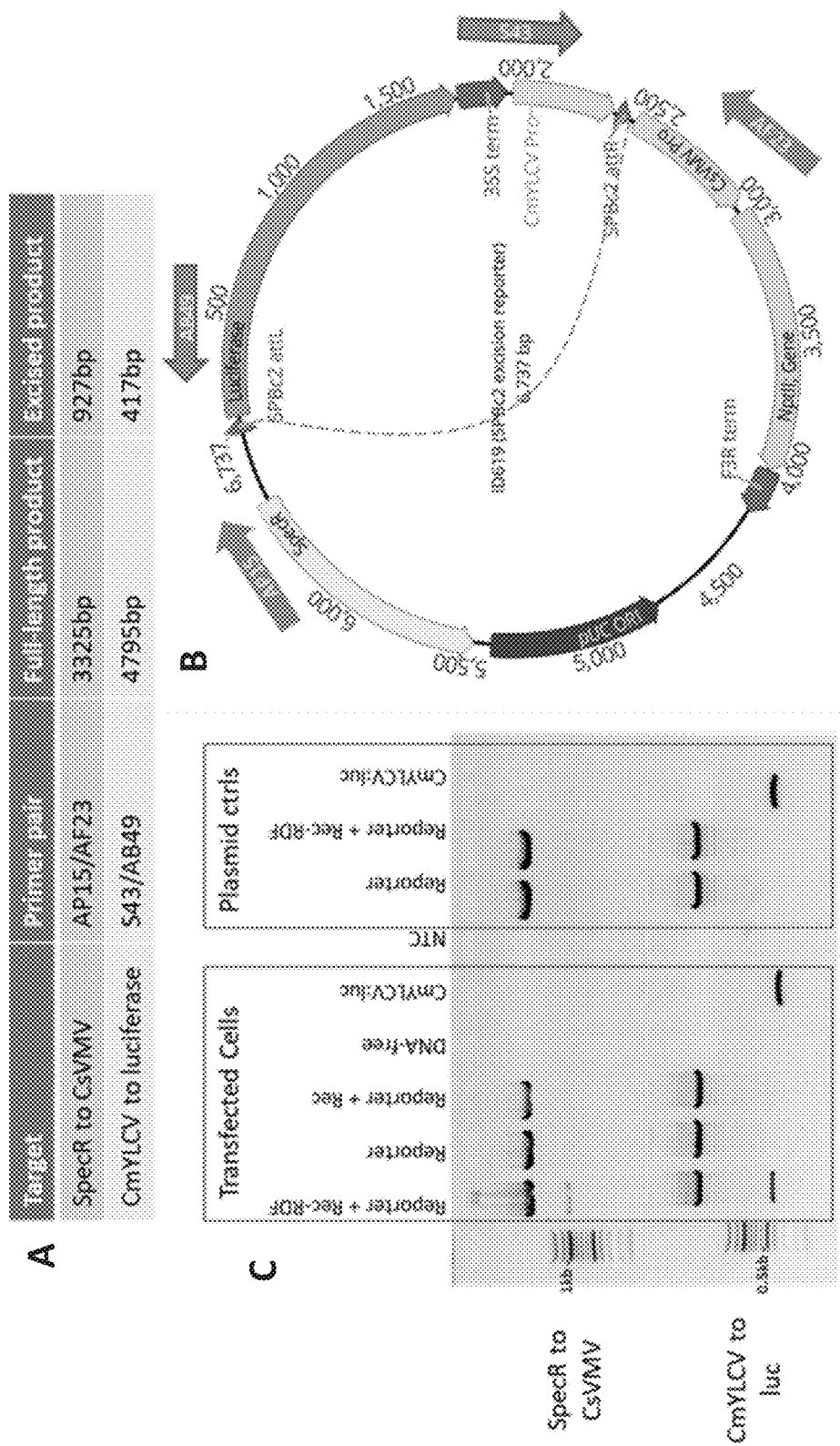
FIG. 24: PCR confirmation of SPβc2 Rec-RDF mediated vector excision. Total genomic DNA was isolated from transfected protoplasts and queried with two distinct primer sets with the expected sizes for the full length excision reporter vector or excised circular products shown in the Panel A. Panel B shows the excision reporter vector map with approximate primer locations shown with arrows outside the circular vector map. Panel C shows PCR results with the expected excision product amplicons observed only after co-transfection with the excision reporter vector+ SPβc2 Rec-RDF fusion expression vector.

To confirm the specificity of the RDF-mediated excision in the Excision Reporter Vector, total genomic DNA was isolated from transfected protoplasts and queried with two distinct primer sets, with the expected sizes for the full length excision reporter vector or excised circular products shown in FIG. 24A. FIG. 24B shows the Excision Reporter Vector map with approximate primer locations shown with arrows on the outside of the vector. PCR results from the experiment are shown in FIG. 24C, with the expected excision product amplicons observed only after co-transfection with the excision reporter vector+SPβc2 Rec-RDF fusion expression vector.

Figure 25A:
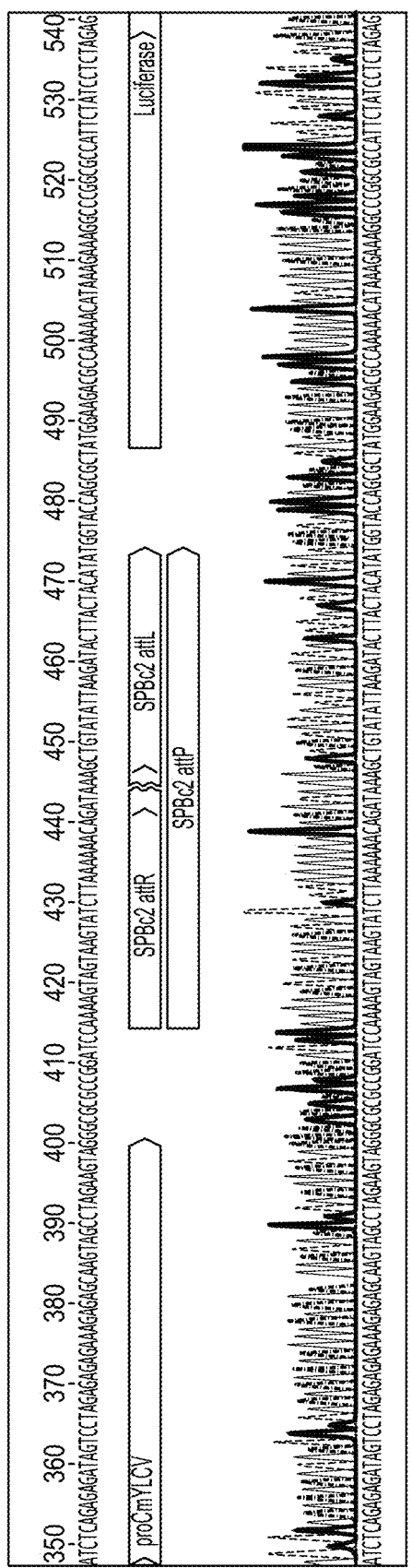
FIG. 25: Sequence Confirmation of SPβc2 Rec-RDF mediated vector excision and canonical attP/B creation. Sanger Sequencing of excision specific amplicons obtained after co-transfection with the attL/attR excision reporter vector and Rec-RDF expression vector. Panel A shows the newly formed attP site flanked by the CmYLCV promoter and Luciferase ORF. For the sequences in Panel A: both correspond to SEQ ID NO:201. Panel B shows the newly formed attB site within the backbone mini-plasmid. For the sequences shown in Panel B: both correspond to SEQ ID NO:202. Panel C-F show the canonical SPβc2 attP (top sequence corresponds to SEQ ID NO: 203; bottom sequence corresponds to SEQ ID NO:204), attB (top sequence corresponds to nucleotides 8-57 of SEQ ID NO:6; bottom sequence corresponds to SEQ ID NO:205), attL (top sequence corresponds to SEQ ID NO:206; bottom sequence corresponds to SEQ ID NO:207), and attR (top sequence corresponds to SEQ ID NO:208; bottom sequence corresponds to SEQ ID NO: 209) sites, respectively, (adapted from Abe et al. (2014) PLOS genetics, 10 (10), e1004636).
Figure 25B:
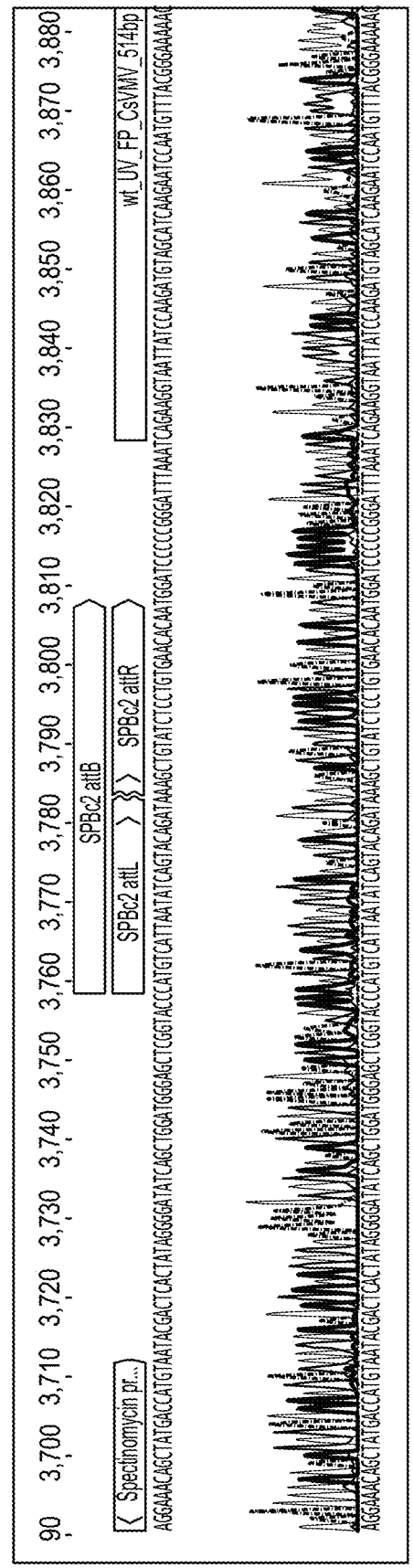

FIG. 25 shows the results of Sanger sequencing of excision specific amplicons obtained after co-transfection with the attL/attR excision reporter vector and Rec-RDF expression vector. FIG. 25A shows the newly formed attP site flanked by the CmYLCV promoter and Luciferase ORF. FIG. 25B shows the newly formed attB site within the backbone mini-plasmid. FIGS. 25C-F show the canonical SPβc2 attP, attB, attL, and attR sites, respectively, with black and grey boxes corresponding to sequence elements from the attP and attB site respectively (adapted from Abe et. al. 2014).

Example 16. Gene Switch Controlled RDF-Mediated Excision

Figure 26:
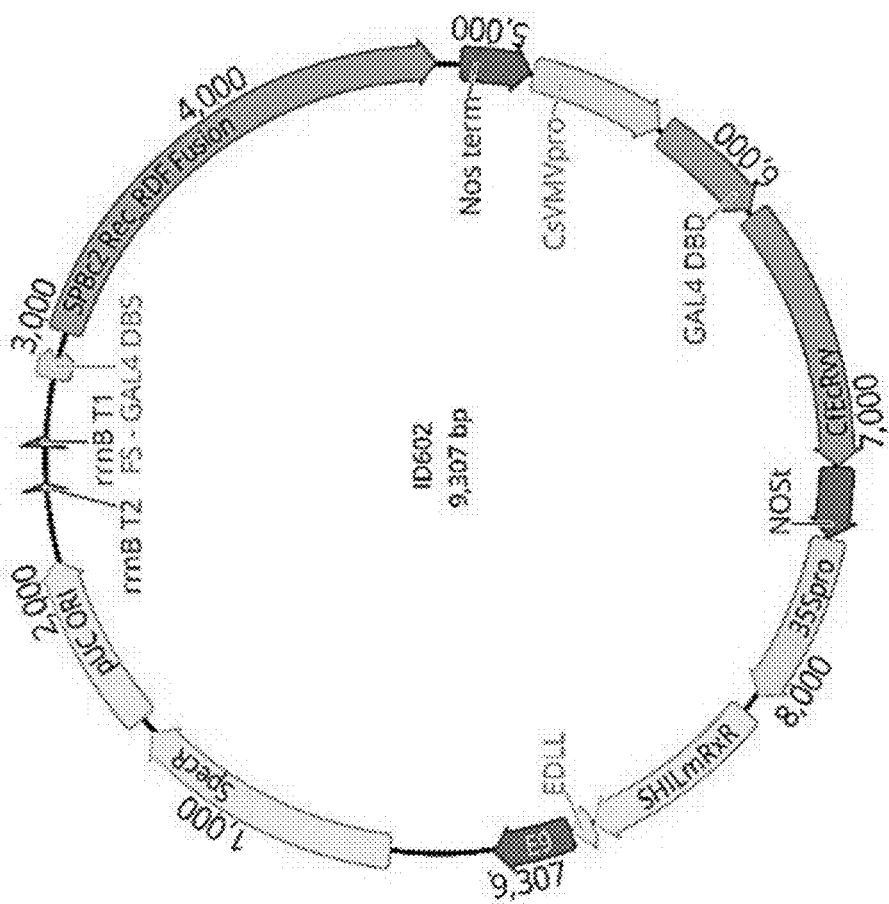
FIG. 26: Gene Switch controlled SPβc2 Rec-RDF ligand inducible vector map. SPβc2 Rec-RDF fusion ORF was cloned downstream of the modified gene switch promoter with GAL4 DNA binding sites (FS-GAL4 DBS), together with ligand-responsive ecdysone receptor (CfEcRvy) and RxR-EDLL domains.

To demonstrate the ability to control RDF-mediated excision on demand, a SPβc2 Rec_RDF fusion ORF was cloned in front of a gene switch promoter with GAL4 DNA binding Sites (GS-GAL4 DBS), together with ligand responsive Ecdysone Receptor (CfEcRvy) and RxR_EDLL domains (FIG. 26). The ability of the gene switch to control RDF-mediated excision was tested in lettuce and avocado protoplasts. Lettuce protoplasts were isolated as described in Example 10. For avocado, leaf tissue was sliced into thin strips with a razor blade, placed in an enzyme solution (1% Cellulase R10, 0.25% Macerozyme R10, 0.4M mannitol, 20 mM KCl, 20 mM MES pH 5.7, 10 mM $CaCl_2$), and 0.1% BSA), and vacuum infiltrated for 20 minutes in low-light. After vacuum infiltration, digests were carried out with gentle agitation at room temperature in the dark. Digestion was carried out in 1 mg/ml MES with enzyme solution (2% Cellulase RS, 1% Hemicellulase, 1% Macerozyme R10, and 0.5%, Pectinase) and vacuum infiltrated for 20 minutes. Digests were carried out overnight, and protoplasts were subsequently filtered through a 40 micron filter to remove debris and washed 2× to remove residual enzymes. PEG-mediated transfection was carried out as described in Example 11.

Figure 27:
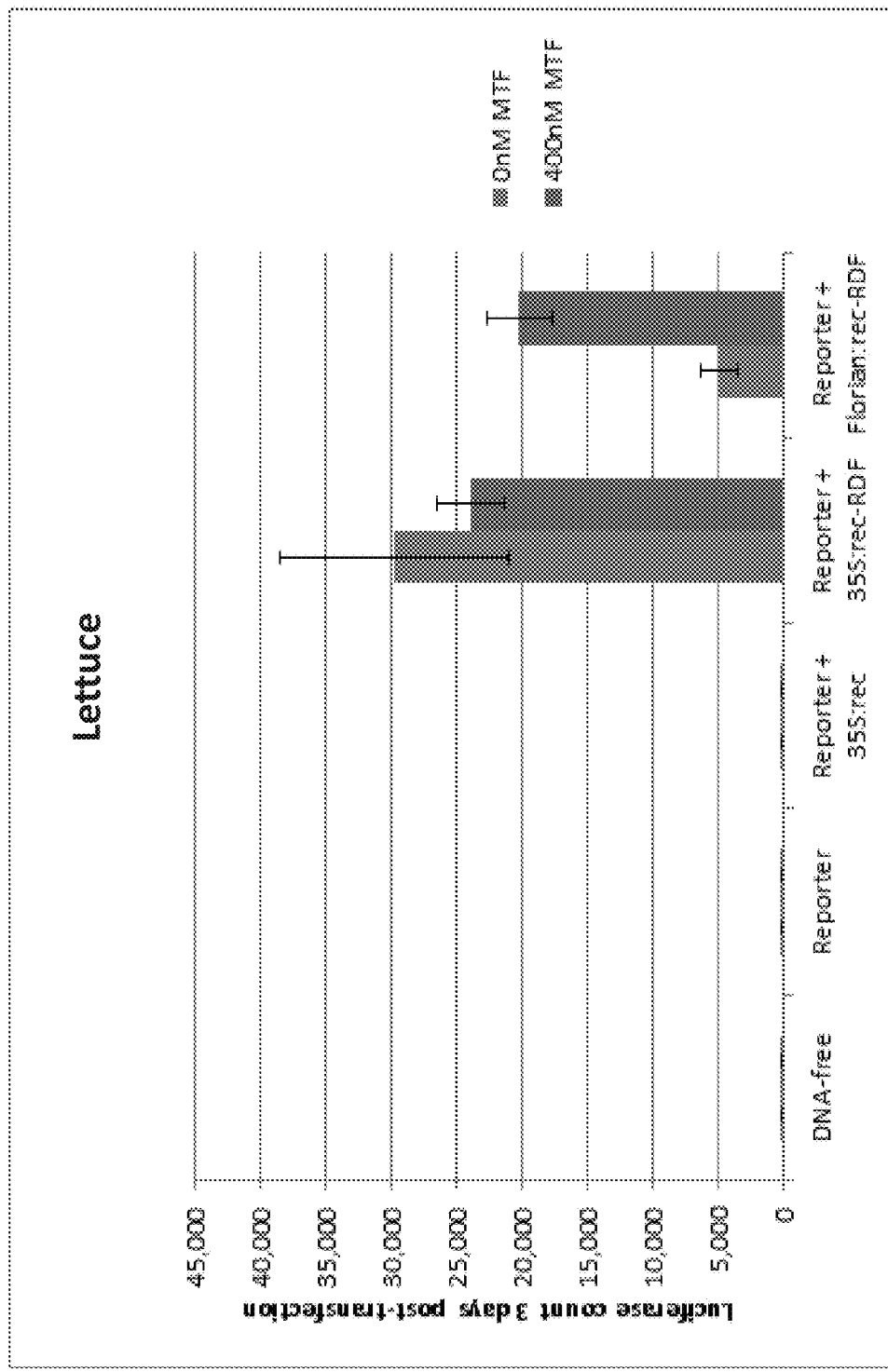
FIG. 27. Ligand inducible expression of SPβc2 Rec-RDF in lettuce and avocado protoplasts. Excision reporter vector was co-transfected into WT lettuce or avocado protoplasts together with 35S-Rec, 35S-Rec-RDF, or Gene Switch-Rec-RDF and each treatment was incubated with or without methoxyfenozide (MTF). In lettuce, at 3 days post transfection, a luciferase assay showed a 4-5 fold induction for the gene switch in the presence of MTF, while all other treatments were unchanged or showed reduced luciferase activity in the presence of ligand (Panel A). In avocado, the gene switch-Rec-RDF induction in the presence of MTF was approximately 10×compared to control treatment without ligand (Panel B).
Figure 27:
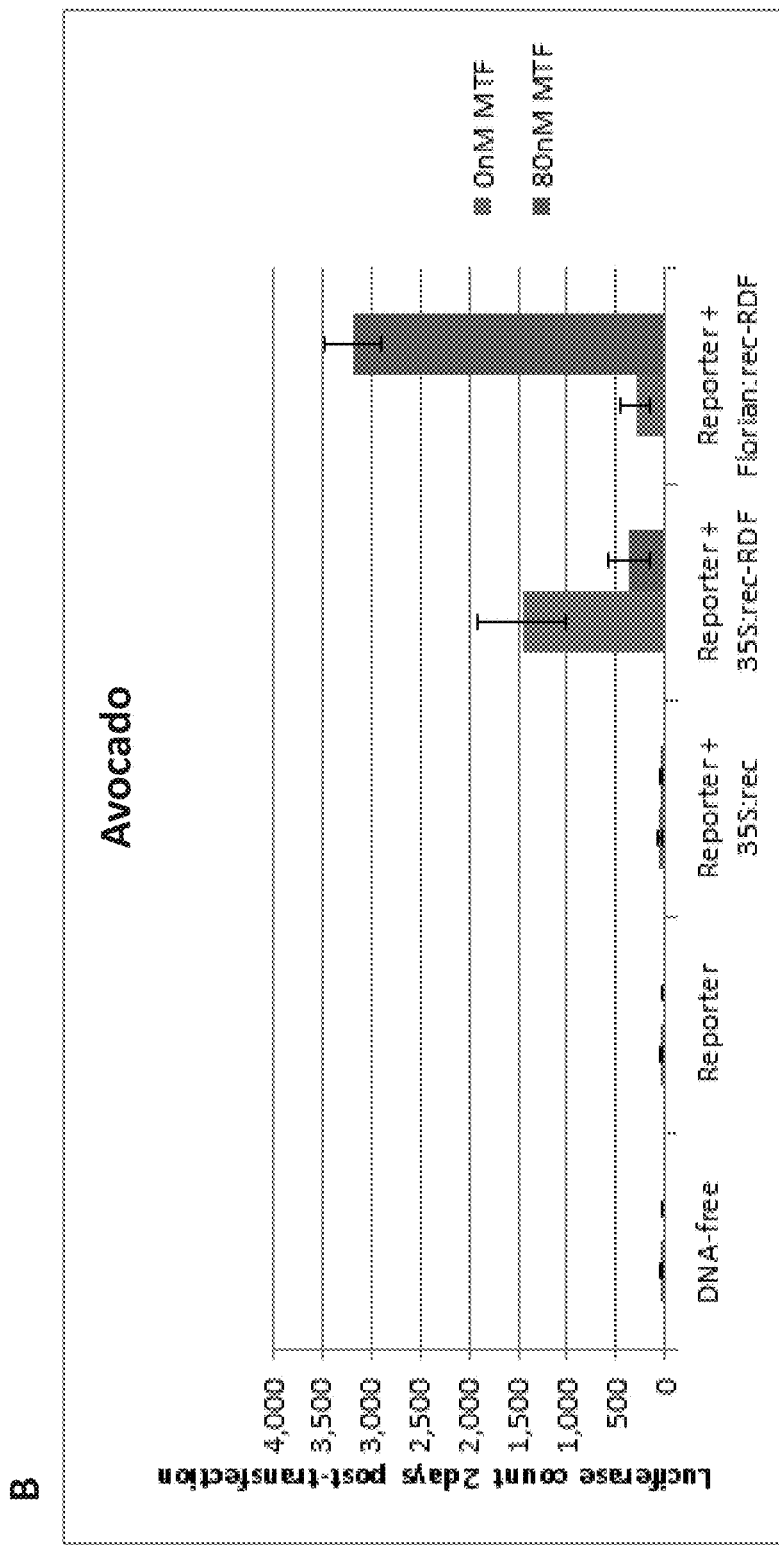

Excision reporter vector was co-transfected into WT lettuce or avocado protoplasts together with 35S-Rec, 35S-Rec-RDF, or Gene Switch/Rec-RDF and each treatment was incubated with or without methoxyfenozide (MTF). In lettuce, at 3 days post transfection, a luciferase assay showed a 4-5 fold induction for the gene switch in the presence of MTF, while all other treatments were unchanged or showed reduced luciferase activity in the presence of ligand (FIG. 27A). In avocado, Gene Switch/Rec-RDF induction in the presence of MTF was approximately 10×compared to control (not treated with MTF (FIG. 27B).

Example 17. Transgenic Events Mediated by Serine Recombinases in Monocots

1. Corn

Immature corn embryos (*Zea mays* B105) were used as an embryogenic tissue source to evaluate ATTR based integration via gold particle biolistic delivery of SPβc2 attP integration vector and Recombinase Expression Vector.

Corn plants (*Zea mays* B105) were grown under glasshouse conditions and immature ears were harvested at 11 days post pollination and stored at 4° C. until embryo excision, typically 3-7 days post-harvest. Husk and silk were removed, 2-3 cm were excised from both ends and ears were submerged in 70% ethanol with mild shaking for 10 minutes. Ears were then rinsed 3×with sterile DI water and embryos were excised from kernels and separated from remaining endosperm. Embryos were transferred scutellum side up onto Induction Media) and cultured in the dark for 5 days at 28° C.

In an effort to minimize the number of biolistic events derived from genomic shearing or random integration, preliminary experiments were conducted to determine the minimal amount of DNA required to consistently induce GFP fluorescent foci at 24 hours post bombardment (not shown). Plasmids for SPβc2 Recombinase expression and attP integration were delivered into immature corn embryos as previously described using the PDS-100/He Particle Bombardment system with 0.6 uM gold Microcarriers and an 1100 PSI rupture disc (Lowe, B.A., Prakash, N. S., Way, M., Mann, M. T., Spencer, T. M., & Boddupalli, R. S. (2009). Enhanced single copy integration events in corn via particle bombardment using low quantities of DNA. Transgenic research, 18 (6), 831). A final concentration of 10 ng each vector (attP-GFP-NptII integration vector and Recombinase Expression Vector)/shot was used for subsequent experiments. At 72 hours post bombardment, there was no clear difference in GFP foci number or intensity when the attP-GFP-NptII integration vector was delivered on its own or co-delivered with the SPβc2 expression vector (not shown).

Immature embryos were harvested and co-bombarded on a weekly basis, with a total of 1,120 embryos co-bombarded with both vectors. Following particle bombardment, embryos were transferred, scutellum side up, to Rest Media, and cultured for 5 days at 28° C. in the dark. Embryos were transferred to Selection Media and cultured for 28 days at 28° C. in the dark. Healthy calli emerging on selection media was transferred to Shoot Proliferation Media and cultured for 7 days at 28° C. with 18:6 light-dark schedule. Calli were then transferred to Shoot Elongation Media and cultured for 14-28 days at 28° C. with 18:6 light-dark schedule. Finally, shoots ≥2 cm were transferred to Rooting Media and cultured until vigorous and healthy roots formed.

Figure 28:
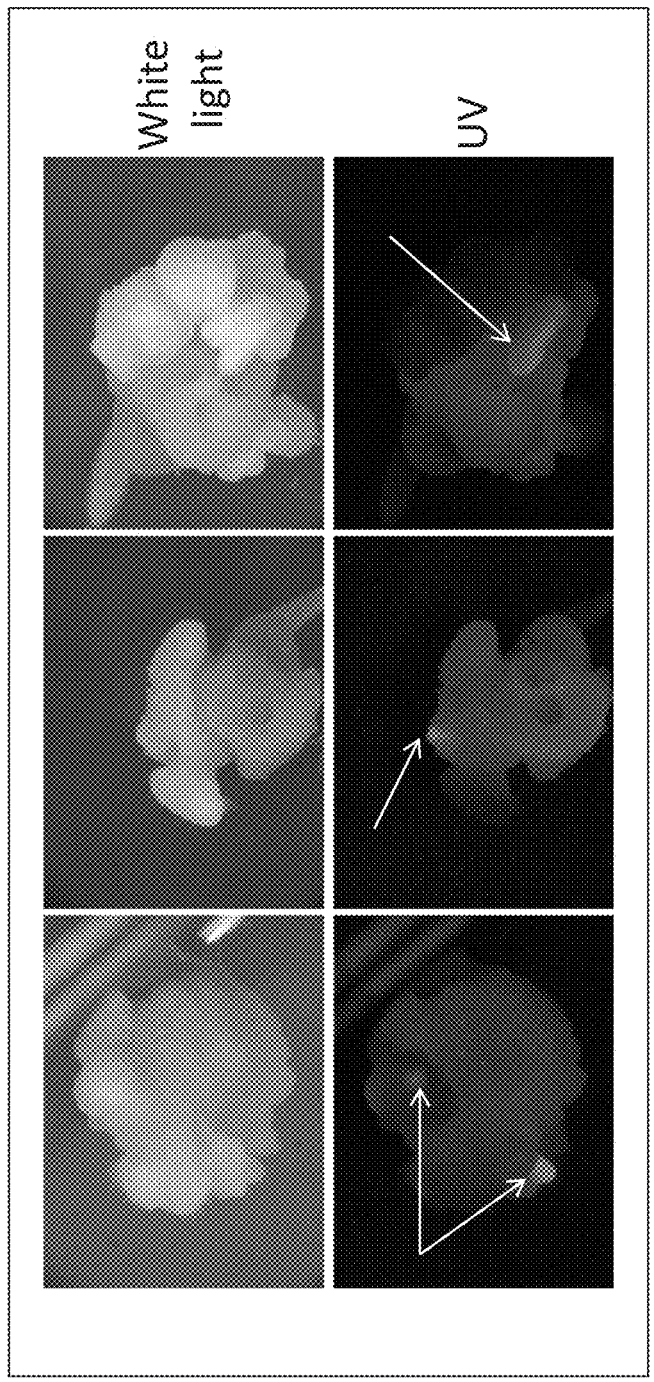
FIG. 28: Formation of GFP fluorescent somatic embryos 3 weeks post bombardment with attP-GFP-NptII integration vector plus SPβc2 expression vector. Bombarded corn embryos were induced to undergo somatic embryogenesis. The top panels show the embryos, three weeks post bombardment, viewed under bright field. GFP fluorescent sectors are clearly visible at 3 weeks post bombardment when viewed under GFP filter (Bottom panels as indicated by arrows).

At 3 weeks post-bombardment, tissues were undergoing somatic embryogenesis and GFP fluorescent sectors were clearly visible under a blue light with appropriate filter (FIG. 28). Somatic embryos were induced to germinate under NptII selection and leaf tissue was collected from individual events for characterization. A total of 20 attP+SPβc2 events, regenerated on NptII selection were chosen for initial analysis. Frozen leaf tissue was ground under liquid nitrogen and incubated for 30 minutes at 60° C. in 2×CTAB buffer (2% cetyltrimethylammonium bromide, 100 mM Tris pH 8.0, 20 mM EDTA, 1.4M NaCl, and 1% PVP MW 40K). Debris was pelleted, and clarified lysates were treated with RNaseA for 15 minutes at 37° C. followed by chloroform extraction and ethanol precipitation. DNA pellets were rehydrated in water, quantitated by Nano-drop, and visualized on a 0.6% TBE agarose gel. Gene specific primer sets for NptII and GFP were used to screen events for the presence of both transgenes. PCR was performed using Phusion Green Hot Start II High-Fidelity PCR Mastermix (Thermo #F566) and adhering to the manufacturer's recommendations for reaction set-up and cycling conditions. GenomeWalker was performed using the Clontech Universal GenomeWalker™ 2.0 kit (#636405) according to the manufacturer's instructions. Libraries were prepared using DraI from NEB. All primers used for genetic characterization of corn events are listed in Table 14.

Figure 31:
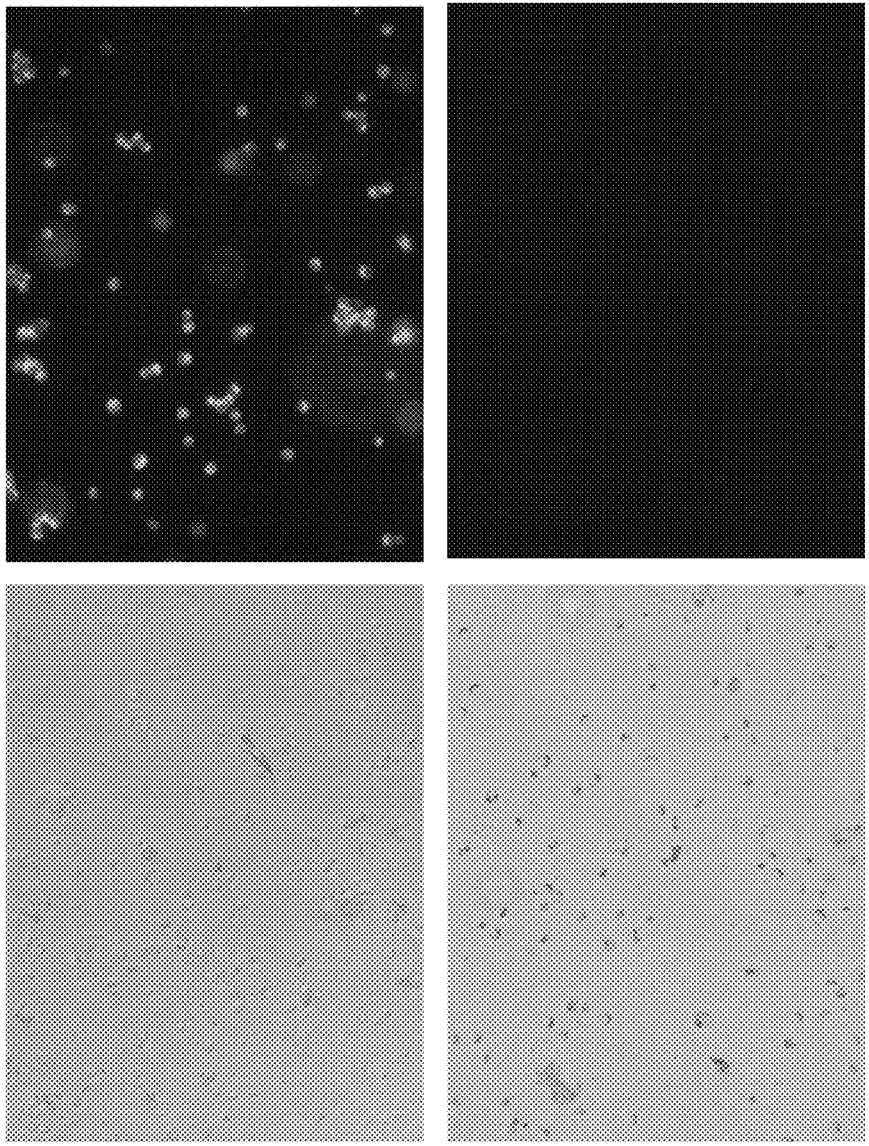
FIG. 31: Protoplasts isolated from 1 week old etiolated rice seedlings and transfected with a 35S-GFP-NOS plasmid. At 16 hours post-transfection, protoplasts were visualized under bright field (Left) or under blue light with GFP filter (Right).

MS with 7 g/L phytoblend in phytatrays under 24-hour dark at 25° C. Protoplast isolation and DNA transfection from etiolated rice seedlings was validated through 35S-GFP-NOS expression (FIG. 31). Stem and sheath tissue from etiolated seedlings were sliced into thin strips with a razor

TABLE 14

Primers used for Corn Genetic Characterization

|  | Oligo ID | Oligo Name | Sequence |
|---|---|---|---|
| Genotyping: endogenous | PDSAP23 | RS_Z.m. PDS_F | CGGTTCGGTTGTCTGACAGA (SEQ ID NO: 45) |
|  | AP24 | RS_Z.m. PDS_R | GGTGCTGGCAAAGTTTCTGG (SEQ ID NO: 46) |
| Genotyping: GFP | Y6 | GFP_ZL_F1 | CTCGTGACCACCTTCACCTAC (SEQ ID NO: 47) |
|  | AK03 | GFP_DS_AT_F | GTGTTCTGCTGGTAGTGGTC (SEQ ID NO: 48) |
| Genotyping: NptII | Z93 | Kan_ZL_F1 | GTACTCTTGCCGACTACAACATC (SEQ ID NO: 49) |
|  | Z94 | Kan_ZL_R1 | CGTGCAATCCATCTTGTTCAATC (SEQ ID NO: 50) |
| Genome Walker Primary PCR | AL34 | SPβc2-ATTP_GSP1_AT_R | GAAGGGTCTTGCGAAGGATAGTGGGAT (SEQ ID NO: 51) |
|  | AL36 | SPβc2-ATTP_GSP1_AT_F | TGCAATGTAACATCAGAGATTTTGAGACAC (SEQ ID NO: 52) |
| Genome Walker Secondary PCR | AL33 | SPβc2-ATTP_GSP2_AT_R | CCTTACGTCAGTGGAGATATCACATCAATC (SEQ ID NO: 53) |
|  | AL35 | SPβc2-ATTP_GSP2_AT_F | AGGAAACAGCTATGACCATGTAATACGACT (SEQ ID NO: 54) |
| Junction confirmation | AQ85 | AQ85: Corn 183 F'_35S | CCGAAGCCTGTGAGGAACAT (SEQ ID NO: 55) |

PCR products of interest were purified with either the Zymo DNA Clean & Concentrator 5 (#D4014) or the Qiagen QIAquick PCR & Gel Cleanup Kit (#28506) and submitted for Sanger sequencing by Genewiz. Sequencing results were analyzed using Geneious and *Zea mays* reference genomes available on NCBI. Primers to genomic flanking sequence were designed with Primer3.

Figure 29:
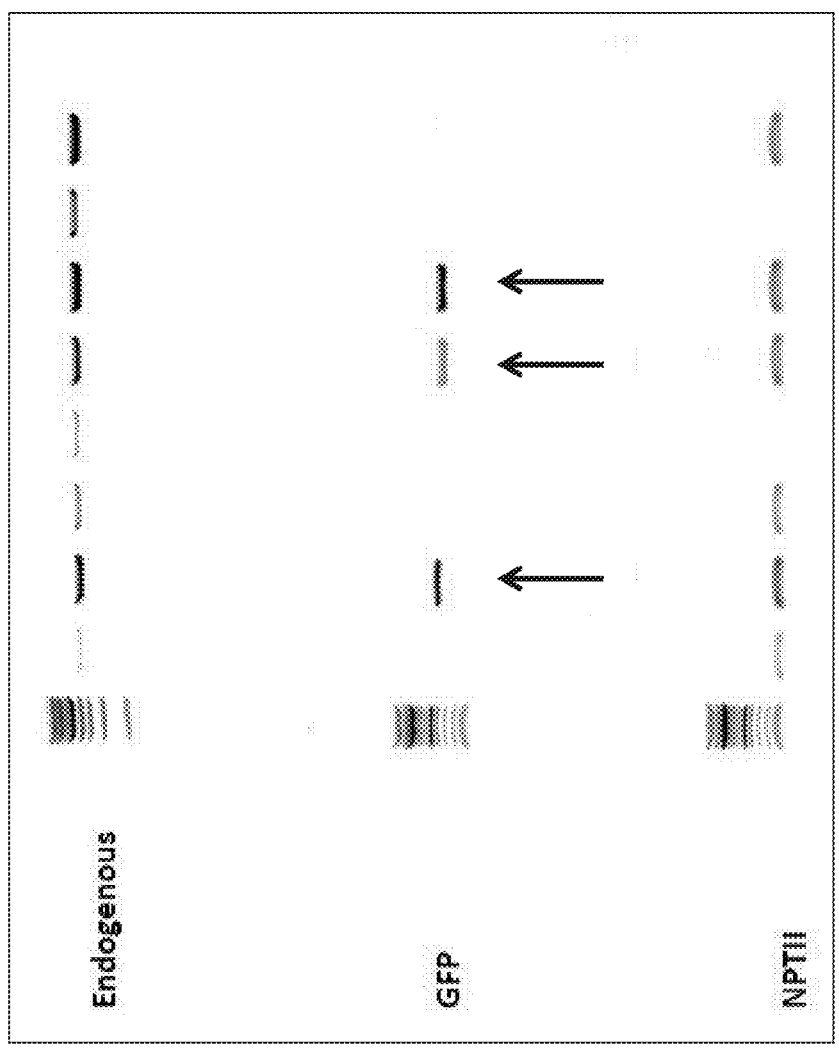
FIG. 29: An example of a PCR pre-screen of corn events regenerated on selection. Putative transformed somatic embryos were induced to germinate under selection and vegetative tissues were harvested for gDNA isolation. All germinated events were pre-screened by PCR to identify events stably transformed with both GFP and NptII expression cassettes. Arrows indicate events that were moved forward for Genome Walker Analysis.
Figure 30A:
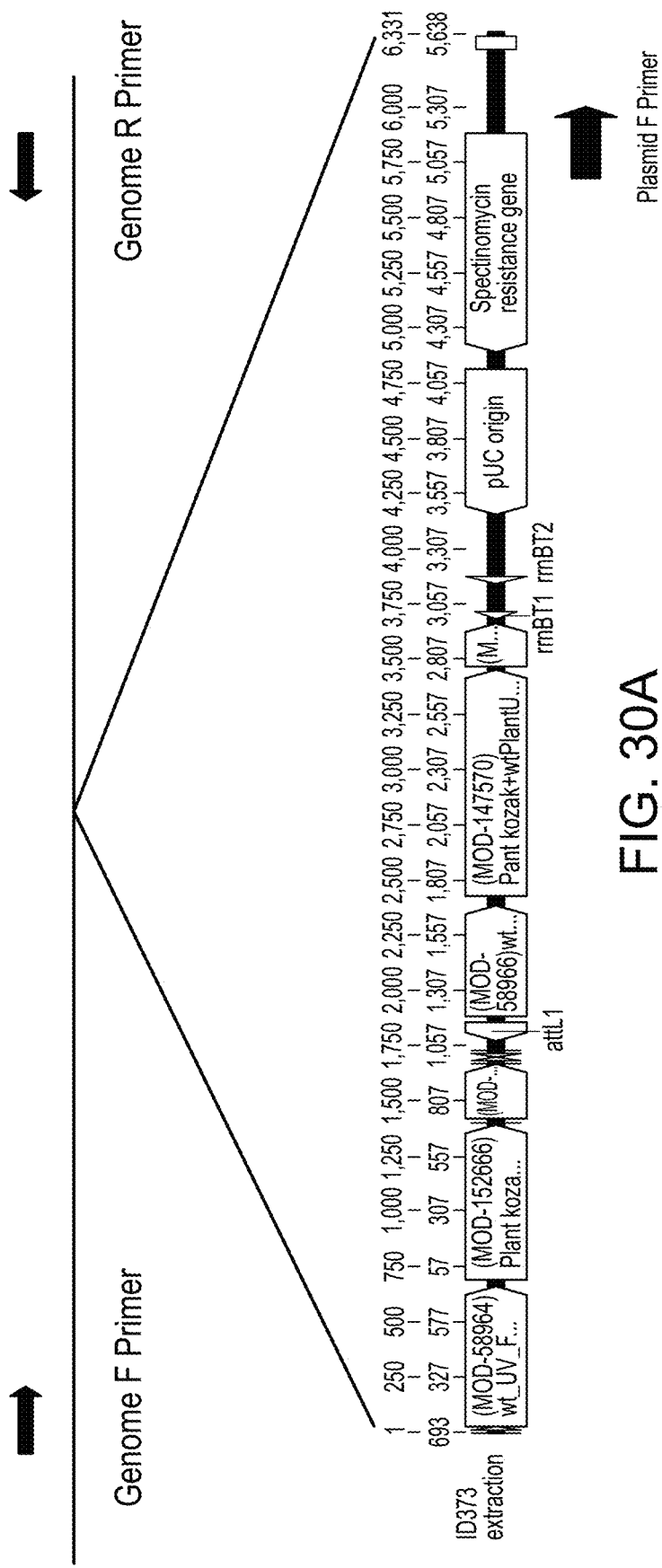
FIG. 30: Direct PCR amplification and sequence validation of gDNA::attP vector junction. Panel A is a schematic showing primer design for junction specific PCR amplification. Panel B shows PCR results showing event specific amplification of the transgene::gDNA junction. The two bands listed with ATTR are sister events derived from the same embryo. Panel C shows sequences derived from (top to bottom) WT genomic reference sequence (SEQ ID NO:210), WT amplified sequence (SEQ ID NO:211), attP vector sequence ("attP integration vector" nucleotides 5596-5705 of SEQ ID NO:4), junction specific PCR amplicon (SEQ ID NO:212), and Genome Walker Assay (SEQ ID NO:212). Panel D shows the pseudo-site sequence for corn ATTR integration with junction site underlined and in boldface.
Figure 30B:
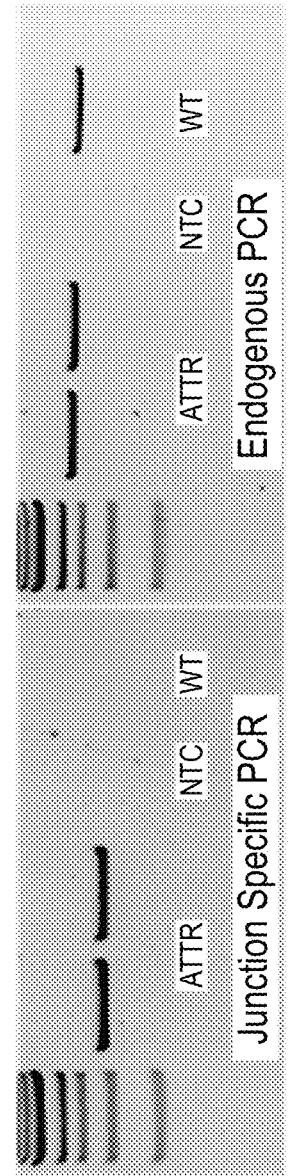
Figures 30C, 30D:
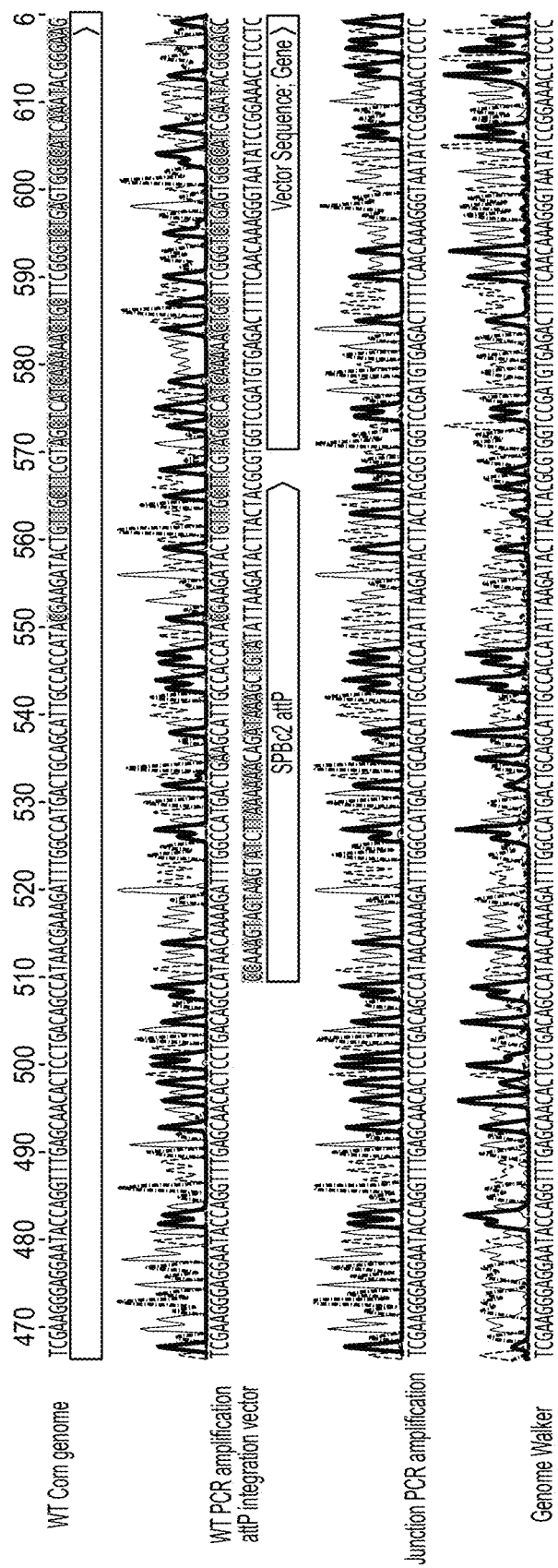

A PCR pre-screen was used to identify events with both transgene cassettes stably integrated (FIG. 29) and a Genome Walker Assay (Clontech) was used to identify the vector integration locus. A single event was identified through Genome Walker Assay and direct PCR amplification as having a transgene::gDNA junction consistent with an SPβc2 ATTR integration mechanism (FIG. 30). FIG. 30A shows a schematic of primer design for junction specific PCR amplification. FIG. 30B shows PCR results showing event specific amplification of the transgene::gDNA junction. The two bands listed with ATTR are sister events derived from the same embryo. FIG. 30C shows sequences derived from (top to bottom) WT genomic reference sequence, WT amplified sequence, attP vector sequence, junction specific PCR amplicon, and Genome Walker Assay. The pseudosite sequence for corn ATTR integration with junction site is shown in FIG. 30D.

2. Rice

Carolina Gold Rice Seed (Baker Creek Heirloom Seeds) were dehusked and sterilized 75% ethanol for 1 minute, 3% sodium hypochlorite with tween20 for 1 hour, and rinsed 5×with sterile DI water with a 20 minute soak between the 4th and 5th rinses. Seeds were blotted dry and placed on ½ blade, placed in an enzyme solution (1.5% Cellulase RS, 0.75% Macerozyme R10, 0.6M mannitol, 10 mM MES pH 5.7, 10 mM $CaCl_2$, and 0.1% BSA), and vacuum infiltrated for 20 minutes in low-light. After vacuum infiltration, digests were carried out with gentle agitation at room temperature in the dark. After 4 hours incubation in the enzyme solution, equal volume W5 solution (154 mM NaCl, 125 mM $CaCl_2$, 5 mM KCl, and 2 mM MES pH 5.7) was gently added and digests were filtered through a 40 uM nylon cell strainer. Cells were pelleted by centrifugation at 201×g for 3 minutes, washed once with W5 solution, and resuspended in MMG (400 mM mannitol, 15 mM $MgCl_2$, and 4 mM MES pH 5.7) at $1.6×10^6$ cells/mL.

PEG-mediated transfections were carried out in 48-well deep dish plates with the number of replicate wells being scaled up or down based upon experimental needs. Per well, 100 uL cells were mixed with 9 ug insert DNA and 4.5 ug recombinase expression DNA. 100 uL PEG (40% PEG4000, 0.2M mannitol, 0.1M $CaCl_2$) were added and mixed thoroughly by shaking. After 15 minutes incubation in the dark, 440 uL W5 were added slowly and allowed 8 minutes acclimation before fully mixing. Cells were pelleted at 805×g for 5 minutes, resuspended in 150 uL WI (4 mM MES pH 5.7, 20 mM KCl, and 0.5 M mannitol), and incubated at 25° C. in the dark for 3 days. A total of 2.9 Million rice protoplasts were co-transfected with the SPβc2 attP integration vector and Recombinase expression vector. Genomic DNA was isolated from transfected protoplast pools 3 days post co-transfection and the Genome Walker Assay was performed directly on pooled protoplast DNA. Briefly, total gDNA was isolated from the rice protoplast pool co-transfected with SPβc2 expression vector and SPβc2 attP integration vector by lysis of cells in urea buffer (6.9M urea, 350 mM NaCl, 50 mM Tris-Cl pH8, 20 mM EDTA pH8, and 1% Sarkosyl), extraction with phenol and chloroform, and precipitation with isopropanol. GenomeWalker Assay was performed as described above and primary and secondary amplicons from both the left and right borders were pooled and column cleaned.

Figure 32A:
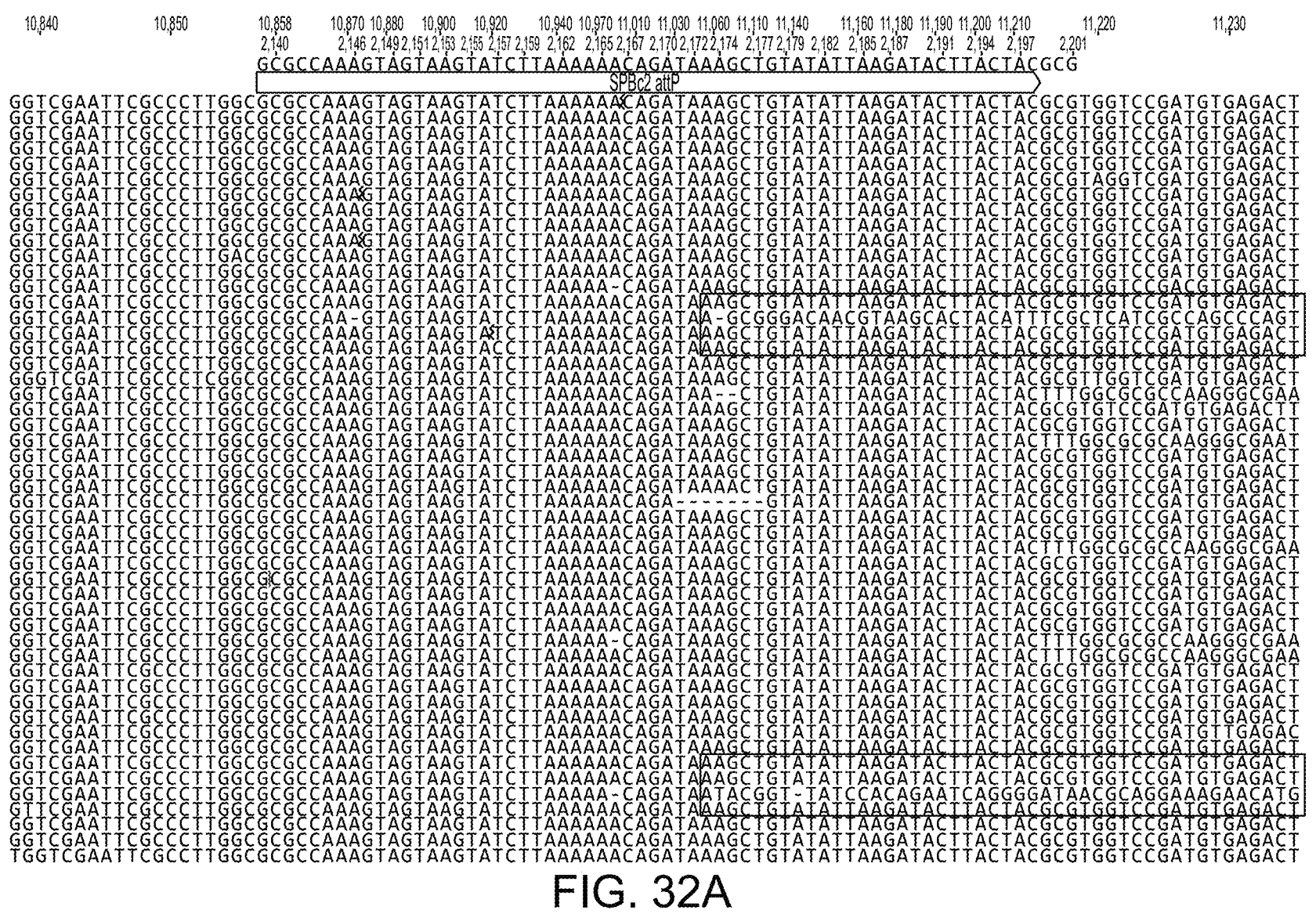
Figure 33:
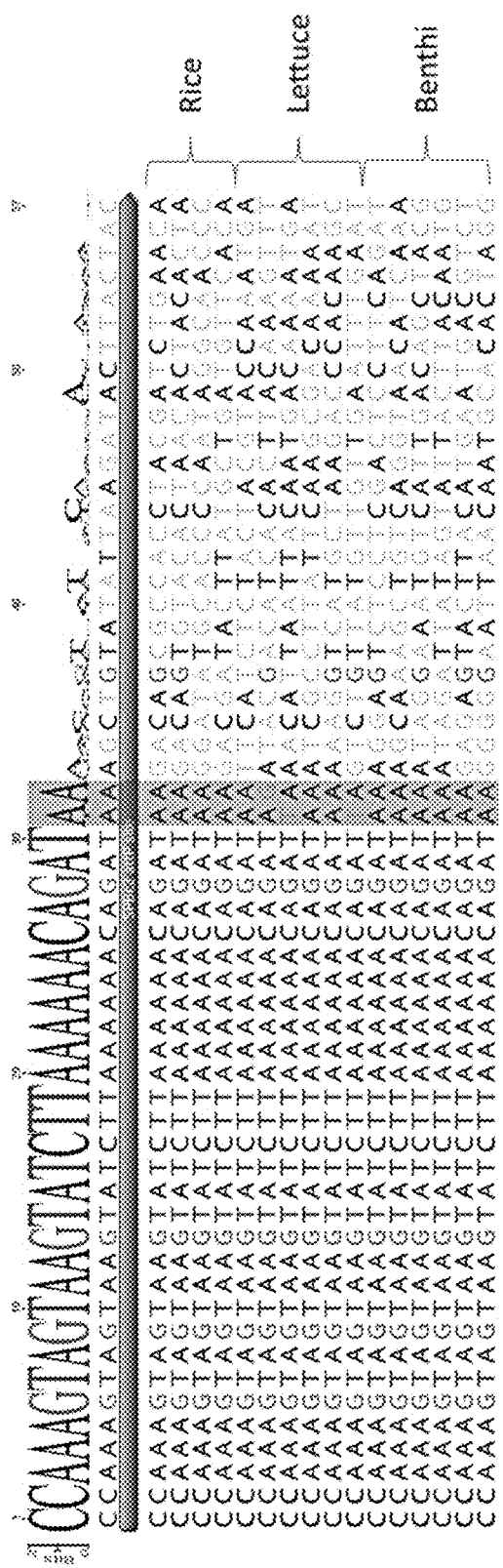
FIG. 33: Cross species alignment of SPβc2 ATTR mediated junctions identified in Rice, Lettuce, and *Nicotiana benthamiana*. Alignment of multiple transgene::gDNA junctions derived from ATTR mediated transformation of Rice, Lettuce, and *N. benthamiana*. Sequence logo at top of the alignment indicates the sequence diversity present at each nucleotide position. First row of aligned sequences shows the canonical SPβc2 attP site for reference. Highlighted nucleotide pairs indicate the canonical SPβc2 attP recombination site. The sequences in order from top to bottom correspond to SEQ ID NOs: 106-122.

Genome Walker amplicon "smear" was sent to Genewiz for next-gen sequencing using the PacBio Sequel Instrument II and Amplicon Sequencing work flow. Total CCS reads were reference assembled to the complete SPβc2 attP site and potential gDNA::transgene junctions were identified visually. Amplicon reads with putative junctions within the attP site were queried against the NCBI reference genome using BLAST to identify genomic integration loci. Cross-species alignment of ATTR junctions was performed in Geneious using the Clustal algorithm with default settings. FIG. 32A shows PacBio CCS sequence reads were reference assembled to the complete SPβc2 attP site. The boxed areas indicate putative gDNA junctions within the attP site. FIG. 32B shows selected amplicon reads that were BLAST searched against the Rice Genome and aligned with genomic sequence (top) and the SPβc2 attP integration vector (bottom). FIG. 32C shows rice SPβc2 pseudosites (junction locations are marked by boldface and underlining). Alignment of the selected rice amplicon reads to previously identified lettuce and *N. benthamiana* junction sites is consistent with an ATTR Large Serine Recombinase integration mechanism (FIG. 33).

Example 18. SF370 Large Serine Recombinase Mediates Integration of DNA into Cells Expression of SF370 large serine recombinase was evaluated for enhanced integration of vectors containing cognate att sites, including co-transfection of two plasmids into lettuce mesophyll protoplasts: (1) Recombinase Expression vector or CAT filler control, and (2) integration vector containing GFP, NptII, and a cognate attP, attB, or siteless control. All vectors were regenerated with or without Kanamycin and GFP expression was evaluated using a blue "biolight" and appropriate emission filter.

Romaine lettuce was used to evaluate the ability of SF370 to integrate DNA into plants. Leaf tissue was sliced into thin strips with a razor blade, placed in an enzyme solution (1% Cellulase R10, 0.25% Macerozyme R10, 0.4 M mannitol, 20 mM KCl, 20 mM MES pH 5.7, 10 mM $CaCl_2$), and 0.1% BSA), and vacuum infiltrated for 20 minutes in low-light. After vacuum infiltration, digests were carried out with gentle agitation at room temperature in the dark.

After 2 hours incubation in the enzyme solution, half volume 200 mM $CaCl_2$) was gently added and digests were filtered through a 70 uM nylon cell strainer. Cells were pelleted by centrifugation at 163×g for 3 minutes, washed once with Francheschi's solution (0.4 M mannitol, 1.5 mM $CaCl_2$), 5 mM HEPES, 1 g/L BSA pH 5.7), and then incubated on ice in the dark for 30 minutes in Francheschi's solution. After the 30 minute ice incubation, cells were pelleted and resuspended in MaMg (0.4 M mannitol, 15 mM $MgCl_2$) at $3 \times 10^5$ cells/mL.

PEG-mediated transfections were carried out in 48-well deep dish plates with the number of replicate wells being scaled up or down based upon experimental needs. Per well, 100 uL cells were mixed with 9 ug insert DNA and 4.5recombinase expression DNA. 100 uL PEG (40% PEG, 0.4 M mannitol, 0.1 M Ca $(NO_3)_2$ adjusted to pH 10) were added and mixed thoroughly by shaking. After 18 minutes incubation in the dark, 800 uL W5 were added slowly and allowed 8 minutes acclimation before fully mixing. Cells were pelleted at 805×g for 5 minutes, resuspended in 150 uL WI (4 mM MES pH 5.7, 20 mM KCl, and 0.5 M mannitol), and incubated at 25° C. in the dark overnight. Colony counts were recorded at 6 weeks post-transfection (Table 15).

TABLE 15

Calli regeneration colony counts were collected 6 weeks after transfection.

| Insert vector | SF370 Recombinase | GFP+ Kan Resistant Colonies |
| --- | --- | --- |
| SF370 attB- | (-) | 0 |
| GFP-NptII | (+) | 0 |
| SF370 attP- | (-) | 1 |
| GFP-NptII | (+) | 4 |
| Siteless- | (-) | 0 |
| GFP-NptII | (+) | 0 |

Figure 34:
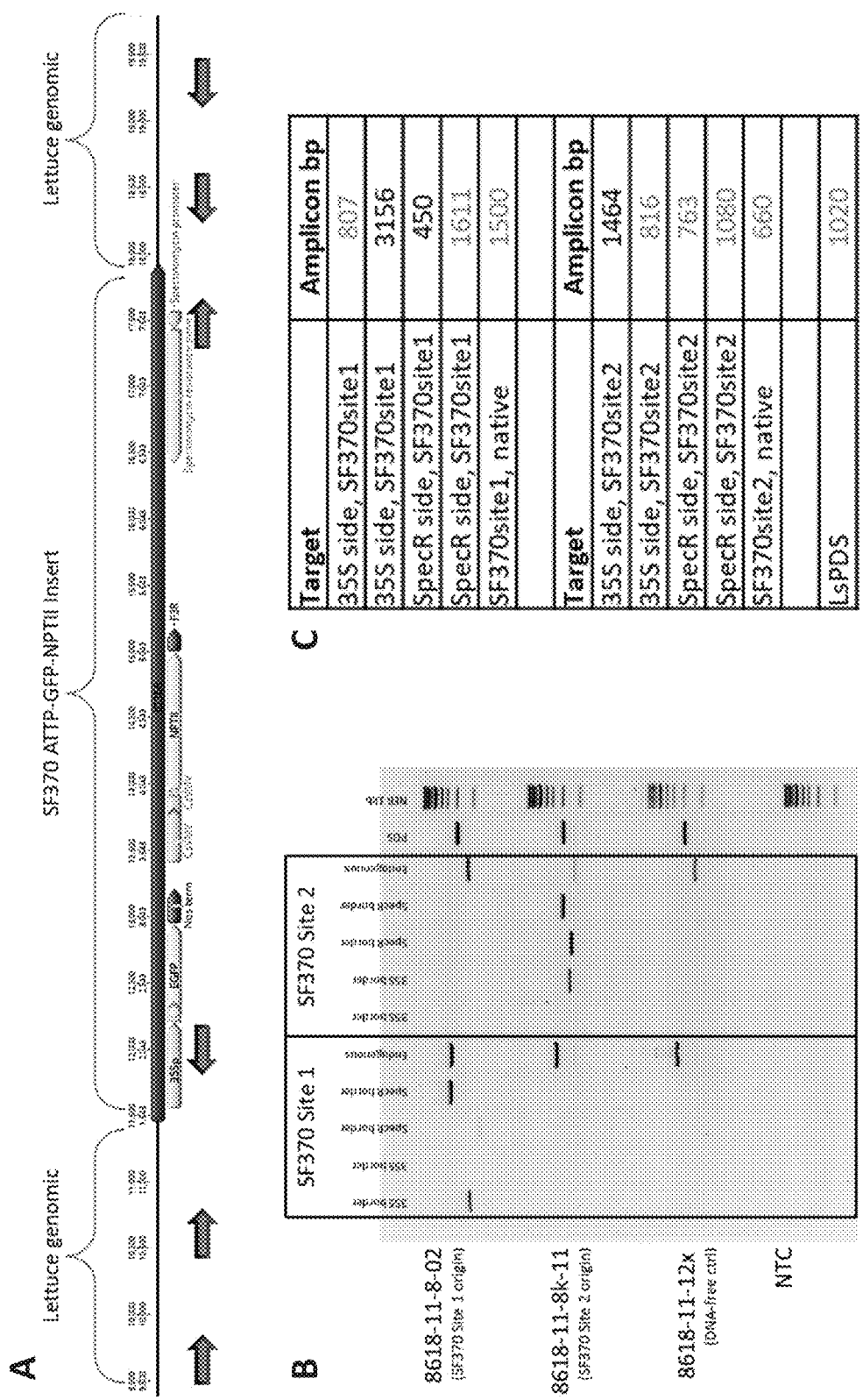
FIG. 34: Panel A shows a schematic of the SF370 attP vector integrated into the lettuce genome site 1. Arrows indicate primers used to directly amplify transgene: gDNA border sequences. Panel B shows PCR results for the two SF370 events along with a DNA free control regenerated without selection. Panel C shows expected amplicon sizes with the grey lettering indicating successful amplification.

Five independent colonies from this condition were analyzed by Genome Walker in order to identify vector integration sites. Based on Genome Walker Analysis, transgene: gDNA borders were identified for two events and insert specific primers were designed to directly amplify and sequence the Left and Right borders for each event (FIG. 34A). Arrows indicate primers used to directly amplify transgene: gDNA border sequences. As both putative integration sites were located within repetitive regions, two separate primers were designed for each Left and Right border. FIG. 34B shows PCR results for the two SF370 events along with a non-transgenic event regenerated without selection (DNA free control). FIG. 34C shows expected amplicon sizes with the grey lettering indicating successful amplification.

Figure 35:
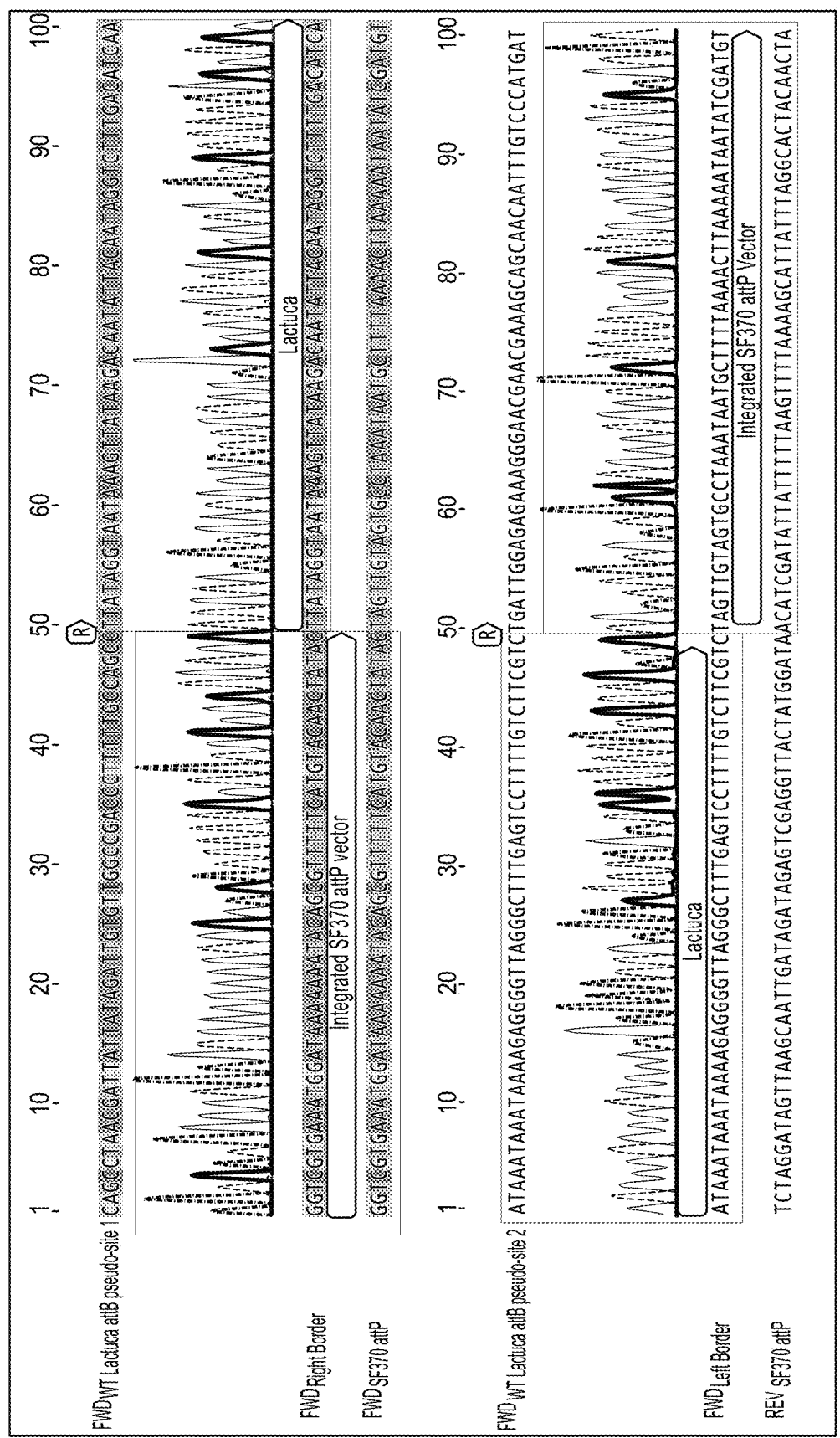
FIG. 35: Alignment of WT lettuce SF370 pseudo-site 1 (top) and pseudo-site 2 (bottom) with transgene: gDNA sequence chromatograms and canonical SF370 attP site. Arrow above each alignment indicates the junction site. For the top panel: "WT *Lactuca* attB pseudo-site 1" corresponds to SEQ ID NO:64, "Right Border" corresponds to SEQ ID NO:232, and "SF 370 attP" corresponds to nucleotides 50-149 of SEQ ID NO: 128. For the bottom panel: "WT *Lactuca* attB pseudo-site 2" corresponds to SEQ ID NO:65, "Left Border" corresponds to SEQ ID NO:233, and "SF370 attP" corresponds to SEQ ID NO:234.

Sanger sequence analysis of both borders for both events was consistent with a large serine recombinase site-specific integration mechanism whereby the SF370 attP vector was linearized in the middle of the attP site and no loss of vector or host genome sequence was observed following integration. FIG. 35 shows alignment of WT lettuce SF370 pseudo-site 1 (top) and pseudo-site 2 (bottom) with transgene: gDNA sequence chromatograms and canonical SF370 attP site. Arrow above each alignment indicates the junction site. Chromatograms for the Left and Right borders are available for both sites, however only a single border is shown for each. Complete sequence for the lettuce integration loci (SF370 pseudo-attB sites) are listed with genome locations according to the unmasked vv8 lettuce genome from UC Davis Genome Center (Table 16). The SF370 attB sites identified in lettuce are shown in Table 17 junction sites highlighted in boldface.

TABLE 16

Diagnostic Primer Sets for confirmation of SF370 sites in lettuce

Transgene:gDNA borders

| | Left (35S) side | | Right (SpecR) side | |
|---|---|---|---|---|
| | Oligo ID | Sequence | Oligo ID | Sequence |
| Insert-specific | AL33 | CCTTACGTCAGTGGAGATAT CACATCAATC (SEQ ID NO: 53) | AL35 | AGGAAACAGCTATGACCATGTAA TACGACT (SEQ ID NO: 54) |
| | AL34 | GAAGGGTCTTGCGAAGGAT AGTGGGAT (SEQ ID NO: 51) | AL36 | TGCAATGTAACATCAGAGATTTT GAGACAC (SEQ ID NO: 52) |
| SF370 site #1: Ls9824521 | AP19 | GGAGGGAGGGTTGTTTTGGT (SEQ ID NO: 57) | AP21 | GCCTACGGAACCAAGACACA (SEQ ID NO: 59) |
| SF370 site #2: Ls76491582 | AP26 | AGGCTTGACTGATTGAGTTT ATGTTGA (SEQ ID NO: 58) | AP27 | CCGGTCCTTATCAATACCACATC AAA (SEQ ID NO: 60) |
| | | | AP28 | ACACATGTTGACGTGTCCTATTT TCC (SEQ ID NO: 61) |

Endogenous Template QC

| | Oligo ID | Sequence |
|---|---|---|
| Lettuce PDS | A178 | ATGTCTCTGTTTGGAAAT GTTTC (SEQ ID NO: 62) |
| | A180 | CAATGGTGCAGGTAAAA CAT (SEQ ID NO: 63) |

TABLE 17

SF370 attB sites identified in lettuce

| Chromosome ID | Position Start | Lettuce SF370 attB recombination site sequence |
|---|---|---|
| Dovetail_09Sept_Map_inspected_12-07-2015_1_v8_1g_8 | 76495830 | CAGCCTAACGATTATTATAGATTGTGT TGGCCGACCCTTTTTGCCAGCCTTATA GGTAATAAAGTTATAAGACAATATTAC AATAGGTCTTTGACATCAA (SEQ ID NO: 64) |
| Dovetail_09Sept_Map_inspected_12-07-2015_1_v8_1g_8 | 9835927 | ATAAATAAATAAAAGAGGGGTTAGGGC TTTGAGTCCTTTTGTCTTCGTCTGATT GGAGAGAAAGGGAACGAACGAAAGCAG CAACAATTTGTCCCATGAT (SEQ ID NO: 65) |

Reference Genome was Michelmore Lab unmasked vv8 from UC Davis Genome Center.
Boldfaced and underlined letters in the sequence indicates the insertion site

Example 19. Analysis of Pseudosites for Serine Recombinase Mediated Integration in Plants Based on data obtained for SPβc2-mediated DNA integration, seven selected insertion sites that were found repeatedly were analyzed for conservation in the region +/−20 bp around the insertion site. A nucleotide distribution matrix was generated from a sequence set where the insertion sites were repeated according to their number of events (31 sequences total).

To analyze the insertion sequences occurring at a high frequency, the insertion sequences were added multiple times to the input sequence file according to their number of events. This resulted in a sequence file consisting of 31 sequences in total. These 31 sequences (+/−20 bp around insertion site) were used as input for MatDefine (Quandt, K. et al. (1995) *Nucleic Acids Res.* 23:4878-4884; Cartharius, K. et al. (2005) Bioinformatics 21:2933-2942) with unanchored alignment of the sequences. To define a matrix from all sequences, the minimum matrix similarity for inclusion in the matrix was reduced to 0.6. The results are shown in Table 18.

TABLE 18

Alignment of 31 Sequences

| Sequence | Position | Alignment | Matrix Sim. |
|---|---|---|---|
| 1 | 3-40 | GTGCTTGTTTAAGGCCATAAATCGCCTTATTCAAGCGA (SEQ ID NO: 66) | 0.606 |
| 2 | 3-40 | GTGCTTGTTTAAGGCCATAAATCGCCTTATTCAAGCGA (SEQ ID NO: 67) | 0.606 |
| 3 | 2-39 | GTTAAGGGGTAAAATCACTAAGGGGGAATTAACAATGC (SEQ ID NO: 68) | 0.690 |
| 4 | 2-39 | GTTAAGGGGTAAAATCACTAAGGGGGAATTAACAATGC (SEQ ID NO: 69) | 0.690 |
| 5 | 3-40 | TCCACTATCAGCAACGATAAAAAGGTCATGCTAAGACC (SEQ ID NO: 70) | 0.857 |
| 6 | 3-40 | TCCACTATCAGCAACGATAAAAAGGTCATGCTAAGACC (SEQ ID NO: 71) | 0.857 |
| 7 | 3-40 | TCCACTATCAGCAACGATAAAAAGGTCATGCTAAGACC (SEQ ID NO: 72) | 0.857 |
| 8 | 3-40 | TCCACTATCAGCAACGATAAAAAGGTCATGCTAAGACC (SEQ ID NO: 73) | 0.857 |
| 9 | 3-40 | TCCACTATCAGCAACGATAAAAAGGTCATGCTAAGACC (SEQ ID NO: 74) | 0.857 |
| 10 | 3-40 | TCCACTATCAGCAACGATAAAAAGGTCATGCTAAGACC (SEQ ID NO: 75) | 0.857 |
| 11 | 3-40 | TCCACTATCAGCAACGATAAAAAGGTCATGCTAAGACC (SEQ ID NO: 76) | 0.857 |
| 12 | 3-40 | TGTATCATGAGAAACAATTAGAAGGTACCTATAATTAT (SEQ ID NO: 77) | 0.974 |
| 13 | 3-40 | TGTATCATGAGAAACAATTAGAAGGTACCTATAATTAT (SEQ ID NO: 78) | 0.974 |
| 14 | 3-40 | TGTATCATGAGAAACAATTAGAAGGTACCTATAATTAT (SEQ ID NO: 79) | 0.974 |
| 15 | 3-40 | TGTATCATGAGAAACAATTAGAAGGTACCTATAATTAT (SEQ ID NO: 80) | 0.974 |
| 16 | 3-40 | TGTATCATGAGAAACAATTAGAAGGTACCTATAATTAT (SEQ ID NO: 81) | 0.974 |
| 17 | 3-40 | TGTATCATGAGAAACAATTAGAAGGTACCTATAATTAT (SEQ ID NO: 82) | 0.974 |
| 18 | 3-40 | TGTATCATGAGAAACAATTAGAAGGTACCTATAATTAT (SEQ ID NO: 83) | 0.974 |
| 19 | 3-40 | TGTATCATGAGAAACAATTAGAAGGTACCTATAATTAT (SEQ ID NO: 84) | 0.974 |
| 20 | 3-40 | TGTATCATGAGAAACAATTAGAAGGTACCTATAATTAT (SEQ ID NO: 85) | 0.974 |
| 21 | 3-40 | TGTATCATGAGAAACAATTAGAAGGTACCTATAATTAT (SEQ ID NO: 86) | 0.974 |
| 22 | 1-38 | CATCATTAGAGAAACAATTAAATAGATTATAGTATTAC (SEQ ID NO: 87) | 0.909 |
| 23 | 1-38 | CATCATTAGAGAAACAATTAAATAGATTATAGTATTAC (SEQ ID NO: 88) | 0.909 |
| 24 | 1-38 | CATCATTAGAGAAACAATTAAATAGATTATAGTATTAC (SEQ ID NO: 89) | 0.909 |
| 25 | 1-38 | CATCATTAGAGAAACAATTAAATAGATTATAGTATTAC (SEQ ID NO: 90) | 0.909 |
| 26 | 1-38 | CATCATTAGAGAAACAATTAAATAGATTATAGTATTAC (SEQ ID NO: 91) | 0.909 |
| 27 | 1-38 | CATCATTAGAGAAACAATTAAATAGATTATAGTATTAC (SEQ ID NO: 92) | 0.909 |
| 28 | 1-37 | .TTCATCAATGATTCTATTAAGGAGATTCTTACATTGA (SEQ ID NO: 93) | 0.717 |
| 29 | 1-37 | .TTCATCAATGATTCTATTAAGGAGATTCTTACATTGA (SEQ ID NO: 94) | 0.717 |
| 30 | 3-40 | ACTTGAAAGTACGACCAAGAAAATGATTATATTTGA.. (SEQ ID NO: 95) | 0.647 |
| 31 | 3-40 | ACTTGAAAGTACGACCAAGAAAATGATTATATTTGA.. (SEQ ID NO: 96) | 0.647 |
| IUPAC Consensus | | tntmnyawgagaaacaATTAaaaggwwhhtataaktay (SEQ ID NO: 97) | |

Base pairs marked red in the IUPAC consensus sequence show a high information content (Ci-value >60). Base pairs in capital letters denote the core sequence used by MatInspector when searching sequence with this nucleotide distribution matrix.

The program MatInspector (Quandt et al. (1995); Cartharius et al. (2005) was used to search all 20 insertion sequences (+/−30 bp around insertion site) and three plant genomes (*Arabidopsis thaliana, Zea mays* and *Glycine max*) for matches to the defined nucleotide distribution matrices. MatInspector has been run several times with different search thresholds (core similarity, matrix similarity). The thresholds were chosen to find all selected seven insertion sequences, preferably the three insertion sequences found more than twice and to reduce the number of genomic matches.

Table 19 shows the number of insertion sequences with a matrix match (from all sequences and from selected sequences). The last column lists the selected insertion sequences that are found by MatInspector with the given parameters.

TABLE 19

Number of Insertion Sequences with Matrix Match

| Search parameters | #found (all seq.) | #found (sel. seq.) |
|---|---|---|
| Core similarity: none Matrix similarity: 0.60 | 15 | 7 |
| Core similarity: 0.85 Matrix similarity: 0.70 | 7 | 4 |
| Core similarity: 0.85 Matrix similarity: 0.85 | 5 | 3 |

To check whether the defined nucleotide distribution matrices are suitable to identify preferred insertion sites, the genomic sequences of three plant genomes have been scanned by MatInspector with the same set of parameters that have been used for scanning the twenty insertion sequences. The genomes searched were: (1) *Arabidopsis thaliana* (TAIR10.1, total length=119,668,634 bp); (2) *Zea mays* (B73 RefGen v4, total length=2,135,083,061 bp); and (3) *Glycine max* (*Glycine max* v2.1, total length=979,046,046 bp). A search with the matrix defined from the 31 sequences yielded the results in Table 20.

TABLE 20

Search with Matrix

| Genome | # Matches (csim = na, msim = 0.6) | #matches (csim = 0.85, msim = 0.7) | #matches (csim = 0.85, msim = 0.85) |
|---|---|---|---|
| A. thaliana | 1,843,719 | 19,311 | 0 |
| Zea mays | 15,024,894 | 136,515 | 16 |
| Glycine max | 17,253,490 | 233,880 | 43 |

The table includes the number of matches found by the matrix (defined from repeated insertion sequences) is very specific when searched with high thresholds that recognize only the three insertion sequences found in more than two events. As it looks like the matches found in the genomes of *Zea mays* and *Glycine max* could be candidates for preferred insertion sites, these matches were inspected further.

The GenomatixSuite task "Annotation & Statistics" has been used to annotate the 16 matrix matches in *Zea mays* and the 43 matrix matches in *Glycine max*. Furthermore, the sequences of the matches have been extracted and aligned with the multiple alignment program DiAlign (Morgenstern, B. et al. (1996) *Proc. Natl. Acd. Sci. USA* 93:12098-12103; Morgenstern, B. et al. (1998) *Bioinformatics* 14:290-294; Morgenstern, B. (1998) *Bioinformatics* 15:211-218). The alignment of the sequences was done to exclude the possibility that the matches are genomic repeats.

Annotation of the 16 matches in *Zea mays* is shown in Table 21.

TABLE 21

Annotation of 16 matches in *Zea mays*

| Genomic element | Number of Regions | Percentage of Regions |
|---|---|---|
| Exon | 2 | 12.5% |
| Partial Exon | 1 | 6.2% |
| Intron | 2 | 12.5% |
| Intergenic Regions | 11 | 68.8% |
| Sum of the above | 16 | 100% |
| Promoters | 3 | 18.8% |

Partial Exons means that the region is overlapping with an exon. Promoters are located in intergenic regions and therefore annotated additionally. Matches are found in 8 of the 10 chromosomes of the *Zea mays* genome (chromosomes 1, 3, 4, 5, 7, 8, 9, 10).

Annotation of the 43 matches in *Glycine max* is shown in Table 22.

TABLE 22

Annotation of 43 matches in *Glycine max*

| Genomic element | Number of Regions | Percentage of Regions |
|---|---|---|
| Exon | 0 | 0.0% |
| Partial Exon | 0 | 0.0% |
| Intron | 7 | 16.3% |
| Intergenic Regions | 36 | 83.7% |
| Sum of the above | 43 | 100 |
| Promoters | 5 | 11.6 |

Partial Exons means that the region is overlapping with an exon. Promoters are located in intergenic regions and therefore annotated additionally. Matches are found in 18 of the 20 chromosomes of the *Glycine max* genome (all chromosomes except chr. 18 and chr. 20).

The alignment of the 16 *Zea mays* matches is shown in FIG. 36. A consensus sequence for FIG. 36 is:

```
                                          (SEQ ID NO: 98)
mhrdhnndwn wrmAAChATw AAdnnGhdhh whnvAdhnhn
``` with a core sequence of:

```
                                          (SEQ ID NO: 99)
mhrdhnndwn wrmAAChATw AAdnnGhdhh w
```

The alignment of the 43 *Glycine max* matches is shown in FIG. 37. A consensus sequence for FIG. 37 is:

```
                                         (SEQ ID NO: 100)
nnnnnnnnnw nhAAChATwA hdnnrnnnnn nnnwddnnn
``` with a core sequence of:

(SEQ ID NO: 101)
wnhAAChATw Ahdnnr.

The '*' signs below the alignment show the nucleotide similarity at each position of the alignment. If all nucleotides are identical, 10 '*' signs are displayed. In the *Zea mays* alignment, for nine positions within the alignment, all nucleotides are identical. For the *Glycine max* alignment, for six positions within the alignment, all nucleotides are identical. All other positions of the alignment have a lower nucleotide similarity.

Example 20. Flipped Inserts

Figure 38:
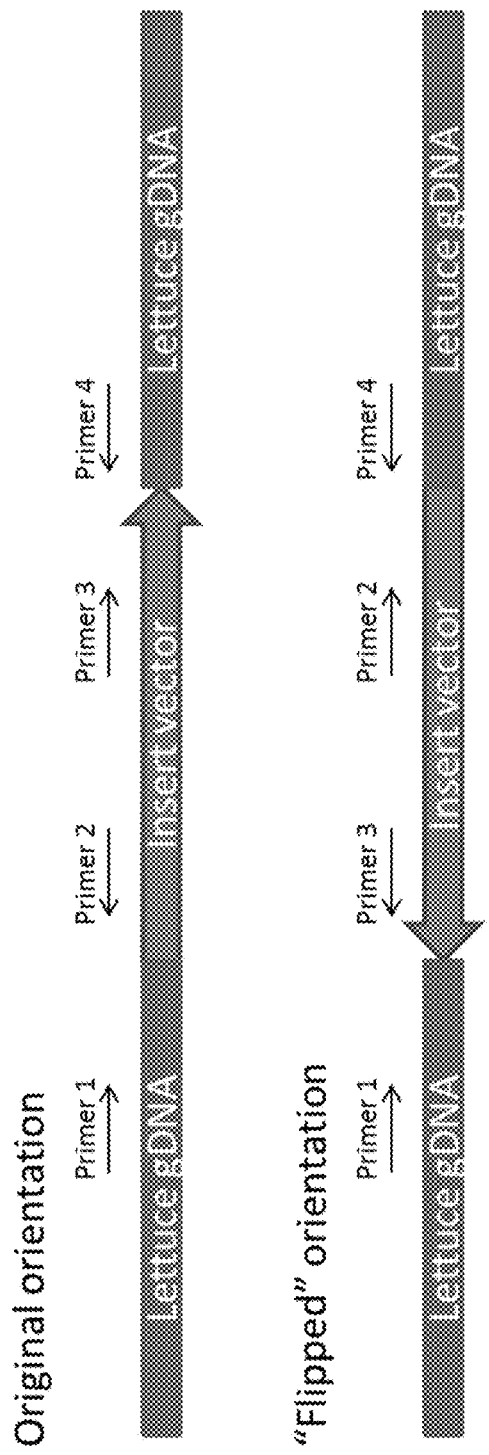
FIG. 38: Diagram of PCR screening strategy to identify any inserts in the reverse orientation.

To determine whether the insert always integrates in the same orientation, the population was also screened by end-point PCR by pairing a primer on the opposite side of the insert to the original endogenous primer. For example, Primer 3 was paired with Primer 4 to screen for the right border (SpecR side) in the original orientation. Primer 2 was paired with Primer 4 to screen for the right border (35S side) in the "flipped" orientation (FIG. 38). Screening for flipped insertions was performed for all 7 "preferred" integration sites that were repeated in multiple events in both lettuce and *N. benthamiana*. Flipped inserts were found in 3 events for site 7493878 in lettuce; of the sites screened this was the only one with flipped inserts.

While no gain or loss of sequence was seen for either the insert or gDNA when ID373 was inserted in site 7493878 in the original orientation, a 350 bp gap was seen from the left (35S side) gDNA: insert border in one of the events with ID373 inserted in the flipped orientation.

What is claimed is:

1. A method for incorporating an exogenous DNA into a plant genome, comprising:
co-transfecting a plant cell with:
(a) an exogenous DNA comprising an attP or attB site and
(b) a polynucleotide encoding an SPβc2 serine recombinase comprising a nucleotide sequence of SEQ ID NO:36, or a nucleotide sequence having at least 95% sequence identity to SEQ ID NO:36, operably linked to a promoter that is active in the plant;
selecting for integration of the exogenous DNA into the plant cell genome at a plant att pseudosite comprising a core sequence of SEQ ID NO:99 or SEQ ID NO:101 or a consensus sequence of SEQ ID NO:97, SEQ ID NO:98, SEQ ID NO: 100, SEQ ID NO: 130, or SEQ ID NO: 131; and
growing the plant cell.

2. The method of claim 1, wherein the exogenous DNA is up to 25 kb, up to 50 kb, up to 75 kb up to 100 kb, up to 150 kb, up to 200 kb, up to 250 kb or up to 300 kb.

3. The method of claim 1, wherein the target att pseudosite is a pseudo attB or pseudo attP site.

4. The method of claim 1, wherein the exogenous DNA comprises an attP site.

5. The method of claim 4, wherein the attP site has the sequence of SEQ ID NO:7.

6. The method of claim 1, wherein said plant cell comprises the exogenous DNA and the polynucleotide, further comprising introducing into the plant cell a polynucleotide encoding a second SPβc2 serine recombinase and a cognate Recombinase Directionality Factor (RDF) wherein the second SPβc2 serine recombinase and RDF are under the control of an inducible promoter or gene switch, wherein when activated, the promoter drives expression of the second SPβc2 serine recombinase and the RDF to excise the exogenous DNA from the plant genome.

7. The method of claim 6 wherein the RDF comprises the amino acid sequence of SEQ ID NO:31.

8. A transgenic plant cell obtained by the method of claim 1.

9. A transgenic plant obtained by culturing the transgenic plant cell of claim 8.

10. A method for obtaining site-specific recombination in a lettuce plant cell comprising:
contacting a lettuce plant cell with:
(a) an exogenous DNA comprising an attP or attB site; and
(b) a serine recombinase polypeptide that is active in a lettuce plant, wherein the serine recombinase is SPβc2;
selecting for integration of the exogenous DNA into the lettuce plant cell genome at a lettuce plant att pseudosite; and
growing the lettuce plant cell.

11. The method of claim 10, further comprising selecting for the integration of the exogenous DNA into one or more target att pseudosites on the lettuce chromosome.

12. The method of claim 10, wherein the exogenous DNA is up to 25 kb, up to 50 kb, up to 75 kb, up to 100 kb, up to 125 kb, up to 150 kb, or more than 150 kb, up to 150 kb, up to 200 kb, up to 250 kb or up to 300 kb.

13. The method of claim 10, wherein the target att pseudosite is a pseudo attB or pseudo attP site.

14. The method of claim 10, wherein the exogenous DNA comprises an attP site.

15. The method of claim 14, wherein the attP site has the sequence of SEQ ID NO:7.

16. The method of claim 10, wherein the SPβc2 serine recombinase has an amino acid sequence at least 65%, 70%, 75%, 80%, 85% or 90% identical to SEQ ID NO: 1.

17. The method of claim 10, wherein the SPβc2 serine recombinase is encoded by a plasmid that is co-transfected into the lettuce plant cell with the exogenous DNA.

18. A transgenic lettuce plant cell obtained by the method of claim 10, wherein said lettuce plant cell comprises the exogenous DNA and the polypeptide.

19. A transgenic lettuce plant obtained by culturing the transgenic lettuce plant cell of claim 18.

20. The method of claim 1, wherein said plant att pseudosite comprises the nucleic acid sequence of any one of SEQ ID NOs: 56, 66-96, 107-116, 132-139, or 140-146.

21. The method of claim 10, wherein the lettuce plant att pseudosite comprises the nucleic acid sequence of any one of SEQ ID NOs: 66-96, 130, 131, or 140-146.

* * * * *

SEQUENCE LISTING

```
<160> NUMBER OF SEQ ID NOS: 291

<210> SEQ ID NO 1
<211> LENGTH: 545
<212> TYPE: PRT
<213> ORGANISM: Bacillus subtilis

<400> SEQUENCE: 1

Met Glu Leu Lys Asn Ile Val Asn Ser Tyr Asn Ile Thr Asn Ile Leu
1               5                   10                  15

Gly Tyr Leu Arg Arg Ser Arg Gln Asp Met Glu Arg Glu Lys Arg Thr
            20                  25                  30

Gly Glu Asp Thr Leu Thr Glu Gln Lys Glu Leu Met Asn Lys Ile Leu
        35                  40                  45

Thr Ala Ile Glu Ile Pro Tyr Glu Leu Lys Met Glu Ile Gly Ser Gly
    50                  55                  60

Glu Ser Ile Asp Gly Arg Pro Val Phe Lys Glu Cys Leu Lys Asp Leu
65                  70                  75                  80

Glu Glu Gly Lys Tyr Gln Ala Ile Ala Val Lys Glu Ile Thr Arg Leu
                85                  90                  95

Ser Arg Gly Ser Tyr Ser Asp Ala Gly Gln Ile Val Asn Leu Leu Gln
            100                 105                 110

Ser Lys Arg Leu Ile Ile Ile Thr Pro Tyr Lys Val Tyr Asp Pro Arg
        115                 120                 125

Asn Pro Val Asp Met Arg Gln Ile Arg Phe Glu Leu Phe Met Ala Arg
    130                 135                 140

Glu Glu Phe Glu Met Thr Arg Glu Arg Met Thr Gly Ala Lys Tyr Thr
145                 150                 155                 160

Tyr Ala Ala Gln Gly Lys Trp Ile Ser Gly Leu Ala Pro Tyr Gly Tyr
                165                 170                 175

Gln Leu Asn Lys Lys Thr Ser Lys Leu Asp Pro Val Glu Asp Glu Ala
            180                 185                 190

Lys Val Val Gln Leu Ile Phe Asn Ile Phe Leu Asn Gly Leu Asn Gly
        195                 200                 205

Lys Asp Tyr Ser Tyr Thr Ala Ile Ala Ser His Leu Thr Asn Leu Gln
    210                 215                 220

Ile Pro Thr Pro Ser Gly Lys Lys Arg Trp Asn Gln Tyr Thr Ile Lys
225                 230                 235                 240

Ala Ile Leu Gln Asn Glu Val Tyr Ile Gly Thr Val Lys Tyr Lys Val
```

```
                    245                 250                 255
Arg Glu Lys Thr Lys Asp Gly Lys Arg Thr Ile Arg Pro Glu Lys Glu
            260                 265                 270

Gln Ile Val Val Gln Asp Ala His Ala Pro Ile Ile Asp Lys Glu Gln
        275                 280                 285

Phe Gln Gln Ser Gln Val Lys Ile Ala Asn Lys Val Pro Leu Leu Pro
    290                 295                 300

Asn Lys Asp Glu Phe Glu Leu Ser Glu Leu Ala Gly Val Cys Thr Cys
305                 310                 315                 320

Ser Lys Cys Gly Glu Pro Leu Ser Lys Tyr Glu Ser Lys Arg Ile Arg
                325                 330                 335

Lys Asn Lys Asp Gly Thr Glu Ser Val Tyr His Val Lys Ser Leu Thr
            340                 345                 350

Cys Lys Lys Asn Lys Cys Thr Tyr Val Arg Tyr Asn Asp Val Glu Asn
        355                 360                 365

Ala Ile Leu Asp Tyr Leu Ser Ser Leu Asn Asp Leu Asn Asp Ser Thr
    370                 375                 380

Leu Thr Lys His Ile Asn Ser Met Leu Ser Lys Tyr Glu Asp Asp Asn
385                 390                 395                 400

Ser Asn Met Lys Thr Lys Lys Gln Met Ser Glu His Leu Ser Gln Lys
                405                 410                 415

Glu Lys Glu Leu Lys Asn Lys Asn Phe Ile Phe Asp Lys Tyr Glu
            420                 425                 430

Ser Gly Ile Tyr Ser Asp Glu Leu Phe Leu Lys Arg Lys Ala Ala Leu
        435                 440                 445

Asp Glu Glu Phe Lys Glu Leu Gln Asn Ala Lys Asn Glu Leu Asn Gly
    450                 455                 460

Leu Gln Asp Thr Gln Ser Glu Ile Asp Ser Asn Thr Val Arg Asn Asn
465                 470                 475                 480

Ile Asn Lys Ile Ile Asp Gln Tyr His Ile Glu Ser Ser Ser Glu Lys
                485                 490                 495

Lys Asn Glu Leu Leu Arg Met Val Leu Lys Asp Val Ile Val Asn Met
            500                 505                 510

Thr Gln Lys Arg Lys Gly Pro Ile Pro Ala Gln Phe Glu Ile Thr Pro
        515                 520                 525

Ile Leu Arg Phe Asn Phe Ile Phe Asp Leu Thr Ala Thr Asn Ser Phe
    530                 535                 540

His
545

<210> SEQ ID NO 2
<211> LENGTH: 576
<212> TYPE: PRT
<213> ORGANISM: Artificial Sequence
<220> FEATURE:
<223> OTHER INFORMATION: Bacillus subtilis SPbeta2 with HA tag and NLS
      sequence

<400> SEQUENCE: 2

Met Glu Leu Lys Asn Ile Val Asn Ser Tyr Asn Ile Thr Asn Ile Leu
1               5                   10                  15

Gly Tyr Leu Arg Arg Ser Arg Gln Asp Met Glu Arg Glu Lys Arg Thr
            20                  25                  30

Gly Glu Asp Thr Leu Thr Glu Gln Lys Glu Leu Met Asn Lys Ile Leu
        35                  40                  45
```

```
Thr Ala Ile Glu Ile Pro Tyr Glu Leu Lys Met Glu Ile Gly Ser Gly
    50              55                  60

Glu Ser Ile Asp Gly Arg Pro Val Phe Lys Glu Cys Leu Lys Asp Leu
65              70              75                  80

Glu Glu Gly Lys Tyr Gln Ala Ile Ala Val Lys Glu Ile Thr Arg Leu
                85              90                  95

Ser Arg Gly Ser Tyr Ser Asp Ala Gly Gln Ile Val Asn Leu Leu Gln
                100             105             110

Ser Lys Arg Leu Ile Ile Ile Thr Pro Tyr Lys Val Tyr Asp Pro Arg
            115                 120             125

Asn Pro Val Asp Met Arg Gln Ile Arg Phe Glu Leu Phe Met Ala Arg
    130             135             140

Glu Phe Glu Met Thr Arg Glu Arg Met Thr Gly Ala Lys Tyr Thr
145             150             155                 160

Tyr Ala Ala Gln Gly Lys Trp Ile Ser Gly Leu Ala Pro Tyr Gly Tyr
                165             170             175

Gln Leu Asn Lys Lys Thr Ser Lys Leu Asp Pro Val Glu Asp Glu Ala
            180             185             190

Lys Val Val Gln Leu Ile Phe Asn Ile Phe Leu Asn Gly Leu Asn Gly
            195             200             205

Lys Asp Tyr Ser Tyr Thr Ala Ile Ala Ser His Leu Thr Asn Leu Gln
            210             215             220

Ile Pro Thr Pro Ser Gly Lys Lys Arg Trp Asn Gln Tyr Thr Ile Lys
225             230             235                 240

Ala Ile Leu Gln Asn Glu Val Tyr Ile Gly Thr Val Lys Tyr Lys Val
                245             250             255

Arg Glu Lys Thr Lys Asp Gly Lys Arg Thr Ile Arg Pro Glu Lys Glu
            260             265             270

Gln Ile Val Val Gln Asp Ala His Ala Pro Ile Ile Asp Lys Glu Gln
            275             280             285

Phe Gln Gln Ser Gln Val Lys Ile Ala Asn Lys Val Pro Leu Leu Pro
    290             295             300

Asn Lys Asp Glu Phe Glu Leu Ser Glu Leu Ala Gly Val Cys Thr Cys
305             310             315                 320

Ser Lys Cys Gly Glu Pro Leu Ser Lys Tyr Glu Ser Lys Arg Ile Arg
            325             330             335

Lys Asn Lys Asp Gly Thr Glu Ser Val Tyr His Val Lys Ser Leu Thr
            340             345             350

Cys Lys Lys Asn Lys Cys Thr Tyr Val Arg Tyr Asn Asp Val Glu Asn
            355             360             365

Ala Ile Leu Asp Tyr Leu Ser Ser Leu Asn Asp Leu Asn Asp Ser Thr
    370             375             380

Leu Thr Lys His Ile Asn Ser Met Leu Ser Lys Tyr Glu Asp Asp Asn
385             390             395                 400

Ser Asn Met Lys Thr Lys Lys Gln Met Ser Glu His Leu Ser Gln Lys
            405             410             415

Glu Lys Glu Leu Lys Asn Lys Glu Asn Phe Ile Phe Asp Lys Tyr Glu
            420             425             430

Ser Gly Ile Tyr Ser Asp Glu Leu Phe Leu Lys Arg Lys Ala Ala Leu
            435             440             445

Asp Glu Glu Phe Lys Glu Leu Gln Asn Ala Lys Asn Glu Leu Asn Gly
    450             455             460

Leu Gln Asp Thr Gln Ser Glu Ile Asp Ser Asn Thr Val Arg Asn Asn
```

```
              465                 470                 475                 480
Ile Asn Lys Ile Ile Asp Gln Tyr His Ile Glu Ser Ser Ser Glu Lys
                    485                 490                 495

Lys Asn Glu Leu Leu Arg Met Val Leu Lys Asp Val Ile Val Asn Met
            500                 505                 510

Thr Gln Lys Arg Lys Gly Pro Ile Pro Ala Gln Phe Glu Ile Thr Pro
            515                 520                 525

Ile Leu Arg Phe Asn Phe Ile Phe Asp Leu Thr Ala Thr Asn Ser Phe
            530                 535                 540

His Gly Tyr Pro Tyr Asp Val Pro Asp Tyr Ala Gly Leu Asp Ser Thr
545                 550                 555                 560

Ala Pro Lys Lys Lys Arg Lys Val Gly Ile His Gly Val Pro Ala Ala
                565                 570                 575
```

<210> SEQ ID NO 3
<211> LENGTH: 1751
<212> TYPE: DNA
<213> ORGANISM: Artificial Sequence
<220> FEATURE:
<223> OTHER INFORMATION: Bacillus subtilis with HA tag and NLS sequence

<400> SEQUENCE: 3

```
cctgcagggc caccatggaa cttaaaaaca ttgttaattc ttataacatt accaatatcc     60
tcggataccT tagaaggtcc aggcaggata tggagagaga gaaaaggact ggagaagata    120
ctcttactga gcagaaggaa cttatgaaca aaatcctcac cgccatcgaa atcccttacg    180
aacttaaaat ggaaatcggt tctggtgagt ccatcgacgg aaggccagtg ttcaaagagt    240
gtctcaagga tcttgaggaa ggaaaatacc aggctattgc tgtgaaggaa atcactaggc    300
tctctagggg atcttactcc gatgccggac agatcgtgaa cctccttcag tctaaaaggc    360
tcatcattat cactccatat aaggtgtacg acccaaggaa cccagttgac atgagacaaa    420
ttaggtttga acttttcatg gctagagagg agtttgaaat gactagggag aggatgaccg    480 gagctaaaata cacttacgcc gctcaaggaa agtggatttc tggtcttgcc ccatacggat    540
accaactcaa caaaaagact tctaaacttg acccagtgga ggacgaggcc aaggtggttc    600
agcttatttt caatatcttt cttaatggac tcaacggtaa ggactactcc tacactgcta    660
ttgcttccca cctcaccaat cttcagatcc ctaccccttc tggtaagaaa aggtggaacc    720
agtacactat caaagctatt cttcagaacg aagtttatat cggaaccgtg aagtataagg    780
tgagggagaa aaccaaggac ggaaaaagga ctatcagacc agaaaaggaa caaattgttg    840
tgcaagacgc tcatgctcct atcattgata agagcagtt ccagcaatcc caagtgaaga    900
ttgctaataa ggtgccactc cttcctaaca agatgagtt cgagctttcc gagttagctg    960
gtgtttgtac ctgttctaaa tgcggtgagc ctctttccaa gtatgagtcc aagagaatca   1020
gaaagaataa ggacggaact gagtccgttt atcacgttaa gtcccttact tgcaaaaaga   1080
ataagtgtac ctatgttaga tacaatgatg tggagaatgc tattcttgac tacctttctt   1140
ctcttaatga tctcaacgac tctactctta ctaagcatat caattctatg ctttccaagt   1200
atgaggacga taattctaat atgaaaacca aaaagcagat gtccgagcat ctttctcaaa   1260
aagagaaaga gctaaagaat aaggaaaact ttatctttga taaatacgaa tctggtatct   1320
attctgacga gctgttcctc aagagaaagg ccgctctcga tgaggagttt aaggaacttc   1380
agaacgccaa gaatgagttg aacggacttc aagatactca atccgagatt gattccaaca   1440
ctgttagaaa caatatcaat aagattatcg accaatatca cattgagtct agctctgaga   1500
```

```
aaaagaatga gcttcttaga atggtgctta aagatgtgat cgtgaacatg acccagaaaa    1560
ggaagggtcc aattccagcc caatttgaga ttaccoctat cctcaggttt aactttatct    1620
ttgatctcac cgccaccaat tcttttcacg gatacccta cgatgttcct gattacgctg     1680
ggctggacag caccgctccc aaaagaaaa ggaaggtggg cattcacggc gtgcctgcgg     1740
cctgaatcga t                                                         1751

<210> SEQ ID NO 4
<211> LENGTH: 6331
<212> TYPE: DNA
<213> ORGANISM: Artificial Sequence
<220> FEATURE:
<223> OTHER INFORMATION: attP-GFP Reporter plasmid

<400> SEQUENCE: 4
gcaagggcga ggagctgttc accggggtgg tgcccatcct ggtcgagctg gacggcgacg      60
taaacggcca caagttcagc gtgtccggcg agggcgaggg cgatgccacc tacggcaagc     120
tgaccctgaa gttcatctgc accaccggca agctgcccgt gccctggccc accctcgtga     180
ccaccttcac ctacggcgtg cagtgcttca gccgctaccc cgaccacatg aagcagcacg     240
acttcttcaa gtccgccatg cccgaaggct acgtccagga gcgcaccatc ttcttcaagg     300
acgacggcaa ctacaagacc cgcgccgagg tgaagttcga gggcgacacc ctggtgaacc     360
gcatcgagct gaagggcatc gacttcaagg aggacggcaa catcctgggg cacaagctgg     420
agtacaacta caacagccac aacgtctata tcatggccga caagcagaag aacggcatca     480
aggtgaactt caagatccgc cacaacatcg aggacggcag cgtgcagctc gccgaccact     540
accagcagaa cacccccatc ggcgacggcc ccgtgctgct gcccgacaac cactacctga     600
gcacccagtc cgccctgagc aaagacccca acgagaagcg cgatcacatg gtcctgctgg     660
agttcgtgac cgccgccggg atcactcacg gcatggacga gctgtacaag taaatcgatg     720
acttcccgat cgttcaaaca tttggcaata aagtttctta agattgaatc ctgttgccgg     780
tcttgcgatg attatcatat aatttctgtt gaattacgtt aagcatgtaa taattaacat     840
gtaatgcatg acgttattta tgagatgggt ttttatgatt agagtcccgc aattatacat     900
ttaatacgcg atagaaaaca aaatatagcg cgcaaactag gataaattat cgcgcgcggt     960
gtcatctatg ttactagatc ggggctcgag gaatggagct gtaacgtgag caacgcggtc    1020
cggttcggct gcggccgccc gggctcgagc ggtccggcga tcgcaagggc gaattcggag    1080
cctgcttttt tgtacaaagt tggcattata aaaaagcatt gctcatcaat tgttgcaac     1140 gaacaggtca ctatcagtca aaataaaatc attatttggg ccccagaag gtaattatcc     1200 aagatgtagc atcaagaatc caatgtttac gggaaaaact atggaagtat tatgtgaact    1260
cagcaagaag cagatcaata tgcggcacat attcaaccta tgttcaaaaa tgaagaatgt    1320
acagatacaa gatcctatac tgccagaata cgaagaagaa tacatagaaa ttgaaaagaa    1380
agaaccaggc gaagaaaaga atcttgaaga cgtaagcact gacgacaaca atgaaaagaa    1440
gaagataagg tcggtgattg tgaaagagac atagaggaca catgtaaggt ggaaaatgta    1500
agggcggaaa gtaaccttat cacaaaggaa tcttatcccc cactactat cctttatat     1560 tttccgtgt catttttgcc cttgagtttt cctatataag gaaccaagtt cggcatttgt    1620
gaaaacaaga aaaatttggg tgtaagctat tttctttgaa gtactgagga tacaacttca    1680
gagaaatttg taagtttgcc tgcagggcat tgtgtgcttt tcgggctagc gcaaaaatgc    1740
```

```
agatcttcgt gaagacctta acggggaaga cgatcaccct agaggttgag tcttccgaca    1800
ccatcgacaa tgtcaaagcc aagatccagg acaaggaagg gattccccca gaccagcagc    1860
gtttgatttt cgccggaaag cagcttgagg atggtcgtac tcttgccgac tacaacatcc    1920
agaaggagtc aactctccat ctcgtgctcc gtctccgtgg tggtagttta aacatgattg    1980
aacaagatgg attgcacgca ggttctccgg ccgcttgggt ggagaggcta ttcggctatg    2040
actgggcaca acagacaatc ggctgctctg atgccgccgt gttccggctg tcagcgcagg    2100
gaaggccagt tcttttttgtc aagaccgacc tgtccggtgc cctgaatgaa cttcaagacg    2160
aggcagcgcg gctatcgtgg ctggccacga cgggcgttcc ttgcgctgct gtgctcgacg    2220
ttgtcactga agcgggaagg gactggctgc tattgggcga agtgccgggg caggatctcc    2280
tgtcatctca ccttgctcct gccgagaaag tatccatcat ggctgatgca atgcggcggc    2340
tgcatacgct tgatccggct acctgcccat tcgaccacca agcgaaacat cgcatcgagc    2400
gagcacgtac tcggatggaa gccggtcttg tcgatcagga tgatctggac gaagagcatc    2460
aggggctcgc gccagccgaa ctgttcgcca ggctcaaggc gaggatgcca gacggcgagg    2520
atctcgtcgt gacccatggc gatgcctgct tgccgaatat catggtggaa atggccgct    2580 tttctggatt catcgactgt ggaaggcttg gtgtggctga taggtatcag gacatagcgt    2640
tggctacccg tgatattgct gaagagcttg gcggcgaatg ggctgaccgc ttcctcgtgc    2700
tttacggtat cgccgctccc gattcgcagc gcatcgcctt ctatcgcctt cttgacgagt    2760
tcttctgaat cgatttttaa tgtttagcaa atgtcttatc agttttcttt tttgtcgaac    2820
ggtaatttag agttttttt tgctatatgg attttcgttt tgatgtata tgtgacaacc    2880 ctcgggattg ttgatttatt tcaaaactaa gagttttgc ttattgttct cgtctatttt    2940
ggatatcaaa gttaacgcga gagtaggaa ctgccaggca tcaaataaaa cgaaaggctc    3000
agtcggaaga ctgggccttt cgttttatct gttgtttgtc ggtgaacgct ctcctgagta    3060
ggacaaatcc gccgggagcg gatttgaacg ttgtgaagca acggcccgga gggtggcggg    3120
caggacgccc gccataaact gccaggcatc aaactaagca gaaggccatc ctgacggatg    3180
gcctttttgc gtttctacaa actcttcctg gctagcggta cgcgtattaa ttgcgttgcg    3240
ctcactgccc gctttccagt cgggaaacct gtcgtgccag ctgcattaat gaatcggcca    3300
acgcgcgggg agaggcggtt tgcgtattgg gcgctcttcc gcttcctcgc tcactgactc    3360
gctgcgctcg tcgttcggc tgcggcgagc ggtatcagct cactcaaagg cggtaatacg    3420
gttatccaca gaatcagggg ataacgcagg aaagaacatg tgagcaaaag gccagcaaaa    3480
ggccaggaac cgtaaaaagg ccgcgttgct ggcgtttttc cataggctcc gcccccctga    3540
cgagcatcac aaaaatcgac gctcaagtca gaggtggcga aacccgacag gactataaag    3600
ataccaggcg tttccccctg gaagctccct cgtgcgctct cctgttccga ccctgccgct    3660
taccggatac ctgtccgcct ttctcccttc gggaagcgtg cgctttctc aatgctcacg    3720 ctgtaggtat ctcagttcgg tgtaggtcgt tcgctccaag ctgggctgtg tgcacgaacc    3780
ccccgttcag cccgaccgct gcgccttatc cggtaactat cgtcttgagt ccaacccggt    3840
aagacacgac ttatcgccac tggcagcagc cactggtaac aggattagca gagcgaggta    3900
tgtaggcggt gctacagagt tcttgaagtg gtggcctaac tacggctaca ctagaaggac    3960
agtatttggt atctgcgctc tgctgaagcc agttaccttc ggaaaaagag ttggtagctc    4020
ttgatccggc aaacaaacca ccgctggtag cggtggtttt tttgtttgca agcagcagat    4080
tacgcgcaga aaaaaaggat ctcaagaaga tcctttgatc ttttctacgg ggtctgacgc    4140
```

```
tcagtggaac gacgcgtaac tcacgttaag ggattttggt catgggtggc tcgagggtta    4200
tttgccgact accttggtga tctcgccttt cacgtagtgg acaaattctt ccaactgatc    4260
tgcgcgcgag gccaagcgat cttcttcttg tccaagataa gcctgtctag cttcaagtat    4320
gacgggctga tactgggccg gcaggcgctc cattgcccag tcggcagcga catccttcgg    4380
cgcgattttg ccggttactg cgctgtacca aatgcgggac aacgtaagca ctacatttcg    4440
ctcatcgcca gcccagtcgg gcggcgagtt ccatagcgtt aaggtttcat ttagcgcctc    4500
aaatagatcc tgttcaggaa ccggatcaaa gagttcctcc gccgctggac ctaccaaggc    4560
aacgctatgt tctcttgctt ttgtcagcaa gatagccaga tcaatgtcga tcgtggctgg    4620
ctcgaagata cctgcaagaa tgtcattgcg ctgccattct ccaaattgca gttcgcgctt    4680
agctggataa cgccacggaa tgatgtcgtc gtgcacaaca atggtgactt ctacagcgcg    4740
gagaatctcg ctctctccag gggaagccga agtttccaaa aggtcgttga tcaaagctcg    4800
ccgcgttgtt tcatcaagcc ttacggtcac cgtaaccagc aaatcaatat cactgtgtgg    4860
cttcaggccg ccatccactg cggagccgta caaatgtacg ccagcaacg tcggttcgag    4920
atggcgctcg atgacgccaa ctacctctga tagttgagtc gatacttcgg cgatcaccgc    4980
ttccctcatg atgtttaact tgttttagg gcgactgccc tgctgcgtaa catcgttgct    5040
gctccataac atcaaacatc gacccacggc gtaacgcgct tgctgcttgg atgcccgagg    5100
catagactgt accccaaaaa aacagtcata acaagccatg aaaaccgcca ctgcgccgtt    5160
accaccgctg cgttcggtca aggttctgga ccagttgcgt gagcgcatac gctacttgca    5220
ttacagctta cgaaccgaac aggcttatgt ccactgggtt cgtgccttca tccgtttcca    5280
cggtgtgcgt cacccggcaa ccttgggcag cagcgaagtc gaggcatttc tgtcctggct    5340
ggtctagagg aggcatgatg atatattttt atcttgtgca atgtaacatc agagattttg    5400
agacacgggc cagagctgcc aggaaacagc tatgaccatg taatacgact cactataggg    5460
gatatcagct ggatggcaaa taatgatttt attttgactg atagtgacct gttcgttgca    5520
acaaattgat gagcaattat tttttataat gccaactttg tacaagaaag ctgggtcgaa    5580
ttcgcccttg gcgcgccaaa gtagtaagta tcttaaaaaa cagataaagc tgtatattaa    5640
gatacttact acgcgtggtc cgatgtgaga cttttcaaca aagggtaata tccggaaacc    5700
tcctcggatt ccattgccca gctatctgtc actttattgt gaagatagtg gaaaggaag    5760
gtggctccta caaatgccat cattgcgata aggaaaggc catcgttgaa gatgcctctg    5820
ccgacagtgg tcccaaagat ggaccccac ccacgaggag catcgtggaa aaagaagacg    5880
ttccaaccac gtcttcaaag caagtggatt gatgtgatgg tccgatgtga gactttcaa    5940
caaagggtaa tatccggaaa cctcctcgga ttccattgcc cagctatctg tcactttatt    6000
gtgaagatag tggaaaagga aggtggctcc tacaaatgcc atcattgcga taaggaaag    6060
gccatcgttg aagatgcctc tgccgacagt ggtcccaaag atggaccccc acccacgagg    6120
agcatcgtgg aaaaagaaga cgttccaacc acgtcttcaa agcaagtgga ttgatgtgat    6180
atctccactg acgtaaggga tgacgcacaa tcccactatc cttcgcaaga cccttcctct    6240
atataaggaa gttcatttca tttggagagg acacgcgaca agctgactct agcagatcct    6300
ccagactgca gggctagcgc aaaaatggtg a                                   6331
```

<210> SEQ ID NO 5
<211> LENGTH: 5617
<212> TYPE: DNA

<213> ORGANISM: Artificial Sequence
<220> FEATURE:
<223> OTHER INFORMATION: 35S SPBc2-NOS plasmid

<400> SEQUENCE: 5

| | | | | | |
|---|---|---|---|---|---|
| aacatgtgag | caaaaggcca | gcaaaaggcc | aggaaccgta | aaaaggccgc | gttgctggcg | 60 |
| ttttttccata | ggctccgccc | ccctgacgag | catcacaaaa | atcgacgctc | aagtcagagg | 120 |
| tggcgaaacc | cgacaggact | ataaagatac | caggcgtttc | ccctggaag | ctccctcgtg | 180 |
| cgctctcctg | ttccgaccct | gccgcttacc | ggatacctgt | ccgcctttct | cccttcggga | 240 |
| agcgtggcgc | tttctcaatg | ctcacgctgt | aggtatctca | gttcggtgta | ggtcgttcgc | 300 |
| tccaagctgg | gctgtgtgca | cgaaccccc | gttcagcccg | accgctgcgc | cttatccggt | 360 |
| aactatcgtc | ttgagtccaa | cccggtaaga | cacgacttat | cgccactggc | agcagccact | 420 |
| ggtaacagga | ttagcagagc | gaggtatgta | ggcggtgcta | cagagttctt | gaagtggtgg | 480 |
| cctaactacg | gctacactag | aaggacagta | tttggtatct | gcgctctgct | gaagccagtt | 540 |
| accttcggaa | aaagagttgg | tagctcttga | tccggcaaac | aaaccaccgc | tggtagcggt | 600 |
| ggtttttttg | tttgcaagca | gcagattacg | cgcagaaaaa | aaggatctca | agaagatcct | 660 |
| ttgatctttt | ctacggggtc | tgacgctcag | tggaacgacg | cgtaactcac | gttaagggat | 720 |
| tttggtcatg | ggtggctcga | gggttatttg | ccgactacct | tggtgatctc | gcctttcacg | 780 |
| tagtggacaa | attcttccaa | ctgatctgcg | cgcgaggcca | agcgatcttc | ttcttgtcca | 840 |
| agataagcct | gtctagcttc | aagtatgacg | ggctgatact | gggccggcag | gcgctccatt | 900 |
| gcccagtcgg | cagcgacatc | cttcggcgcg | attttgccgg | ttactgcgct | gtaccaaatg | 960 |
| cgggacaacg | taagcactac | atttcgctca | tcgccagccc | agtcgggcgg | cgagttccat | 1020 |
| agcgttaagg | tttcatttag | cgcctcaaat | agatcctgtt | caggaaccgg | atcaaagagt | 1080 |
| tcctccgccg | ctggacctac | caaggcaacg | ctatgttctc | ttgcttttgt | cagcaagata | 1140 |
| gccagatcaa | tgtcgatcgt | ggctggctcg | aagatacctg | caagaatgtc | attgcgctgc | 1200 |
| cattctccaa | attgcagttc | gcgcttagct | ggataacgcc | acggaatgat | gtcgtcgtgc | 1260 |
| acaacaatgg | tgacttctac | agcgcggaga | atctcgctct | ctccagggga | agccgaagtt | 1320 |
| tccaaaggt | cgttgatcaa | agctcgccgc | gttgtttcat | caagccttac | ggtcaccgta | 1380 |
| accagcaaat | caatatcact | gtgtggcttc | aggccgccat | ccactgcgga | gccgtacaaa | 1440 |
| tgtacggcca | gcaacgtcgg | ttcgagatgg | cgctcgatga | cgccaactac | ctctgatagt | 1500 |
| tgagtcgata | cttcggcgat | caccgcttcc | ctcatgatgt | ttaactttgt | tttagggcga | 1560 |
| ctgccctgct | gcgtaacatc | gttgctgctc | cataacatca | aacatcgacc | cacggcgtaa | 1620 |
| cgcgcttgct | gcttggatgc | ccgaggcata | gactgtaccc | caaaaaaaca | gtcataacaa | 1680 |
| gccatgaaaa | ccgccactgc | gccgttacca | ccgctgcgtt | cggtcaaggt | tctggaccag | 1740 |
| ttgcgtgagc | gcatacgcta | cttgcattac | agcttacgaa | ccgaacaggc | ttatgtccac | 1800 |
| tgggttcgtg | ccttcatccg | tttccacggt | gtgcgtcacc | cggcaacctt | gggcagcagc | 1860 |
| gaagtcgagg | catttctgtc | ctggctggtc | tagaggaggc | atgatgatat | atttttatct | 1920 |
| tgtgcaatgt | aacatcagag | attttgagac | acgggccaga | gctgccagga | acagctatg | 1980 |
| accatgtaat | acgactcact | atagggagata | tcagctggat | ggcaaataat | gattttattt | 2040 |
| tgactgatag | tgacctgttc | gttgcaacaa | attgatgagc | aattattttt | tataatgcca | 2100 |
| actttgtaca | agaaagctgg | gtcgaattcg | cccttgcgc | gcctgggat | agcgatcgcc | 2160 |
| acgatccgaa | atacctcaac | tgtgacgcgt | ggtccgatgt | gagacttttc | aacaaagggt | 2220 |

```
aatatccgga aacctcctcg gattccattg cccagctatc tgtcacttta ttgtgaagat   2280
agtggaaaag gaaggtggct cctacaaatg ccatcattgc gataaaggaa aggccatcgt   2340
tgaagatgcc tctgccgaca gtggtcccaa agatggaccc ccacccacga ggagcatcgt   2400
ggaaaaagaa gacgttccaa ccacgtcttc aaagcaagtg gattgatgtg atggtccgat   2460
gtgagacttt tcaacaaagg gtaatatccg gaaacctcct cggattccat tgcccagcta   2520
tctgtcactt tattgtgaag atagtggaaa aggaaggtgg ctcctacaaa tgccatcatt   2580
gcgataaagg aaaggccatc gttgaagatg cctctgccga cagtggtccc aaagatggac   2640
ccccacccac gaggagcatc gtggaaaaag aagacgttcc aaccacgtct caaagcaag   2700 tggattgatg tgatatctcc actgacgtaa gggatgacgc acaatcccac tatccttcgc   2760
aagacccttc ctctatataa ggaagttcat ttcatttgga gaggacacgc gacaagctga   2820
ctctagcaga tcctccagac ctgcagggcc accatggaac ttaaaaacat tgttaattct   2880
tataacatta ccaatatcct cggataccett agaaggtcca ggcaggatat ggagagagag   2940
aaaaggactg gagaagatac tcttactgag cagaaggaac ttatgaacaa aatcctcacc   3000
gccatcgaaa tcccttacga acttaaaatg gaaatcggtt ctggtgagtc catcgacgga   3060
aggccagtgt tcaaagagtg tctcaaggat cttgaggaag gaaaatacca ggctattgct   3120
gtgaaggaaa tcactaggct ctctagggga tcttactccg atgccggaca gatcgtgaac   3180
ctccttcagt ctaaaaggct catcattatc actccatata aggtgtacga cccaaggaac   3240
ccagttgaca tgagacaaat taggtttgaa cttttcatgg ctagagagga gtttgaaatg   3300
actagggaga ggatgaccgg agctaaatac acttacgccg ctcaaggaaa gtggatttct   3360
ggtcttgccc catacggata ccaactcaac aaaaagactt ctaaacttga cccagtggag   3420
gacgaggcca aggtggttca gcttattttc aatatctttc ttaatggact caacggtaag   3480
gactactcct acactgctat tgcttcccac ctcaccaatc ttcagatccc taccccttct   3540
ggtaagaaaa ggtggaacca gtacactatc aaagctattc ttcagaacga gtttatatc   3600 ggaaccgtga gtataaggt gagggagaaa accaaggacg gaaaaaggac tatcagacca   3660
gaaaaggaac aaattgttgt gcaagacgct catgctccta tcattgataa agagcagttc   3720
cagcaatccc aagtgaagat tgctaataag gtgccactcc ttcctaacaa agatgagttc   3780
gagctttccg agttagctgg tgtttgtacc tgttctaaat gcggtgagcc tctttccaag   3840
tatgagtcca agagaatcag aaagaataag gacggaactg agtccgttta tcacgttaag   3900
tcccttactt gcaaaaagaa taagtgtacc tatgttagat acaatgatgt ggagaatgct   3960
attcttgact accttctctc tcttaatgat ctcaacgact ctactcttac taagcatatc   4020
aattctatgc tttccaagta tgaggacgat aattctaata tgaaaccaa aaagcagatg   4080 tccgagcatc tttctcaaaa agagaaagag ctaaagaata aggaaaactt tatctttgat   4140
aaatacgaat ctggtatcta ttctgacgag ctgttcctca agagaaaggc cgctctcgat   4200
gaggagttta aggaacttca gaacgccaag aatgagttga acggacttca agatactcaa   4260
tccgagattg attccaacac tgttagaaac aatatcaata agattatcga ccaatatcac   4320
attgagtcta gctctgagaa aaagaatgag cttcttagaa tggtgcttaa agatgtgatc   4380
gtgaacatga cccagaaaag gaagggtcca attccagccc aatttgagat taccccctatc   4440 ctcaggttta actttatctt tgatctcacc gccaccaatt ctttttcacgg ataccccttac   4500 gatgttcctg attacgctgg gctggacagc accgctccca aaaagaaaag gaaggtgggc   4560
```

-continued

```
attcacggcg tgcctgcggc ctgaatcgat gacttcccga tcgttcaaac atttggcaat    4620
aaagtttctt aagattgaat cctgttgccg gtcttgcgat gattatcata taatttctgt    4680
tgaattacgt taagcatgta ataattaaca tgtaatgcat gacgttattt atgagatggg    4740
ttttttatgat tagagtcccg caattataca tttaatacgc gatagaaaac aaaatatagc   4800
gcgcaaacta ggataaatta tcgcgcgcgg tgtcatctat gttactagat cggggctcga    4860
ggaatggagc tgtaacgtga gcaacgcggt ccggttcggc tgcggccgcc cgggctcgag    4920
cggtccggcg atcgcaaggg cgaattcgga gcctgctttt ttgtacaaag ttggcattat    4980
aaaaaagcat tgctcatcaa tttgttgcaa cgaacaggtc actatcagtc aaaataaaat    5040
cattatttgg ggcccgagct taagactggc cgtcgtttta caacgtcgtg actgggaaaa    5100
catccatgct agcgttaacg cgagagtagg gaactgccag gcatcaaata aaacgaaagg    5160
ctcagtcgga agactgggcc tttcgtttta tctgttgttt gtcggtgaac gctctcctga    5220
gtaggacaaa tccgccggga gcggatttga acgttgtgaa gcaacggccc ggagggtggc    5280
gggcaggacg cccgccataa actgccaggc atcaaactaa gcagaaggcc atcctgacgg    5340
atggcctttt tgcgttccta caaactcttc ctggctagcg gtacgcgtat taattgcgtt    5400
gcgctcactg cccgctttcc agtcgggaaa cctgtcgtgc cagctgcatt aatgaatcgg    5460
ccaacgcgcg gggagaggcg gtttgcgtat tgggcgctct ccgcttcct cgctcactga    5520
ctcgctgcgc tcggtcgttc ggctgcggcg agcggtatca gctcactcaa aggcggtaat    5580
acggttatcc acagaatcag gggataacgc aggaaag                             5617
```

```
<210> SEQ ID NO 6
<211> LENGTH: 62
<212> TYPE: DNA
<213> ORGANISM: Bacillus subtilis

<400> SEQUENCE: 6
agtgcagcat gtcattaata tcagtacaga taaagctgta tctcctgtga acacaatggg    60
tg                                                                   62

<210> SEQ ID NO 7
<211> LENGTH: 55
<212> TYPE: DNA
<213> ORGANISM: Bacillus subtilis

<400> SEQUENCE: 7
aaagtagtaa gtatcttaaa aaacagataa agctgtatat taagatactt actac         55

<210> SEQ ID NO 8
<211> LENGTH: 200
<212> TYPE: DNA
<213> ORGANISM: Streptococcus pyogenes

<400> SEQUENCE: 8
gttttccatt gttttttga agtgtctgat gttctgtgat atgataaaag ggataataac     60
gtttgtaaag gagactgata atggcatgta caactatact cgtcggtaaa aaggcatctt    120
atgatggctc aaccatggtt gctcgaacag aagattctca aaatggtgat ttcacgccta    180
aaaaaatgat tgtggtgaaa                                                200

<210> SEQ ID NO 9
<211> LENGTH: 200
<212> TYPE: DNA
<213> ORGANISM: Streptococcus pyogenes
```

```
<400> SEQUENCE: 9 attttttgtat ccagttcaat ggatatttga tataatcgtc ttaaaaagga ggtcgtgaaa        60
tggataaaaa aatacagcgt ttttcatgta caactatact agttgtagtg cctaaataat       120
gcttttaaaa cttaaaaata atatcgatgt tatccatagt aacctcgact ctatctatca       180
attgcttaac tatcctagat                                                    200

<210> SEQ ID NO 10
<211> LENGTH: 49
<212> TYPE: DNA
<213> ORGANISM: Listeria monocytogenes

<400> SEQUENCE: 10
aacttttcgg atcaagctat gaaggacgca aagagggaac taaacactt                     49

<210> SEQ ID NO 11
<211> LENGTH: 49
<212> TYPE: DNA
<213> ORGANISM: Listeria monocytogenes

<400> SEQUENCE: 11
ttagttcctc gttttctctc gttggaagaa gaagaaacga gaaactaaa                     49

<210> SEQ ID NO 12
<211> LENGTH: 50
<212> TYPE: DNA
<213> ORGANISM: Mycobacterium avium

<400> SEQUENCE: 12
tcggccggct tgtcgacgac ggcggtctcc gtcgtcagga tcatccgggc                    50

<210> SEQ ID NO 13
<211> LENGTH: 58
<212> TYPE: DNA
<213> ORGANISM: Mycobacterium avium

<400> SEQUENCE: 13
gtcgtggttt gtctggtcaa ccaccgcggt ctcagtggtg tacggtacaa accccgac           58

<210> SEQ ID NO 14
<211> LENGTH: 45
<212> TYPE: DNA
<213> ORGANISM: Streptomyces phage C31

<400> SEQUENCE: 14
tgcgggtgcc agggcgtgcc cttgggctcc ccgggcgcgt actcc                         45

<210> SEQ ID NO 15
<211> LENGTH: 42
<212> TYPE: DNA
<213> ORGANISM: Streptomyces phage C31

<400> SEQUENCE: 15
gtgccccaac tggggtaacc tttgagttct ctcagttggg gg                            42

<210> SEQ ID NO 16
<211> LENGTH: 20
<212> TYPE: PRT
<213> ORGANISM: Simian virus 40

<400> SEQUENCE: 16
```

```
Ala Val Lys Arg Pro Ala Ala Thr Lys Lys Ala Gly Gln Ala Lys Lys
1               5                   10                  15

Lys Lys Leu Asp
            20

<210> SEQ ID NO 17
<211> LENGTH: 25
<212> TYPE: PRT
<213> ORGANISM: Caenorhabditis elegans

<400> SEQUENCE: 17

Met Ser Arg Arg Arg Lys Ala Asn Pro Thr Lys Leu Ser Glu Asn Ala
1               5                   10                  15

Lys Lys Leu Ala Lys Glu Val Glu Asn
            20                  25

<210> SEQ ID NO 18
<211> LENGTH: 9
<212> TYPE: PRT
<213> ORGANISM: Homo sapiens

<400> SEQUENCE: 18

Pro Ala Ala Lys Arg Val Lys Leu Asp
1               5

<210> SEQ ID NO 19
<211> LENGTH: 9
<212> TYPE: PRT
<213> ORGANISM: Escherichia coli

<400> SEQUENCE: 19

Lys Leu Lys Ile Lys Arg Pro Val Lys
1               5

<210> SEQ ID NO 20
<211> LENGTH: 5
<212> TYPE: PRT
<213> ORGANISM: Artificial Sequence
<220> FEATURE:
<223> OTHER INFORMATION: Epitope tag sequence

<400> SEQUENCE: 20

Phe His His Thr Thr
1               5

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 21
catttcattt ggagaggaca                                            20

<210> SEQ ID NO 22
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 22
gaaaactgat aagacatttg ctaaac                                     26
```

```
<210> SEQ ID NO 23
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 23
gtactcttgc cgactacaac atc                                            23

<210> SEQ ID NO 24
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 24
gaacccagtg gacataagc                                                 19

<210> SEQ ID NO 25
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 25
aggtttcatt tagcgcctc                                                 19

<210> SEQ ID NO 26
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 26
gataatcatc gcaagaccg                                                 19

<210> SEQ ID NO 27
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 27
atgtctctgt ttggaaatgt ttc                                            23

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 28
caatggtgca ggtaaaacat                                                20

<210> SEQ ID NO 29
<211> LENGTH: 174
<212> TYPE: DNA
<213> ORGANISM: Artificial Sequence
<220> FEATURE:
<223> OTHER INFORMATION: Codon-optimized Recombinase Directionality
```

Factor

<400> SEQUENCE: 29
atggaaccat atcaaagata tgaagaactt aagaagaaga ctattaaggt tgttcaaaag     60
gaaaattatt ctattagata tattactcaa gatgaagctt ctaatgatct tgatgaattt    120
tataagcaat ttgctcaaca tcttcttgaa gctgctcttg aaagaaaggc tgaa          174

<210> SEQ ID NO 30
<211> LENGTH: 270
<212> TYPE: DNA
<213> ORGANISM: Artificial Sequence
<220> FEATURE:
<223> OTHER INFORMATION: Codon-optimized Recombinase Directionality
      Factor with HA tag and NLS

<400> SEQUENCE: 30
atggaaccat atcaaagata tgaagaactt aagaagaaga ctattaaggt tgttcaaaag     60
gaaaattatt ctattagata tattactcaa gatgaagctt ctaatgatct tgatgaattt    120
tataagcaat ttgctcaaca tcttcttgaa gctgctcttg aaagaaaggc tgaaggatac   180
ccttacgatg ttcctgatta cgctgggctg gacagcaccg ctcccaaaaa gaaaaggaag   240
gtgggcattc acggcgtgcc tgcggcctga                                    270

<210> SEQ ID NO 31
<211> LENGTH: 58
<212> TYPE: PRT
<213> ORGANISM: Bacillus subtilis

<400> SEQUENCE: 31

Met Glu Pro Tyr Gln Arg Tyr Glu Glu Leu Lys Lys Lys Thr Ile Lys
1               5                   10                  15

Val Val Gln Lys Glu Asn Tyr Ser Ile Arg Tyr Ile Thr Gln Asp Glu
            20                  25                  30

Ala Ser Asn Asp Leu Asp Glu Phe Tyr Lys Gln Phe Ala Gln His Leu
        35                  40                  45

Leu Glu Ala Ala Leu Glu Arg Lys Ala Glu
    50                  55

<210> SEQ ID NO 32
<211> LENGTH: 89
<212> TYPE: PRT
<213> ORGANISM: Artificial Sequence
<220> FEATURE:
<223> OTHER INFORMATION: Recombinase Directionality Factor with HA tag
      and NLS

<400> SEQUENCE: 32

Met Glu Pro Tyr Gln Arg Tyr Glu Glu Leu Lys Lys Lys Thr Ile Lys
1               5                   10                  15

Val Val Gln Lys Glu Asn Tyr Ser Ile Arg Tyr Ile Thr Gln Asp Glu
            20                  25                  30

Ala Ser Asn Asp Leu Asp Glu Phe Tyr Lys Gln Phe Ala Gln His Leu
        35                  40                  45

Leu Glu Ala Ala Leu Glu Arg Lys Ala Glu Gly Tyr Pro Tyr Asp Val
    50                  55                  60

Pro Asp Tyr Ala Gly Leu Asp Ser Thr Ala Pro Lys Lys Lys Arg Lys
65                  70                  75                  80

Val Gly Ile His Gly Val Pro Ala Ala
            85

<210> SEQ ID NO 33
<211> LENGTH: 63
<212> TYPE: DNA
<213> ORGANISM: Artificial Sequence
<220> FEATURE:
<223> OTHER INFORMATION: NLS sequence

<400> SEQUENCE: 33
gggctggaca gcaccgctcc caaaaagaaa aggaaggtgg gcattcacgg cgtgcctgcg    60
gcc                                                                  63

<210> SEQ ID NO 34
<211> LENGTH: 30
<212> TYPE: DNA
<213> ORGANISM: Artificial Sequence
<220> FEATURE:
<223> OTHER INFORMATION: HA tag sequence

<400> SEQUENCE: 34
ggataccctt acgatgttcc tgattacgct                                     30

<210> SEQ ID NO 35
<211> LENGTH: 1923
<212> TYPE: DNA
<213> ORGANISM: Artificial Sequence
<220> FEATURE:
<223> OTHER INFORMATION: Synthetic construct containing SPBc2 serine
      recombinase and RDF

<400> SEQUENCE: 35
atggaactta aaacattgt taattcttat aacattacca atatcctcgg ataccttaga    60
aggtccaggc aggatatgga gagagagaaa aggactggag aagatactct tactgagcag   120
aaggaactta tgaacaaaat cctcaccgcc atcgaaatcc cttacgaact aaaatggaa    180 atcggttctg gtgagtccat cgacggaagg ccagtgttca agagtgtct caaggatctt   240 gaggaaggaa ataccaggc tattgctgtg aaggaaatca ctaggctctc tagggatct    300 tactccgatg ccggacagat cgtgaacctc cttcagtcta aaaggctcat cattatcact   360
ccatataagg tgtacgaccc aaggaaccca gttgacatga gacaaattag gtttgaactt   420
ttcatggcta gagaggagtt tgaaatgact agggagagga tgaccggagc taaatacact   480
tacgccgctc aaggaaagtg gatttctggt cttgccccat acggatacca actcaacaaa   540
aagacttcta aacttgaccc agtggaggac gaggccaagg tggttcagct tattttcaat   600
atctttctta atggactcaa cggtaaggac tactcctaca ctgctattgc ttcccacctc   660
accaatcttc agatccctac ccttctggt aagaaaaggt ggaaccagta cactatcaaa   720
gctattcttc agaacgaagt ttatatcgga accgtgaagt ataaggtgag ggagaaaacc   780
aaggacggaa aaaggactat cagaccagaa aggaacaaa ttgttgtgca agacgctcat   840
gctcctatca ttgataaaga gcagttccag caatcccaag tgaagattgc taataaggtg   900
ccactccttc ctaacaaaga tgagttcgag cttttccgagt tagctggtgt ttgtacctgt   960
tctaaatgcg gtgagcctct ttccaagtat gagtccaaga aatcagaaa gaataaggac  1020 ggaactgagt ccgtttatca cgttaagtcc cttacttgca aaaagaataa gtgtacctat  1080
gttagataca atgatgtgga gaatgctatt cttgactacc tttcttctct taatgatctc  1140
aacgactcta ctcttactaa gcatatcaat tctatgcttt ccaagtatga ggacgataat  1200
tctaatatga aaaccaaaaa gcagatgtcc gagcatcttt ctcaaaaaga gaaagagcta  1260

```
aagaataagg aaaactttat ctttgataaa tacgaatctg gtatctattc tgacgagctg   1320
ttcctcaaga gaaaggccgc tctcgatgag gagtttaagg aacttcagaa cgccaagaat   1380
gagttgaacg gacttcaaga tactcaatcc gagattgatt ccaacactgt tagaaacaat   1440
atcaataaga ttatcgacca atatcacatt gagtctagct ctgagaaaaa gaatgagctt   1500
cttagaatgg tgcttaaaga tgtgatcgtg aacatgaccc agaaaaggaa gggtccaatt   1560
ccagcccaat ttgagattac ccctatcctc aggtttaact ttatctttga tctcaccgcc   1620
accaattctt ttcacactag tagatctggt accatggaac catatcaaag atatgaagaa   1680
cttaagaaga agactattaa ggttgttcaa aggaaaatt attctattag atatattact    1740
caagatgaag cttctaatga tcttgatgaa ttttataagc aatttgctca acatcttctt   1800
gaagctgctc ttgaaagaaa ggctgaagga taccccttacg atgttcctga ttacgctggg   1860
ctggacagca ccgctcccaa aaagaaaagg aaggtgggca ttcacggcgt gcctgcggcc   1920
tga                                                                 1923

<210> SEQ ID NO 36
<211> LENGTH: 1635
<212> TYPE: DNA
<213> ORGANISM: Streptococcus pyogenes

<400> SEQUENCE: 36
atggaactta aaaacattgt taattcttat aacattacca atatcctcgg ataccttaga    60
aggtccaggc aggatatgga gagagagaaa aggactggag aagatactct tactgagcag   120
aaggaactta tgaacaaaat cctcaccgcc atcgaaatcc cttacgaact taaaatggaa   180
atcggttctg gtgagtccat cgacggaagg ccagtgttca agagtgtct caaggatctt    240 gaggaaggaa ataccaggc tattgctgtg aaggaaatca ctaggctctc taggggatct   300
tactccgatg ccggacagat cgtgaacctc cttcagtcta aaaggctcat cattatcact   360
ccatataagg tgtacgaccc aaggaaccca gttgacatga gacaaattag gttgaacttt   420
tcatggctga gagggagtt tgaaatgact agggagagga tgaccggagc taaatacact   480
tacgccgctc aaggaaagtg gatttctggt cttgccccat acggatacca actcaacaaa   540
aagacttcta aacttgaccc agtggaggac gaggccaagg tggttcagct tattttcaat   600
atctttctta atggactcaa cggtaaggac tactcctaca ctgctattgc ttcccacctc   660
accaatcttc agatccctac cccttctggt aagaaaaggt ggaaccagta cactatcaaa   720
gctattcttc agaacgaagt ttatatcgga accgtgaagt ataaggtgag ggagaaaacc   780
aaggacggaa aaggactat cagaccagaa aaggaacaaa ttgttgtgca agacgctcat   840
gctcctatca ttgataaaga gcagttccag caatcccaag tgaagattgc taataaggtg   900
ccactccttc ctaacaaaga tgagttcgag cttttccgagt tagctggtgt ttgtacctgt   960
tctaaatgcg gtgagcctct ttccaagtat gagtccaaga gaatcagaaa gaataaggac   1020
ggaactgagt ccgtttatca cgttaagtcc cttacttgca aaaagaataa gtgtacctat   1080
gttagataca atgatgtgga gaatgctatt cttgactacc tttcttctct taatgatctc   1140
aacgactcta ctcttactaa gcatatcaat tctatgcttt ccaagtatga ggacgataat   1200
tctaatatga aaccaaaaa gcagatgtcc gagcatcttt ctcaaaaaga gaaagagcta   1260
aagaataagg aaaactttat ctttgataaa tacgaatctg gtatctattc tgacgagctg   1320
ttcctcaaga gaaaggccgc tctcgatgag gagtttaagg aacttcagaa cgccaagaat   1380
```

```
gagttgaacg gacttcaaga tactcaatcc gagattgatt ccaacactgt tagaaacaat   1440
atcaataaga ttatcgacca atatcacatt gagtctagct ctgagaaaaa gaatgagctt   1500
cttagaatgg tgcttaaaga tgtgatcgtg aacatgaccc agaaaaggaa gggtccaatt   1560
ccagcccaat ttgagattac ccctatcctc aggtttaact ttatctttga tctcaccgcc   1620
accaattctt ttcac                                                    1635

<210> SEQ ID NO 37
<211> LENGTH: 18
<212> TYPE: DNA
<213> ORGANISM: Artificial Sequence
<220> FEATURE:
<223> OTHER INFORMATION: oligomeric linker

<400> SEQUENCE: 37
actagtagat ctggtacc                                                 18

<210> SEQ ID NO 38
<211> LENGTH: 174
<212> TYPE: DNA
<213> ORGANISM: Streptococcus pyogenes

<400> SEQUENCE: 38
atggaaccat atcaaagata tgaagaactt aagaagaaga ctattaaggt tgttcaaaag    60
gaaaattatt ctattagata tattactcaa gatgaagctt ctaatgatct tgatgaattt   120
tataagcaat tgctcaaca tcttcttgaa gctgctcttg aaagaaaggc tgaa          174

<210> SEQ ID NO 39
<211> LENGTH: 96
<212> TYPE: DNA
<213> ORGANISM: Artificial Sequence
<220> FEATURE:
<223> OTHER INFORMATION: HA and NLS tags

<400> SEQUENCE: 39
ggataccctt acgatgttcc tgattacgct gggctggaca gcaccgctcc caaaaagaaa    60
aggaaggtgg gcattcacgg cgtgcctgcg gcctga                             96

<210> SEQ ID NO 40
<211> LENGTH: 640
<212> TYPE: PRT
<213> ORGANISM: Artificial Sequence
<220> FEATURE:
<223> OTHER INFORMATION: Synthetic fusion construct of SPBc2 Serine
      recombinase and RDF with linker, HA tag and NLS tag

<400> SEQUENCE: 40

Met Glu Leu Lys Asn Ile Val Asn Ser Tyr Asn Ile Thr Asn Ile Leu
1               5                   10                  15

Gly Tyr Leu Arg Arg Ser Arg Gln Asp Met Glu Arg Glu Lys Arg Thr
            20                  25                  30

Gly Glu Asp Thr Leu Thr Glu Gln Lys Glu Leu Met Asn Lys Ile Leu
        35                  40                  45

Thr Ala Ile Glu Ile Pro Tyr Glu Leu Lys Met Glu Ile Gly Ser Gly
    50                  55                  60

Glu Ser Ile Asp Gly Arg Pro Val Phe Lys Glu Cys Leu Lys Asp Leu
65                  70                  75                  80

Glu Glu Gly Lys Tyr Gln Ala Ile Ala Val Lys Glu Ile Thr Arg Leu
                85                  90                  95
```

```
Ser Arg Gly Ser Tyr Ser Asp Ala Gly Gln Ile Val Asn Leu Leu Gln
            100                 105                 110

Ser Lys Arg Leu Ile Ile Ile Thr Pro Tyr Lys Val Tyr Asp Pro Arg
        115                 120                 125

Asn Pro Val Asp Met Arg Gln Ile Arg Phe Glu Leu Phe Met Ala Arg
130                 135                 140

Glu Phe Glu Met Thr Arg Glu Arg Met Thr Gly Ala Lys Tyr Thr
145                 150                 155                 160

Tyr Ala Ala Gln Gly Lys Trp Ile Ser Gly Leu Ala Pro Tyr Gly Tyr
                165                 170                 175

Gln Leu Asn Lys Lys Thr Ser Lys Leu Asp Pro Val Glu Asp Glu Ala
                180                 185                 190

Lys Val Val Gln Leu Ile Phe Asn Ile Phe Leu Asn Gly Leu Asn Gly
                195                 200                 205

Lys Asp Tyr Ser Tyr Thr Ala Ile Ala Ser His Leu Thr Asn Leu Gln
        210                 215                 220

Ile Pro Thr Pro Ser Gly Lys Lys Arg Trp Asn Gln Tyr Thr Ile Lys
225                 230                 235                 240

Ala Ile Leu Gln Asn Glu Val Tyr Ile Gly Thr Val Lys Tyr Lys Val
                245                 250                 255

Arg Glu Lys Thr Lys Asp Gly Lys Arg Thr Ile Arg Pro Glu Lys Glu
                260                 265                 270

Gln Ile Val Val Gln Asp Ala His Ala Pro Ile Ile Asp Lys Glu Gln
        275                 280                 285

Phe Gln Gln Ser Gln Val Lys Ile Ala Asn Lys Val Pro Leu Leu Pro
        290                 295                 300

Asn Lys Asp Glu Phe Glu Leu Ser Glu Leu Ala Gly Val Cys Thr Cys
305                 310                 315                 320

Ser Lys Cys Gly Glu Pro Leu Ser Lys Tyr Glu Ser Lys Arg Ile Arg
                325                 330                 335

Lys Asn Lys Asp Gly Thr Glu Ser Val Tyr His Val Lys Ser Leu Thr
            340                 345                 350

Cys Lys Lys Asn Lys Cys Thr Tyr Val Arg Tyr Asn Asp Val Glu Asn
        355                 360                 365

Ala Ile Leu Asp Tyr Leu Ser Ser Leu Asn Asp Leu Asn Asp Ser Thr
        370                 375                 380

Leu Thr Lys His Ile Asn Ser Met Leu Ser Lys Tyr Glu Asp Asp Asn
385                 390                 395                 400

Ser Asn Met Lys Thr Lys Lys Gln Met Ser Glu His Leu Ser Gln Lys
                405                 410                 415

Glu Lys Glu Leu Lys Asn Lys Glu Asn Phe Ile Phe Asp Lys Tyr Glu
                420                 425                 430

Ser Gly Ile Tyr Ser Asp Glu Leu Phe Leu Lys Arg Lys Ala Ala Leu
        435                 440                 445

Asp Glu Glu Phe Lys Glu Leu Gln Asn Ala Lys Asn Glu Leu Asn Gly
        450                 455                 460

Leu Gln Asp Thr Gln Ser Glu Ile Asp Ser Asn Thr Val Arg Asn Asn
465                 470                 475                 480

Ile Asn Lys Ile Ile Asp Gln Tyr His Ile Glu Ser Ser Ser Glu Lys
                485                 490                 495

Lys Asn Glu Leu Leu Arg Met Val Leu Lys Asp Val Ile Val Asn Met
                500                 505                 510

Thr Gln Lys Arg Lys Gly Pro Ile Pro Ala Gln Phe Glu Ile Thr Pro
```

```
            515                 520                 525
Ile Leu Arg Phe Asn Phe Ile Phe Asp Leu Thr Ala Thr Asn Ser Phe
    530                 535                 540

His Thr Ser Arg Ser Gly Thr Met Glu Pro Tyr Gln Arg Tyr Glu Glu
545                 550                 555                 560

Leu Lys Lys Lys Thr Ile Lys Val Val Gln Lys Glu Asn Tyr Ser Ile
                565                 570                 575

Arg Tyr Ile Thr Gln Asp Glu Ala Ser Asn Asp Leu Asp Glu Phe Tyr
                580                 585                 590

Lys Gln Phe Ala Gln His Leu Leu Glu Ala Ala Leu Glu Arg Lys Ala
                595                 600                 605

Glu Gly Tyr Pro Tyr Asp Val Pro Asp Tyr Ala Gly Leu Asp Ser Thr
                610                 615                 620

Ala Pro Lys Lys Lys Arg Lys Val Gly Ile His Gly Val Pro Ala Ala
625                 630                 635                 640

<210> SEQ ID NO 41
<211> LENGTH: 545
<212> TYPE: PRT
<213> ORGANISM: Streptococcus pyogenes

<400> SEQUENCE: 41

Met Glu Leu Lys Asn Ile Val Asn Ser Tyr Asn Ile Thr Asn Ile Leu
1               5                   10                  15

Gly Tyr Leu Arg Arg Ser Arg Gln Asp Met Glu Arg Glu Lys Arg Thr
                20                  25                  30

Gly Glu Asp Thr Leu Thr Glu Gln Lys Glu Leu Met Asn Lys Ile Leu
            35                  40                  45

Thr Ala Ile Glu Ile Pro Tyr Glu Leu Lys Met Glu Ile Gly Ser Gly
        50                  55                  60

Glu Ser Ile Asp Gly Arg Pro Val Phe Lys Glu Cys Leu Lys Asp Leu
65                  70                  75                  80

Glu Glu Gly Lys Tyr Gln Ala Ile Ala Val Lys Glu Ile Thr Arg Leu
                85                  90                  95

Ser Arg Gly Ser Tyr Ser Asp Ala Gly Gln Ile Val Asn Leu Leu Gln
            100                 105                 110

Ser Lys Arg Leu Ile Ile Ile Thr Pro Tyr Lys Val Tyr Asp Pro Arg
        115                 120                 125

Asn Pro Val Asp Met Arg Gln Ile Arg Phe Glu Leu Phe Met Ala Arg
130                 135                 140

Glu Glu Phe Glu Met Thr Arg Glu Arg Met Thr Gly Ala Lys Tyr Thr
145                 150                 155                 160

Tyr Ala Ala Gln Gly Lys Trp Ile Ser Gly Leu Ala Pro Tyr Gly Tyr
                165                 170                 175

Gln Leu Asn Lys Lys Thr Ser Lys Leu Asp Pro Val Glu Asp Glu Ala
            180                 185                 190

Lys Val Val Gln Leu Ile Phe Asn Ile Phe Leu Asn Gly Leu Asn Gly
        195                 200                 205

Lys Asp Tyr Ser Tyr Thr Ala Ile Ala Ser His Leu Thr Asn Leu Gln
    210                 215                 220

Ile Pro Thr Pro Ser Gly Lys Lys Arg Trp Asn Gln Tyr Thr Ile Lys
225                 230                 235                 240

Ala Ile Leu Gln Asn Glu Val Tyr Ile Gly Thr Val Lys Tyr Lys Val
                245                 250                 255
```

-continued

Arg Glu Lys Thr Lys Asp Gly Lys Arg Thr Ile Arg Pro Glu Lys Glu
            260                 265                 270

Gln Ile Val Val Gln Asp Ala His Ala Pro Ile Asp Lys Glu Gln
    275                 280                 285

Phe Gln Gln Ser Gln Val Lys Ile Ala Asn Lys Val Pro Leu Leu Pro
    290                 295                 300

Asn Lys Asp Glu Phe Glu Leu Ser Glu Leu Ala Gly Val Cys Thr Cys
305                 310                 315                 320

Ser Lys Cys Gly Glu Pro Leu Ser Lys Tyr Glu Ser Lys Arg Ile Arg
                325                 330                 335

Lys Asn Lys Asp Gly Thr Glu Ser Val Tyr His Val Lys Ser Leu Thr
            340                 345                 350

Cys Lys Lys Asn Lys Cys Thr Tyr Val Arg Tyr Asn Asp Val Glu Asn
        355                 360                 365

Ala Ile Leu Asp Tyr Leu Ser Ser Leu Asn Asp Leu Asn Asp Ser Thr
    370                 375                 380

Leu Thr Lys His Ile Asn Ser Met Leu Ser Lys Tyr Glu Asp Asp Asn
385                 390                 395                 400

Ser Asn Met Lys Thr Lys Lys Gln Met Ser Glu His Leu Ser Gln Lys
                405                 410                 415

Glu Lys Glu Leu Lys Asn Lys Glu Asn Phe Ile Phe Asp Lys Tyr Glu
            420                 425                 430

Ser Gly Ile Tyr Ser Asp Glu Leu Phe Leu Lys Arg Lys Ala Ala Leu
        435                 440                 445

Asp Glu Glu Phe Lys Glu Leu Gln Asn Ala Lys Asn Glu Leu Asn Gly
    450                 455                 460

Leu Gln Asp Thr Gln Ser Glu Ile Asp Ser Asn Thr Val Arg Asn Asn
465                 470                 475                 480

Ile Asn Lys Ile Ile Asp Gln Tyr His Ile Glu Ser Ser Ser Glu Lys
                485                 490                 495

Lys Asn Glu Leu Leu Arg Met Val Leu Lys Asp Val Ile Val Asn Met
            500                 505                 510

Thr Gln Lys Arg Lys Gly Pro Ile Pro Ala Gln Phe Glu Ile Thr Pro
        515                 520                 525

Ile Leu Arg Phe Asn Phe Ile Phe Asp Leu Thr Ala Thr Asn Ser Phe
    530                 535                 540

His
545

<210> SEQ ID NO 42
<211> LENGTH: 58
<212> TYPE: PRT
<213> ORGANISM: Streptococcus pyogenes

<400> SEQUENCE: 42

Met Glu Pro Tyr Gln Arg Tyr Glu Glu Leu Lys Lys Lys Thr Ile Lys
1               5                   10                  15

Val Val Gln Lys Glu Asn Tyr Ser Ile Arg Tyr Ile Thr Gln Asp Glu
            20                  25                  30

Ala Ser Asn Asp Leu Asp Glu Phe Tyr Lys Gln Phe Ala Gln His Leu
        35                  40                  45

Leu Glu Ala Ala Leu Glu Arg Lys Ala Glu
    50                  55

<210> SEQ ID NO 43

```
<211> LENGTH: 6
<212> TYPE: PRT
<213> ORGANISM: Artificial Sequence
<220> FEATURE:
<223> OTHER INFORMATION: Polypeptide linker

<400> SEQUENCE: 43

Thr Ser Arg Ser Gly Thr
1               5

<210> SEQ ID NO 44
<211> LENGTH: 31
<212> TYPE: PRT
<213> ORGANISM: Artificial Sequence
<220> FEATURE:
<223> OTHER INFORMATION: Polypeptide tags

<400> SEQUENCE: 44

Gly Tyr Pro Tyr Asp Val Pro Asp Tyr Ala Gly Leu Asp Ser Thr Ala
1               5                   10                  15

Pro Lys Lys Lys Arg Lys Val Gly Ile His Gly Val Pro Ala Ala
            20                  25                  30

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 45
cggttcggtt gtctgacaga                                          20

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 46
ggtgctggca aagtttctgg                                          20

<210> SEQ ID NO 47
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 47
ctcgtgacca ccttcaccta c                                        21

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 48
gtgttctgct ggtagtggtc                                          20

<210> SEQ ID NO 49
<211> LENGTH: 23
<212> TYPE: DNA
```

```
<213> ORGANISM: Artificial Sequence
<220> FEATURE:
<223> OTHER INFORMATION: Oligonucleotide Primer

<400> SEQUENCE: 49
gtactcttgc cgactacaac atc                                          23

<210> SEQ ID NO 50
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 50
cgtgcaatcc atcttgttca atc                                          23

<210> SEQ ID NO 51
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 51
gaagggtctt gcgaaggata gtgggat                                      27

<210> SEQ ID NO 52
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 52
tgcaatgtaa catcagagat tttgagacac                                   30

<210> SEQ ID NO 53
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 53
ccttacgtca gtggagatat cacatcaatc                                   30

<210> SEQ ID NO 54
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 54
aggaaacagc tatgaccatg taatacgact                                   30

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 55
ccgaagcctg tgaggaacat                                              20
```

<210> SEQ ID NO 56
<211> LENGTH: 99
<212> TYPE: DNA
<213> ORGANISM: Nicotiana benthamiana

<400> SEQUENCE: 56
ataacgaaag atttggccat gactgcagca ttgccaccat acgaagatac tgttgcttcg    60
tagctcatca aaaactgctt cgggtctgag tggccatca                           99

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 57
ggagggaggg ttgttttggt                                                20

<210> SEQ ID NO 58
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 58
aggcttgact gattgagttt atgttga                                        27

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 59
gcctacggaa ccaagacaca                                                20

<210> SEQ ID NO 60
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 60
ccggtcctta tcaataccac atcaaa                                         26

<210> SEQ ID NO 61
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 61
acacatgttg acgtgtccta ttttcc                                         26

<210> SEQ ID NO 62
<211> LENGTH: 23
<212> TYPE: DNA
<213> ORGANISM: Artificial Sequence
<220> FEATURE:

<223> OTHER INFORMATION: Oligonucleotide Primer

<400> SEQUENCE: 62
atgtctctgt ttggaaatgt ttc                                                23

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 63
caatggtgca ggtaaaacat                                                    20

<210> SEQ ID NO 64
<211> LENGTH: 100
<212> TYPE: DNA
<213> ORGANISM: Lactuca sativa

<400> SEQUENCE: 64
cagcctaacg attattatag attgtgttgg ccgaccctttt ttgccagcct tataggtaat        60
aaagttataa dacaatatta caataggtct ttgacatcaa                              100

<210> SEQ ID NO 65
<211> LENGTH: 100
<212> TYPE: DNA
<213> ORGANISM: Lactuca sativa

<400> SEQUENCE: 65
ataaataaat aaaagagggg ttagggcttt gagtcctttt gtcttcgtct gattggagag        60
aaagggaacg aacgaaagca gcaacaattt gtcccatgat                              100

<210> SEQ ID NO 66
<211> LENGTH: 38
<212> TYPE: DNA
<213> ORGANISM: Lactuca sativa

<400> SEQUENCE: 66
gtgcttgttt aaggccataa atcgccttat tcaagcga                                38

<210> SEQ ID NO 67
<211> LENGTH: 38
<212> TYPE: DNA
<213> ORGANISM: Lactuca sativa

<400> SEQUENCE: 67
gtgcttgttt aaggccataa atcgccttat tcaagcga                                38

<210> SEQ ID NO 68
<211> LENGTH: 38
<212> TYPE: DNA
<213> ORGANISM: Lactuca sativa

<400> SEQUENCE: 68
gttaaggggt aaaatcacta aggggaatt aacaatgc                                 38

<210> SEQ ID NO 69
<211> LENGTH: 38
<212> TYPE: DNA
<213> ORGANISM: Lactuca sativa

<400> SEQUENCE: 69

```
gttaaggggt aaaatcacta aggggggaatt aacaatgc                            38
```

<210> SEQ ID NO 70
<211> LENGTH: 38
<212> TYPE: DNA
<213> ORGANISM: Lactuca sativa

<400> SEQUENCE: 70

```
tccactatca gcaacgataa aaaggtcatg ctaagacc                             38
```

<210> SEQ ID NO 71
<211> LENGTH: 38
<212> TYPE: DNA
<213> ORGANISM: Lactuca sativa

<400> SEQUENCE: 71

```
tccactatca gcaacgataa aaaggtcatg ctaagacc                             38
```

<210> SEQ ID NO 72
<211> LENGTH: 38
<212> TYPE: DNA
<213> ORGANISM: Lactuca sativa

<400> SEQUENCE: 72

```
tccactatca gcaacgataa aaaggtcatg ctaagacc                             38
```

<210> SEQ ID NO 73
<211> LENGTH: 38
<212> TYPE: DNA
<213> ORGANISM: Lactuca sativa

<400> SEQUENCE: 73

```
tccactatca gcaacgataa aaaggtcatg ctaagacc                             38
```

<210> SEQ ID NO 74
<211> LENGTH: 38
<212> TYPE: DNA
<213> ORGANISM: Lactuca sativa

<400> SEQUENCE: 74

```
tccactatca gcaacgataa aaaggtcatg ctaagacc                             38
```

<210> SEQ ID NO 75
<211> LENGTH: 38
<212> TYPE: DNA
<213> ORGANISM: Lactuca sativa

<400> SEQUENCE: 75

```
tccactatca gcaacgataa aaaggtcatg ctaagacc                             38
```

<210> SEQ ID NO 76
<211> LENGTH: 38
<212> TYPE: DNA
<213> ORGANISM: Lactuca sativa

<400> SEQUENCE: 76

```
tccactatca gcaacgataa aaaggtcatg ctaagacc                             38
```

<210> SEQ ID NO 77
<211> LENGTH: 38
<212> TYPE: DNA
<213> ORGANISM: Lactuca sativa

```
<400> SEQUENCE: 77
tgtatcatga gaaacaatta gaaggtacct ataattat                              38

<210> SEQ ID NO 78
<211> LENGTH: 38
<212> TYPE: DNA
<213> ORGANISM: Lactuca sativa

<400> SEQUENCE: 78
tgtatcatga gaaacaatta gaaggtacct ataattat                              38

<210> SEQ ID NO 79
<211> LENGTH: 38
<212> TYPE: DNA
<213> ORGANISM: Lactuca sativa

<400> SEQUENCE: 79
tgtatcatga gaaacaatta gaaggtacct ataattat                              38

<210> SEQ ID NO 80
<211> LENGTH: 38
<212> TYPE: DNA
<213> ORGANISM: Lactuca sativa

<400> SEQUENCE: 80
tgtatcatga gaaacaatta gaaggtacct ataattat                              38

<210> SEQ ID NO 81
<211> LENGTH: 38
<212> TYPE: DNA
<213> ORGANISM: Lactuca sativa

<400> SEQUENCE: 81
tgtatcatga gaaacaatta gaaggtacct ataattat                              38

<210> SEQ ID NO 82
<211> LENGTH: 38
<212> TYPE: DNA
<213> ORGANISM: Lactuca sativa

<400> SEQUENCE: 82
tgtatcatga gaaacaatta gaaggtacct ataattat                              38

<210> SEQ ID NO 83
<211> LENGTH: 38
<212> TYPE: DNA
<213> ORGANISM: Lactuca sativa

<400> SEQUENCE: 83
tgtatcatga gaaacaatta gaaggtacct ataattat                              38

<210> SEQ ID NO 84
<211> LENGTH: 38
<212> TYPE: DNA
<213> ORGANISM: Lactuca sativa

<400> SEQUENCE: 84
tgtatcatga gaaacaatta gaaggtacct ataattat                              38

<210> SEQ ID NO 85
<211> LENGTH: 38
<212> TYPE: DNA
<213> ORGANISM: Lactuca sativa
```

```
<400> SEQUENCE: 85
tgtatcatga gaaacaatta gaaggtacct ataattat                              38

<210> SEQ ID NO 86
<211> LENGTH: 38
<212> TYPE: DNA
<213> ORGANISM: Lactuca sativa

<400> SEQUENCE: 86
tgtatcatga gaaacaatta gaaggtacct ataattat                              38

<210> SEQ ID NO 87
<211> LENGTH: 38
<212> TYPE: DNA
<213> ORGANISM: Lactuca sativa

<400> SEQUENCE: 87
catcattaga gaaacaatta aatagattat agtattac                              38

<210> SEQ ID NO 88
<211> LENGTH: 38
<212> TYPE: DNA
<213> ORGANISM: Lactuca sativa

<400> SEQUENCE: 88
catcattaga gaaacaatta aatagattat agtattac                              38

<210> SEQ ID NO 89
<211> LENGTH: 38
<212> TYPE: DNA
<213> ORGANISM: Lactuca sativa

<400> SEQUENCE: 89
catcattaga gaaacaatta aatagattat agtattac                              38

<210> SEQ ID NO 90
<211> LENGTH: 38
<212> TYPE: DNA
<213> ORGANISM: Lactuca sativa

<400> SEQUENCE: 90
catcattaga gaaacaatta aatagattat agtattac                              38

<210> SEQ ID NO 91
<211> LENGTH: 38
<212> TYPE: DNA
<213> ORGANISM: Lactuca sativa

<400> SEQUENCE: 91
catcattaga gaaacaatta aatagattat agtattac                              38

<210> SEQ ID NO 92
<211> LENGTH: 38
<212> TYPE: DNA
<213> ORGANISM: Lactuca sativa

<400> SEQUENCE: 92
catcattaga gaaacaatta aatagattat agtattac                              38

<210> SEQ ID NO 93
<211> LENGTH: 37
<212> TYPE: DNA
```

<213> ORGANISM: Lactuca sativa

<400> SEQUENCE: 93
ttcatcaatg attctattaa ggagattctt acattga        37

<210> SEQ ID NO 94
<211> LENGTH: 37
<212> TYPE: DNA
<213> ORGANISM: Lactuca sativa

<400> SEQUENCE: 94
ttcatcaatg attctattaa ggagattctt acattga        37

<210> SEQ ID NO 95
<211> LENGTH: 36
<212> TYPE: DNA
<213> ORGANISM: Lactuca sativa

<400> SEQUENCE: 95
acttgaaagt acgaccaaga aaatgattat atttga         36

<210> SEQ ID NO 96
<211> LENGTH: 36
<212> TYPE: DNA
<213> ORGANISM: Lactuca sativa

<400> SEQUENCE: 96
acttgaaagt acgaccaaga aaatgattat atttga         36

<210> SEQ ID NO 97
<211> LENGTH: 38
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 97
tntmnyawga gaaacaatta aaaggwwhht ataaktay      38

<210> SEQ ID NO 98
<211> LENGTH: 40
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

```
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 98
mhrdhnndwn wrmaachatw aadnnghdhh whnvadhnhn                                40

<210> SEQ ID NO 99
<211> LENGTH: 31
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t

<400> SEQUENCE: 99
mhrdhnndwn wrmaachatw aadnnghdhh w                                         31

<210> SEQ ID NO 100
<211> LENGTH: 39
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(33)
<223> OTHER INFORMATION: n is a, c, g, or t
<220> FEATURE:
<221> NAME/KEY: misc_feature
<222> LOCATION: (37)..(39)
<223> OTHER INFORMATION: n is a, c, g, or t

<400> SEQUENCE: 100
nnnnnnnnnw nhaachatwa hdnnrnnnnn nnnwddnnn                                 39

<210> SEQ ID NO 101
<211> LENGTH: 16
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(2)
```

```
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t

<400> SEQUENCE: 101
wnhaachatw ahdnnr                                                   16

<210> SEQ ID NO 102
<211> LENGTH: 100
<212> TYPE: DNA
<213> ORGANISM: Oryza sativa

<400> SEQUENCE: 102
tccgattgaa gtttagtagg agtatagtgt agtgttagtg tacactgtct ttaagatcac    60
attaagaact aatagacctg taaacccttt catctagcag                        100

<210> SEQ ID NO 103
<211> LENGTH: 99
<212> TYPE: DNA
<213> ORGANISM: Oryza sativa

<400> SEQUENCE: 103
ggtaaaggcg atgatgtgta ctcttgggtt gcctattggg tgcatatcct tggcagggct    60
catgttgttc agttaataaa gatattaagt agctaccta                         99

<210> SEQ ID NO 104
<211> LENGTH: 99
<212> TYPE: DNA
<213> ORGANISM: Oryza sativa

<400> SEQUENCE: 104
tacctttaat ttagtacatg acattgtgaa catcagcata agtatcgtct tattgagata    60
catattttat ctcacgttag cacgttttt taagtacta                          99

<210> SEQ ID NO 105
<211> LENGTH: 99
<212> TYPE: DNA
<213> ORGANISM: Oryza sativa

<400> SEQUENCE: 105
accgaatgct gcgtggagta cattgttcag atcgtaggtg gcgctgtctt gtctgcccgc    60
ccatttaact tccttccgcc atcacgaacc tgatcaacg                         99

<210> SEQ ID NO 106
<211> LENGTH: 57
<212> TYPE: DNA
<213> ORGANISM: Artificial Sequence
<220> FEATURE:
<223> OTHER INFORMATION: Consensus sequence

<400> SEQUENCE: 106
ccaaagtagt aagtatctta aaaacagat aaagctgtat attaagatac ttactac       57

<210> SEQ ID NO 107
<211> LENGTH: 57
<212> TYPE: DNA
<213> ORGANISM: Oryza sativa

<400> SEQUENCE: 107
ccaaagtagt aagtatctta aaaacagat aagacagcgc cacctacgat ctgaaca       57
```

<210> SEQ ID NO 108
<211> LENGTH: 57
<212> TYPE: DNA
<213> ORGANISM: Oryza sativa

<400> SEQUENCE: 108
ccaaagtagt aagtatctta aaaaacagat aagacagtgt acactaacac tacacta        57

<210> SEQ ID NO 109
<211> LENGTH: 57
<212> TYPE: DNA
<213> ORGANISM: Oryza sativa

<400> SEQUENCE: 109
ccaaagtagt aagtatctta aaaaacagat aaggatatgc accccaatag gcaaccc        57

<210> SEQ ID NO 110
<211> LENGTH: 57
<212> TYPE: DNA
<213> ORGANISM: Oryza sativa

<400> SEQUENCE: 110
ccaaagtagt aagtatctta aaaaacagat aagacgatac ttatgctgat gttcaca        57

<210> SEQ ID NO 111
<211> LENGTH: 57
<212> TYPE: DNA
<213> ORGANISM: Lactuca sativa

<400> SEQUENCE: 111
ccaaagtagt aagtatctta aaaaacagat aattcatctc tactacgtac caaatga        57

<210> SEQ ID NO 112
<211> LENGTH: 57
<212> TYPE: DNA
<213> ORGANISM: Lactuca sativa

<400> SEQUENCE: 112
ccaaagtagt aagtatctta aaaaacagat agatacgaca tcacacttac aaagttt        57

<210> SEQ ID NO 113
<211> LENGTH: 57
<212> TYPE: DNA
<213> ORGANISM: Lactuca sativa

<400> SEQUENCE: 113
ccaaagtagt aagtatctta aaaaacagat taaacattaa ttacaatgac aaaatga        57

<210> SEQ ID NO 114
<211> LENGTH: 57
<212> TYPE: DNA
<213> ORGANISM: Lactuca sativa

<400> SEQUENCE: 114
ccaaagtagt aagtatctta aaaaacagat aaatcgcctt attcaagcga caaaaat        57

<210> SEQ ID NO 115
<211> LENGTH: 57
<212> TYPE: DNA
<213> ORGANISM: Lactuca sativa

<400> SEQUENCE: 115

-continued ccaaagtagt aagtatctta aaaaacagat aaaaaggtca tgctaagacc cacaagc    57

<210> SEQ ID NO 116
<211> LENGTH: 57
<212> TYPE: DNA
<213> ORGANISM: Lactuca sativa

<400> SEQUENCE: 116
ccaaagtagt aagtatctta aaaaacagat tagtctgtta tgttgttgaa tttgaat    57

<210> SEQ ID NO 117
<211> LENGTH: 57
<212> TYPE: DNA
<213> ORGANISM: Nicotiana benthamiana

<400> SEQUENCE: 117
ccaaagtagt aagtatctta aaaaacagat aaaggagtct cctcgactcc ttcagat    57

<210> SEQ ID NO 118
<211> LENGTH: 57
<212> TYPE: DNA
<213> ORGANISM: Nicotiana benthamiana

<400> SEQUENCE: 118
ccaaagtagt aagtatctta aaaaacagat aaagcaaagc tgtcaggtaa catcaaa    57

<210> SEQ ID NO 119
<211> LENGTH: 57
<212> TYPE: DNA
<213> ORGANISM: Nicotiana benthamiana

<400> SEQUENCE: 119
ccaaagtagt aagtatctta aaaaacagat aaataggaaa tgtcattgac agctacg    57

<210> SEQ ID NO 120
<211> LENGTH: 57
<212> TYPE: DNA
<213> ORGANISM: Nicotiana benthamiana

<400> SEQUENCE: 120
ccaaagtagt aagtatctta aaaaacagat aaatagatta tagtattact tacaatg    57

<210> SEQ ID NO 121
<211> LENGTH: 57
<212> TYPE: DNA
<213> ORGANISM: Nicotiana benthamiana

<400> SEQUENCE: 121
ccaaagtagt aagtatctta aaaaacagat aagagagtac ttacatgaat gacgtct    57

<210> SEQ ID NO 122
<211> LENGTH: 57
<212> TYPE: DNA
<213> ORGANISM: Nicotiana benthamiana

<400> SEQUENCE: 122
ccaaagtagt aagtatctta aaaaacagat aaggggggaat taacaatgca cactagg    57

<210> SEQ ID NO 123
<211> LENGTH: 100
<212> TYPE: DNA
<213> ORGANISM: Lactuca sativa

<400> SEQUENCE: 123

```
ataaataaat aaaagagggg ttagggcttt gagtcctttt gtcttcgtct tataggtaat        60
aaagttataa gacaatatta caataggtct ttgacatcaa                             100

<210> SEQ ID NO 124
<211> LENGTH: 22
<212> TYPE: DNA
<213> ORGANISM: Lactuca sativa

<400> SEQUENCE: 124
tgtcttcgtc tttataggtaa ta                                                22

<210> SEQ ID NO 125
<211> LENGTH: 471
<212> TYPE: PRT
<213> ORGANISM: Streptococcus pyogenes

<400> SEQUENCE: 125
```

Met Arg Lys Val Ala Ile Tyr Ser Arg Val Ser Thr Ile Asn Gln Ala
1               5                   10                  15

Glu Glu Gly Tyr Ser Ile Gln Gly Gln Ile Glu Ala Leu Thr Lys Tyr
            20                  25                  30

Cys Glu Ala Met Glu Trp Lys Ile Tyr Lys Asn Tyr Ser Asp Ala Gly
        35                  40                  45

Phe Ser Gly Gly Lys Leu Glu Arg Pro Ala Ile Thr Glu Leu Ile Glu
    50                  55                  60

Asp Gly Lys Asn Asn Lys Phe Asp Thr Ile Leu Val Tyr Lys Leu Asp
65                  70                  75                  80

Arg Leu Ser Arg Asn Val Lys Asp Thr Leu Tyr Leu Val Lys Asp Val
                85                  90                  95

Phe Thr Ala Asn Asn Ile His Phe Val Ser Leu Lys Glu Asn Ile Asp
            100                 105                 110

Thr Ser Ser Ala Met Gly Asn Leu Phe Leu Thr Leu Leu Ser Ala Ile
        115                 120                 125

Ala Glu Phe Glu Arg Glu Gln Ile Lys Glu Arg Met Gln Phe Gly Val
    130                 135                 140

Met Asn Arg Ala Lys Ser Gly Lys Thr Thr Ala Trp Lys Thr Pro Pro
145                 150                 155                 160

Tyr Gly Tyr Arg Tyr Asn Lys Asp Glu Lys Thr Leu Ser Val Asn Glu
                165                 170                 175

Leu Glu Ala Ala Asn Val Arg Gln Met Phe Asp Met Ile Ile Ser Gly
            180                 185                 190

Cys Ser Ile Met Ser Ile Thr Asn Tyr Ala Arg Asp Asn Phe Val Gly
        195                 200                 205

Asn Thr Trp Thr His Val Lys Val Lys Arg Ile Leu Glu Asn Glu Thr
    210                 215                 220

Tyr Lys Gly Leu Val Lys Tyr Arg Glu Gln Thr Phe Ser Gly Asp His
225                 230                 235                 240

Gln Ala Ile Ile Asp Glu Lys Thr Tyr Asn Lys Ala Gln Ile Ala Leu
                245                 250                 255

Ala His Arg Thr Asp Thr Lys Thr Asn Thr Arg Pro Phe Gln Gly Lys
            260                 265                 270

Tyr Met Leu Ser His Ile Ala Lys Cys Gly Tyr Cys Gly Ala Pro Leu
        275                 280                 285

Lys Val Cys Thr Gly Arg Ala Lys Asn Asp Gly Thr Arg Arg Gln Thr
    290                 295                 300

-continued

```
Tyr Val Cys Val Asn Lys Thr Glu Ser Leu Ala Arg Arg Ser Val Asn
305                 310                 315                 320

Asn Tyr Asn Asn Gln Lys Ile Cys Asn Thr Gly Arg Tyr Glu Lys Lys
            325                 330                 335

His Ile Glu Lys Tyr Val Ile Asp Val Leu Tyr Lys Leu Gln His Asp
        340                 345                 350

Lys Glu Tyr Leu Lys Lys Ile Lys Lys Asp Asn Ile Ile Asp Ile
    355                 360                 365

Thr Pro Leu Lys Lys Glu Ile Glu Ile Ile Asp Lys Lys Ile Asn Arg
370                 375                 380

Leu Asn Asp Leu Tyr Ile Asn Asp Leu Ile Asp Leu Pro Lys Leu Lys
385                 390                 395                 400

Lys Asp Ile Glu Glu Leu Asn His Leu Lys Asp Tyr Asn Lys Ala
            405                 410                 415

Ile Lys Leu Asn Tyr Leu Asp Lys Lys Asn Glu Asp Ser Leu Gly Met
        420                 425                 430

Leu Met Asp Asn Leu Asp Ile Arg Lys Ser Ser Tyr Asp Val Gln Ser
    435                 440                 445

Arg Ile Val Lys Gln Leu Ile Asp Arg Val Glu Val Thr Met Asp Asn
450                 455                 460

Ile Asp Ile Ile Phe Lys Phe
465                 470

<210> SEQ ID NO 126
<211> LENGTH: 1416
<212> TYPE: DNA
<213> ORGANISM: Streptococcus pyogenes

<400> SEQUENCE: 126
atgagaaaag tagctatttta ctctagagta tcaacaataa atcaagccga agaaggatat      60
tccattcaag acagattga agctttaaca aagtattgtg aggcaatgga atggaaaatt      120
tacaaaaact actctgatgc aggttttttca ggcggtaaac ttgaacgacc ggcaataaca     180
gaattgattg aagacggtaa aaacaataaa tttgatacta ttttagtcta taaactagac      240
aggctatcaa gaaatgtaaa agacacactt tacttagtca agatgtatt tactgctaac      300 aatatccatt tgtcagcttt aaaagaaaat atcgacactt cttcagcaat gggaaatctc      360
tttctcactc tcttgtcagc tattgcagag tttgaaagag aacagattaa agagcgaatg      420
cagtttggtg ttatgaatag agcaaaatct ggaaaaacaa cggcttggaa acaccacct      480 tatggatata gatcaacaa agacgaaaaa acattgtcgg tcaacgagtt agaggctgct      540
aatgtcaggc agatgtttga catgataatc tctggctgct caatcatgtc aattacaaat      600
tacgcgagag acaatttcgt cgggaatacg tggacacatg taaaagtaaa agaatatta      660 gaaaacgaaa catataaagg attagtgaag tataggaac aaactttctc aggtgatcat      720
caagccatta tcgacgaaaa aacatataat aaagcgcaaa tagctttagc acataggaca      780
gatacgaaaa caaatactag accttttcaa gggaaatata tgctttctca catagcaaaa      840
tgcggttatt gtggtgcccc tttaaaagta tgcacaggaa gagctaagaa cgatggtacg      900
agaaggcaaa cttacgtttg tgttaataaa acagaaagtt tggctagacg aagtgttaat      960
aattataata accaaaagat tgtaacact ggtcgatatg aaaaaaaca catcgaaaaa      1020 tatgttattg atgttcttta taacttcaa cacgataaag aatatcttaa aaaaataaaa      1080
aaagatgaca atataattga tattacacct ttaaaaaaag aaatagagat aatcgataaa      1140
```

```
aaaatcaatc gtctaaacga tttatatatt aatgatttga ttgacctacc aaaactaaaa    1200
aaagacatcg aagaactcaa tcatttaaaa gatgattata acaaagcaat taaattgaat    1260
tatttagaca agaaaaacga agactctctt ggaatgctga tggataacct tgacattaga    1320
aaatcttcgt atgatgttca atctaggata gttaagcaat tgatagatag agtcgaggtt    1380
actatggata acatcgatat tatttttaag ttttaa                              1416
```

<210> SEQ ID NO 127
<211> LENGTH: 2442
<212> TYPE: DNA
<213> ORGANISM: Artificial Sequence
<220> FEATURE:
<223> OTHER INFORMATION: Polynucleotide construct to express SF370

<400> SEQUENCE: 127

```
gtccgatgtg agacttttca acaaagggta atatccggaa acctcctcgg attccattgc     60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg aaaaagaag acgttccaac cacgtcttca    240
aagcaagtgg attgatgtga tggtccgatg tgagactttt caacaaaggg taatatccgg    300
aaacctcctc ggattccatt gcccagctat ctgtcacttt attgtgaaga tagtggaaaa    360
ggaaggtggc tcctacaaat gccatcattg cgataaagga aaggccatcg ttgaagatgc    420
ctctgccgac agtggtccca agatggacc cccacccacg aggagcatcg tggaaaaaga    480
agacgttcca accacgtctt caaagcaagt ggattgatgt gatatctcca ctgacgtaag    540
ggatgacgca caatcccact atccttcgca agacccttcc tctatataag gaagttcatt    600
tcatttggag aggacacgcg acaagctgac tctagcagat cctccagacc tgcagggcca    660
ccatgagaaa ggtggctatt tactccaggg tgtctactat caatcaagcc gaggaaggat    720
attctattca aggtcaaatt gaggccctta ctaagtattg cgaagctatg gagtggaaga    780
tttacaaaaa ctattctgac gctggtttct ctggtggtaa gttggaaaga ccagccatca    840
ctgagcttat cgaagatggt aagaataaca aattcgacac cattcttgtg tacaaacttg    900
acaggctctc taggaacgtg aaggacaccc tctacctcgt taaagatgtg ttcactgcta    960
ataacattca ctttgtttct cttaaagaga atatcgacac ctcctctgct atgggtaacc    1020 tttcctcac cctcctttcc gctattgctg agttcgagag ggagcaaatt aaggaaagga    1080
tgcaatttgg agtgatgaat agggccaagt ctggaaaaac cactgcttgg aaaactccac    1140
cttacggtta cagatacaat aaggacgaga aactctctc tgtgaacgaa cttgaagctg    1200
ccaacgtgag gcagatgttt gatatgatta tctctggttg ctccatcatg tctattacca    1260
attacgccag ggacaacttt gttggtaaca cttggactca cgttaaggtt aagaggatct    1320
tggagaatga gacttacaaa ggactcgtta atacagaga gcagaccttt tctggagatc    1380
accaagccat cattgatgaa aagacttaca ataaggctca atcgctctc gctcatagga    1440 ctgatactaa gactaacact aggccattcc aaggaaagta catgctttct cacattgcta    1500
aatgcggtta ctgtggagcc ccactcaagg tttgcaccgg aagggctaaa acgacggaa    1560 ctaggagaca aacttacgtg tgcgtgaaca aaaccgaatc tctcgctaga aggtccgtta    1620
ataactataa caatcaaaag atttgcaaca ctggaagata cgaaaagaaa cacattgaga    1680
aatacgtgat cgacgttctc tacaaacttc agcacgacaa ggaataccte aagaaaatca    1740
```

-continued

| | |
|---|---|
| aaaaggacga taatatcatt gatattaccc ctcttaaaaa ggaaatcgaa atcattgata | 1800 |
| aaaagattaa cagacttaat gatctctaca ttaacgacct tattgatctt ccaaagctca | 1860 |
| aaaaggacat cgaggagctt aaccatctta aagatgacta caataaggcc atcaaactta | 1920 |
| attacctcga taaaaagaat gaggactctc tcggaatgct tatggataat cttgacatca | 1980 |
| gaaagtcctc ttatgatgtg caatccagga ttgttaaaca actcatcgac agggtggagg | 2040 |
| tgactatgga taatatcgac atcattttca aattcggata cccttacgat gttcctgatt | 2100 |
| acgctgggct ggacagcacc gctcccaaaa agaaaaggaa ggtgggcatt cacggcgtgc | 2160 |
| ctgcggcctg aatcgatgac ttcccgatcg ttcaaacatt tggcaataaa gtttcttaag | 2220 |
| attgaatcct gttgccggtc ttgcgatgat tatcatataa tttctgttga attacgttaa | 2280 |
| gcatgtaata attaacatgt aatgcatgac gttatttatg agatgggttt ttatgattag | 2340 |
| agtcccgcaa ttatacattt aatacgcgat agaaaacaaa atatagcgcg caaactagga | 2400 |
| taaattatcg cgcgcggtgt catctatgtt actagatcgg gg | 2442 |

<210> SEQ ID NO 128
<211> LENGTH: 198
<212> TYPE: DNA
<213> ORGANISM: Streptococcus pyogenes

<400> SEQUENCE: 128

| | |
|---|---|
| tttttgtatc cagttcaatg gatatttgat ataatcgtct taaaaggag gtcgtgaaat | 60 |
| ggataaaaaa atacagcgtt tttcatgtac aactatacta gttgtagtgc ctaaataatg | 120 |
| cttttaaaac ttaaaaataa tatcgatgtt atccatagta acctcgactc tatctatcaa | 180 |
| ttgcttaact atcctaga | 198 |

<210> SEQ ID NO 129
<211> LENGTH: 200
<212> TYPE: DNA
<213> ORGANISM: Streptococcus pyogenes

<400> SEQUENCE: 129

| | |
|---|---|
| gttttccatt gttttttttga agtgtctgat gttctgtgat atgataaaag ggataataac | 60 |
| gtttgtaaag gagactgata atggcatgta caactatact cgtcggtaaa aaggcatctt | 120 |
| atgatggctc aaccatggtt gctcgaacag aagattctca aaatggtgat ttcacgccta | 180 |
| aaaaaatgat tgtggtgaaa | 200 |

<210> SEQ ID NO 130
<211> LENGTH: 32
<212> TYPE: DNA
<213> ORGANISM: Lactuca sativa

<400> SEQUENCE: 130

| | |
|---|---|
| ccaaagtagt aagtatctta aaaaacagat wr | 32 |

<210> SEQ ID NO 131
<211> LENGTH: 32
<212> TYPE: DNA
<213> ORGANISM: Nicotiana benthamiana

<400> SEQUENCE: 131

| | |
|---|---|
| ccaaagtagt aagtatctta aaaaacagat aa | 32 |

<210> SEQ ID NO 132
<211> LENGTH: 100

```
<212> TYPE: DNA
<213> ORGANISM: Nicotiana benthamiana

<400> SEQUENCE: 132
gttatagtca gttgaattca aactctctga ctcatcatta gagaaacaat taaatagatt    60
atagtattac ttacaatgcg cgcgacgcat tgtatgaacc                         100

<210> SEQ ID NO 133
<211> LENGTH: 100
<212> TYPE: DNA
<213> ORGANISM: Nicotiana benthamiana

<400> SEQUENCE: 133
ttgctgtctt ttcatacttt tctaagttga aagtacttga aagtacgacc aagaaaatga    60
ttatatttga cacagaaaat gcaaggtact ttgaatgtga                         100

<210> SEQ ID NO 134
<211> LENGTH: 100
<212> TYPE: DNA
<213> ORGANISM: Nicotiana benthamiana

<400> SEQUENCE: 134
ggataaggga gggtttagat attttgaaag ggttaagggg taaaatcact aaggggggaat   60 taacaatgca cactagggtt gccttaaaag tgcctatata                         100

<210> SEQ ID NO 135
<211> LENGTH: 100
<212> TYPE: DNA
<213> ORGANISM: Nicotiana benthamiana

<400> SEQUENCE: 135
ctaatataca ttgacagtgt taaaaaaaat ctattaacga caatatagag aagagagtac    60
ttacatgaat gacgtctact ttgactccgt caattccaac                         100

<210> SEQ ID NO 136
<211> LENGTH: 100
<212> TYPE: DNA
<213> ORGANISM: Nicotiana benthamiana

<400> SEQUENCE: 136
taggcttaca ttcctgatgt actatcccat tatgcaataa taaagatgca aaataggaaa    60
tgtcattgac agctacgaga tctatctttta ttgattcact                        100

<210> SEQ ID NO 137
<211> LENGTH: 100
<212> TYPE: DNA
<213> ORGANISM: Nicotiana benthamiana

<400> SEQUENCE: 137
acatggagca atgatggaga aaaatggtgg tcattactac tgaagttgtc aaagcaaagc    60
tgtcaggtaa catcaaatga tctctaaatc aattagtctt                         100

<210> SEQ ID NO 138
<211> LENGTH: 100
<212> TYPE: DNA
<213> ORGANISM: Nicotiana benthamiana

<400> SEQUENCE: 138
gccacaacct aggccaggca aaggtttcac taatacctgt gatgtttgtc aaaggagtct    60
```

```
cctcgactcc ttcagattct gctctcttgg ctgtaaggta                         100
```

<210> SEQ ID NO 139
<211> LENGTH: 100
<212> TYPE: DNA
<213> ORGANISM: Nicotiana benthamiana

<400> SEQUENCE: 139

```
gaagagacga ttacatatat gtgtacgcgt tggataatca tttgaacctt aaagtctgtc    60
tctctcttaa catgtgttca atagcaatac aaagtgtata                         100
```

<210> SEQ ID NO 140
<211> LENGTH: 100
<212> TYPE: DNA
<213> ORGANISM: Nicotiana benthamiana

<400> SEQUENCE: 140

```
attaaggagg agaatataac atgtattttg tgtgtatcat gagaaacaat tagaaggtac    60
ctataattat gaagtcaaag cacaaggata ttcttgtaaa                         100
```

<210> SEQ ID NO 141
<211> LENGTH: 100
<212> TYPE: DNA
<213> ORGANISM: Nicotiana benthamiana

<400> SEQUENCE: 141

```
caatggtgaa tatagtccgg cgaccaactc tgtccactat cagcaacgat aaaaaggtca    60
tgctaagacc cacaagccca gtcaccactg ctgacataag                         100
```

<210> SEQ ID NO 142
<211> LENGTH: 100
<212> TYPE: DNA
<213> ORGANISM: Nicotiana benthamiana

<400> SEQUENCE: 142

```
ataagtttag atcttattga actaggcttg tggtgcttgt ttaaggccat aaatcgcctt    60
attcaagcga caaaaatgag acgaataggt ggagtcttca                         100
```

<210> SEQ ID NO 143
<211> LENGTH: 100
<212> TYPE: DNA
<213> ORGANISM: Nicotiana benthamiana

<400> SEQUENCE: 143

```
tccgtcacaa attgcatcac tacgactaag atcttcatca atgattctat taaggagatt    60
cttacattga aggagaagtt acataaattc tttattattt                         100
```

<210> SEQ ID NO 144
<211> LENGTH: 100
<212> TYPE: DNA
<213> ORGANISM: Nicotiana benthamiana

<400> SEQUENCE: 144

```
tgaatttctt atgaaggtta caacgcatcg tggattacaa gcaattctgt ttagtctgtt    60
atgttgttga atttgaatgg atcttgtcct cagttactca                         100
```

<210> SEQ ID NO 145
<211> LENGTH: 100
<212> TYPE: DNA
<213> ORGANISM: Nicotiana benthamiana

<400> SEQUENCE: 145
cacaaaaaat tgaccatttc tagcaacttc ctatgatacg ttgatacttt ctaaacatta       60
attacaatga caaatgaag tctaccaaat cattcataga                              100

<210> SEQ ID NO 146
<211> LENGTH: 101
<212> TYPE: DNA
<213> ORGANISM: Nicotiana benthamiana

<400> SEQUENCE: 146
tatttgtgat gtgacatgac aaataatgat gttacaatat tatgtacctc taaatgagat       60
ctagcattga agattgcatg aatattcttg agtgtgttat t                           101

<210> SEQ ID NO 147
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 147
cccggaaaca cctaacagct                                                   20

<210> SEQ ID NO 148
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 148
agtcccgtca tcaaacccac                                                   20

<210> SEQ ID NO 149
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 149
ttttgcaaac tccaacgcca                                                   20

<210> SEQ ID NO 150
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 150
gtggagaggg gagagatcga                                                   20

<210> SEQ ID NO 151
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 151
ccgctctcat ccctggtttt                                                   20

```
<210> SEQ ID NO 152
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 152
ggatgttaga gacggtatta tgttcac                                        27

<210> SEQ ID NO 153
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 153
cacaaacacc gtcatcaccg                                                20

<210> SEQ ID NO 154
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 154
atgccaaagt tgccaaagt ct                                              22

<210> SEQ ID NO 155
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 155
cttgtgggtt gtggaattgt ca                                             22

<210> SEQ ID NO 156
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 156
tgctattcgt acggaaggcg                                                20

<210> SEQ ID NO 157
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 157
tcgaactcac caagctccac                                                20

<210> SEQ ID NO 158
<211> LENGTH: 20
<212> TYPE: DNA
<213> ORGANISM: Artificial Sequence
<220> FEATURE:
<223> OTHER INFORMATION: Oligonucleotide primer
```

-continued

<400> SEQUENCE: 158
gcacctacgt tcagaggctt                                        20

<210> SEQ ID NO 159
<211> LENGTH: 30
<212> TYPE: DNA
<213> ORGANISM: Artificial
<220> FEATURE:
<223> OTHER INFORMATION: Primer

<400> SEQUENCE: 159
gaaaactgac caaccgtatg ttctcactaa                             30

<210> SEQ ID NO 160
<211> LENGTH: 30
<212> TYPE: DNA
<213> ORGANISM: Artificial
<220> FEATURE:
<223> OTHER INFORMATION: Primer

<400> SEQUENCE: 160
gagatgagtt ttgcgtactt caagaggatg                             30

<210> SEQ ID NO 161
<211> LENGTH: 30
<212> TYPE: DNA
<213> ORGANISM: Artificial
<220> FEATURE:
<223> OTHER INFORMATION: Primer

<400> SEQUENCE: 161
caagttcatt ggattttgac tgactcacca                             30

<210> SEQ ID NO 162
<211> LENGTH: 30
<212> TYPE: DNA
<213> ORGANISM: Artificial
<220> FEATURE:
<223> OTHER INFORMATION: Primer

<400> SEQUENCE: 162
tcccaactta acaatacgaa aactagsggt                             30

<210> SEQ ID NO 163
<211> LENGTH: 30
<212> TYPE: DNA
<213> ORGANISM: Artificial
<220> FEATURE:
<223> OTHER INFORMATION: Primer

<400> SEQUENCE: 163
gtaggctatc gtcatttcct aagatgtgga                             30

<210> SEQ ID NO 164
<211> LENGTH: 30
<212> TYPE: DNA
<213> ORGANISM: Artificial
<220> FEATURE:
<223> OTHER INFORMATION: Primer

<400> SEQUENCE: 164
tagtcaatgc acgccttttc gatctatatc                             30

<210> SEQ ID NO 165

-continued

```
<211> LENGTH: 30
<212> TYPE: DNA
<213> ORGANISM: Artificial
<220> FEATURE:
<223> OTHER INFORMATION: Primer

<400> SEQUENCE: 165
ccccttacaa gtaccctcat atttctcaca                                        30

<210> SEQ ID NO 166
<211> LENGTH: 22
<212> TYPE: DNA
<213> ORGANISM: Artificial
<220> FEATURE:
<223> OTHER INFORMATION: Primer

<400> SEQUENCE: 166
ttaacgaggc aaccaataag gc                                                22

<210> SEQ ID NO 167
<211> LENGTH: 30
<212> TYPE: DNA
<213> ORGANISM: Artificial
<220> FEATURE:
<223> OTHER INFORMATION: Primer

<400> SEQUENCE: 167
atgatagaat ccgccttgtt tatctagacg                                        30

<210> SEQ ID NO 168
<211> LENGTH: 30
<212> TYPE: DNA
<213> ORGANISM: Artificial
<220> FEATURE:
<223> OTHER INFORMATION: Primer

<400> SEQUENCE: 168
aatgcaaatt caccgtatca gtaaagttcg                                        30

<210> SEQ ID NO 169
<211> LENGTH: 30
<212> TYPE: DNA
<213> ORGANISM: Artificial
<220> FEATURE:
<223> OTHER INFORMATION: Primer

<400> SEQUENCE: 169
accgtaacgt gatcttcaaa ttaacaatct                                        30

<210> SEQ ID NO 170
<211> LENGTH: 30
<212> TYPE: DNA
<213> ORGANISM: Artificial
<220> FEATURE:
<223> OTHER INFORMATION: Primer

<400> SEQUENCE: 170
ggtgatgatc catacagctt ggttaaagat                                        30

<210> SEQ ID NO 171
<211> LENGTH: 30
<212> TYPE: DNA
<213> ORGANISM: Artificial
<220> FEATURE:
<223> OTHER INFORMATION: Primer

<400> SEQUENCE: 171
```
atccaagaat aagaatccca cctcatgttc                                30

<210> SEQ ID NO 172
<211> LENGTH: 30
<212> TYPE: DNA
<213> ORGANISM: Artificial
<220> FEATURE:
<223> OTHER INFORMATION: Primer

<400> SEQUENCE: 172
aattaacaga ccatgagcca caataactga                                30

<210> SEQ ID NO 173
<211> LENGTH: 22
<212> TYPE: DNA
<213> ORGANISM: Artificial
<220> FEATURE:
<223> OTHER INFORMATION: Primer

<400> SEQUENCE: 173
agagggaatt aacgcaactg tg                                        22

<210> SEQ ID NO 174
<211> LENGTH: 95
<212> TYPE: DNA
<213> ORGANISM: Artificial
<220> FEATURE:
<223> OTHER INFORMATION: Transgene Integration Site

<400> SEQUENCE: 174
atagtcagtt gaattcaaac tctctgactc atcattagag aaacaattaa agctgtatat    60
taagatactt actacgcgtg gtccgatgtg agact                              95

<210> SEQ ID NO 175
<211> LENGTH: 95
<212> TYPE: DNA
<213> ORGANISM: Artificial
<220> FEATURE:
<223> OTHER INFORMATION: Transgene Integration Site

<400> SEQUENCE: 175
gaattcgccc ttggcgcgcc aaagtagtaa gtatcttaaa aaacagataa atagattata    60
gtattactta caatgcgcgc gacgcattgt atgaa                              95

<210> SEQ ID NO 176
<211> LENGTH: 179
<212> TYPE: DNA
<213> ORGANISM: Artificial
<220> FEATURE:
<223> OTHER INFORMATION: Niben101Scf00732_Event 7_L Border

<400> SEQUENCE: 176
attatcaaca gtgcaaaggt tgtcttcttg aatgagaggc cacaacctag gccaggcaaa    60
ggtttcacta atacctgtga tgtttgtcaa agctgtatat taagatactt actacgcgtg   120
gtccgatgtg agactttttca acaaagggta atatccggaa acctcctcgg attccattg   179

<210> SEQ ID NO 177
<211> LENGTH: 178
<212> TYPE: DNA
<213> ORGANISM: Artificial
<220> FEATURE:
<223> OTHER INFORMATION: Niben101Scf00773_Event 9_L Border -continued

```
<400> SEQUENCE: 177
gaagaaaaag atgaaacaaa tccaaggagg aagattagac atggagcaat gatggagaaa    60
aatggtggtc attactactg aagttgtcaa agctgtatat taagatactt actacgcgtg   120
gtccgatgtg agacttttca acaaagggta atatccggaa acctcctcgg attccatt    178

<210> SEQ ID NO 178
<211> LENGTH: 178
<212> TYPE: DNA
<213> ORGANISM: Artificial
<220> FEATURE:
<223> OTHER INFORMATION: Niben101Scf04574_Event 5_L Border

<400> SEQUENCE: 178
aactttttga gatcatagaa gatatcaaat gtaaatgata ggcttacatt cctgatgtac    60
tatcccatta tgcaataata aagatgcaaa agctgtatat taagatactt actacgcgtg   120
gtccgatgtg agacttttca acaaagggta atatccggaa acctcctcgg attccatt    178

<210> SEQ ID NO 179
<211> LENGTH: 178
<212> TYPE: DNA
<213> ORGANISM: Artificial
<220> FEATURE:
<223> OTHER INFORMATION: Niben101Scf05124_Event 6_L Border

<400> SEQUENCE: 179
aagtacatta aatagactgc taagcaatat tattaaagtt atagtcagtt gaattcaaac    60
tctctgactc atcattagag aaacaattaa agctgtatat taagatactt actacgcgtg   120
gtccgatgtg agacttttca acaaagggta atatccggaa acctcctcgg attccatt    178

<210> SEQ ID NO 180
<211> LENGTH: 178
<212> TYPE: DNA
<213> ORGANISM: Artificial
<220> FEATURE:
<223> OTHER INFORMATION: Niben101Scf11415_Event 3_L Border

<400> SEQUENCE: 180
cagcaactat atatcaagta cgtaaattaa aaacttaact aatatacatt gacagtgtta    60
aaaaaaatct attaacgaca atatagagaa agctgtatat taagatactt actacgcgtg   120
gtccgatgtg agacttttca acaaagggta atatccggaa acctcctcgg attccatt    178

<210> SEQ ID NO 181
<211> LENGTH: 178
<212> TYPE: DNA
<213> ORGANISM: Artificial
<220> FEATURE:
<223> OTHER INFORMATION: Niben101Scf13522_Event 9_L Border

<400> SEQUENCE: 181
gaagcttcta gaggataagg ttaggctagt ttgttaaggg ataagggagg gtttagatat    60
tttgaaaggg ttaaggggta aaatcactaa agctgtatat taagatactt actacgcgtg   120
gtccgatgtg agacttttca acaaagggta atatccggaa acctcctcgg attccatt    178

<210> SEQ ID NO 182
<211> LENGTH: 178
<212> TYPE: DNA
<213> ORGANISM: Artificial
<220> FEATURE:
<223> OTHER INFORMATION: Niben101Scf00732_Event 7_R Border
```

<400> SEQUENCE: 182 ttattttta taatgccaac tttgtacaag aaagctgggt cgaattcgcc cttggcgcgc      60
caaagtagta agtatcttaa aaaacagata aaggagtctc ctcgactcct tcagattctg    120
ctctcttggc tgtaaggtaa ttactgacta attgcttttt gctccattct cacaaatt     178

<210> SEQ ID NO 183
<211> LENGTH: 178
<212> TYPE: DNA
<213> ORGANISM: Artificial
<220> FEATURE:
<223> OTHER INFORMATION: Niben101Scf00773_Event 9_R Border

<400> SEQUENCE: 183 ttattttta taatgccaac tttgtacaag aaagctgggt cgaattcgcc cttggcgcgc      60
caaagtagta agtatcttaa aaaacagata aagcaaagct gtcaggtaac atcaaatgat    120
ctctaaatca attagtcttg agggctattt ttgtctctat aaagacagag tatctaaa     178

<210> SEQ ID NO 184
<211> LENGTH: 178
<212> TYPE: DNA
<213> ORGANISM: Artificial
<220> FEATURE:
<223> OTHER INFORMATION: Niben101Scf04574_Event 5_R Border

<400> SEQUENCE: 184 ttattttta taatgccaac tttgtacaag aaagctgggt cgaattcgcc cttggcgcgc      60
caaagtagta agtatcttaa aaaacagata aataggaaat gtcattgaca gctacgagat    120
ctatctttat tgattcacta ttcacgatta caaagatttg catccaagat ctaaactt     178

<210> SEQ ID NO 185
<211> LENGTH: 178
<212> TYPE: DNA
<213> ORGANISM: Artificial
<220> FEATURE:
<223> OTHER INFORMATION: Niben101Scf05124_Event 6_R Border

<400> SEQUENCE: 185 ttattttta taatgccaac tttgtacaag aaagctgggt cgaattcgcc cttggcgcgc      60
caaagtagta agtatcttaa aaaacagata aatagattat agtattactt acaatgcgcg    120
cgacgcattg tatgaaccag cgtgcggatc gtgtgaatca atattgtat tgatgatt      178

<210> SEQ ID NO 186
<211> LENGTH: 178
<212> TYPE: DNA
<213> ORGANISM: Artificial
<220> FEATURE:
<223> OTHER INFORMATION: Niben101Scf11415_Event 3_R Border

<400> SEQUENCE: 186 ttattttta taatgccaac tttgtacaag aaagctgggt cgaattcgcc cttggcgcgc      60
caaagtagta agtatcttaa aaaacagata agagagtact tacatgaatg acgtctactt    120
tgactccgtc aattccaacc gactccaagt gggtgtgtag accctcatat agcttatc     178

<210> SEQ ID NO 187
<211> LENGTH: 178
<212> TYPE: DNA
<213> ORGANISM: Artificial
<220> FEATURE:

<223> OTHER INFORMATION: Niben101Scf13522_Event 9_R_border

<400> SEQUENCE: 187 ttattttta taatgccaac tttgtacaag aaagctgggt cgaattcgcc cttggcgcgc    60
caaagtagta agtatcttaa aaaacagata aggggaatt aacaatgcac actaggttg    120 ccttaaaagt gcctatataa ggcccatttt ccttcatttt ttggcagacg ttgagaac    178

<210> SEQ ID NO 188
<211> LENGTH: 80
<212> TYPE: DNA
<213> ORGANISM: Artificial
<220> FEATURE:
<223> OTHER INFORMATION: Scarless Excision Site

<400> SEQUENCE: 188
tcaaagtaga cgtcattcat gtaagtactc tcttctctat attgtcgtta atagattttt    60
tttaacactg tcaatgtata    80

<210> SEQ ID NO 189
<211> LENGTH: 80
<212> TYPE: DNA
<213> ORGANISM: Artificial
<220> FEATURE:
<223> OTHER INFORMATION: DNA Free Protoplast

<400> SEQUENCE: 189
tcaaagtaga cgtcattcat gtaagtactc tcttatctgt tttttaagat acttactact    60
ttggcgcgcc aagggcgaat    80

<210> SEQ ID NO 190
<211> LENGTH: 46
<212> TYPE: DNA
<213> ORGANISM: Artificial
<220> FEATURE:
<223> OTHER INFORMATION: attP Donor Vector

<400> SEQUENCE: 190
atctgttttt taagatactt actactttgg cgcgccaagg gcgaat    46

<210> SEQ ID NO 191
<211> LENGTH: 95
<212> TYPE: DNA
<213> ORGANISM: Artificial
<220> FEATURE:
<223> OTHER INFORMATION: Left Border

<400> SEQUENCE: 191
aaggaggaga atataacatg tattttgtgt gtatcatgag aaacaattaa gctgtatatt    60
aagatactta ctacgcgtgg tccgatgtga gactt    95

<210> SEQ ID NO 192
<211> LENGTH: 95
<212> TYPE: DNA
<213> ORGANISM: Artificial
<220> FEATURE:
<223> OTHER INFORMATION: Right Border

<400> SEQUENCE: 192
aattcgccct tggcgcgcca agtagtaag tatcttaaaa aacagataag aaggtaccta    60
taattatgaa gtcaaagcac aaggatattc ttgta    95

```
<210> SEQ ID NO 193
<211> LENGTH: 65
<212> TYPE: DNA
<213> ORGANISM: Artificial
<220> FEATURE:
<223> OTHER INFORMATION: 7493878 with ID373 Insert or 1627-17a-4-1-
      AL33.ab1

<400> SEQUENCE: 193
tattttgtgt gtatcatgag aaacaataaa gctgtatatt aagatactta ctacgcgtgg      60
tccga                                                                 65

<210> SEQ ID NO 194
<211> LENGTH: 65
<212> TYPE: DNA
<213> ORGANISM: Artificial
<220> FEATURE:
<223> OTHER INFORMATION: 1627-19-1-042-AL33.ab1 or 1627-19-1-200-1-
      AL33.ab1

<400> SEQUENCE: 194
tattttgtgt gtatcatgag aaacaattaa gctgtatatt aagatactta ctacgcgtgg      60
tccga                                                                 65

<210> SEQ ID NO 195
<211> LENGTH: 65
<212> TYPE: DNA
<213> ORGANISM: Artificial
<220> FEATURE:
<223> OTHER INFORMATION: 1627-19-1-170-AO34.ab1
<220> FEATURE:
<221> NAME/KEY: misc_feature
<222> LOCATION: (36)..(36)
<223> OTHER INFORMATION: n is a, c, g, or t

<400> SEQUENCE: 195
tattttgtgt gtatcatgag aaacaattaa gctgtntatt aagatactta ctacgcgtgg      60
tccga                                                                 65

<210> SEQ ID NO 196
<211> LENGTH: 66
<212> TYPE: DNA
<213> ORGANISM: Artificial
<220> FEATURE:
<223> OTHER INFORMATION: 7493878 with ID373 Insert, or 1627-17a-4-1-
      AO33.ab1

<400> SEQUENCE: 196
tggcgcgcca aagtagtaag tatcttaaaa aacagattag aaggtaccta taattatgaa      60
gtcaaa                                                                66

<210> SEQ ID NO 197
<211> LENGTH: 66
<212> TYPE: DNA
<213> ORGANISM: Artificial
<220> FEATURE:
<223> OTHER INFORMATION: 1627-19-1-042-1-AO33.ab1, 1627-19-1-170-
      AO33.ab1, or 1627-19-1-200-1-AO33.ab1

<400> SEQUENCE: 197
tggcgcgcca aagtagtaag tatcttaaaa aacagataag aaggtaccta taattatgaa      60
gtcaaa                                                                66

<210> SEQ ID NO 198
```

```
<211> LENGTH: 100
<212> TYPE: DNA
<213> ORGANISM: Artificial
<220> FEATURE:
<223> OTHER INFORMATION: ATTR transgenic N. benthi locus

<400> SEQUENCE: 198
gttatagtca gttgaattca aactctctga ctcatcatta gagaaacaat taaagctgta      60
tattaagata cttactacgc gtggtccgat gtgagacttt                           100

<210> SEQ ID NO 199
<211> LENGTH: 93
<212> TYPE: DNA
<213> ORGANISM: Artificial
<220> FEATURE:
<223> OTHER INFORMATION: ATTR Transgenic Lettuce

<400> SEQUENCE: 199
tcgaattcgc ccttggcgcg ccaaagtagt aagtatctta aaaacagat aaaaaggtca       60 tgctaagacc cacaagccca gtcaccactg ctg                                   93

<210> SEQ ID NO 200
<211> LENGTH: 77
<212> TYPE: DNA
<213> ORGANISM: Artificial
<220> FEATURE:
<223> OTHER INFORMATION: attP Integration Vector

<400> SEQUENCE: 200
tcgaattggc ccttggcgcg ccaaagtagt aagtatctta aaaacagat aaagctgtat       60 attaagatac ttactac                                                     77

<210> SEQ ID NO 201
<211> LENGTH: 193
<212> TYPE: DNA
<213> ORGANISM: Artificial
<220> FEATURE:
<223> OTHER INFORMATION: Newly Formed attP Site Flanked by the CmYLCV
      Promoter and Luciferase ORF

<400> SEQUENCE: 201
atctcagaga gatagtccta gagagagaaa gagagcaagt agcctagaag tagggcgcgc      60
cggatccaaa agtagtaagt atcttaaaaa acagataaag ctgtatatta agatacttac    120
tacatatggt accagcgcta tggaagacgc caaaaacata agaaaggcc cggcgccatt     180 ctatcctcta gag                                                       193

<210> SEQ ID NO 202
<211> LENGTH: 192
<212> TYPE: DNA
<213> ORGANISM: Artificial
<220> FEATURE:
<223> OTHER INFORMATION: Newly Formed attB site within the Backbone
      Mini-plasmid

<400> SEQUENCE: 202
aggaaacagc tatgaccatg taatacgact cactataggg gatatcagct ggatgggagc      60
tcggtaccca tgtcattaat atcagtacag ataaagctgt atctcctgtg aacacaatgg    120
atcccccggg atttaaatca gaaggtaatt atccaagatg tagcatcaag aatccaatgt    180
ttacgggaaa aa                                                         192
```

```
<210> SEQ ID NO 203
<211> LENGTH: 60
<212> TYPE: DNA
<213> ORGANISM: Artificial
<220> FEATURE:
<223> OTHER INFORMATION: Canonical SPBc2 attP Site

<400> SEQUENCE: 203
aaaagtagta agtatcttaa aaaacagata aagctgtata ttaagatact tactacatat      60

<210> SEQ ID NO 204
<211> LENGTH: 60
<212> TYPE: DNA
<213> ORGANISM: Artificial
<220> FEATURE:
<223> OTHER INFORMATION: Reverse Complement of Canonical SPBc2 attP Site

<400> SEQUENCE: 204
atatgtagta agtatcttaa tatacagctt tatctgtttt ttaagatact tactactttt      60

<210> SEQ ID NO 205
<211> LENGTH: 50
<212> TYPE: DNA
<213> ORGANISM: Artificial
<220> FEATURE:
<223> OTHER INFORMATION: Reverse complement of Canonical SPBc2 attB Site

<400> SEQUENCE: 205
attgtgttca caggagatac agctttatct gtactgatat taatgacatg      50

<210> SEQ ID NO 206
<211> LENGTH: 55
<212> TYPE: DNA
<213> ORGANISM: Artificial
<220> FEATURE:
<223> OTHER INFORMATION: Canonical SPBc2 attL Site

<400> SEQUENCE: 206
catgtcatta atatcagtac agataaagct gtatattaag atacttacta catat      55

<210> SEQ ID NO 207
<211> LENGTH: 55
<212> TYPE: DNA
<213> ORGANISM: Artificial
<220> FEATURE:
<223> OTHER INFORMATION: Reverse complement of Canonical SPBc2 attL Site

<400> SEQUENCE: 207
atatgtagta agtatcttaa tatacagctt tatctgtact gatattaatg acatg      55

<210> SEQ ID NO 208
<211> LENGTH: 55
<212> TYPE: DNA
<213> ORGANISM: Artificial
<220> FEATURE:
<223> OTHER INFORMATION: Canonical SPBc2 attR Site

<400> SEQUENCE: 208
aaaagtagta agtatcttaa aaaacagata aagctgtatc tcctgtgaac acaat      55

<210> SEQ ID NO 209
<211> LENGTH: 55
<212> TYPE: DNA
<213> ORGANISM: Artificial
<220> FEATURE:
<223> OTHER INFORMATION: Reverse complement of Canonical SPBc2 attR Site
```

```
<400> SEQUENCE: 209
attgtgttca caggagatac agctttatct gttttttaag atacttacta ctttt         55

<210> SEQ ID NO 210
<211> LENGTH: 153
<212> TYPE: DNA
<213> ORGANISM: Zea mays

<400> SEQUENCE: 210
tcgaagggag gaataccagg tttgagcaac actcctgaca gccataacga aagatttggc    60
catgactgca gcattgccac catacgaaga tactgttgct tcgtagctca tcaaaaactg   120
cttcgggtct gagtggccat caaatacggg aag                                153

<210> SEQ ID NO 211
<211> LENGTH: 153
<212> TYPE: DNA
<213> ORGANISM: Artificial
<220> FEATURE:
<223> OTHER INFORMATION: WT PCR Amplification

<400> SEQUENCE: 211
tcgaagggag gaataccagg tttgagcaac actcctgaca gccataacaa aagatttggc    60
catgactgaa gcattgccac catacgaaga tactgttgct tcgtagctca tcaaaaactg   120
cttcgggtct gagtggccat cgaatacggg agc                                153

<210> SEQ ID NO 212
<211> LENGTH: 153
<212> TYPE: DNA
<213> ORGANISM: Artificial
<220> FEATURE:
<223> OTHER INFORMATION: Junction Specific PCR Amplicon or Genome Walker

<400> SEQUENCE: 212
tcgaagggag gaataccagg tttgagcaac actcctgaca gccataacaa aagatttggc    60
catgactgca gcattgccac catattaaga tacttactac gcgtggtccg atgtgagact   120
tttcaacaaa gggtaatatc cggaaacctc ctc                                153

<210> SEQ ID NO 213
<211> LENGTH: 99
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 213
ggtcgaattc gcccttggcg cgccaaagta gtaagtatct taaaaaacag ataaagctgt    60
atattaagat acttactacg cgtaggtcga tgtgagact                           99

<210> SEQ ID NO 214
<211> LENGTH: 99
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 214
ggtcgaattc gcccttgacg cgccaaagta gtaagtatct taaaaaacag ataaagctgt    60
atattaagat acttactacg cgtggtccga tgtgagact                           99
```

<210> SEQ ID NO 215
<211> LENGTH: 98
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 215
ggtcgaattc gcccttggcg cgccaaagta gtaagtatct taaaaacaga taaagctgta       60
tattaagata cttactacgc gtggtccgac gtgagact                              98

<210> SEQ ID NO 216
<211> LENGTH: 97
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 216
ggtcgaattc gcccttggcg cgccaagtag taagtatctt aaaaaacaga taagcgggac       60
aacgtaagca ctacatttcg ctcatcgcca gcccagt                               97

<210> SEQ ID NO 217
<211> LENGTH: 99
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 217
ggtcgaattc gcccttggcg cgccaaagta gtaagtacct taaaaaacag ataaagctgt       60
atattaagat acttactacg cgtggtccga tgtgagact                             99

<210> SEQ ID NO 218
<211> LENGTH: 99
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 218
gggtcgattc gccctcggcg cgccaaagta gtaagtatct taaaaaacag ataaagctgt       60
atattaagat acttactacg cgttggtcga tgtgagact                             99

<210> SEQ ID NO 219
<211> LENGTH: 97
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 219
ggtcgaattc gcccttggcg cgccaaagta gtaagtatct taaaaaacag ataactgtat       60
attaagatac ttactacttt ggcgcgccaa gggcgaa                               97

<210> SEQ ID NO 220
<211> LENGTH: 99

```
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 220
ggtcgaattc gcccttggcg cgccaaagta gtaagtatct taaaaaacag ataaagctgt      60
atattaagat acttactacg cgtgtccgat gtgagactt                              99

<210> SEQ ID NO 221
<211> LENGTH: 99
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 221
ggtcgaattc gcccttggcg cgccaaagta gtaagtatct taaaaaacag ataaagctgt      60
atattaagat acttactact ttggcgcgca agggcgaat                             99

<210> SEQ ID NO 222
<211> LENGTH: 99
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 222
ggtcgaattc gcccttggcg cgccaaagta gtaagtatct taaaaaacag ataaaactgt      60
atattaagat acttactacg cgtggtccga tgtgagact                             99

<210> SEQ ID NO 223
<211> LENGTH: 92
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 223
ggtcgaattc gcccttggcg cgccaaagta gtaagtatct taaaaaacag agtatattaa      60
gatacttact acgcgtggtc cgatgtgaga ct                                    92

<210> SEQ ID NO 224
<211> LENGTH: 99
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 224
ggtcgaattc gcccttggcg cgccaaagta gtaagtatct taaaaaacag ataaagctgt      60
atattaagat acttactact ttggcgcgcc aagggcgaa                             99

<210> SEQ ID NO 225
<211> LENGTH: 98
<212> TYPE: DNA
<213> ORGANISM: Artificial
<220> FEATURE:
<223> OTHER INFORMATION: PacBio CCS Sequence Reads Reference Assembled
``` to the Complete SPBc2 attP Site

<400> SEQUENCE: 225
ggtcgaattc gcccttggcg cgccaaagta gtaagtatct taaaaacaga taaagctgta      60
tattaagata cttactactt tggcgcgcca agggcgaa                              98

<210> SEQ ID NO 226
<211> LENGTH: 99
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 226
ggtcgaattc gcccttggcg cgccaaagta gtaagtatct taaaaacag ataaagctgt       60 atattaagat acttactacg cgtggtccga tgttgagac                             99

<210> SEQ ID NO 227
<211> LENGTH: 97
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 227
ggtcgaattc gcccttggcg cgccaaagta gtaagtatct taaaaacaga taatacggtt      60
atccacagaa tcaggggata acgcaggaaa gaacatg                               97

<210> SEQ ID NO 228
<211> LENGTH: 99
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 228
gttcgaattc gcccttggcg cgccaaagta gtaagtatct taaaaacag ataaagctgt       60 atattaagat acttactacg cgtggtccga tgtgagact                             99

<210> SEQ ID NO 229
<211> LENGTH: 99
<212> TYPE: DNA
<213> ORGANISM: Artificial
<220> FEATURE:
<223> OTHER INFORMATION: PacBio CCS Sequence Reads Reference Assembled
      to the Complete SPBc2 attP Site

<400> SEQUENCE: 229
tggtcgaatt cgccttggcg cgccaaagta gtaagtatct taaaaacag ataaagctgt       60 atattaagat acttactacg cgtggtccga tgtgagact                             99

<210> SEQ ID NO 230
<211> LENGTH: 119
<212> TYPE: DNA
<213> ORGANISM: Oryza minuta

<400> SEQUENCE: 230
atgtgttgaa ttcacagtgg ttgctacttg gtgctaattg ctaccagttg ctaagctagc      60
tagtgctatt acaggattgg tgaactactc gggttcctct cccacggatt tgcctggcc     119

<210> SEQ ID NO 231
<211> LENGTH: 119
<212> TYPE: DNA
<213> ORGANISM: Artificial
<220> FEATURE:
<223> OTHER INFORMATION: Selected Amplicon Reads

<400> SEQUENCE: 231

```
atgtgtcgaa ttcacagtgg tttgctactt ggtgctaatt gctaccagtt gctagctagc    60
tagtgctatt acaggattgg tgagctactc ggctgtatat taagatactt actacgcgt    119
```

<210> SEQ ID NO 232
<211> LENGTH: 100
<212> TYPE: DNA
<213> ORGANISM: Artificial
<220> FEATURE:
<223> OTHER INFORMATION: FWD Right Border

<400> SEQUENCE: 232

```
ggtcgtgaaa tggataaaaa aatacagcgt ttttcatgta caactatact tataggtaat    60
aaagttataa gacaatatta caataggtct tttgacatca                          100
```

<210> SEQ ID NO 233
<211> LENGTH: 100
<212> TYPE: DNA
<213> ORGANISM: Artificial
<220> FEATURE:
<223> OTHER INFORMATION: FWD Left Border

<400> SEQUENCE: 233

```
ataaataaat aaaagagggg ttagggcttt gagtcctttt gtcttcgtct agttgtagtg    60
cctaaataat gcttttaaaa cttaaaaata atatcgatgt                          100
```

<210> SEQ ID NO 234
<211> LENGTH: 100
<212> TYPE: DNA
<213> ORGANISM: Artificial
<220> FEATURE:
<223> OTHER INFORMATION: REV SF370 attP

<400> SEQUENCE: 234

```
tctaggatag ttaagcaatt gatagataga gtcgaggtta ctatggataa catcgatatt    60
atttttaagt tttaaaagca ttatttaggc actacaacta                          100
```

<210> SEQ ID NO 235
<211> LENGTH: 39
<212> TYPE: DNA
<213> ORGANISM: Zea mays

<400> SEQUENCE: 235

```
aattacatga gaaacaatta agaagagttt agaaaagaa                            39
```

<210> SEQ ID NO 236
<211> LENGTH: 39
<212> TYPE: DNA
<213> ORGANISM: Zea mays

<400> SEQUENCE: 236

```
attattttta gaaacaataa atgggttttt aaaatagca                            39
```

<210> SEQ ID NO 237

```
<211> LENGTH: 39
<212> TYPE: DNA
<213> ORGANISM: Zea mays

<400> SEQUENCE: 237
tgtatctagt gaaactataa attggtaatt ctaagtaac                              39

<210> SEQ ID NO 238
<211> LENGTH: 39
<212> TYPE: DNA
<213> ORGANISM: Zea mays

<400> SEQUENCE: 238
tgttgcgtga gaaacaatta aatagatcca acaatacaa                              39

<210> SEQ ID NO 239
<211> LENGTH: 39
<212> TYPE: DNA
<213> ORGANISM: Zea mays

<400> SEQUENCE: 239
tgaaatttta gaaaccatta aaatgtattt agaagcttc                              39

<210> SEQ ID NO 240
<211> LENGTH: 39
<212> TYPE: DNA
<213> ORGANISM: Zea mays

<400> SEQUENCE: 240
tgtcatgaaa gcaacaataa aattgattttt ctaattaat                             39

<210> SEQ ID NO 241
<211> LENGTH: 39
<212> TYPE: DNA
<213> ORGANISM: Zea mays

<400> SEQUENCE: 241
tggcatatga gaaacaataa aagcgatcat atcatatta                              39

<210> SEQ ID NO 242
<211> LENGTH: 39
<212> TYPE: DNA
<213> ORGANISM: Zea mays

<400> SEQUENCE: 242
tgttgtgtga gaaacaatta aacagatcca acaatacaa                              39

<210> SEQ ID NO 243
<211> LENGTH: 39
<212> TYPE: DNA
<213> ORGANISM: Zea mays

<400> SEQUENCE: 243
tgttgcatga gaaacaatta aacagatcca acaatacaa                              39

<210> SEQ ID NO 244
<211> LENGTH: 39
<212> TYPE: DNA
<213> ORGANISM: Zea mays

<400> SEQUENCE: 244
ataaaaaaca gaaactatta aacagaaact atgattgta                              39
```

```
<210> SEQ ID NO 245
<211> LENGTH: 39
<212> TYPE: DNA
<213> ORGANISM: Zea mays

<400> SEQUENCE: 245
acaaaaaaca gaaactatta aacagaaact atgattgta                              39

<210> SEQ ID NO 246
<211> LENGTH: 39
<212> TYPE: DNA
<213> ORGANISM: Zea mays

<400> SEQUENCE: 246
cataggataa aaacaataa aagcgattat ataagtcca                               39

<210> SEQ ID NO 247
<211> LENGTH: 39
<212> TYPE: DNA
<213> ORGANISM: Zea mays

<400> SEQUENCE: 247
agtcatttga gaaacaataa aggagttatt ttgattatg                              39

<210> SEQ ID NO 248
<211> LENGTH: 39
<212> TYPE: DNA
<213> ORGANISM: Zea mays

<400> SEQUENCE: 248
tatacttaaa aaacaatta aaaggctctt agcagtcac                               39

<210> SEQ ID NO 249
<211> LENGTH: 39
<212> TYPE: DNA
<213> ORGANISM: Glycine max

<400> SEQUENCE: 249
aggaatataa gaaacaataa aaatgacact aatatgaag                              39

<210> SEQ ID NO 250
<211> LENGTH: 39
<212> TYPE: DNA
<213> ORGANISM: Glycine max

<400> SEQUENCE: 250 actaaaaga taaacaatta aatagtttat ataagaata                               39

<210> SEQ ID NO 251
<211> LENGTH: 39
<212> TYPE: DNA
<213> ORGANISM: Glycine max

<400> SEQUENCE: 251
aactatagga gaaacaatta agaagaatct acaatttgt                              39

<210> SEQ ID NO 252
<211> LENGTH: 39
<212> TYPE: DNA
<213> ORGANISM: Glycine max

<400> SEQUENCE: 252
tttaatataa aaacaataa agaggaaaat catattgaa                               39
```

<210> SEQ ID NO 253
<211> LENGTH: 39
<212> TYPE: DNA
<213> ORGANISM: Glycine max

<400> SEQUENCE: 253
tataacaagt aaacaataa aaaggaaaat aataatgat                                    39

<210> SEQ ID NO 254
<211> LENGTH: 39
<212> TYPE: DNA
<213> ORGANISM: Glycine max

<400> SEQUENCE: 254
taaaataaaa gaaacaataa aagcgttttt tttattaaa                                   39

<210> SEQ ID NO 255
<211> LENGTH: 39
<212> TYPE: DNA
<213> ORGANISM: Glycine max

<400> SEQUENCE: 255
gatagggaaa aaaactataa aaaggatttt ttaattata                                   39

<210> SEQ ID NO 256
<211> LENGTH: 39
<212> TYPE: DNA
<213> ORGANISM: Glycine max

<400> SEQUENCE: 256
catattatta aaaactatta atcggttttt ataattatt                                   39

<210> SEQ ID NO 257
<211> LENGTH: 39
<212> TYPE: DNA
<213> ORGANISM: Glycine max

<400> SEQUENCE: 257
attaatacga gaaacaatta aaaaaatctt ataaaaaag                                   39

<210> SEQ ID NO 258
<211> LENGTH: 39
<212> TYPE: DNA
<213> ORGANISM: Glycine max

<400> SEQUENCE: 258
aagataataa gaaacaatta aaaagtttat aatatgaat                                   39

<210> SEQ ID NO 259
<211> LENGTH: 39
<212> TYPE: DNA
<213> ORGANISM: Glycine max

<400> SEQUENCE: 259
tggattaaaa taaacaatta aaaggatcat taaagtcag                                   39

<210> SEQ ID NO 260
<211> LENGTH: 39
<212> TYPE: DNA
<213> ORGANISM: Glycine max

<400> SEQUENCE: 260
tttattatta gaaactataa atagggtttt ctaattttt                                   39

<210> SEQ ID NO 261
<211> LENGTH: 39
<212> TYPE: DNA
<213> ORGANISM: Glycine max

<400> SEQUENCE: 261
gagcataaaa gaaacaatta aagggatt ggaataaaa                              39

<210> SEQ ID NO 262
<211> LENGTH: 39
<212> TYPE: DNA
<213> ORGANISM: Glycine max

<400> SEQUENCE: 262
ttttataaaa aaacaatta aagggtcat aatagtgct                              39

<210> SEQ ID NO 263
<211> LENGTH: 39
<212> TYPE: DNA
<213> ORGANISM: Glycine max

<400> SEQUENCE: 263
ttaaatatta gaaactatta aaagttatt aaaaaattt                             39

<210> SEQ ID NO 264
<211> LENGTH: 39
<212> TYPE: DNA
<213> ORGANISM: Glycine max

<400> SEQUENCE: 264
tttataaaga aaacaataa aagggagtat attataatg                             39

<210> SEQ ID NO 265
<211> LENGTH: 39
<212> TYPE: DNA
<213> ORGANISM: Glycine max

<400> SEQUENCE: 265
tgtaaataaa gtaacaatta aacgatctt gtcattact                             39

<210> SEQ ID NO 266
<211> LENGTH: 39
<212> TYPE: DNA
<213> ORGANISM: Glycine max

<400> SEQUENCE: 266
tgtacatttt taacaatta aaggttagt ataagaata                              39

<210> SEQ ID NO 267
<211> LENGTH: 39
<212> TYPE: DNA
<213> ORGANISM: Glycine max

<400> SEQUENCE: 267
tgtaataaaa aaacaataa taaagaagtt ataattctc                             39

<210> SEQ ID NO 268
<211> LENGTH: 39
<212> TYPE: DNA
<213> ORGANISM: Glycine max

<400> SEQUENCE: 268

```
catcaaatga aaacaatta aaaggtctta aaatacac                            39
```

<210> SEQ ID NO 269
<211> LENGTH: 39
<212> TYPE: DNA
<213> ORGANISM: Glycine max

<400> SEQUENCE: 269

```
tttaaatgca gaaactataa caaagttctt ataattaaa                          39
```

<210> SEQ ID NO 270
<211> LENGTH: 39
<212> TYPE: DNA
<213> ORGANISM: Glycine max

<400> SEQUENCE: 270

```
ttgtttgtta aaacaatta aaaggtcatt aaaattagt                           39
```

<210> SEQ ID NO 271
<211> LENGTH: 39
<212> TYPE: DNA
<213> ORGANISM: Glycine max

<400> SEQUENCE: 271

```
acttacataa gaaacaatta agttgttgct caaattata                          39
```

<210> SEQ ID NO 272
<211> LENGTH: 39
<212> TYPE: DNA
<213> ORGANISM: Glycine max

<400> SEQUENCE: 272

```
tttttttatca gcaactatta aaatgatagt aaaaattaa                         39
```

<210> SEQ ID NO 273
<211> LENGTH: 39
<212> TYPE: DNA
<213> ORGANISM: Glycine max

<400> SEQUENCE: 273

```
tttcttaata caaacaatta aaaggttaac aaaaatata                          39
```

<210> SEQ ID NO 274
<211> LENGTH: 39
<212> TYPE: DNA
<213> ORGANISM: Glycine max

<400> SEQUENCE: 274

```
cattgattaa gaaactataa aaaagtattt attatgaaa                          39
```

<210> SEQ ID NO 275
<211> LENGTH: 39
<212> TYPE: DNA
<213> ORGANISM: Glycine max

<400> SEQUENCE: 275

```
tttctgcata aaaacaataa aaaggaaagt attagtaag                          39
```

<210> SEQ ID NO 276
<211> LENGTH: 39
<212> TYPE: DNA
<213> ORGANISM: Glycine max

<400> SEQUENCE: 276

```
tttaagtgaa gaaacaatta aagagagggt agaagaaca                                  39

<210> SEQ ID NO 277
<211> LENGTH: 39
<212> TYPE: DNA
<213> ORGANISM: Glycine max

<400> SEQUENCE: 277
gactcgaagt gaaacaatta aaaagtatct aggattaaa                                  39

<210> SEQ ID NO 278
<211> LENGTH: 39
<212> TYPE: DNA
<213> ORGANISM: Glycine max

<400> SEQUENCE: 278
gatattgata aaacaatta aaaggagatt atcatttgt                                   39

<210> SEQ ID NO 279
<211> LENGTH: 39
<212> TYPE: DNA
<213> ORGANISM: Glycine max

<400> SEQUENCE: 279
gactcgaagt gaaacaatta aaaagtatct aagattaaa                                  39

<210> SEQ ID NO 280
<211> LENGTH: 39
<212> TYPE: DNA
<213> ORGANISM: Glycine max

<400> SEQUENCE: 280
tgtagtattt gaaaccatta caatgaaatt atgattcag                                  39

<210> SEQ ID NO 281
<211> LENGTH: 39
<212> TYPE: DNA
<213> ORGANISM: Glycine max

<400> SEQUENCE: 281
aattgtcaga gaaacaatta aatggaattg tatattgtc                                  39

<210> SEQ ID NO 282
<211> LENGTH: 39
<212> TYPE: DNA
<213> ORGANISM: Glycine max

<400> SEQUENCE: 282
gacttgaagt gaaacaatta aaaagtatct aggattaaa                                  39

<210> SEQ ID NO 283
<211> LENGTH: 39
<212> TYPE: DNA
<213> ORGANISM: Glycine max

<400> SEQUENCE: 283
aattgtcaga gaaacaatta aatggaattg cacattgcc                                  39

<210> SEQ ID NO 284
<211> LENGTH: 39
<212> TYPE: DNA
<213> ORGANISM: Glycine max
```

```
<400> SEQUENCE: 284
tctttactga gaaacaatta aatggaaaga aaaataaga                                   39

<210> SEQ ID NO 285
<211> LENGTH: 39
<212> TYPE: DNA
<213> ORGANISM: Glycine max

<400> SEQUENCE: 285
gttatcattt gaaacaatta taatgcactt attataaac                                   39

<210> SEQ ID NO 286
<211> LENGTH: 39
<212> TYPE: DNA
<213> ORGANISM: Glycine max

<400> SEQUENCE: 286
ctcttcaata gaaaccatta aaaggatct agaattaaa                                    39

<210> SEQ ID NO 287
<211> LENGTH: 39
<212> TYPE: DNA
<213> ORGANISM: Glycine max

<400> SEQUENCE: 287
tttataaaaa aaaactatta aaatgtattg attatttct                                   39

<210> SEQ ID NO 288
<211> LENGTH: 39
<212> TYPE: DNA
<213> ORGANISM: Glycine max

<400> SEQUENCE: 288
tctgaatgca gaaaccataa aatagaatat agaattgag                                   39

<210> SEQ ID NO 289
<211> LENGTH: 39
<212> TYPE: DNA
<213> ORGANISM: Glycine max

<400> SEQUENCE: 289
aaaaatatta gaaactatta aaagttact aaaaaaaac                                    39

<210> SEQ ID NO 290
<211> LENGTH: 39
<212> TYPE: DNA
<213> ORGANISM: Glycine max

<400> SEQUENCE: 290
actacctaaa gcaacaataa aagggaaat atcattcta                                    39

<210> SEQ ID NO 291
<211> LENGTH: 39
<212> TYPE: DNA
<213> ORGANISM: Glycine max

<400> SEQUENCE: 291
tctaaactga taaacaatta aacggtgttt atatttata                                   39
```